United States Patent
Bencsik et al.

(10) Patent No.: US 9,409,886 B2
(45) Date of Patent: *Aug. 9, 2016

(54) PYRIMIDYL CYCLOPENTANES AS AKT PROTEIN KINASE INHIBITORS

(71) Applicants: Array BioPharma Inc., Boulder, CO (US); Genentech, Inc., South San Francisco, CA (US)

(72) Inventors: Josef Bencsik, Boulder, CO (US); James F. Blake, Boulder, CO (US); James M. Graham, Boulder, CO (US); Martin F. Hentemann, Boulder, CO (US); Nicholas C. Kallan, Boulder, CO (US); Ian S. Mitchell, Boulder, CO (US); Stephen T. Schlachter, Boulder, CO (US); Keith L. Spencer, Boulder, CO (US); Dengming Xiao, Boulder, CO (US); Rui Xu, Boulder, CO (US); Mike Welch, Boulder, CO (US); Jun Liang, South San Francisco, CA (US); Brian S. Safina, South San Francisco, CA (US)

(73) Assignees: ARRAY BIOPHARMA INC., Boulder, CO (US); GENENTECH, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/086,717

(22) Filed: Nov. 21, 2013

(65) Prior Publication Data

US 2014/0080829 A1    Mar. 20, 2014
US 2016/0152601 A9    Jun. 2, 2016

Related U.S. Application Data

(63) Continuation of application No. 12/667,848, filed as application No. PCT/US2008/069144 on Jul. 3, 2008, now Pat. No. 8,618,097.

(60) Provisional application No. 61/020,088, filed on Jan. 9, 2008, provisional application No. 60/948,138, filed on Jul. 5, 2007.

(51) Int. Cl.
| | |
|---|---|
| *C07D 403/12* | (2006.01) |
| *C07D 401/12* | (2006.01) |
| *C07D 405/14* | (2006.01) |
| *C07D 409/14* | (2006.01) |
| *C07D 413/12* | (2006.01) |

(Continued)

(52) U.S. Cl.
CPC ............ *C07D 403/12* (2013.01); *C07D 401/12* (2013.01); *C07D 403/14* (2013.01); *C07D 405/14* (2013.01); *C07D 409/14* (2013.01); *C07D 413/12* (2013.01)

(58) Field of Classification Search
CPC .. C07D 401/12; C07D 403/12; C07D 405/14; C07D 413/12; C07D 403/14; C07D 409/14
USPC ................... 544/253; 514/252.15, 252.16
See application file for complete search history.

(56) References Cited

U.S. PATENT DOCUMENTS

| | | | |
|---|---|---|---|
| 3,885,035 | A | 5/1975 | Simpson |
| 3,956,495 | A | 5/1976 | Lacefield |

(Continued)

FOREIGN PATENT DOCUMENTS

| | | | |
|---|---|---|---|
| EP | 0194161 | A2 | 9/1986 |
| EP | 1803710 | A1 | 7/2007 |

(Continued)

OTHER PUBLICATIONS

Alessi et al., "Characterization of a 3-phosphoinositide-dependent protein kinase which phosphorylates and activates protein kinase Bα", Curr. Biol., 7, 261-269 (1997).

(Continued)

*Primary Examiner* — Susanna Moore
(74) *Attorney, Agent, or Firm* — Viksnins Harris & Padys PLLP

(57) ABSTRACT

The present invention provides compounds of Formula I, including tautomers, resolved enantiomers, diastereomers, solvates, metabolites, salts and pharmaceutically acceptable prodrugs thereof.

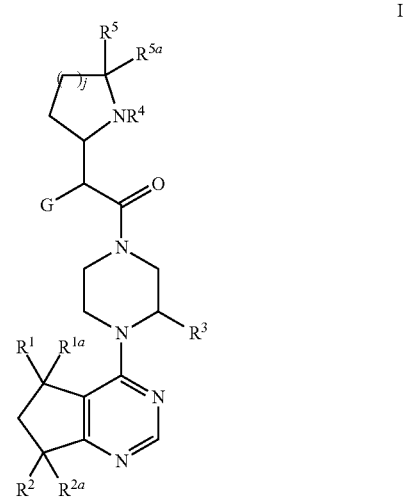

Also provided are methods of using the compounds of this invention as AKT protein kinase inhibitors and for the treatment of hyperproliferative diseases such as cancer.

50 Claims, No Drawings

(51) Int. Cl.
*C07D 403/14* (2006.01)
*A61P 35/02* (2006.01)
*A61P 35/04* (2006.01)
*A61P 29/00* (2006.01)
*A61P 9/00* (2006.01)
*A61P 25/28* (2006.01)
*A61P 35/00* (2006.01)
*A61P 25/16* (2006.01)
*A61P 31/04* (2006.01)
*A61P 37/06* (2006.01)
*A61P 37/08* (2006.01)
*A61P 17/06* (2006.01)
*A61P 11/06* (2006.01)

(56) References Cited

U.S. PATENT DOCUMENTS

| | | |
|---|---|---|
| 3,966,936 A | 6/1976 | Cronin et al. |
| 4,060,615 A | 11/1977 | Matier et al. |
| 4,352,928 A | 10/1982 | Hiranuma et al. |
| 5,051,412 A | 9/1991 | Macor |
| 5,525,625 A | 6/1996 | Bridges et al. |
| 5,563,152 A | 10/1996 | Kulagowski et al. |
| 5,610,303 A | 3/1997 | Kimura et al. |
| 5,750,531 A | 5/1998 | Lee et al. |
| 5,750,545 A | 5/1998 | Akahoshi et al. |
| 5,817,671 A | 10/1998 | Filla et al. |
| 6,310,060 B1 | 10/2001 | Barrett et al. |
| 6,423,716 B1 | 7/2002 | Matsuno et al. |
| 6,469,004 B1 | 10/2002 | Barrett et al. |
| 6,506,798 B1 | 1/2003 | Barrett et al. |
| 6,627,628 B1 | 9/2003 | Schindler et al. |
| 6,831,175 B2 | 12/2004 | Li et al. |
| 7,041,687 B2 | 5/2006 | Binch et al. |
| 7,067,664 B1 | 6/2006 | Chen |
| 7,115,741 B2 | 10/2006 | Levy et al. |
| 7,125,880 B1 | 10/2006 | Chen |
| 7,223,738 B2 | 5/2007 | Bilodeau et al. |
| 7,223,767 B2 | 5/2007 | Clark et al. |
| 8,003,651 B2 | 8/2011 | Mitchell et al. |
| 8,063,050 B2 | 11/2011 | Mitchell et al. |
| 8,329,701 B2 | 12/2012 | Mitchell et al. |
| 8,329,709 B2 | 12/2012 | Banka et al. |
| 8,377,937 B2 | 2/2013 | Bencsik et al. |
| 8,618,097 B2 | 12/2013 | Bencsik et al. |
| 8,680,114 B2 | 3/2014 | Mitchell et al. |
| 8,835,434 B2 | 9/2014 | Bencsik et al. |
| 8,846,681 B2 | 9/2014 | Mitchell et al. |
| 8,846,683 B2 | 9/2014 | Bencsik et al. |
| 8,853,199 B2 | 10/2014 | Mitchell et al. |
| 8,853,216 B2 | 10/2014 | Bencsik et al. |
| 2003/0004193 A1 | 1/2003 | Barrett et al. |
| 2003/0045521 A1 | 3/2003 | Tecle |
| 2003/0078428 A1 | 4/2003 | Barrett et al. |
| 2003/0092748 A1 | 5/2003 | Barrett et al. |
| 2003/0199511 A1 | 10/2003 | Li et al. |
| 2003/0216460 A1 | 11/2003 | Wallace et al. |
| 2003/0232869 A1 | 12/2003 | Wallace et al. |
| 2004/0009968 A1 | 1/2004 | Binch et al. |
| 2004/0053933 A1 | 3/2004 | Pontillo et al. |
| 2004/0102360 A1 | 5/2004 | Barnett et al. |
| 2004/0116710 A1 | 6/2004 | Wallace et al. |
| 2004/0176400 A1 | 9/2004 | Capelli et al. |
| 2005/0059687 A1 | 3/2005 | Makings et al. |
| 2005/0130954 A1 | 6/2005 | Mitchell et al. |
| 2005/0182061 A1 | 8/2005 | Green et al. |
| 2006/0025074 A1 | 2/2006 | Liang et al. |
| 2006/0062400 A1 | 3/2006 | Chia-Chun |
| 2007/0004708 A1 | 1/2007 | Andreotti et al. |
| 2007/0027156 A1 | 2/2007 | Nakai et al. |
| 2007/0135466 A1 | 6/2007 | Ledeboer et al. |
| 2008/0051399 A1 | 2/2008 | Mitchell et al. |
| 2008/0058327 A1 | 3/2008 | Mitchell et al. |
| 2008/0076774 A1 | 3/2008 | Anand et al. |
| 2008/0188482 A1 | 8/2008 | Rice et al. |
| 2009/0131436 A1 | 5/2009 | Imbach et al. |
| 2010/0168123 A1 | 7/2010 | Mitchell et al. |
| 2010/0222321 A1 | 9/2010 | Armstrong et al. |
| 2010/0292244 A1 | 11/2010 | Bencsik et al. |
| 2011/0065716 A1 | 3/2011 | Bencsik et al. |
| 2011/0086842 A1 | 4/2011 | Stadtmueller et al. |
| 2011/0160221 A1 | 6/2011 | Bencsik et al. |
| 2011/0245230 A1 | 10/2011 | Mitchell et al. |
| 2011/0251181 A1 | 10/2011 | Banka et al. |
| 2011/0269773 A1 | 11/2011 | Mitchell et al. |
| 2012/0329808 A1 | 12/2012 | Mitchell et al. |
| 2013/0065908 A1 | 3/2013 | Mitchell et al. |
| 2013/0085135 A1 | 4/2013 | Banka et al. |
| 2014/0148436 A1 | 5/2014 | Mitchell et al. |
| 2014/0315887 A1 | 10/2014 | Bencsik et al. |

FOREIGN PATENT DOCUMENTS

| | | |
|---|---|---|
| JP | 2004512277 | 4/2004 |
| WO | WO 95/03286 A1 | 2/1995 |
| WO | WO 98/43960 A1 | 10/1998 |
| WO | WO 99/01421 A1 | 1/1999 |
| WO | WO 99/01426 A1 | 1/1999 |
| WO | WO 00/40235 A2 | 7/2000 |
| WO | WO 00/40237 A1 | 7/2000 |
| WO | WO 00/41505 A2 | 7/2000 |
| WO | WO 00/41994 A1 | 7/2000 |
| WO | WO 00/42002 A1 | 7/2000 |
| WO | WO 00/42003 A1 | 7/2000 |
| WO | WO 00/42022 A1 | 7/2000 |
| WO | WO 00/42029 A1 | 7/2000 |
| WO | WO 00/68201 A1 | 11/2000 |
| WO | WO 01/05390 A2 | 1/2001 |
| WO | WO 01/05391 A2 | 1/2001 |
| WO | WO 01/05392 A2 | 1/2001 |
| WO | WO 01/05393 A2 | 1/2001 |
| WO | WO 01/68619 A1 | 9/2001 |
| WO | WO 02/06213 A2 | 1/2002 |
| WO | WO 02/18319 A1 | 3/2002 |
| WO | WO 02/22604 | 3/2002 |
| WO | WO 02/44166 A1 | 6/2002 |
| WO | WO 02/083139 A1 | 10/2002 |
| WO | WO 03/022214 A2 | 3/2003 |
| WO | WO 03/064397 A1 | 8/2003 |
| WO | WO 03/077855 A2 | 9/2003 |
| WO | WO 03/077914 A1 | 9/2003 |
| WO | WO 03/086279 A2 | 10/2003 |
| WO | WO 03/086394 A1 | 10/2003 |
| WO | WO 03/086403 A1 | 10/2003 |
| WO | WO 03/086404 A1 | 10/2003 |
| WO | WO 03/094918 A1 | 11/2003 |
| WO | WO 2004/041162 A2 | 5/2004 |
| WO | WO 2004/096130 A2 | 11/2004 |
| WO | WO 2005/014558 A1 | 2/2005 |
| WO | WO 2005/113762 A1 | 12/2005 |
| WO | WO 2005/117909 A2 | 12/2005 |
| WO | WO 2006/046023 A1 | 5/2006 |
| WO | WO 2006/071819 A1 | 7/2006 |
| WO | WO 2006/090261 A1 | 8/2006 |
| WO | WO 2006/136830 A1 | 12/2006 |
| WO | WO 2007/042298 A1 | 4/2007 |
| WO | WO 2007/077961 A2 | 7/2007 |
| WO | WO 2007/125320 A1 | 11/2007 |
| WO | WO 2008/003697 A1 | 1/2008 |
| WO | WO 2008/003958 A2 | 1/2008 |
| WO | WO 2008/003978 A2 | 1/2008 |
| WO | WO 2008/005511 A2 | 1/2008 |
| WO | WO 2008/005964 A2 | 1/2008 |
| WO | WO 2008/006032 A1 | 1/2008 |
| WO | WO 2008/006040 A1 | 1/2008 |
| WO | WO 2008/012635 A2 | 1/2008 |

OTHER PUBLICATIONS

Balendran et al., "PDK1 acquires PDK2 activity in the presence of a synthetic peptide derived from the carboxyl terminus of PRK2", Curr. Biol., 9, 393-404 (1999).

(56) References Cited

OTHER PUBLICATIONS

Bellacosa et al., "Molecular Alterations of the AKT2 Oncogene in Ovarian and Breast Carcinomas", Int. J. Cancer, (Pred. Oncol.) 64, 280-285 (1995).
Brodbeck et al., "A Human Protein Kinase Bγ with Regulatory Phosphorylation Sites in the Activation Loop and in the C-terminal Hydrophobic Domain", J. Biol. Chem., 274, No. 14, 9133-9136 (1999).
Brognard et al., "Akt/Protein Kinase B is Constitutively Active in Non-Small Cell Lung Cancer Cells and Promotes Cellular Survival and Resistance to Chemotherapy and Radiation", Cancer Res., 61, 3986-3997 (2001).
Cheng et al., "AKT2, a putative oncogene encoding a member of a subfamily of protein-serine/threonine kinases, is amplified in human ovarian carcinomas", Proc. Natl. Acad. Sci. USA, vol. 89, 9267-9271 (1992).
Cheng et al., "Amplification of AKT2 in human pancreatic cancer cells and inhibition of AKT2 expression and tumorigenicity by antisense RNA", Proc. Natl. Acad. Sci., USA, vol. 93, 3636-3641 (1996).
Chilean Patent Office Examination Report for CL Application No. 1974-2008, 9 pages, May 9, 2011.
Coffer et al., "Molecular cloning and characterization of a novel putative protein-serine kinase related to the cAMP-dependent and protein kinase C families", Eur. J. Biochem., 201, 475-481 (1991).
Cohen, "Protein kinases—the major drug targets of the twenty-first century?" Nature Rev. Drug Discovery, vol. 1, 309-315 (2002).
Delcommenne et al., "Phosphoinositide-3-OH kinase-dependent regulation of glycogen synthase kinase 3 and protein kinase B/AKT by the integrin-linked kinase", Proc. Natl. Acad. Sci. USA, vol. 95, 11211-11216 (1998).
Expert Scientific Group on Phase One Clinical Trials Final Report, pp. C1, C35-C38 (Nov. 30, 2006).
GCC Patent Office Examination Report for Application No. GCC/P/2008/11234, 6 pages, Jul. 24, 2011.
Georgakis et al., Expert Rev. Anticancer Ther. 6 (1), pp. 131-140, 2006.
Graff et al., "Increased AKT Activity Contributes to Prostate Cancer Progression by Dramatically Accelerating Prostate Tumor Growth and Diminishing p27Kip1 Expression", J. Biol. Chem., vol. 275, No. 32, 24500-24505 (2000).
Granville et al., Clin. Cancer Res. 12 (3), pp. 679-689, 2006.
Gura, Science vol. 278 (5340), 1041-1042 (1997).
Hardie et al., "The Protein Kinase Facts Book. I and II", Academic Press, San Diego, CA., 48-56 (1995).
Hass-Kogan et al., "Protein kinase B (PKB/AKT) activity is elevated in glioblastoma cells due to mutation of the tumor suppressor PTEN/MMAC", Current Biology, 8, 1195-1198 and Supp. page (1998).
Hay, "The Akt-mTOR tango and its relevance to cancer", Cancer Cell, vol. 8, 179-183 (2005).
Hemmings, "Akt Signaling: Linking Membrane Events to Life and Death Decisions", Science, vol. 275, 628-630 (1997).
Kamb, Nature Reviews Drug Discovery 4, 161-165 (2005).
Kim et al., Current Opinion in Investig. Drugs 6 (12), pp. 1250-1258, 2005.
Kola, Nature Reviews Drug Discovery 3, 711-715 (2004).
Li et al., "Targeting Serine/Threonine Protein Kinase B/Akt and Cell-cycle Checkpoint Kinases for Treating Cancer", Current Topics in Med. Chem., 2, 939-971 (2002).
Leaf, Clifton, Health Administrator vol. XVII (1), 172-183 (2005).
Li, Q., "Recent progress in the discovery of Akt inhibitors as anti-cancer agents", Expert Opinion: Informa Healthcare 17(9), pp. 1077-1130, 2007.
Luo et al., Molecular Cancer Ther. 4 (6), pp. 977-896, 2005.
Nakatani et al., "Identification of a Human Akt3 (Protein Kinase Bγ) Which Contains the Regulatory Serine Phosphorylation Site", Biochem. Biophys. Res. Commun., 257, 906-910 (1999).
Neidle, Cancer Drug Design and Discover, ed. (Elsevier/Academic Press), 427-431 (2008).
New Zealand Patent Office Examination Report for NZ Application No. 582692, 2 pages, Nov. 5, 2010.
New Zealand Patent Office Examination Report for NZ Application No. 599501, 2 pages, Apr. 26, 2012.
Ohno, S. et al., "Synthesis and Hypoglycemic Activity of 7,8-Dihydro-6H-thiopyrano[3,2-d]pyrimidine Derivatives and Related Compounds", Chem. Pharm. Bull. 34(10), pp. 4150-4165, 1986.
Pages et al., Expert Opin. Ther. Patents 19 (11), 1501-1519 (2009).
Patent Cooperation Treaty, International Search Report and Written Opinion for PCT/US200/069144, 13 pages, Feb. 6, 2009.
Patent Office of the Russian Federation, Office Action for Russian Application No. 2010103813, 8 pages, Apr. 13, 2012.
Roberts et al., JAMA 292(17), 2130-2140 (2004).
Ross, L.O. et al., "Potential Anticancer Agents. XVIII. Synthesis of Substituted 4,5-Trimethylenepyrimidines", J.Am. Chem. Soc., vol. 81, pp. 3108-3113, 1959.
Staal, "Molecular cloning of the akt oncogene and its human homologues AKT1 and AKT2: Amplification of AKT1 in a primary human gastric adenocarcinoma", Proc. Natl. Acad. Sci., USA, vol. 84, 5034-5037 (1987).
Sunahara, Hisato (Examiner), Office Action and translation thereof issued by the Japanese Patent Office in corresponding Application No. 2010-515269, Jun. 4, 2013 (mailing date), 7 pages.
Toker et al., "Akt/Protein Kinase B is Regulated by Autophosphorylation at the Hypothetical PDK-2 Site", J. Biol. Chem., vol. 275, No. 12, 8271-8274 (2000).
Toker et al., "Akt Signaling and Cancer: Surviving but not Moving On", Cancer Res. 66 (8), 3963-3966 (2006).
Tyukavkina et al., Bioorganic Chemistry, 4th edition, Drofa Publisher, Moscow, pp. 83-85, (2005).
Vippagunta, S.R., Advanced Drug Delivery Reviews, vol. 48, pp. 3-26, 2001.
Zhao, Z. et al., "Discovery of 2,3,5-trisubstituted pyridine derivatives as potent Akt1 and Akt2 dual inhibitors", Bioorganic & Medicinal Chemistry Letters, vol. 15, pp. 905-909, 2005.
Zinda et al., "AKT-1, -2, and -3 are Expressed in Both Normal and Tumor Tissues of the Lung, Breast, Prostate, and Colon," Clin. Cancer Res., vol. 7, 2475-2479 (2001).
U.S. Appl. No. 14/456,670.
U.S. Appl. No. 14/458,062.
U.S. Appl. No. 14/516,443.
U.S. Appl. No. 14/473,336.
U.S. Appl. No. 14/457,582.

PYRIMIDYL CYCLOPENTANES AS AKT PROTEIN KINASE INHIBITORS

PRIORITY OF INVENTION

This application is a continuation of U.S. application Ser. No. 12/667,848, filed 3 Jul. 2008, which is a national phase entry under 35 U.S.C. §371 of PCT/US08/69144, filed 3 Jul. 2008, which claims benefit of U.S. Provisional Application No. 60/948,138, filed 5 Jul. 2007, and U.S. Provisional Application No. 61/020,088, filed 9 Jan. 2008, each of which are hereby incorporated herein by reference in their entirety.

BACKGROUND OF THE INVENTION

1. Field of the Invention

This invention relates to novel inhibitors of serine/threonine protein kinases (e.g., AKT and related kinases), pharmaceutical compositions containing the inhibitors, and methods for preparing these inhibitors. The inhibitors are useful, for example, for the treatment of hyperproliferative diseases, such as cancer and inflammation, in mammals.

2. Description of the State of the Art

Protein kinases (PK) are enzymes that catalyze the phosphorylation of hydroxy groups on tyrosine, serine and threonine residues of proteins by transfer of the terminal (gamma) phosphate from ATP. Through signal transduction pathways, these enzymes modulate cell growth, differentiation and proliferation, i.e., virtually all aspects of cell life in one way or another depend on PK activity (Hardie, G. and Hanks, S. (1995) *The Protein Kinase Facts Book. I and II*, Academic Press, San Diego, Calif.). Furthermore, abnormal PK activity has been related to a host of disorders, ranging from relatively non-life threatening diseases such as psoriasis to extremely virulent diseases such as glioblastoma (brain cancer). Protein kinases are an important target class for therapeutic modulation (Cohen, P. (2002) Nature Rev. Drug Discovery 1:309).

Significantly, atypical protein phosphorylation and/or expression is often reported to be one of the causative effects of abnormal cellular proliferation, metastasis and cell survival in cancer. The abnormal regulation and/or expression of various kinases, including Akt, VEGF, ILK, ROCK, p70S6K, Bcl, PKA, PKC, Raf, Src, PDK1, ErbB2, MEK, IKK, Cdk, EGFR, BAD, CHK1, CHK2 and GSK3 amongst numerous others, has been specifically implicated in cancer.

Protein kinases include two classes; protein tyrosine kinases (PTK) and serine-threonine kinases (STK). The Protein Kinase B/Akt enzymes are a group of serine/threonine kinases that are overexpressed in a variety of human tumors. One of the best-characterized targets of the PI3K lipid products is the 57 KD serine/threonine protein kinase Akt, downstream of PI3K in the signal transduction pathway (Hemmings, B. A. (1997) Science 275:628; Hay N. (2005) Cancer Cell 8:179-183). Akt is the human homologue of the protoon-cogene v-akt of the acutely transforming retrovirus AKT8. Due to its high sequence homology to protein kinases A and C, Akt is also called Protein Kinase B (PKB) and Related to A and C (RAC). Three isoforms of Akt are known to exist, namely Akt1, Akt2 and Akt3, which exhibit an overall homology of 80% (Staal, S. P. (1987) Proc. Natl. Acad. Sci. 84:5034; Nakatani, K. (1999) Biochem. Biophys. Res. Commun. 257:906; Li et al (2002) Current Topics in Med. Chem. 2:939-971; WO 2005/113762). The Akt isoforms share a common domain organization that consists of a pleckstrin homology domain at the N-terminus, a kinase catalytic domain, and a short regulatory region at the C-terminus. In addition, both Akt2 and Akt3 exhibit splice variants. Upon recruitment to the cell membrane by PtdInd(3, 4, 5)$P_3$, Akt is phosphorylated (activated) by PDK1 at T308, T309 and T305 for isoforms Akt1 (PKBα), Akt2 (PKBβ) and Akt3 (PKBγ), respectively, and at S473, S474 and S472 for isoforms Akt1, Akt2 and Akt3, respectively. Such phosphorylation occurs by an as yet unknown kinase (putatively named PDK2), although PDK1 (Balendran, A., (1999) Curr. Biol. 9:393), autophosphorylation (Toker, A. (2000) J. Biol. Chem. 275:8271) and integrin-linked kinase (ILK) (Delcommenne, M. (1998) Proc. Natl. Acad. Sci. USA, 95:11211) have been implicated in this process. Akt activation requires its phosphorylation on residue Ser 473 in the C-terminal hydrophobic motif (Brodbeck et al (1999) J. Biol. Chem. 274:9133-9136; Coffer et al (1991) Eur. J. Biochem. 201:475-481; Alessi et al (1997) Curr. Biol. 7:261-269). Although monophosphorylation of Akt activates the kinase, bis(phosphorylation) is required for maximal kinase activity.

Akt is believed to assert its effect on cancer by suppressing apoptosis and enhancing both angiogenesis and proliferation (Toker et al (2006) Cancer Res. 66(8):3963-3966). Akt is overexpressed in many forms of human cancer including, but not limited to, colon (Zinda et al (2001) Clin. Cancer Res. 7:2475), ovarian (Cheng et al (1992) Proc. Natl. Acad. Sci. USA 89:9267), brain (Haas Kogan et al (1998) Curr. Biol. 8:1195), lung (Brognard et al (2001) Cancer Res. 61:3986), pancreatic (Bellacosa et al (1995) Int. J. Cancer 64:280-285; Cheng et al (1996) Proc. Natl. Acad. Sci. 93:3636-3641), prostate (Graff et al (2000) J. Biol. Chem. 275:24500) and gastric carcinomas (Staal et al (1987) Proc. Natl. Acad. Sci. USA 84:5034-5037).

The PI3K/Akt/mammalian target of rapamycin (mTOR) pathway has been explored for targeted small molecule inhibitor therapy (Georgakis, G. and Younes, A. (2006) Expert Rev. Anticancer Ther. 6(1):131-140; Granville et al (2006) Clin. Cancer Res. 12(3):679-689). Inhibition of PI3K/Akt signaling induces apoptosis and inhibits the growth of tumor cells that have elevated Akt levels (Kim et al (2005) Current Opinion in Investig. Drugs 6(12):1250-1258; Luo et al (2005) Molecular Cancer Ther. 4(6):977-986).

The development of kinase inhibitors that target abnormally regulated pathways and ultimately result in disease is of enormous ethical and commercial interest to the medical and pharmaceutical community. A compound that inhibits (1) recruitment of Akt to the cell membrane, (2) activation by PDK1 or PDK2, (3) substrate phosphorylation, or (4) one of the downstream targets of Akt could be a valuable anticancer agent, either as a stand-alone therapy or in conjunction with other accepted procedures.

United States Patent Application Publication 2005/0130954 discloses inter alia, a variety of compounds that act as AKT inhibitors. The compounds are said to be useful in the treatment of hyperproliferative diseases such as cancer.

United States Patent Application Publication 2008/0058327 and United States Patent Application Publication 2008/0051399 disclose inter alia, a variety of compounds that act as AKT inhibitors.

SUMMARY OF THE INVENTION

This invention provides novel compounds that inhibit AKT protein kinases. The compounds of the present invention have utility as therapeutic agents for diseases and conditions that can be treated by the inhibition of AKT protein kinases.

The present invention includes compounds having the general Formula I:

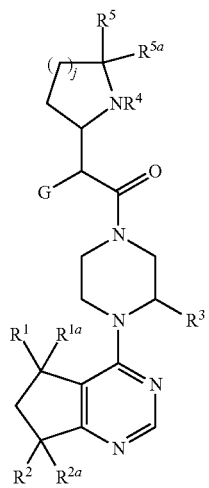

and enantiomers and salts thereof, wherein G, $R^1$, $R^{1a}$, $R^2$, $R^{2a}$, $R^3$, $R^4$, $R^5$, $R^{5a}$ and j are as defined below.

The invention also provides pharmaceutical compositions comprising a compound of Formula I, or an enantiomer or pharmaceutically acceptable salt thereof.

In a further aspect, the present invention provides a method of treating diseases or medical conditions in a mammal mediated by AKT protein kinases, comprising administering to said mammal one or more compounds of Formula I, or an enantiomer or pharmaceutically acceptable salt thereof, in an amount effective to treat or prevent said disorder. AKT protein kinase mediated conditions that can be treated according to the methods of this invention include, but are not limited to, inflammatory, hyperproliferative, cardiovascular, neurodegenerative, gynecological, and dermatological diseases and disorders.

In a further aspect, the present invention provides a method of inhibiting the production of AKT protein kinases in a mammal, which comprises administering to said mammal a compound of Formula I, or an enantiomer or pharmaceutically acceptable salt thereof in an amount effective to inhibit production of an AKT protein kinase.

In a further aspect, the present invention provides methods of inhibiting the activity of AKT protein kinases, comprising contacting said kinase with a compound of Formula I.

The inventive compounds may be used advantageously in combination with other known therapeutic agents. Accordingly, this invention also provides pharmaceutical compositions comprising a compound of Formula I or an enantiomer or pharmaceutically acceptable salt thereof, in combination with a second therapeutic agent.

This invention also provides compounds of Formula I and enantiomers and pharmaceutically acceptable salts thereof for use as medicaments in the treatment of AKT protein kinase-mediated conditions.

An additional aspect of the invention is the use of a compound of Formula I, or an enantiomer or pharmaceutically acceptable salt thereof, for therapy. In one embodiment, the therapy comprises the treatment of an AKT protein kinase-mediated condition.

This invention further provides kits for the treatment of an AKT protein kinase-mediated disease or disorder, said kit comprising a compound of Formula I, or an enantiomer or pharmaceutically acceptable salt thereof, a container, and optionally a package insert or label indicating a treatment. The kits may further comprise a second compound or formulation comprising a second pharmaceutical agent useful for treating said disease or disorder.

Another aspect of the present invention provides a compound for Formula I for use in the treatment of hyperproliferative diseases. In a further aspect, the hyperproliferative disease is cancer.

This invention further includes methods of preparing, methods of separating, and methods of purifying of the compounds of this invention.

Additional advantages and novel features of this invention shall be set forth in part in the description that follows, and in part will become apparent to those skilled in the art upon examination of the following specification, or may be learned by the practice of the invention. The advantages of the invention may be realized and attained by means of the instrumentalities, combinations, compositions, and methods particularly pointed out in the appended claims.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

DEFINITIONS

The term "alkyl" as used herein refers to a saturated linear or branched-chain monovalent hydrocarbon radical of one to twelve carbon atoms, wherein the alkyl radical may be optionally substituted independently with one or more substituents described below. In an embodiment, alkyl includes $C_1$-$C_4$ alkyl groups. In other embodiment, alkyl includes $C_1$-$C_3$ alkyl groups. In other embodiment, alkyl includes $C_1$-$C_6$ alkyl groups. Examples of alkyl groups include, but are not limited to, methyl ("Me", —$CH_3$), ethyl ("Et", —$CH_2CH_3$), 1-propyl ("n-Pr", n-propyl, —$CH_2CH_2CH_3$), 2-propyl ("i-Pr", i-propyl, —$CH(CH_3)_2$), 1-butyl ("n-Bu", n-butyl, —$CH_2CH_2CH_2CH_3$), 2-methyl-1-propyl ("i-Bu", i-butyl, —$CH_2CH(CH_3)_2$), 2-butyl ("s-Bu", s-butyl, —$CH(CH_3)CH_2CH_3$), 2-methyl-2-propyl ("t-Bu", t-butyl, tert-butyl, —$C(CH_3)_3$), 2,2-dimethylpropyl ($CH_2C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)$ $CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)$ ($CH_2CH_2CH_3$)), 2-methyl-2-pentyl (—$C(CH_3)_2$ $CH_2CH_2CH_3$), 3-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, 1-heptyl, 1-octyl, and the like.

The term "cycloalkyl" refers to saturated or partially unsaturated cyclic hydrocarbon radical having from three to twelve carbon atoms. In one embodiment, cycloalkyl includes 5-6 membered cycloalkyl groups. In another embodiment, cycloalkyl includes C$_3$-C$_6$ cycloalkyl groups. In another embodiment, cycloalkyl includes a 5-membered cycloalkyl. In another embodiment, cycloalkyl includes a 6 membered cycloalkyl. The term "cycloalkyl" includes monocyclic and polycyclic (e.g., bicyclic and tricyclic) cycloalkyl structures, wherein the polycyclic structures optionally include a saturated or partially unsaturated cycloalkyl ring fused to a saturated, partially unsaturated or aromatic cycloalkyl or heterocyclic ring. The cycloalkyl may be optionally substituted independently with one or more substituents described herein.

Examples of cycloalkyl groups include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, bicyclo[2.2.1]heptane, bicyclo[2.2.2]octane, and bicyclo[3.2.2]nonane.

The abbreviations are sometimes used in conjunction with elemental abbreviations and chemical structures, for example, methanol ("MeOH") or ethanol ("EtOH").

The elemental abbreviation for hydrogen, i.e., "H", is used throughout the application.

The term "heteroaryl" as used herein refers to a monovalent aromatic radical of a 5-, 6-, or 7-membered ring and includes fused ring systems (at least one of which is aromatic) of 5-10 atoms containing at least one heteroatom independently selected from nitrogen, oxygen, and sulfur. The heteroaryl may be C-attached or N-attached where such is possible. Heteroaryl groups may be optionally substituted independently with one or more substituents described herein. In one embodiment, heteroaryl is a 5-6 membered heteroaryl. In another embodiment, heteroaryl is a 9-10 membered bicyclic heteroaryl.

Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The terms "heterocycle" refers to a saturated or partially unsaturated carbocyclic radical of 3 to 8 ring atoms in which at least one ring atom is a heteroatom independently selected from nitrogen, oxygen and sulfur, the remaining ring atoms being C, where one or more ring atoms may be optionally substituted independently with one or more substituents described herein. In one embodiment, heterocycle is a 4-6 membered group. In other embodiments, heterocycle is a 5-6 membered group, a 5-membered group or a 6-membered group. "Heterocycle" includes radicals where heterocycle radicals are fused with a saturated, partially unsaturated, or aromatic cyclic groups.

Exemplary heterocyclyl groups include, but are not limited to, oxiranyl, aziridinyl, thiiranyl, azetidinyl, oxetanyl, thietanyl, 1,2-dithietanyl, 1,3-dithietanyl, pyrrolidinyl, piperidinyl, morpholinyl, thiomorpholinyl, thioxanyl, piperazinyl, homopiperazinyl, homopiperidinyl, oxepanyl, thiepanyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, dioxanyl, 1,3-dioxolanyl, pyrazolinyl, pyrazolidinyl, dithianyl, dithiolanyl, pyrazolidinylimidazolinyl, imidazolidinyl, 3-azabicyco[3.1.0]hexanyl, 3-azabicyclo[4.1.0]heptanyl and azabicyclo[2.2.2]hexanyl.

The term "halogen" as used herein means fluoro, chloro, bromo or iodo.

The term "enantiomer" refers to two stereoisomers of a compound which are non-superimposable mirror images of one another.

The term "diastereomer" refers to a pair of optical isomers which are not mirror images of one another.

The term "tautomer" or "tautomeric form" refers to structural isomers of different energies which are interconvertible via a low energy barrier.

The phrase "pharmaceutically acceptable" indicates that the substance or composition is compatible chemically and/or toxicologically with the other ingredients comprising a formulation, and/or the mammal being treated therewith.

The phrase "effective amount" means an amount of compound that, when administered to a mammal in need of such treatment, is sufficient to (i) treat or prevent a particular disease, condition, or disorder mediated by the activity of one or more AKT protein kinases, tyrosine kinases, additional serine/threonine kinases, and/or dual specificity kinases, (ii) attenuate, ameliorate, or eliminate one or more symptoms of the particular disease, condition, or disorder, or (iii) prevent or delay the onset of one or more symptoms of the particular disease, condition, or disorder described herein.

"Treating" is intended to mean at least the mitigation of a disease condition in a mammal, such as a human, that is affected, at least in part, by the activity of one or more AKT protein kinases, tyrosine kinases, additional serine/threonine kinases, and/or dual specificity kinases. The terms "treat" and "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those found to be predisposed to having the disease condition but have not yet been diagnosed as having it; modulating and/or inhibiting the disease condition. The terms "treating", "treat", or "treatment" embrace both preventative, i.e., prophylactic, and palliative treatment.

As used herein, the term "mammal" refers to a warm-blooded animal that has or is at risk of developing a disease described herein and includes, but is not limited to, guinea pigs, dogs, cats, rats, mice, hamsters, and primates, including humans.

The term "package insert" is used to refer to instructions customarily included in commercial packages of therapeutic products, that contain information about the indications, usage, dosage, administration, contraindications and/or warnings concerning the use of such therapeutic products.

The term "a" as used herein means one or more.

As used herein, the terms "compound of this invention," "compounds of the present invention" and "compounds of Formula I" includes compounds of Formula I and tautomers, resolved enantiomers, resolved diastereomers, racemic mixtures, solvates, metabolites, salts (including pharmaceutically acceptable salts) and pharmaceutically acceptable prodrugs thereof.

It is to be understood that in instances where two or more radicals are used in succession to define a substituent attached to a structure, the first named radical is considered to be terminal and the last named radical is considered to be attached to the structure in question. Thus, for example, an heteroarylalkyl radical is attached to the structure in question by the alkyl group.

AKT Inhibitors

The inventive compounds of Formula I are useful for inhibiting AKT protein kinases. The compounds of Formula I may also be useful as inhibitors of tyrosine kinases as well as serine and threonine kinases in addition to AKT. Such compounds have utility as therapeutic agents for diseases that can be treated by the inhibition of the AKT protein kinase signaling pathway and tyrosine and serine/threonine kinase receptor pathways.

In general, the invention includes compounds of the Formula I:

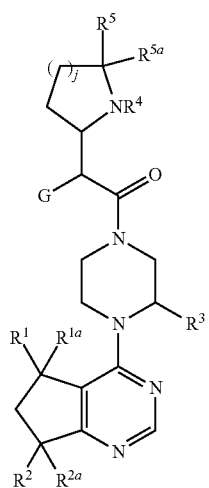

and resolved enantiomers, resolved diastereomers, and pharmaceutically acceptable salts thereof, wherein:

G is phenyl, naphthalene, a 5-6 membered heteroaryl or a 9-10 membered bicyclic heteroaryl, wherein the phenyl, naphthalene, or heteroaryls are optionally substituted with one to four $R^a$ groups;

$R^1$ and $R^{1a}$ are independently selected from H, Me, Et, —CH═CH$_2$, —CH$_2$OH, CF$_3$, CHF$_2$ or CH$_2$F;

$R^2$ is selected from H, —OH, —OMe or F;

$R^{2a}$ is selected from H, Me or F, or $R^2$ and $R^{2a}$ are oxo;

$R^3$ is H, Me, Et, or CF$_3$;

$R^4$ is H, 4-6 membered heterocycle, cyclopropylmethyl or $C_1$-$C_4$ alkyl optionally substituted with F, —OH or —O($C_1$-$C_3$ alkyl);

$R^5$ and $R^{5a}$ are independently selected from H and $C_1$-$C_4$ alkyl, or $R^5$ and $R^{5a}$ together with the atom to which they are attached form a carbonyl group, a 5-6 membered cycloalkyl or 5-6 membered heterocycle, wherein the heterocycle has an oxygen heteroatom;

each $R^a$ is independently halogen, $C_1$-$C_6$ alkyl, $C_3$-$C_6$ cycloalkyl, —O—($C_1$-$C_6$ alkyl), CF$_3$, —OCF$_3$, S($C_1$-$C_6$ alkyl), CN, phenyl, —OCH$_2$-phenyl, NH$_2$, —NO$_2$, —NH—($C_1$-$C_6$ alkyl), —N—($C_1$-$C_6$ alkyl)$_2$, piperidine, pyrrolidine, pyrazole, pyridine, 2-aminopyridine, CH$_2$F, CHF$_2$, —OCH$_2$F, —OCHF$_2$, —OH, —SO$_2$($C_1$-$C_6$ alkyl), C(O)NH$_2$, C(O)NH($C_1$-$C_6$-alkyl), and C(O)N($C_1$-$C_6$ alkyl)$_2$; and j is 1 or 2; and when j is 2, the j ring carbon opposite NR$^4$ may be replaced with an O heteroatom.

In general, the invention includes compounds of the Formula I:

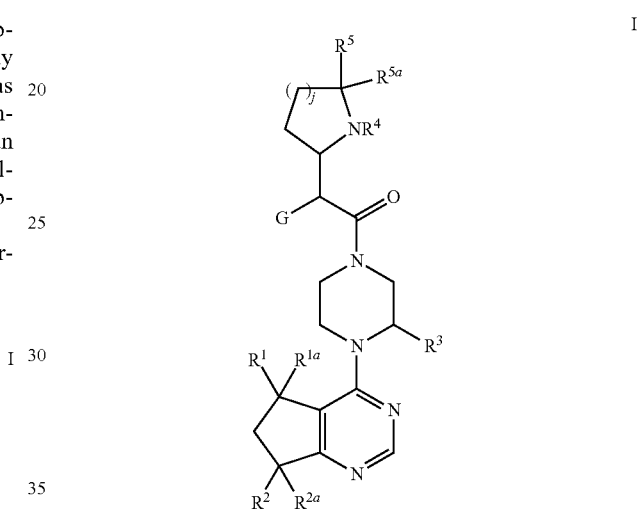

and resolved enantiomers, resolved diastereomers, and pharmaceutically acceptable salts thereof, wherein:

G is phenyl optionally substituted with one to four $R^a$ groups or a 5-6 membered heteroaryl optionally substituted by a halogen;

$R^1$ and $R^{1a}$ are independently selected from H, Me, Et, —CH═CH$_2$, —CH$_2$OH, CF$_3$, CHF$_2$ or CH$_2$F;

$R^2$ is selected from H, —OH, —OMe or F;

$R^{2a}$ is selected from H, Me or F, or $R^2$ and $R^{2a}$ are oxo;

$R^3$ is H, Me, Et, or CF$_3$;

$R^4$ is H, 4-6 membered heterocycle, cyclopropylmethyl or $C_1$-$C_4$ alkyl optionally substituted with F, —OH or —O($C_1$-$C_3$ alkyl);

$R^5$ and $R^{5a}$ are independently selected from H and $C_1$-$C_4$ alkyl, or $R^5$ and $R^{5a}$ together with the atom to which they are attached form a 5-6 membered cycloalkyl or 5-6 membered heterocycle, wherein the heterocycle has an oxygen heteroatom;

each $R^a$ is independently halogen, $C_1$-$C_6$-alkyl, $C_3$-$C_6$-cycloalkyl, —O—($C_1$-$C_6$-alkyl), CF$_3$, —OCF$_3$, S($C_1$-$C_6$-alkyl), CN, —OCH$_2$-phenyl, NH$_2$, —NO$_2$, —NH—($C_1$-$C_6$-alkyl), —N—($C_1$-$C_6$-alkyl)$_2$, piperidine, pyrrolidine, CH$_2$F, CHF$_2$, —OCH$_2$F, —OCHF$_2$, —OH, —SO$_2$($C_1$-$C_6$-alkyl), C(O)NH$_2$, C(O)NH($C_1$-$C_6$-alkyl), and C(O)N($C_1$-$C_6$-alkyl)$_2$;

j is 1 or 2; and when j is 2, the j ring carbon opposite NR$^4$ may be replaced with an O heteroatom.

In a further embodiment of Formula I, $R^2$ is selected from H, —OH, —OMe or F;

$R^{2a}$ is selected from H, Me or F;

$R^4$ is H, 4-6 membered heterocycle, cyclopropylmethyl or $C_1$-$C_4$ alkyl optionally substituted with —OH or —O($C_1$-$C_3$ alkyl);

$R^5$ and $R^{5a}$ are independently selected from H and $C_1$-$C_4$ alkyl; and j is 1 or 2.

Referring to the G group of Formula I, examples include phenyl ("Ph") optionally substituted with one or more $R^a$ groups independently selected from F, Cl, Br, I, methyl, ethyl, isopropyl, tert-butyl, cyclopropyl, CN, $CF_3$, —OMe, —OEt, —OCF$_3$, —NO$_2$, —SMe and —OCH$_2$Ph. Exemplary embodiments of G include phenyl, 2-chlorophenyl, 3-chlorophenyl, 4-chlorophenyl, 4-fluorophenyl, 4-bromophenyl, 4-methylphenyl, 4-ethylphenyl, 4-isopropylphenyl, 4-trifluoromethylphenyl, 4-cyanophenyl, 4-methoxyphenyl, 4-ethoxyphenyl, 4-thiomethylphenyl, 4-trifluoromethoxyphenyl, 4-cyclopropylphenyl, 4-chloro-3-fluorophenyl, 3,4-difluorophenyl, 4-bromo-3-fluorophenyl, 3-fluoro-4-methylphenyl, 3-fluoro-4-methoxyphenyl, 3-fluoro-4-trifluoromethylphenyl, 4-cyano-3-fluorophenyl, 3,4-dichlorophenyl, 2,4-dichlorophenyl, 2,4-difluorophenyl, 2-chloro-4-fluorophenyl, 2-fluoro-4-chlorophenyl, 3,5-dichlorophenyl. 3,5-difluorophenyl, 3-chloro-5-fluorophenyl, 3-chloro-4-fluorophenyl, 3-bromo-4-fluorophenyl, 3,5-difluoro-4-chlorophenyl, 2,3-difluoro-4-chlorophenyl, 2,5-difluoro-4-chlorophenyl, 3,5-difluoro-4-bromophenyl, 2,3-difluoro-4-bromophenyl, 2,5-difluoro-4-bromophenyl, 4-(OCH$_2$Ph)-phenyl, 4-chlorophenyl, 2,4-dichlorophenyl, 3,4-dichlorophenyl, 4-chloro-3-fluorophenyl, 3-chloro-4-fluorophenyl, 3-fluoro-4-bromophenyl, 4-fluorophenyl, 3,4-difluorophenyl, 2,4-difluorophenyl 4-bromophenyl, 4-chloro-2-fluorophenyl, 4-methoxyphenyl, 4-methylphenyl, 4-cyanophenyl, 4-trifluoromethylphenyl, 4-iodophenyl, 4-nitrophenyl, 4-tert-butylphenyl, 2-fluorophenyl, 3-trifluoromethylphenyl, 2-fluoro-4-trifluoromethylphenyl, 3-fluoro-4-trifluoromethoxyphenyl, 3-fluoro-4-trifluoromethylphenyl and 4-trifluoromethoxyphenyl.

Referring to the G group of Formula I, the phrase "5-6 membered heteroaryl optionally substituted by a halogen" includes thiophenes and pyridines, optionally substituted by halogens. Particular examples include, but are not limited to, the structures:

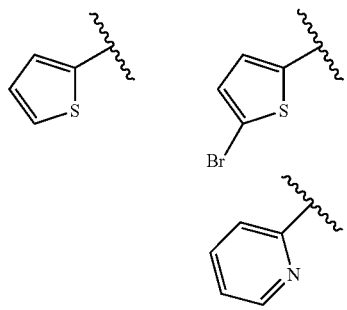

In one embodiment of Formula I, $R^3$ is H.

In another embodiment of Formula I, $R^3$ is methyl, wherein said methyl is optionally in the (S) configuration.

In another embodiment of Formula I, $R^3$ is ethyl.

In one embodiment, $R^5$ is H. In a further embodiment, $R^{5a}$ is H.

In another embodiment, $R^5$ is methyl. In a further embodiment $R^{1a}$ is methyl.

In another embodiment, $R^5$ is ethyl. In a further embodiment $R^{5a}$ is ethyl.

In one embodiment, $R^{5a}$ is H.

In another embodiment, $R^{5a}$ is methyl.

In another embodiment, $R^{5a}$ is ethyl.

In certain embodiments, $R^5$ and $R^{5a}$ are independently selected from H and $C_1$-$C_4$ alkyl, or $R^5$ and $R^{5a}$ together with the atom to which they are attached form a carbonyl group, a 5-6 membered cycloalkyl or 5-6 membered heterocycle, wherein the heterocycle has an oxygen heteroatom.

In certain embodiments, $R^5$ and $R^{5a}$ are independently selected from H and $C_1$-$C_4$ alkyl, or $R^5$ and $R^{5a}$ are oxo or together with the atom to which they are attached form a 5-6 membered cycloalkyl or 5-6 membered heterocycle, wherein the heterocycle has an oxygen heteroatom.

In certain embodiments, $R^5$ and $R^{5a}$ together with the atom to which they are attached form a carbonyl group, having the structure:

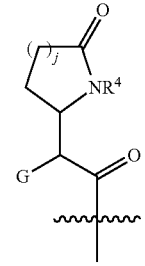

wherein the wavy line is where the structure attaches to the required piperazine of Formula I.

In certain embodiments, $R^5$ and $R^{5a}$ together with the atom to which they are attached form a 5-6 membered cycloalkyl. This embodiment forms a bicyclic spirocycle. In certain embodiments, $R^5$ and $R^{5a}$ together with the atom to which they are attached form a 5-6 membered cycloalkyl, having the structure:

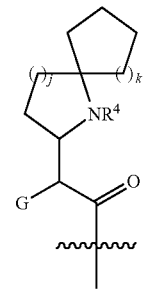

wherein k is 1 or 2 and the wavy line is where the structure attaches to the required piperazine of Formula I.

In certain embodiments, $R^5$ and $R^{5a}$ together with the atom to which they are attached form a 5 membered cycloalkyl, having the structure:

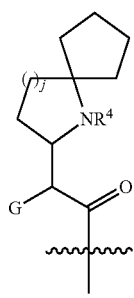

wherein the wavy line is where the structure attaches to the required piperazine of Formula I.

In certain embodiments, $R^5$ and $R^{5a}$ together with the atom to which they are attached form a 6 membered cycloalkyl, having the structure:

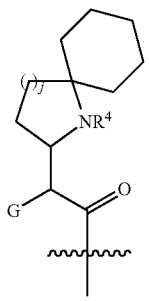

wherein the wavy line is where the structure attaches to the required piperazine of Formula I.

In certain embodiments, $R^5$ and $R^{5a}$ together with the atom to which they are attached form a 5-6 membered heterocycle, wherein the heterocycle has an oxygen heteroatom. This embodiment forms a spirocycle. In certain embodiments, $R^5$ and $R^{5a}$ together with the atom to which they are attached form a 5-6 membered heterocycle, wherein the heterocycle has an oxygen heteroatom, having the structure:

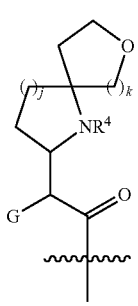

wherein k is 1 or 2 and the wavy line is where the structure attaches to the required piperazine of Formula I.

In certain embodiments, $R^5$ and $R^{5a}$ together with the atom to which they are attached form a 5 membered heterocycle, wherein the heterocycle has an oxygen heteroatom, having the structure:

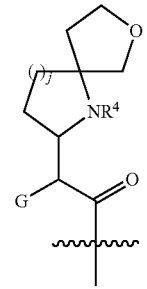

wherein the wavy line is where the structure attaches to the required piperazine of Formula I.

In certain embodiments, $R^5$ and $R^{5a}$ together with the atom to which they are attached form a 6 membered heterocycle, wherein the heterocycle has an oxygen heteroatom, having the structure:

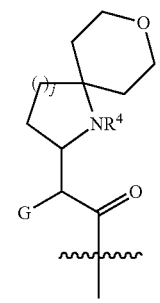

wherein the wavy line is where the structure attaches to the required piperazine of Formula I.

In certain embodiments, $R^1$ is in the (R) configuration.

In one embodiment of Formula I, $R^1$ is methyl, wherein said methyl is optionally in the (R) configuration. In certain embodiments of Formula I, $R^{1a}$ is H. In certain embodiments of Formula I, $R^1$ and $R^{1a}$ are both methyl.

In another embodiment of Formula I, $R^1$ is H. In certain embodiments of Formula I, $R^{1a}$ is H.

In another embodiment of Formula I, $R^1$ is ethyl. In certain embodiments of Formula I, $R^{1a}$ is H.

In another embodiment of Formula I, $R^1$ is $CH=CH_2$ (vinyl). In certain embodiments of Formula I, $R^{1a}$ is H.

In another embodiment of Formula I, $R^1$ is $CH_2OH$. In certain embodiments of Formula I, $R^{1a}$ is H.

In certain embodiments, $R^1$ is $CH_2F$. In certain embodiments of Formula I, $R^{1a}$ is H.

In one embodiment of Formula I, $R^{1a}$ is H.

In certain embodiments, $R^2$ is in the (R) configuration.
In certain embodiments, $R^2$ is in the (S) configuration.
In certain embodiments, $R^2$ is H.
In one embodiment of Formula I, $R^2$ and $R^{2a}$ are H.
In certain embodiments, $R^2$ is F.
In another embodiment of Formula I, $R^2$ and $R^{2a}$ are F.
In another embodiment of Formula I, $R^2$ is F and $R^{2a}$ is H.
In certain embodiments, $R^2$ is F in the (R) configuration. In certain embodiments, $R^2$ is F in the (S) configuration.

In another embodiment of Formula I, $R^2$ is OH. In certain embodiments of Formula I, $R^{2a}$ is H. In certain embodiments, $R^2$ is OH in the (R) configuration. In certain embodiments, $R^2$ is OH in the (S) configuration.

In another embodiment of Formula I, $R^2$ is OH. In certain embodiments of Formula I, $R^{2a}$ is $CH_3$. In certain embodiments, R² is OH in the (R) configuration. In certain embodiments, R² is OH in the (S) configuration.

In another embodiment of Formula I, R² is —OMe. In certain embodiments, R² is —OMe in the (R) configuration.

In certain embodiments, R² and R²ᵃ are oxo.
In certain embodiments, R²ᵃ is in the (R) configuration.
In certain embodiments, R²ᵃ is in the (S) configuration.
In certain embodiments, R²ᵃ is H.
In certain embodiments, R²ᵃ is CH₃.
In certain embodiments, R²ᵃ is F.

In certain embodiments, G is phenyl, naphthalene, a 5-6 membered heteroaryl or a 9-10 membered bicyclic heteroaryl, wherein the phenyl, naphthalene, or heteroaryls are optionally substituted with one to four Rᵃ groups. In certain embodiments, G is phenyl, naphthalene, a 5-6 membered heteroaryl or a 9-10 membered bicyclic heteroaryl, wherein the phenyl, naphthalene, or heteroaryls are optionally substituted with one to four Rᵃ groups, wherein the heteroaryl contains one or two heteroatoms selected from nitrogen and oxygen. In certain embodiments, G is phenyl, naphthalene, a 5-6 membered heteroaryl or a 9-10 membered bicyclic heteroaryl, wherein the phenyl, naphthalene, or heteroaryls are optionally substituted with one to four Rᵃ groups, wherein the 5-6 membered heteroaryl is a thiophene, and the 9-10 membered bicyclic heteroaryl is an indole or a benzisoxazole. In certain embodiments, G is phenyl, naphthalene, a 5-6 membered heteroaryl or a 9-10 membered bicyclic heteroaryl, wherein the phenyl, naphthalene, or heteroaryls are optionally substituted with one to four Rᵃ groups, wherein the 5-6 membered heteroaryl is a thiophene, and the 9-10 membered bicyclic heteroaryl is an indole.

In certain embodiments, G is phenyl optionally substituted with one to four Rᵃ groups, a 5-6 membered heteroaryl optionally substituted with halogen, naphthalene, or a 9-10 membered bicyclic heteroaryl.

In one embodiment of Formula I, G is phenyl optionally substituted with one to four Rᵃ groups. In certain embodiments, each Rᵃ is independently halogen, C₁-C₆-alkyl, C₃-C₆-cycloalkyl, —O—(C₁-C₆-alkyl), CF₃, —OCF₃, S(C₁-C₆-alkyl), CN, phenyl, —OCH₂-phenyl, NH₂, —NO₂, —NH—(C₁-C₆-alkyl), —N—(C₁-C₆-alkyl)₂, piperidine, pyrrolidine, pyrazole, pyridine, 2-aminopyridine, CH₂F, CHF₂, —OCH₂F, —OCHF₂, —OH, —SO₂(C₁-C₆-alkyl), C(O)NH₂, C(O)NH(C₁-C₆-alkyl), and C(O)N(C₁-C₆-alkyl)₂. Exemplary embodiments of G include phenyl, 2-chlorophenyl, 3-chlorophenyl, 4-chlorophenyl, 4-fluorophenyl, 4-bromophenyl, 4-methylphenyl, 4-ethylphenyl, 4-isopropylphenyl, 4-trifluoromethylphenyl, 4-cyanophenyl, 4-methoxyphenyl, 4-ethoxyphenyl, 4-thiomethylphenyl, 4-trifluoromethoxyphenyl, 4-cyclopropylphenyl, 4-chloro-3-fluorophenyl, 3,4-difluorophenyl, 4-bromo-3-fluorophenyl, 3-fluoro-4-methylphenyl, 3-fluoro-4-methoxyphenyl, 3-fluoro-4-trifluoromethylphenyl, 4-cyano-3-fluorophenyl, 3,4-dichlorophenyl, 2,4-dichlorophenyl, 2,4-difluorophenyl, 2-chloro-4-fluorophenyl, 2-fluoro-4-chlorophenyl, 3,5-dichlorophenyl. 3,5-difluorophenyl, 3-chloro-5-fluorophenyl, 3-chloro-4-fluorophenyl, 3-bromo-4-fluorophenyl, 3,5-difluoro-4-chlorophenyl, 2,3-difluoro-4-chlorophenyl, 2,5-difluoro-4-chlorophenyl, 3,5-difluoro-4-bromophenyl, 2,3-difluoro-4-bromophenyl, 2,5-difluoro-4-bromophenyl, 4-(OCH₂Ph)-phenyl, 3-fluoro-4-bromophenyl, 4-iodophenyl, 4-nitrophenyl, 4-tert-butylphenyl, 2-fluorophenyl, 3-trifluoromethylphenyl, 2-fluoro-4-trifluoromethylphenyl, 3-fluoro-4-trifluoromethoxyphenyl, 4-trifluoromethoxyphenyl, 4-bromo-2-fluorophenyl, 2-fluoro-4-methylphenyl, 4-fluoro-3-trifluoromethylphenyl, 3-bromophenyl, 3-fluorophenyl, 2-fluoro-4-methoxyphenyl, 4-(1H-pyrazol-4-yl) phenyl, biphenyl-4-yl, 4-(2-aminopyrimidin-5-yl)phenyl, 2,3-difluoro-4-trifluoromethylphenyl, 2-fluoro-3-(trifluoromethyl)phenyl, and 2-fluoro-5-(trifluoromethyl)phenyl.

In one embodiment of Formula I, G is phenyl optionally substituted with one or more groups independently selected from F, Cl, Br, I, methyl, ethyl, isopropyl, tert-butyl, cyclopropyl, CN, CF₃, OMe, OEt, OCF₃, NO₂, SMe and OCH₂Ph. Exemplary embodiments of G include phenyl, 2-chlorophenyl, 3-chlorophenyl, 4-chlorophenyl, 4-fluorophenyl, 4-bromophenyl, 4-methylphenyl, 4-ethylphenyl, 4-isopropylphenyl, 4-trifluoromethylphenyl, 4-cyanophenyl, 4-methoxyphenyl, 4-ethoxyphenyl, 4-thiomethylphenyl, 4-trifluoromethoxyphenyl, 4-cyclopropylphenyl, 4-chloro-3-fluorophenyl, 3,4-difluorophenyl, 4-bromo-3-fluorophenyl, 3-fluoro-4-methylphenyl, 3-fluoro-4-methoxyphenyl, 3-fluoro-4-trifluoromethylphenyl, 4-cyano-3-fluorophenyl, 3,4-dichlorophenyl, 2,4-dichlorophenyl, 2,4-difluorophenyl, 2-chloro-4-fluorophenyl, 2-fluoro-4-chlorophenyl, 3,5-dichlorophenyl. 3,5-difluorophenyl, 3-chloro-5-fluorophenyl, 3-chloro-4-fluorophenyl, 3-bromo-4-fluorophenyl, 3,5-difluoro-4-chlorophenyl, 2,3-difluoro-4-chlorophenyl, 2,5-difluoro-4-chlorophenyl, 3,5-difluoro-4-bromophenyl, 2,3-difluoro-4-bromophenyl, 2,5-difluoro-4-bromophenyl, 4-(OCH₂Ph)-phenyl, 4-chlorophenyl, 2,4-dichlorophenyl, 3,4-dichlorophenyl, 4-chloro-3-fluorophenyl, 3-chloro-4-fluorophenyl, 3-fluoro-4-bromophenyl, 4-fluorophenyl, 3,4-difluorophenyl, 2,4-difluorophenyl, 4-bromophenyl, 4-chloro-2-fluorophenyl, 4-methoxyphenyl, 4-methylphenyl, 4-cyanophenyl, 4-trifluoromethylphenyl, 4-iodophenyl, 4-nitrophenyl, 4-tert-butylphenyl, 2-fluorophenyl, 3-trifluoromethylphenyl, 2-fluoro-4-trifluoromethylphenyl, 3-fluoro-4-trifluoromethoxyphenyl, 3-fluoro-4-trifluoromethylphenyl and 4-trifluoromethoxyphenyl. In particular embodiments, G is selected from 4-chlorophenyl, 3-fluoro-4-chlorophenyl, 3-fluoro-4-trifluoromethylphenyl and 4-cyclopropylphenyl.

In one embodiment of Formula I, G may be a 5-6 membered monocyclic heteroaryl optionally substituted by one or more halogens. In certain embodiments, G may be a thiophene or a pyridine, optionally substituted by halogens. Particular embodiments include:

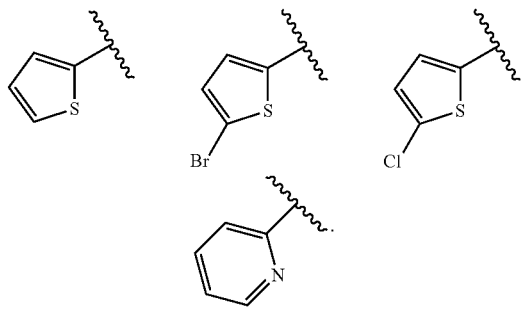

In certain embodiments, G is naphthalene optionally substituted with one to four Rᵃ groups. In certain embodiments, G is naphthalene. In certain embodiments, G is naphthalen-1-yl or naphthalen-2-yl.

In certain embodiments, G is a 9-10 membered bicyclic heteroaryl. In certain embodiments, G is a 9-10 membered bicyclic heteroaryl, wherein the heteroaryl contains one to two heteroatoms selected from nitrogen and oxygen. In certain embodiments, G is a 9-10 membered bicyclic heteroaryl, wherein the heteroaryl contains one nitrogen heteroatom. In certain embodiments, G is a 9-10 membered bicyclic heteroaryl, wherein the heteroaryl is an indole or benzisoxazole. In certain embodiments, G is a 9-10 membered bicyclic heteroaryl, wherein the heteroaryl is an indole. In certain embodiments, G is a 9-10 membered bicyclic heteroaryl, wherein the heteroaryl is a 1H-indol-3-yl.

In certain embodiments, G is substituted by one $R^a$ group.
In certain embodiments, $R^a$ is Cl.
In certain embodiments, $R^a$ is Br.
In certain embodiments, $R^a$ is cyclopropyl.
In certain embodiments, $R^a$ is trifluoromethyl.
In certain embodiments, $R^a$ is cyano.
In certain embodiments, $R^a$ is —$SO_2(C_1-C_6$-alkyl). In certain embodiments, $R^a$ is —$SO_2CH_3$.
In certain embodiments, $R^a$ is $C(O)NH_2$. In certain embodiments, G is benzamide.
In certain embodiments, $R^a$ is F.
In certain embodiments, $R^a$ is phenyl.
In certain embodiments, $R^a$ is 2-aminepyrimidine. In certain embodiments, $R^a$ is 2-aminepyrimidin-5-yl.
In certain embodiments, $R^a$ is $C_1-C_6$ alkyl. In certain embodiments, $R^a$ is methyl or tert-butyl.
In certain embodiments, $R^a$ is 1H-pyrazole. In certain embodiments, $R^a$ is 1H-pyrazol-4-yl.
In certain embodiments, $R^a$ is methoxy.
In certain embodiments, $R^a$ is trifluoromethoxy.
In certain embodiments, G is substituted by two $R^a$ groups. In certain embodiments, $R^a$ is selected from F, Cl, $CF_3$ or CN.

In certain embodiments, G is 4-chlorophenyl, 4-bromophenyl, 4-cyclopropylphenyl, 4-trifluoromethylphenyl, 4-cyanophenyl, 4-benzamide, 4-(methylsulfonyl)phenyl, 2-fluoro-4-trifluoromethylphenyl, 3-fluoro-4-chlorophenyl, 3-fluoro-4-trifluoromethylphenyl, 3-fluoro-4-cyanophenyl, 4-chloro-2,5-difluorophenyl, 4-chloro-2-fluorophenyl, 4-bromo-2-fluorophenyl, 4-bromo-3-fluorophenyl, 3-chlorophenyl, 2-fluoro-4-methylphenyl, 2,4-dichlorophenyl, 3,4-dichlorophenyl, 4-fluorophenyl, 4-fluoro-3-trifluoromethylphenyl, 3-bromophenyl, 3-trifluoromethylphenyl, 3-fluorophenyl, 2-fluoro-4-methoxyphenyl, 4-(1H-pyrazol-4-yl)phenyl, biphenyl-4-yl, 4-(2-aminopyrimidin-5-yl)phenyl, 4-tert-butylphenyl, 2,3-difluoro-4-(trifluoromethyl)phenyl, 2-fluoro-3-(trifluoromethyl)phenyl, 2-fluoro-5-(trifluoromethyl)phenyl, 4-(trifluoromethoxy)phenyl, and 3-fluoro-4-(trifluoromethoxy)phenyl.

In certain embodiments, G is 4-chlorophenyl, 4-bromophenyl, 4-cyclopropylphenyl, 4-trifluoromethylphenyl, 4-cyanophenyl, 4-benzamide, 4-(methylsulfonyl)phenyl, 2-fluoro-4-trifluoromethylphenyl, 3-fluoro-4-chlorophenyl, 3-fluoro-4-trifluoromethylphenyl, 3-fluoro-4-cyanophenyl, 4-chloro-2,5-difluorophenyl, 4-chloro-2-fluorophenyl, 4-bromo-2-fluorophenyl, 4-bromo-3-fluorophenyl, 2-fluoro-4-methylphenyl, 2,4-dichlorophenyl, 3,4-dichlorophenyl, 4-fluorophenyl, 4-fluoro-3-trifluoromethylphenyl, 2-fluoro-4-methoxyphenyl, 4-(1H-pyrazol-4-yl)phenyl, biphenyl-4-yl, 4-(2-aminopyrimidin-5-yl)phenyl, 4-tert-butylphenyl, 2,3-difluoro-4-(trifluoromethyl)phenyl, 2-fluoro-3-(trifluoromethyl)phenyl, 2-fluoro-5-(trifluoromethyl)phenyl, 4-(trifluoromethoxy)phenyl, and 3-fluoro-4-(trifluoromethoxy)phenyl.

In certain embodiments, G is 4-chlorophenyl, 4-bromophenyl, 4-cyclopropylphenyl, 4-trifluoromethylphenyl, 4-cyanophenyl, 4-benzamide, 4-(methylsulfonyl)phenyl, 2-fluoro-4-trifluoromethylphenyl, 3-fluoro-4-chlorophenyl, 3-fluoro-4-trifluoromethylphenyl or 3-fluoro-4-cyanophenyl.

In one embodiment of Formula I, $R^4$ is $C_1-C_4$ alkyl. In particular embodiments, $R^4$ is selected from methyl, ethyl, isopropyl or isobutyl.

In one embodiment of Formula I, $R^4$ is $C_1-C_4$ alkyl optionally substituted with —OH. In particular embodiments, $R^4$ is $CH_2CH_2OH$, $CH_2CH_2CH_2OH$, or $CH_2C(CH_3)_2OH$.

In one embodiment of Formula I, $R^4$ is $C_1-C_4$ alkyl optionally substituted with —$O(C_1-C_3$ alkyl). In a particular embodiment, $R^4$ is $CH_2CH_2OCH_3$.

In one embodiment of Formula I, $R^4$ is $C_1-C_4$ alkyl optionally substituted with F. In particular embodiments, $R^4$ is $CH_2CF_3$, $CH_2CH_2F$ or $CH_2CHF_2$.

In one embodiment of Formula I, $R^4$ is cyclopropylmethyl.

In one embodiment of Formula I, $R^4$ is a 4-6 membered heterocycle. In a particular embodiment, $R^4$ is a 6 membered heterocycle. In a further embodiment, $R^4$ is a 6 membered heterocycle containing an oxygen atom. In a further embodiment, $R^4$ is tetrahydropyranyl.

In a further embodiment, $R^4$ is tetrahydropyran-4-yl.

In another embodiment of Formula I, $R^4$ is H.

In one embodiment of Formula I, j is 1. When j is 1, Formula I has the structure of Formula IA:

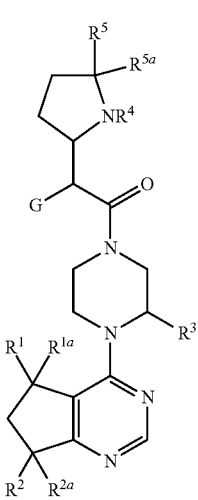

IA

In another embodiment of Formula I, j is 2. When j is 2, Formula I has the structure of Formula IB:

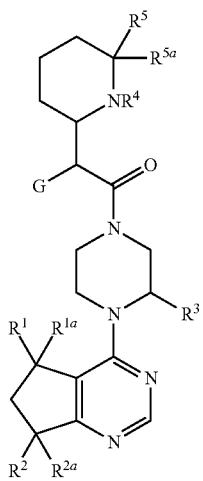

In another embodiment of Formula I, j is 2 and the j ring carbon opposite NR⁴ may be replaced with an O heteroatom. This embodiment of Formula I is shown below as Formula IC:

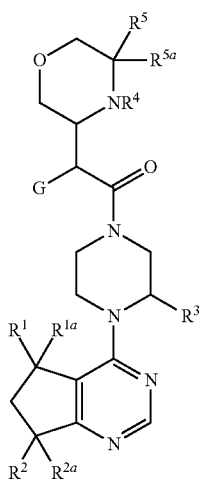

In another embodiment of Formula I, G is 3-substituted phenyl. This embodiment of Formula I is shown below as Formula II:

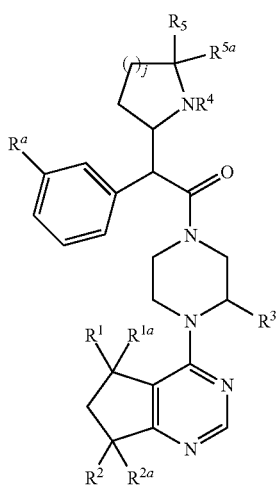

wherein $R^1$, $R^{1a}$, $R^2$, $R^{2a}$, $R^3$, $R^4$, $R^5$, $R^{5a}$, $R^a$ and j are as defined herein.

In certain embodiments of Formula II, $R^a$ is halogen or $CF_3$.

In certain embodiments, compounds of Formula I exclude compounds of Formula II.

In certain embodiments, the salt is a "pharmaceutically acceptable salt" which, unless otherwise indicated, includes salts that retain the biological effectiveness of the corresponding free acid or base of the specified compound and are not biologically or otherwise undesirable.

The compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

Synthesis of Compounds of Formula I

Compounds of the present invention may be synthesized by synthetic routes that include processes analogous to those well-known in the chemical arts, particularly in light of the description contained herein. The starting materials are generally available from commercial sources such as Sigma-Aldrich (St. Louis, Mo.), Alfa Aesar (Ward Hill, Mass.), or TCI (Portland, Oreg.), or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database).

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of Formula I, or salts thereof.

For illustrative purposes, Schemes 1-8 show general methods for preparing the compounds of the present invention, as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1

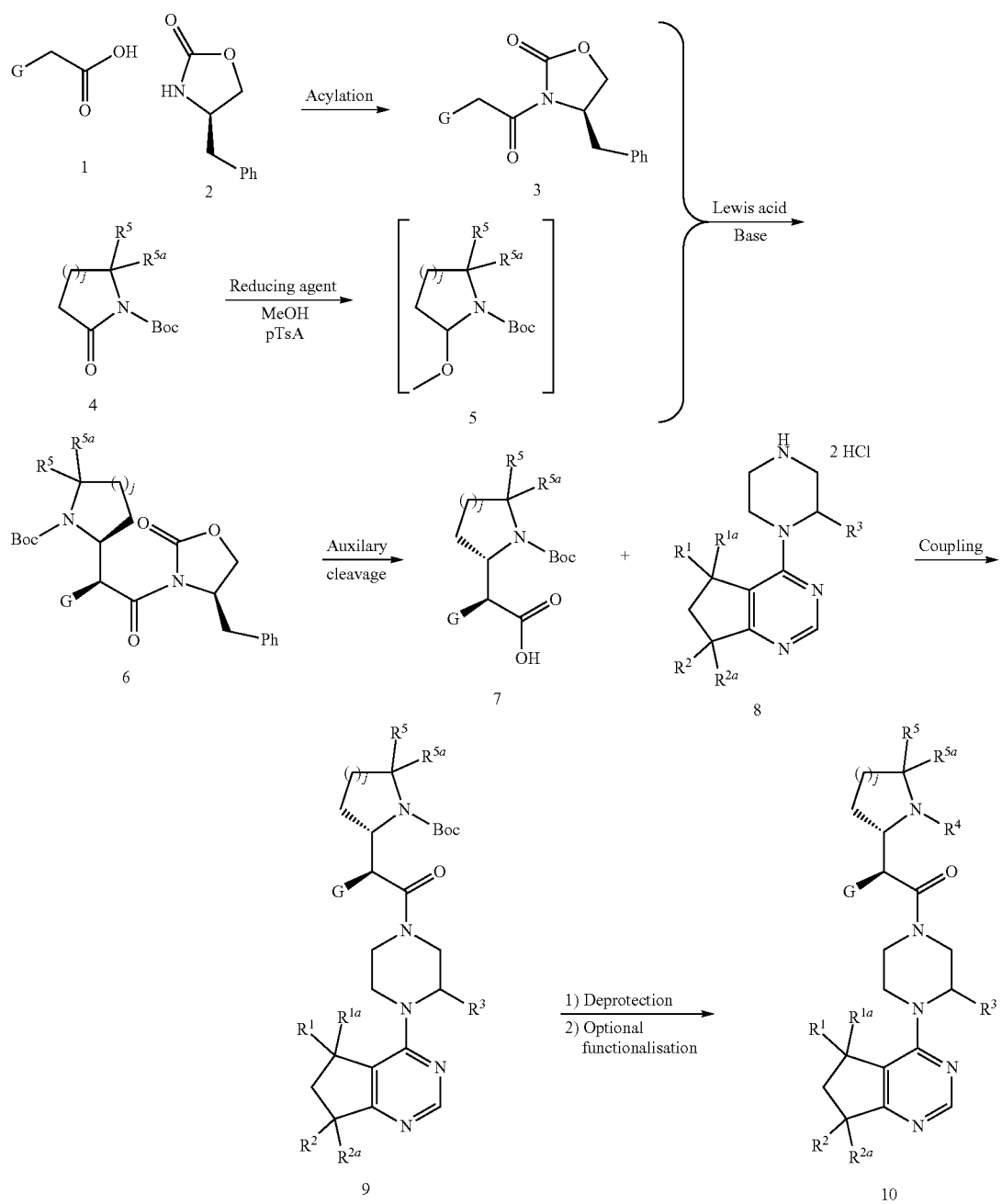

Scheme 1 shows a method of preparing compounds of general formula 10. Condensation of an appropriately substituted phenyl acetic acid (1) with a chiral auxiliary (e.g., an Evans' oxazolidinone (2)) can be performed using an acid chloride, such as pivaloyl chloride as activating agent in the presence of a tertiary amine base, such as Hunig's base. Reduction of lactam (4) with a reducing agent (for example diisobutylaluminium hydride ("DIBAL-H") at −78° C. to 25° C.), and quenching with methanol and in the presence of an acid such as p-toluenesulfonic acid ("pTsA") produces the intermediate methoxyheterocycle (5). Condensation of (3) and (5) can be accomplished using an appropriate Lewis acid and a mild base (e.g., titanium tetrachloride and diisopropylethylamine) to form a 2-substituted heterocycle (6). This reaction may need to be carried out at low temperature (e.g., −100° C. to 0° C.) to obtain acceptable diastereoselectivity in the reaction. Hydrolysis of the chiral auxiliary using a base (e.g., LiOH, $H_2O_2$) at 0° C. to 50° C. produces the carboxylic acid (7). A fully elaborated analog can be synthesized by coupling an acid (7) to the piperazine intermediate (8) using peptide bond forming conditions (e.g., 2-(1H-benzotriazole-1-yl)-1,1,3,3-tetramethyluronium hexafluorophosphate ("HBTU"), N,N-diisopropylethylamine ("DIEA") at 0° C. to 50° C.). Deprotection of compound (9) using anhydrous acid (e.g., HCl in dioxane) produces the free amine. If desired, reductive amination of this amine (using an aldehyde and reducing agent (e.g., NaBH(OAc)$_3$)), alkylation or acylation under standard conditions allows the preparation of the tertiary amine (10).

Use of an alternate chiral auxiliary, a different stereochemistry of the Evans' auxiliary or reaction conditions/reagents may lead to alternate stereoisomers of the product being isolated, providing a general route into alternative absolute stereochemistries of compound 6.

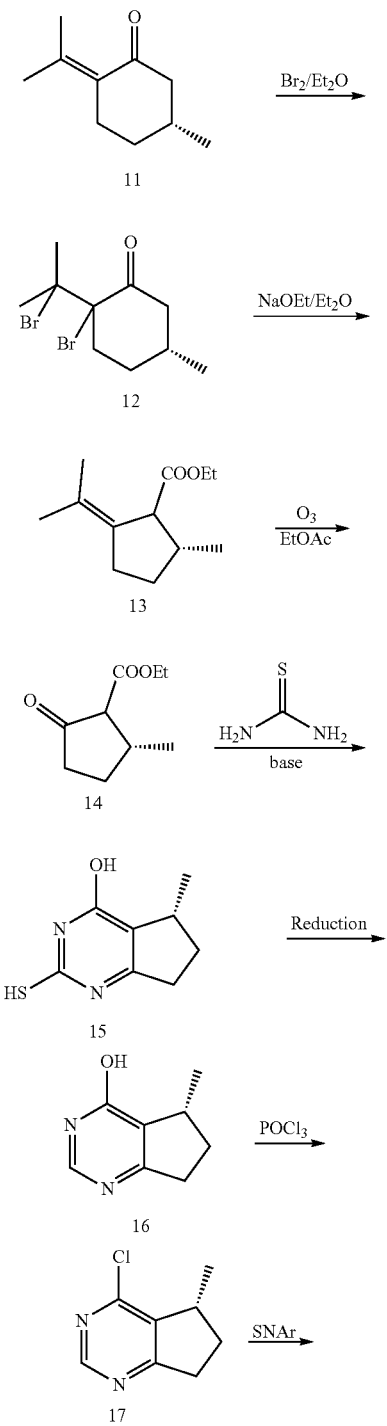

Scheme 2

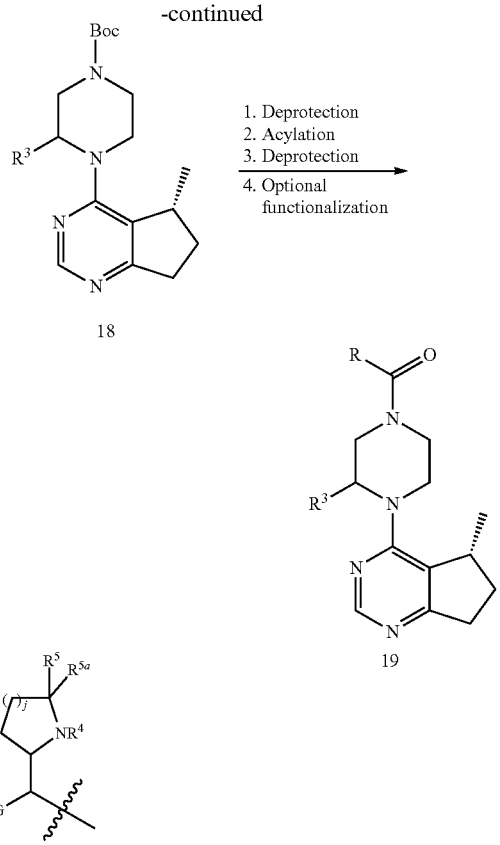

Scheme 2 shows a method of preparing compounds 19 of Formula I wherein $R^2$, $R^{2a}$ and $R^1$ are hydrogen and $R^{1a}$ is methyl. According to Scheme 1, intermediate 13 can be prepared by brominating (+)-pulegone 11 to provide the di-bromide 12, followed by treatment of the di-bromide 12 with a base such as sodium ethoxide. Ozonolysis of the pulegenate 13 gives the ketoester 14. The pyrimidine ring is constructed by reacting the ketoester 14 with thiourea in the presence of base such as KOH. The mercapto group at 2-position of compound 15 is eliminated by reduction with the catalyst such as Raney Ni in ammonia. Chlorination of the hydroxypyrimidine 16 provides the 4-chloropyrimidine 17. S$_N$Ar reaction of the chloropyrimidine 17 with piperazine provides the intermediate 18. After deprotection of intermediate 18, acylation of the piperazine derivatives with an appropriately substituted amino acid followed by second deprotection step and optional additional functionalization provides compound 19.

Scheme 3

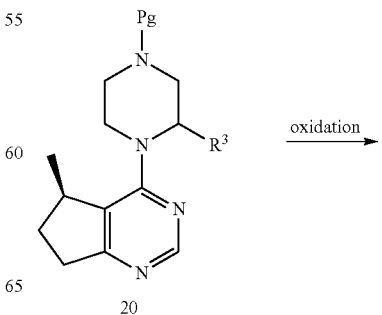

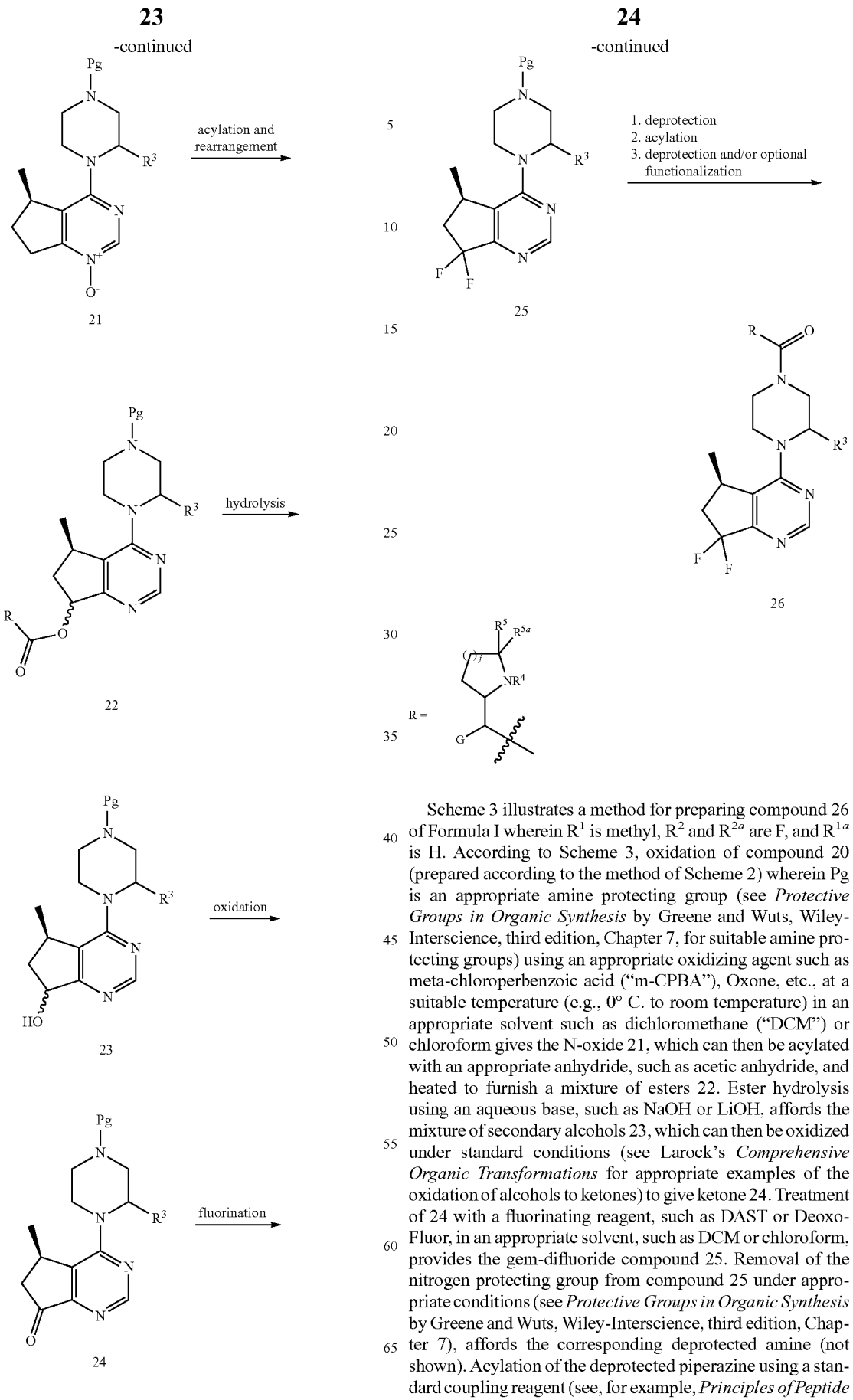

Scheme 3 illustrates a method for preparing compound 26 of Formula I wherein $R^1$ is methyl, $R^2$ and $R^{2a}$ are F, and $R^{1a}$ is H. According to Scheme 3, oxidation of compound 20 (prepared according to the method of Scheme 2) wherein Pg is an appropriate amine protecting group (see *Protective Groups in Organic Synthesis* by Greene and Wuts, Wiley-Interscience, third edition, Chapter 7, for suitable amine protecting groups) using an appropriate oxidizing agent such as meta-chloroperbenzoic acid ("m-CPBA"), Oxone, etc., at a suitable temperature (e.g., 0° C. to room temperature) in an appropriate solvent such as dichloromethane ("DCM") or chloroform gives the N-oxide 21, which can then be acylated with an appropriate anhydride, such as acetic anhydride, and heated to furnish a mixture of esters 22. Ester hydrolysis using an aqueous base, such as NaOH or LiOH, affords the mixture of secondary alcohols 23, which can then be oxidized under standard conditions (see Larock's *Comprehensive Organic Transformations* for appropriate examples of the oxidation of alcohols to ketones) to give ketone 24. Treatment of 24 with a fluorinating reagent, such as DAST or Deoxo-Fluor, in an appropriate solvent, such as DCM or chloroform, provides the gem-difluoride compound 25. Removal of the nitrogen protecting group from compound 25 under appropriate conditions (see *Protective Groups in Organic Synthesis* by Greene and Wuts, Wiley-Interscience, third edition, Chapter 7), affords the corresponding deprotected amine (not shown). Acylation of the deprotected piperazine using a standard coupling reagent (see, for example, *Principles of Peptide*

Synthesis by Miklos Bodanszky), in the presence or absence of a tertiary amine base, and in a suitable solvent (e.g., dimethylformamide ("DMF"), DCM, chloroform, tetrahydrofuran ("THF"), etc) with an appropriately protected amino acid, followed by removal of the protecting group, and additional optional functionalization affords compound 26.
Scheme 4
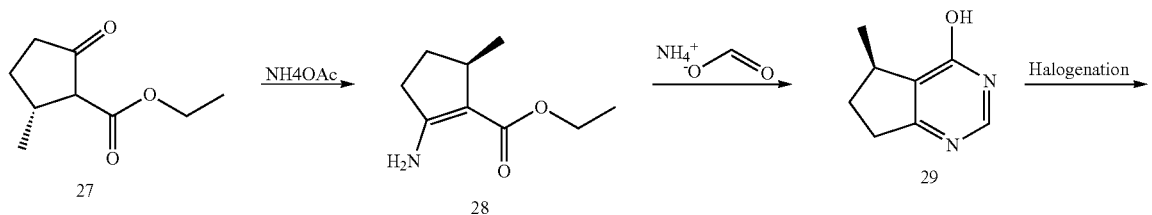
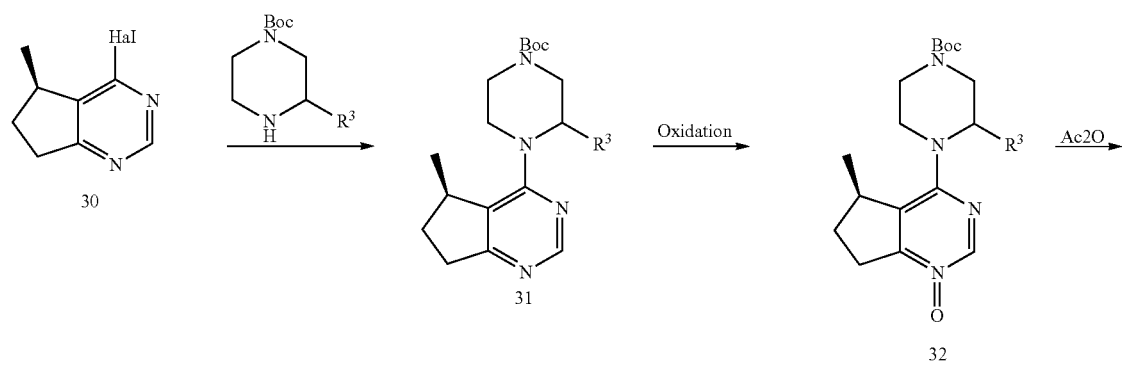
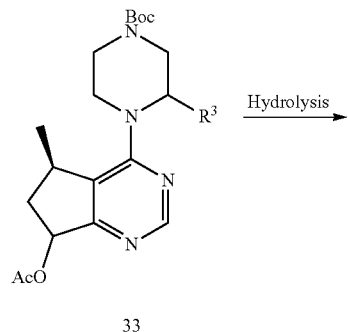
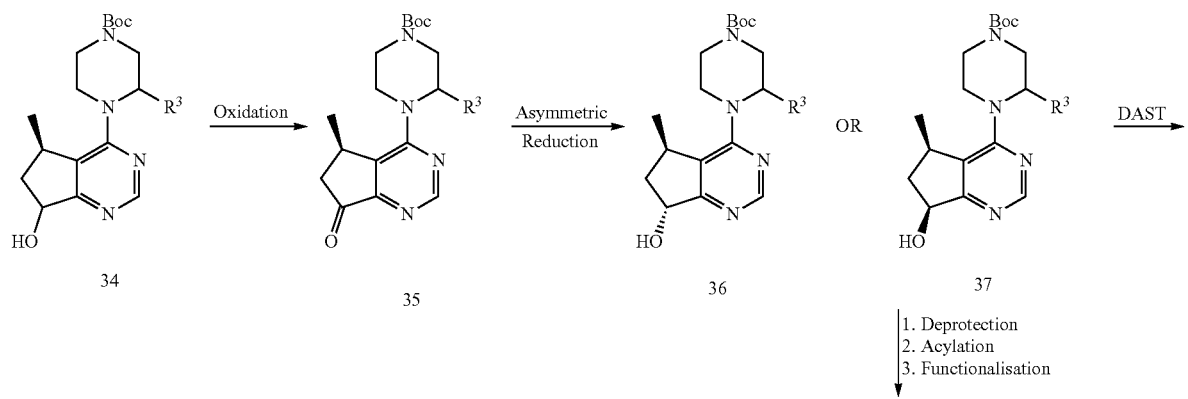

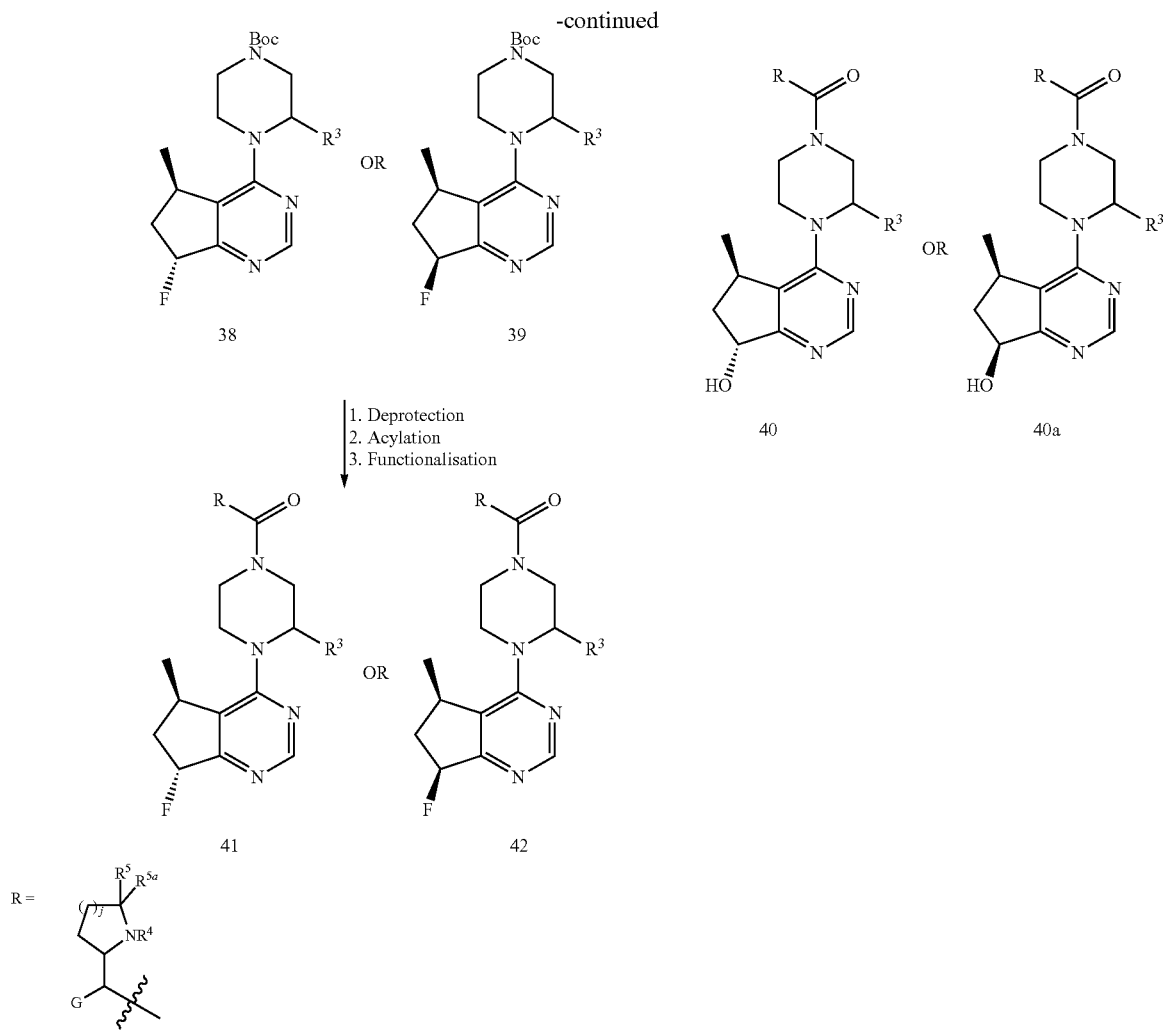

$R^5$ = H, Me, Et, CF3

Scheme 4 shows a method of preparing compounds 40, 40a, 41 and 42. According to Scheme 4, amination of compound 27 using an ammonia synthon gives compound 28. Pyrimidine formation using, for example, ammonium formate in the presence of formamide at 50° C. to 250° C. and/or at high pressure gives the bicyclic unit 29. Activation of compound 29 using, for example, POCl$_3$ or SOCl$_2$ gives the activated pyrimidine 30. Displacement of this leaving group, using a suitable protected/substituted piperidine at 0° C. to 150° C. gives the piperidine 31. Oxidation, using, for example, m-CPBA or Oxone at −20° C. to 50° C. gives the N-oxide 32. Treatment with an acylating agent (e.g., acetic anhydride) followed by heating (40° C. to 200° C.) causes rearrangement to give compound 33. Hydrolysis, using, for example LiOH or NaOH at 0° C. to 50° C. gives the alcohol 34. Oxidation, using for example, Swern conditions, MnO$_4$ or pyridine-SO$_3$ complex at appropriate temperatures gives the ketone 35. Asymmetric reduction using, for example, a catalytic chiral catalyst in the presence of hydrogen, the Corey-Bakshi-Shibata catalyst ("CBS catalyst") or a borohydride reducing agent in the presence of a chiral ligand gives rise to either the (R) or the (S) stereochemistry at the alcohol 36 or 37. Alternatively, a non-chiral reducing agent could be used (e.g., H$_2$, Pd/C), allowing the methyl group on the cyclopentane unit to provide facial selectivity and diastereoselectivity. If the reduction gives a lower diastereoselectivity, the diastereomers could be separated by, for example, chromatography, crystallization or derivitization. Treatment of compound 36 or 37 with a fluorinating agent (e.g., DAST at −20° C. to 100° C.) gives rise to the fluorinated analogues with inverted stereochemistry 38 or 39 respectively. Finally removal of the t-butoxycarbonyl ("Boc") group, using, for example, acid at 0° C. to 50° C., acylation using an appropriately functionalized amino acid and final functionalization of the amine of this amino acid (e.g., removal of any protecting group, alkylation, reductive amination or acylation to introduce new substituents) gives rise to the final compounds 41 and 42.

Alternatively, removal of the Boc-group of 36 or 37, using, for example, acid at 0° C. to 50° C., acylation using an appropriately functionalized amino acid and final functionalization of the amine of this amino acid (e.g., removal of any protecting group, alkylation, reductive amination or acylation to introduce new substituents) gives rise to the final compounds 40 and 40a.

Alternatively, compound 34 could be optionally functionalized and then separated by chromatographic or diastereomeric techniques followed by optional defunctionalization (e.g., see Scheme 8) to give a both compounds 36 and 37.

In Scheme 4, $R^5$ and $R^{5a}$ are independently selected from H and $C_1$-$C_4$ alkyl, or $R^5$ and $R^{5a}$ together with the atom to which they are attached form a 5-6 membered cycloalkyl or 5-6 membered heterocycle, wherein the heterocycle has an oxygen heteroatom.

Scheme 5

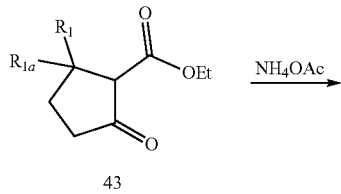

43

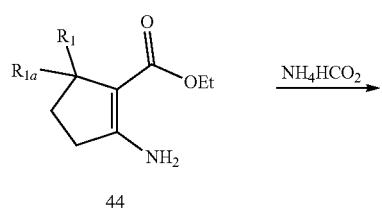

44

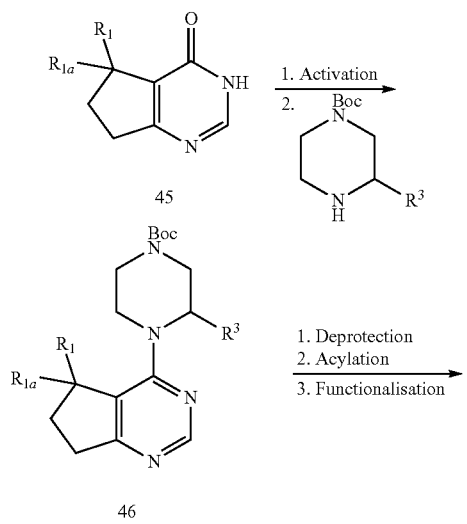

45

46

-continued

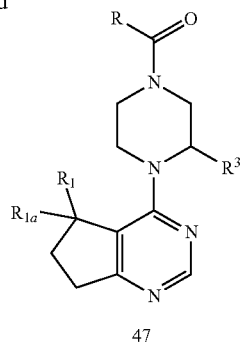

47

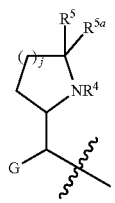

Scheme 5 shows a method of preparing compound 47. According to Scheme 5, amination of compound 43 using an ammonia synthon gives compound 44. Pyrimidine formation using, for example, ammonium formate in the presence of formamide at 50° to 250° C. and/or at high pressure gives the bicyclic unit 45. Activation of compound 45 using, for example, POCl$_3$ or SOCl$_2$ gives the activated pyrimidine and displacement of this leaving group, using a suitable protected/substituted piperidine at 0° C. to 150° C. gives the piperidine 46. Removal of the Boc-group, using, for example, acid at 0° C. to 50° C., acylation using an appropriately functionalized amino acid and final functionalization of the amine of this amino acid (e.g., removal of any protecting group, alkylation, reductive amination or acylation to introduce new substituents) gives rise to the final compounds 47. These analogues may then be subject to separation techniques to give the single enantiomers.

Scheme 6

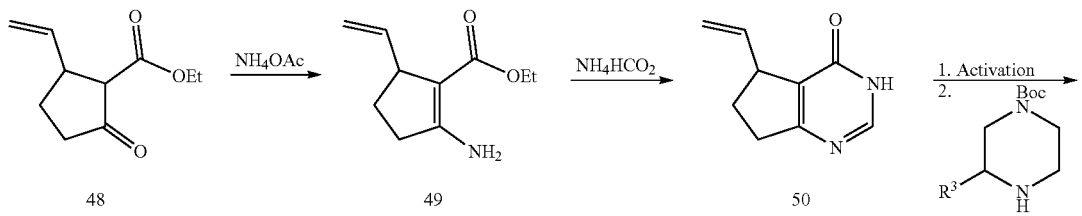

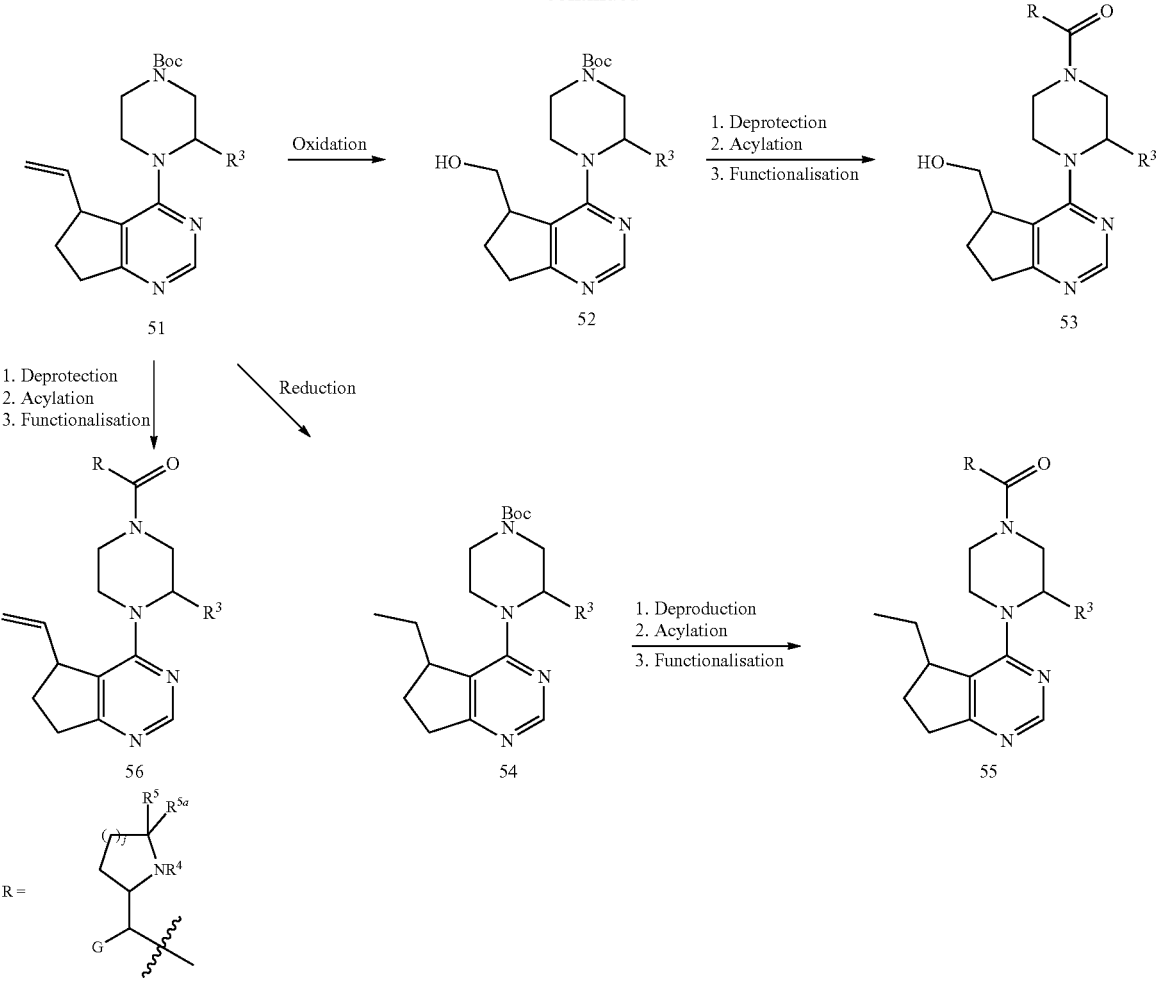

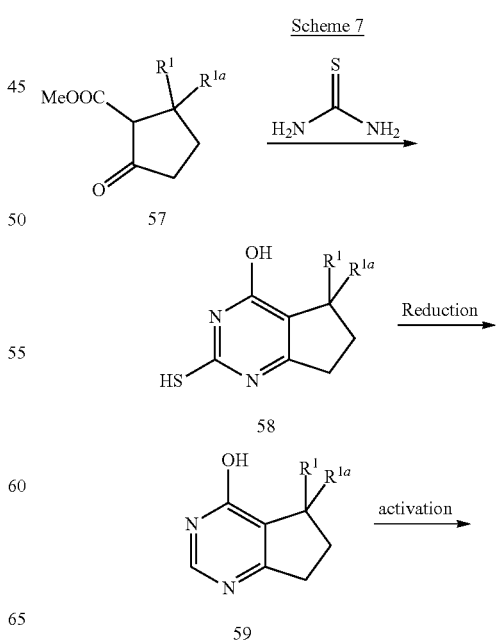

Scheme 6 shows a method of preparing compounds 53, 55 and 56, which include a late stage functionalization of According to Scheme 6, amination of compound 48 using an ammonia synthon gives compound 49. Pyrimidine formation using, for example, ammonium formate in the presence of formamide at 50° C. to 250° C. and/or at high pressure gives the bicyclic unit 50. Activation of compound 50 using, for example, POCl₃ or SOCl₂ gives the activated pyrimidine and displacement of this leaving group, using a suitable protected/substituted piperidine at 0° C. to 150° C. gives the piperidine 51. The olefin may be left intact or functionalized, using for example, ozone at −100° C. to −50° C., followed by a reductive work up (e.g., NaBH₄) may give the hydroxymethyl derivative 52. Alternatively, reduction of the olefin, using, for example, H₂/Pd/C at 0° C. to 50° C. at 1 atm to 50 atm gives rise to the ethyl derivative 54. Subsequent deprotection of the Boc-group, using, for example, acid at 0° C. to 50° C., acylation using an appropriately functionalized amino acid and final functionalization of the amine of this amino acid (e.g., removal of any protecting group, alkylation, reductive amination or acylation to introduce new substituents) gives rise to the final compounds 53, 55 and 56. These analogues may then be subject to separation techniques to give the single enantiomers.

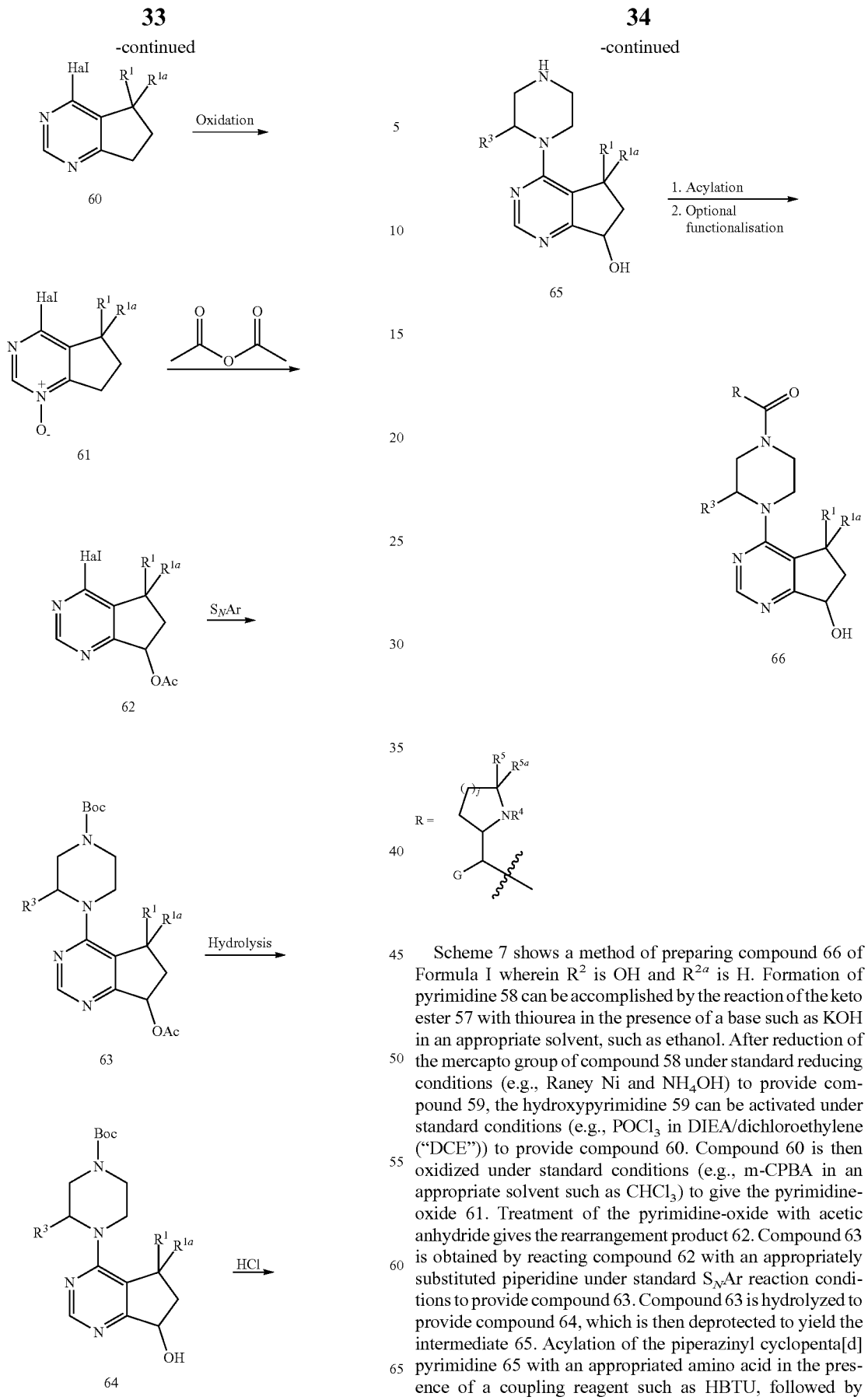

Scheme 7 shows a method of preparing compound 66 of Formula I wherein $R^2$ is OH and $R^{2a}$ is H. Formation of pyrimidine 58 can be accomplished by the reaction of the keto ester 57 with thiourea in the presence of a base such as KOH in an appropriate solvent, such as ethanol. After reduction of the mercapto group of compound 58 under standard reducing conditions (e.g., Raney Ni and $NH_4OH$) to provide compound 59, the hydroxypyrimidine 59 can be activated under standard conditions (e.g., $POCl_3$ in DIEA/dichloroethylene ("DCE")) to provide compound 60. Compound 60 is then oxidized under standard conditions (e.g., m-CPBA in an appropriate solvent such as $CHCl_3$) to give the pyrimidine-oxide 61. Treatment of the pyrimidine-oxide with acetic anhydride gives the rearrangement product 62. Compound 63 is obtained by reacting compound 62 with an appropriately substituted piperidine under standard $S_NAr$ reaction conditions to provide compound 63. Compound 63 is hydrolyzed to provide compound 64, which is then deprotected to yield the intermediate 65. Acylation of the piperazinyl cyclopenta[d] pyrimidine 65 with an appropriated amino acid in the presence of a coupling reagent such as HBTU, followed by optional functionalization, gives compound 66 of Formula I.

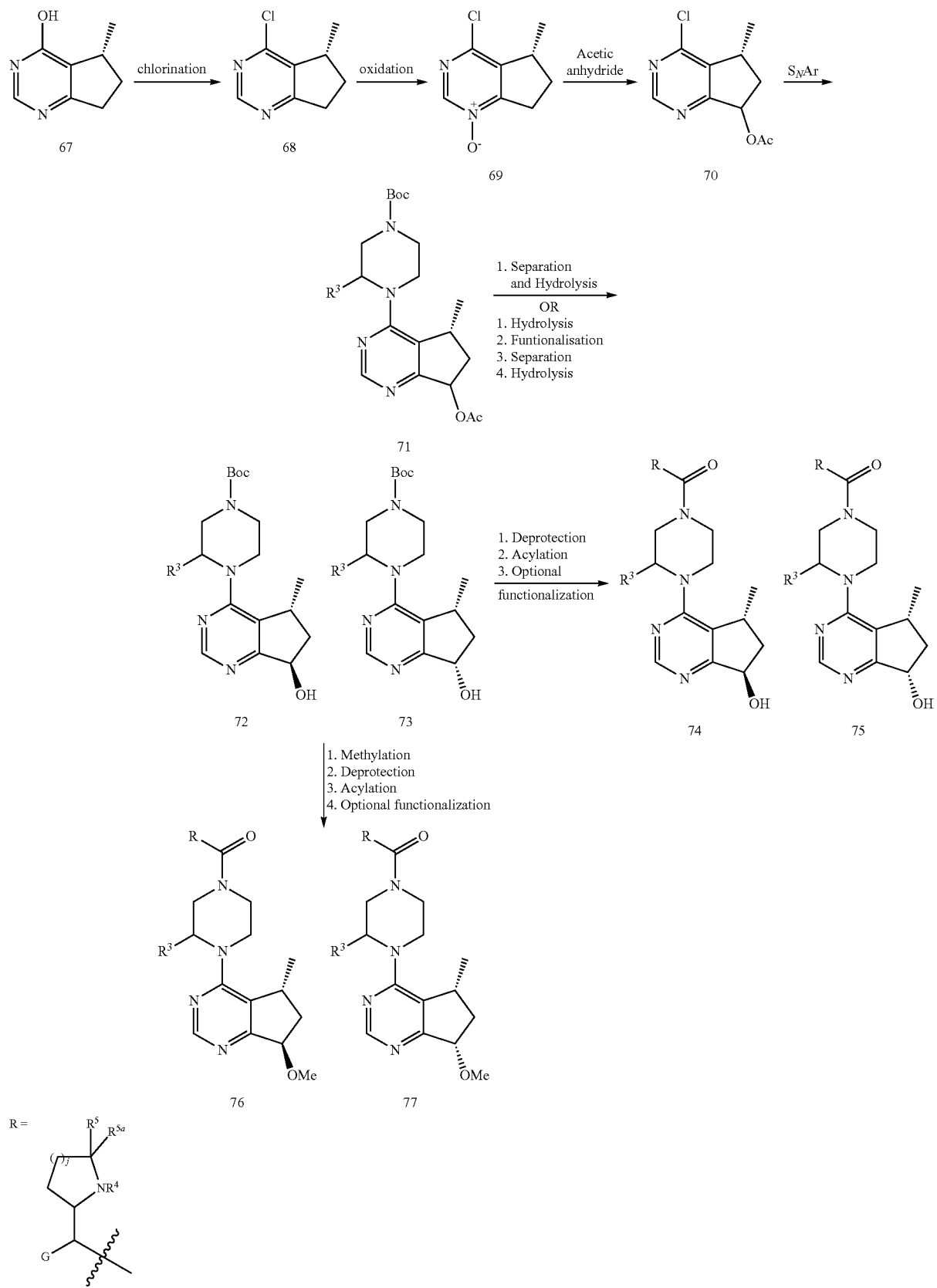
Scheme 8

Scheme 8 shows a method of preparing compounds 74, 75, 76 and 77 of Formula I, wherein $R^1$ is methyl and $R^2$ is either hydroxy or methoxy. According to Scheme 8, chlorination of the hydroxypyrimidine 67 under standard conditions (e.g., $POCl_3$) provides the 4-chloropyrimidine 68. The oxidation of the 4-chloropyrimidine 68 with an oxidizing agent such as m-CPBA or hydrogen peroxide provides the N-oxide 69. Rearrangement of the N-oxide 69 with acetic anhydride yields the intermediate 70. Compound 70 is reacted with the desired piperazine to provide compound 71. Compound 71 is subjected to separation (e.g., HPLC with a chiral stationary phase) and then hydrolyzed upon treatment with a base such as lithium hydroxide to provide compounds 72 and 73, respectively. Compounds 72 and 73 are then subject to deprotection (e.g., 4N HCl/dioxane for a Boc group), and are then reacted with the appropriate amino acid and optionally functionalized (e.g., reductive amination, alkylation, acylation, etc.) to provide compounds 74 and 75, respectively.

Alternatively, the 7-hydroxy group of compounds 72 and 73 may be alkylated with alkylating reagent such as alkyl halide (e.g., MeI) in the presence of a base such as NaH or KOH, followed by deprotection (e.g., 4N HCl/dioxane for a Boc group); reacted with the appropriate amino acid and optionally functionalized (e.g., reductive amination, alkylation, acylation, etc.) to provide compounds 76 and 77, wherein $R^2$ is methoxy.

Alternatively, compound 71 may be hydrolyzed (e.g., a base such as LiOH) and then functionalized to ease separation (e.g., 4-nitrobenzoyl chloride, triethylamine), separated and then hydrolyzed (e.g., a base such as lithium hydroxide) to give the alcohols 72 and 73.

Scheme 9

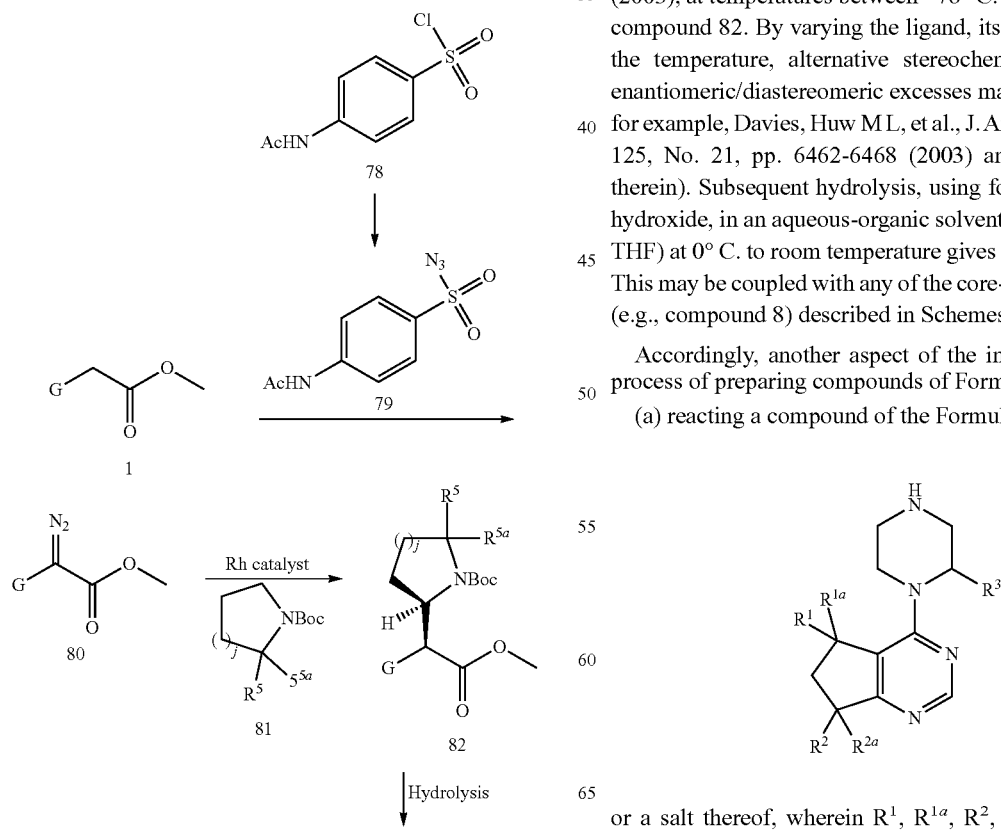

Scheme 9 shows a method of forming the protected amino acid unit 83, with an alternative stereochemistry to that depicted in compound 7. A suitable ester (e.g., compound 1) may be converted to the diazo analogue 80 by treatment with a suitable azide (e.g., 4-acetamidobenzenesulfonyl azide, 79; itself obtained by the treatment of the sulfonyl chloride, 78, with sodium azide in acetone/water at 0° C. to room temperature) in, for example, acetonitrile in the presence of an amine base (e.g., DBU) at −20° C. to room temperature to give compound 80. This compound, 80, may be treated with an appropriately protected and optionally substituted cyclic amine 81 in the presence of a chiral rhodium catalyst (e.g., $Rh_2(S-DOSP)_4$ (Tetrakis[N-[(4-dodecylphenyl)sulfonyl]-(L)-prolinato]dirhodium)) or similar catalysts as reported, for example, in Davies, Huw M L, et al., J. Am. Chem. Soc., Vol. 118, No. 29, pp. 6897-6907 (1996) and Davies, Huw M L, et al., J. Am. Chem. Soc., Vol. 125, No. 21, pp. 6462-6468 (2003), at temperatures between −78° C. and 100° C. to give compound 82. By varying the ligand, its stereochemistry or the temperature, alternative stereochemical outcomes or enantiomeric/diastereomeric excesses may be obtained (see, for example, Davies, Huw M L, et al., J. Am. Chem. Soc., Vol. 125, No. 21, pp. 6462-6468 (2003) and references cited therein). Subsequent hydrolysis, using for example, lithium hydroxide, in an aqueous-organic solvent system (e.g., $H_2O$/THF) at 0° C. to room temperature gives the desired acid 83. This may be coupled with any of the core-piperazine systems (e.g., compound 8) described in Schemes 1-8.

Accordingly, another aspect of the invention provides a process of preparing compounds of Formula I, comprising:

(a) reacting a compound of the Formula 8:

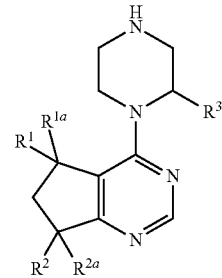

or a salt thereof, wherein $R^1$, $R^{1a}$, $R^2$, $R^{2a}$ and $R^3$ are as defined herein, with a compound of the Formula 7:

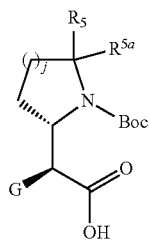

wherein $R^5$, $R^{5a}$ and j are as defined herein to prepare a compound of Formula 9:

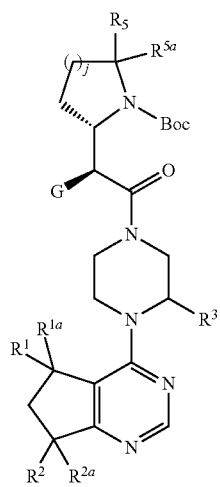

(b) deprotecting the compound of Formula 9; and (c) optionally functionalizing the compound of Formula 9 to prepare a compound of Formula I.

Accordingly, another aspect of the invention provides a process of preparing compounds of Formula I, comprising:

(a) reacting a compound of the Formula 8:

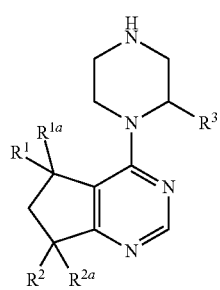

or a salt thereof, wherein $R^1$, $R^{1a}$, $R^2$, $R^{2a}$ and $R^3$ are as defined herein, with a compound of the Formula 83:

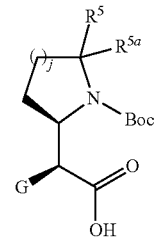

wherein $R^5$, $R^{5a}$ and j are as defined herein to prepare a compound of Formula 84:

(b) deprotecting the compound of Formula 84; and (c) optionally functionalizing the compound of Formula 84 to prepare a compound of Formula I.

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and diastereomers, and mixtures, racemic or otherwise, thereof. Accordingly, this invention also includes all such isomers, including diastereomeric mixtures, pure diastereomers and pure enantiomers of the compounds of this invention. Diastereomers have different physical properties, e.g., melting points, boiling points, spectral properties, and reactivities.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob I I I. J. Org. Chem., (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111).

By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. of Chromatogr., (1990) 513:375-378). Enriched or purified enantiomers can be distinguished by methods used to distinguish other chiral molecules with asymmetric carbon atoms, such as optical rotation and circular dichroism.

The compounds of the present invention may also exist in different tautomeric forms, and all such forms are embraced within the scope of the invention. For example, proton tautomers (also known as prototropic tautomers) include interconversions via migration of a proton, such as keto-enol and imine-enamine isomerizations. Valence tautomers include interconversions by reorganization of some of the bonding electrons.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

Administration and Pharmaceutical Formulations

The compounds of the invention may be administered by any convenient route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal.

The compounds may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents. If parenteral administration is desired, the compositions will be sterile and in a solution or suspension form suitable for injection or infusion.

A typical formulation is prepared by mixing a compound of the present invention and a carrier or excipient. Suitable carriers and excipients are well known to those skilled in the art and are described in detail in, e.g., Howard C. Ansel et al., Pharmaceutical Dosage Forms and Drug Delivery Systems, ($8^{th}$ Ed. 2004); Alfonso R. Gennaro et al., Remington: The Science and Practice of Pharmacy, ($20^{th}$ Ed. 2000); and Raymond C. Rowe, Handbook of Pharmaceutical Excipients, ($5^{th}$ Ed. 2005). The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

One embodiment of the present invention includes a pharmaceutical composition comprising a compound of Formula I, or a stereoisomer or pharmaceutically acceptable salt thereof. In a further embodiment, the present invention provides a pharmaceutical composition comprising a compound of Formula I, or a stereoisomer or pharmaceutically acceptable salt thereof, together with a pharmaceutically acceptable carrier or excipient.

Methods of Treatment with Compounds of Formula I

The compounds of the present invention can be used as prophylactics or therapeutic agents for treating diseases or disorders mediated by modulation or regulation of AKT protein kinases, tyrosine kinases, additional serine/threonine kinases, and/or dual specificity kinases. AKT protein kinase mediated conditions that can be treated according to the methods of this invention include, but are not limited to, inflammatory, hyperproliferative cardiovascular, neurodegenerative, gynecological, and dermatological diseases and disorders.

In one embodiment, said pharmaceutical composition is for the treatment of hyperproliferative disorders, including cancers of the following categories: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell lung, small cell lung; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multifonn. oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); (9) Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; (10) Skin: advanced melanoma, malignant melanoma, basal cell carcinoma, squamous cell carcinoma, Karposi's sarcoma, moles dysplastic nevi, lipoma, angioma, dermatofibroma, keloids, psoriasis; (11) Adrenal glands: neuroblastoma; (12) Breast: metastatic breast; breast adenocarcinoma; (13) Colon; (14) Oral cavity; (15) Hairy cell leukemia; (16) Head and neck; (17) and others including refractory metastatic disease; Kaposi's sarcoma; Bannayan-Zonana syndrome; and Cowden disease or Lhermitte-Duclos disease, among other kinds of hyperproliferative disorders.

Compounds and methods of this invention can be also used to treat diseases and conditions such as rheumatoid arthritis, osteoarthritis, Crohn's disease, angiofibroma, ocular diseases (e.g., retinal vascularisation, diabetic retinopathy, age-related macular degeneration, macular degeneration, etc.), multiple sclerosis, obesity, restenosis, autoimmune diseases, allergy, asthma, endometriosis, atherosclerosis, vein graft stenosis, peri-anastomatic prothetic graft stenosis, prostate hyperplasia, chronic obstructive pulmonary disease, psoriasis, inhibition of neurological damage due to tissue repair, scar tissue formation (and can aid in wound healing), multiple sclerosis, inflammatory bowel disease, infections, particularly bacterial, viral, retroviral or parasitic infections (by increasing apoptosis), pulmonary disease, neoplasm, Parkinson's disease, transplant rejection (as an immunosuppressant), septic shock, etc.

Accordingly, another aspect of this invention provides a method of treating diseases or medical conditions in a mammal mediated by AKT protein kinases, comprising administering to said mammal one or more compounds of Formula I or a pharmaceutically acceptable salt or prodrug thereof in an amount effective to treat or prevent said disorder.

In the case of cancer, an effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

This invention also provides compounds of Formula I for use in the treatment of AKT protein kinase-mediated conditions.

An additional aspect of the invention is the use of a compound of Formula I in the preparation of a medicament for therapy, such as for the treatment or prevention of AKT protein kinase-mediated conditions.

Combination Therapy

The compounds of this invention and stereoisomers and pharmaceutically acceptable salts thereof may be employed alone or in combination with other therapeutic agents for treatment. In one embodiment, compounds of this invention may be employed alone or in combination with chemotherapeutic agents. The compounds of the present invention can be used in combination with one or more additional drugs, for example an anti-inflammatory compound that works by a different mechanism of action. The second compound of the pharmaceutical combination formulation or dosing regimen preferably has complementary activities to the compound of this invention such that they do not adversely affect each other. Such molecules are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

Examples of chemotherapeutic agents include Erlotinib (TARCEVA®, Genentech, Inc./OSI Pharm.), Trastuzumab (HERCEPTIN®, Genentech, Inc.); bevacizumab (AVASTIN®, Genentech, Inc.); Rituximab (RITUXAN®, Genentech, Inc./Biogen Idec, Inc.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide, ADRIAMYCIN® (doxorubicin), TAXOL® (paclitaxel; Bristol-Myers Squibb, Princeton, N.J.), ABRAXANE® (Cremophor-free), and TAXOTERE® (doxetaxel; Rhone-Poulenc Rorer, Antony, France).

Articles of Manufacture

In another embodiment of the invention, an article of manufacture, or "kit", containing materials useful for the treatment of the disorders described above is provided. In one embodiment, the kit comprises a container comprising a compound of this invention. Suitable containers include, for example, bottles, vials, syringes, blister pack, etc. The container may be formed from a variety of materials such as glass or plastic. The container may hold a compound of this invention or a formulation thereof which is effective for treating the condition and may have a sterile access port (for example, the container may be an intravenous solution bag or a vial having a stopper pierceable by a hypodermic injection needle).

The kit may further comprise a label or package insert on or associated with the container. In one embodiment, the label or package inserts indicates that the composition comprising a compound of this invention can be used to treat a disorder mediated, for example, by AKT kinase. The label or package insert may also indicate that the composition can be used to treat other disorders.

In certain embodiments, the kits are suitable for the delivery of solid oral forms of a compound of this invention, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to another embodiment, a kit may comprise (a) a first container with a compound of this invention contained therein; and (b) a second container with a second pharmaceutical formulation contained therein, wherein the second pharmaceutical formulation comprises a second compound useful for treating a disorder mediated by AKT kinase. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of this invention and, if present, the second pharmaceutical formulation. For example, if the kit comprises a first composition comprising a compound of this invention and a second pharmaceutical formulation, the kit may further comprise directions for the simultaneous, sequential or separate administration of the first and second pharmaceutical compositions to a patient in need thereof.

In certain other embodiments wherein the kit comprises a composition of this invention and a second therapeutic agent, the kit may comprise a container for containing the separate compositions such as a divided bottle or a divided foil packet, however, the separate compositions may also be contained within a single, undivided container. In certain embodiments, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Accordingly, a further aspect of this invention provides a kit for treating a disorder or disease mediated by Akt kinase, wherein said kit comprises a) a first pharmaceutical composition comprising a compound of this invention or a pharmaceutically acceptable salt thereof; and b) instructions for use.

In certain embodiments, the kit further comprises (c) a second pharmaceutical composition, wherein the second pharmaceutical composition comprises a second compound suitable for treating a disorder or disease mediated by Akt kinase. In certain embodiment comprising a second pharmaceutical composition, the kit further comprises instructions for the simultaneous, sequential or separate administration of said first and second pharmaceutical compositions to a patient in need thereof. In certain embodiments, said first and second pharmaceutical compositions are contained in separate containers. In other embodiments, said first and second pharmaceutical compositions are contained in the same container.

Although the compounds of Formula I are primarily of value as therapeutic agents for use in mammals, they are also useful whenever it is required to control AKT protein kinases, tyrosine kinases, additional serine/threonine kinases, and/or dual specificity kinases. Thus, they are useful as pharmacological standards for use in the development of new biological tests and in the search for new pharmacological agents.

The activity of the compounds of this invention may be assayed for AKT protein kinases, tyrosine kinases, additional serine/threonine kinases, and/or dual specificity kinases in vitro, in vivo, or in a cell line. In vitro assays include assays that determine inhibition of the kinase activity. Alternate in vitro assays quantitate the ability of the inhibitor to bind to kinases and may be measured either by radiolabelling the inhibitor prior to binding, isolating the inhibitor/kinase complex and determining the amount of radiolabel bound, or by running a competition experiment where new inhibitors are incubated with known radioligands. These and other useful in vitro and cell culture assays are well known to those of skill in the art.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed.

BIOLOGICAL EXAMPLES

AKT-1 Kinase Assay

The activity of the compounds described in the present invention may be determined by the following kinase assay, which measures the phosphorylation of a fluorescently-labeled peptide by full-length human recombinant active AKT-1 by fluorescent polarization using a commercially available IMAP kit.

The assay materials are obtained from an IMAP AKT Assay Bulk Kit, product #R8059, from Molecular Devices, Sunnyvale, Calif. The kit materials include an IMAP Reaction Buffer (5×). The diluted 1×IMAP Reaction Buffer contained 10 mM Tris-HCl, pH 7.2, 10 mM $MgCl_2$, 0.1% BSA, 0.05% $NaN_3$. DTT is routinely added to a final concentration of 1 mM immediately prior to use. Also included is IMAP Binding Buffer (5×), and IMAP Binding Reagent. The Binding Solution is prepared as a 1:400 dilution of IMAP Binding Reagent into 1×IMAP Binding Buffer.

The fluorescein-labeled AKT Substrate (Crosstide) has the sequence (F1)-GRPRTSSFAEG. A stock solution of 20 μM is made up in 1×IMAP Reaction Buffer.

The plates used include a Costar 3657 (382-well made of polypropylene and having a white, v-bottom) that is used for compound dilution and for preparing the compound-ATP mixture. The assay plate is a Packard ProxyPlate™-384 F.

The AKT-1 used is made from full-length, human recombinant AKT-1 that is activated with PDK1 and MAP kinase 2.

To perform the assay, stock solutions of compounds at 10 mM in dimethylsulfoxide ("DMSO") are prepared. The stock solutions and the control compound are serially diluted 1:2 nine times into DMSO (10 μL of compound+10 μL of DMSO) to give 50× dilution series over the desired dosing range. Next, 2.1-4 aliquots of the compounds in DMSO are transferred to a Costar 3657 plate containing 50 μL of 10.4 μM ATP in 1×IMAP Reaction Buffer containing 1 mM DTT. After thorough mixing, 2.5-μL aliquots are transferred to a ProxyPlate™-384 F plate.

The assay is initiated by the addition of 2.5-4 aliquots of a solution containing 200 nM of fluorescently-labeled peptide substrate and 4 nM AKT-1. The plate is centrifuged for 1 minute at 1000 g and incubated for 60 minute at ambient temperature. The reaction is then quenched by the addition of 15 μL of Binding Solution, centrifuged again and incubated for an additional 30 minutes at ambient temperature prior to reading on a Victor 1420 Multilabel HTS Counter configured to measure fluorescence polarization.

The compounds of Examples 1-100 were tested in the above assay and found to have an $IC_{50}$ of less than 1 μM.

The compounds of Examples 1-141 were tested in the above assay and found to have an $IC_{50}$ of less than 1 μM.

PREPARATIVE EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other compounds of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the Examples described below, unless otherwise indicated all temperatures are set forth in degrees Celsius. Reagents were purchased from commercial suppliers such as Sigma-Aldrich, Alfa Aesar, or TCI, and were used without further purification unless otherwise indicated. Tetrahydrofuran ("THF"), dichloromethane ("DCM"), toluene, and dioxane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

$^1$H NMR spectra were recorded on a Varian instrument operating at 400 MHz. $^1$H-NMR spectra were obtained as $CDCl_3$, $CD_3OD$, $D_2O$ or $d_6$-DMSO solutions (reported in ppm), using tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm) as the reference standard. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

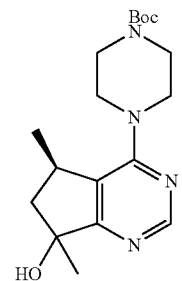 [SMILES: C[C@@H]1CC(C)(O)c2ncnc(N3CCN(C(=O)OC(C)(C)C)CC3)c21]

tert-butyl 4-((5R)-7-hydroxy-5,7-dimethyl-6,7-dihydro-5H-cyclopenta[d]pyrimidin-4-yl)piperazine-1-carboxylate A solution of (R)-tert-butyl 4-(5-methyl-7-oxo-6,7-dihydro-5H-cyclopenta[d]pyrimidin-4-yl)piperazine-1-carboxylate (40 mg, 0.120 mmol; see Example 3, Step 8) in THF (4 mL) was added to a 1.5M solution of methyllithium in diethyl ether (0.088 mL, 0.132 mmol) at −78° C. The resulting mixture was stirred at −78° C. for 1 hour and quenched by saturated aqueous $NH_4Cl$. The aqueous layer was extracted with EtOAc (2x). The organic layer was dried (MgSO₄) and concentrated. The residue was purified by a silica cartridge (5.0 g) eluted by EtOAc to give tert-butyl 4-((5R)-7-hydroxy-5,7-dimethyl-6,7-dihydro-5H-cyclopenta[d]pyrimidin-4-yl)piperazine-1-carboxylate as a solid (29 mg, 69%). LCMS (APCI+) [M-Boc+H]+ 349.1; Retention time: 2.49 minutes.

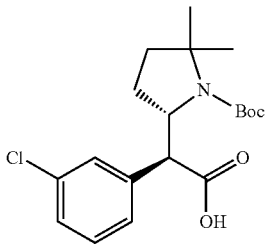 [SMILES: CC(C)(C)OC(=O)N1[C@H]([C@@H](C(=O)O)c2cccc(Cl)c2)CCC1(C)C]

(S)-2-((S)-1-(tert-butoxycarbonyl)-5,5-dimethylpyrrolidin-2-yl)-2-(3-chlorophenyl)acetic acid Step 1:
In a 1000 mL flask under N₂, 2-(3-chlorophenyl)acetic acid (3.50 g, 20.51 mmol) was added to dry THF (300 mL), and the contents were cooled to 0° C. DIEA (3.93 mL, 22.6 mmol) was added to the stirring solution, followed by portionwise addition of trimethylacetyl chloride (2.60 g, 21.5 mmol). In a separate flask, (R)-4-benzyloxazolidin-2-one (3.82 g, 21.5 mmol) was added to dry THF (75 mL) and cooled to −78° C. under N₂. n-BuLi (8.21 mL, 20.5 mmol) was added to this cold stirring solution, and the whole contents were stirred for 30 minutes at −78° C. This solution was then slowly added to the mixed anhydride at 0° C. The reaction was stirred for 2 hours and determined complete by TLC (25% ethyl acetate/hexanes, KMnO₄ stain). The reaction was quenched with water (250 mL) and diluted with ethyl acetate (250 mL). The layers were separated, and the organics were washed with brine (100 mL), dried (MgSO₄) and concentrated to an oil. The oil was purified by flash chromatography (10% ethyl acetate/hexanes to 25% ethyl acetate/hexanes) to give (R)-4-benzyl-3-(2-(3-chlorophenyl)acetyl)oxazolidin-2-one (1.99 g, 6.03 mmol, 29.4% yield). ¹H NMR (400 MHz, CDCl₃) 7.37-7.20 (m, 7H), 7.14 (d, J=6.64 Hz, 2H), 4.73-4.64 (m, 1H), 4.28 (dd, J1=16.00 Hz, J2=33.97 Hz, 2H), 4.22-4.16 (m, 2H), 3.27 (dd, J1=3.12 Hz, J2=13.27 Hz, 1H), 2.77 (dd, J1=9.37 Hz, J2=13.27 Hz, 1H).

Step 2:
A solution of (R)-4-benzyl-3-(2-(3-chlorophenyl)acetyl)oxazolidin-2-one (0.975 g, 2.96 mmol) in dry DCM (125 mL) was cooled to −78° C., and TiCl4 (3.10 mL, 3.10 mmol) was added. DIEA (0.566 mL, 3.25 mmol) was added to this stirring cold solution for 15 minutes. A solution of tert-butyl 5-methoxy-2,2-dimethylpyrrolidine-1-carboxylate (0.881 g, 3.84 mmol) in DCM (20 mL) was added to the cold mixture. The reaction was stirred for 15 minutes at −78° C. and then warmed to −10° C. (ice/acetone) and stirred for 3 hours. The reaction was quenched with NH4Cl, diluted with DCM (50 mL), water (50 mL), and the layers were separated. The aqueous layer was extracted with DCM (25 mL), dried (MgSO₄) and concentrated to an oil. TLC (10% ethyl acetate/hexanes) shows desired product at Rf~0.2. Purification by flash chromatography (5% ethyl acetate/hexanes-10% ethyl acetate/hexanes) gave (S)-tert-butyl 5-((S)-2-((R)-4-benzyl-2-oxooxazolidin-3-yl)-1-(3-chlorophenyl)-2-oxoethyl)-2,2-dimethylpyrrolidine-1-carboxylate (0.98 g, 1.86 mmol, 62.9% yield). HPLC, 254 nm, 100% purity, retention time=3.86 minutes.

Step 3:
30% H₂O₂ (0.447 mL, 4.65 mmol) was added to a solution of LiOH—H₂O (0.156 g, 3.72 mmol) in THF/water (75 mL; 2:1), and the solution was stirred at room temperature for 10 minutes. The solution was cooled to 0° C. and treated with (S)-tert-butyl 5-((S)-2-((R)-4-benzyl-2-oxooxazolidin-3-yl)-1-(3-chlorophenyl)-2-oxoethyl)-2,2-dimethylpyrrolidine-1-carboxylate (0.98 g, 1.9 mmol) in THF (15 mL). The mixture was then stirred at 0° C. for 2 hours and then allowed to warm to room temperature and stirred overnight. The reaction was cooled to 0° C., treated with 1M Na₂SO₃ (10 mL) and stirred for 10 minutes. The reaction was then warmed to room temperature and stirred for 10 minutes. The reaction was concentrated, extracted with ethyl acetate (2×50 mL). The aqueous portion was acidified with HSO₄ (s) to a pH of about 1 to about 2, extracted with DCM/MeOH (3×100 mL; 10:1), and concentrated to provide (S)-2-((S)-1-(tert-butoxycarbonyl)-5,5-dimethylpyrrolidin-2-yl)-2-(3-chlorophenyl)acetic acid (0.330 g, 0.897 mmol, 48.2% yield). LC/MS, retention time=3.59 minutes, (APCI+) m/z=284 [M+H, −100amu, (boc)].

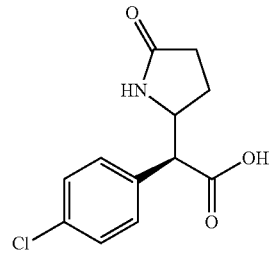 [SMILES: O=C1CCC([C@@H](C(=O)O)c2ccc(Cl)cc2)N1]

(2S)-2-(4-chlorophenyl)-2-(5-oxopyrrolidin-2-yl) acetic acid (2S)-2-(4-Chlorophenyl)-2-(5-oxopyrrolidin-2-yl)acetic acid may be prepared as described in Example B, using 5-methoxy-2-pyrrolidinone (commercially available from suppliers such as TRC Biomedical Research Chemicals of North York, Ontario, Canada).

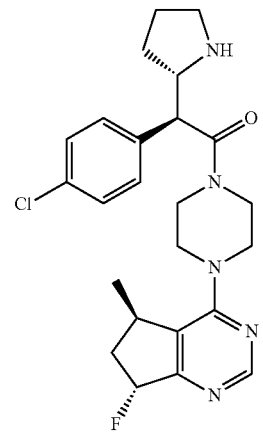 [SMILES: C[C@@H]1C[C@@H](F)c2ncnc(N3CCN(C(=O)[C@@H](c4ccc(Cl)cc4)[C@@H]4CCCN4)CC3)c21]

(S)-2-(4-chlorophenyl)-1-(4-((5R,7R)-7-fluoro-5-methyl-6,7-dihydro-5H-cyclopenta[d]pyrimidin-4-yl)piperazin-1-yl)-2-((S)-pyrrolidin-2-yl)ethanone Step 1:

tert-Butyl 4-((5R,7S)-7-hydroxy-5-methyl-6,7-dihydro-5H-cyclopenta[d]pyrimidin-4-yl)piperazine-1-carboxylate (0.843 g, 2.521 mmol) was dissolved in methylene chloride (40 mL) and cooled to −20° C. The solution was treated with DAST (0.9992 mL, 7.562 mmol) and stirred at −20° C. for 100 minutes. After 3 hours, the reaction was quenched with ice and then warmed to ambient temperature. The mixture was separated. The aqueous phase (pH of about 1) was extracted with methylene chloride (2×), and the combined organics were washed with 6% NaHCO$_3$ (2×), dried over Na$_2$SO$_4$, and concentrated to a dark oil (0.91 g). This material was subjected to chromatography on SiO$_2$ (Biotage 40S, load with eluant) and eluted with 2:1 Hexane/ethyl acetate ("EtOAc"). The desired tert-butyl 4-((5R,7R)-7-fluoro-5-methyl-6,7-dihydro-5H-cyclopenta[d]pyrimidin-4-yl)piperazine-1-carboxylate (0.6138 g, 72%) was recovered cleanly. tert-Butyl 4-((5R,7R)-7-fluoro-5-methyl-6,7-dihydro-5H-cyclopenta[d]pyrimidin-4-yl)piperazine-1-carboxylate (0.6138 g, 1.825 mmol) was dissolved in dioxane (5 mL) and cooled to 0° C. A solution of HCl in dioxane (11.40 mL, 45.61 mmol; 4M) was added dropwise, and then the reaction mixture was allowed to warm to ambient temperature while stirring for 60 hours. The reaction mixture was concentrated in vacuo, re-suspended in MeOH and re-concentrated (3×). The residue was dissolved in MeOH (3.7 mL) and added dropwise to a rapidly stirring flask containing ether (100 mL). The solid was filtered under a blanket of nitrogen gas, washed with ether and dried under nitrogen gas to give (5R,7R)-7-fluoro-5-methyl-4-(piperazin-1-yl)-6,7-dihydro-5H-cyclopenta[d]pyrimidine di-hydrochloride as a solid (539 mg, 96%). LC/MS (APCI)$^+$ m/z 237.2.

Step 2:

2-(4-Chlorophenyl)acetic acid (20.00 g, 117.2 mmol) and (R)-4-benzyloxazolidin-2-one (10.39 g, 58.62 mmol) were combined in toluene (100 mL). Triethylamine (32.68 mL, 234.5 mmol) was added, and the solution was heated to 80° C. A solution of pivaloyl chloride (14.42 mL, 117.2 mmol) in toluene (25 mL) was added dropwise. After addition, the mixture was heated to reflux for 16 hours. The reaction was cooled and washed with 2N HCl (2×), water, 5% Na$_2$CO$_3$ (2×), saturated NaCl, dried over Na$_2$SO$_4$ and concentrated in vacuo to a solid (about 10 g). The crude solid was subjected to chromatography on SiO$_2$ eluting with 4:1 hexane/ethyl acetate. (R)-4-Benzyl-3-(2-(4-chlorophenyl)acetyl)oxazolidin-2-one was recovered as a solid (15.4 g, 80%). $^1$H NMR (CDCl$_3$, 400 MHz) δ 7.34-7.26 (m, 7H), 7.16-7.11 (m, 2H), 4.71-4.64 (m, 1H), 4.35-4.16 (m, 4H), 3.26 (dd, J$_1$=2.9, J$_2$=13.2, 1H), 2.76 (dd, J$_1$=9.3, J$_2$=13.2, 1H).

Step 3:

tert-Butyl 2-oxopyrrolidine-1-carboxylate (12.33 g, 66.57 mmol) was dissolved in Et$_2$O (60 mL) and cooled to −78° C. The suspension was treated dropwise with DIBAL-H (45.27 mL, 67.90 mmol) [1.5M in toluene], and the mixture was stirred at −78° C. for 2 hours. The mixture was allowed to warm to ambient temperature with a bath and stirred overnight. The reaction was quenched by addition of a solution of p-toluenesulfonic acid hydrate (0.075 g) in MeOH (75 mL). The mixture was stirred at ambient temperature for 16 hours. The white suspension was concentrated in vacuo to a white solid. This was re-suspended in a mixture of Rochelle's salt (0.5N) and ethyl acetate. The layers were separated, and the aqueous layer was washed twice with methylene chloride. The combined organic layers were washed with saturated NaCl, dried over Na$_2$SO$_4$ and concentrated in vacuo to provide an oil. A solution of titanium (IV) chloride (10.007 mL, 10.007 mmol) [1 M in toluene] was cooled to 0° C. and treated with a solution of (R)-4-benzyl-3-(2-(4-chlorophenyl)acetyl)oxazolidin-2-one (3.000 g, 9.0970 mmol) dissolved in dichloromethane (20 mL). After 5 minutes, diisopropylethylamine (1.7430 mL, 10.007 mmol) was added. The resultant solution was stirred for 1 hour at 0° C. then cooled to −20° C. A solution of tert-butyl 2-methoxypyrrolidine-1-carboxylate (2.5549 g, 13.646 mmol) dissolved in dichloromethane (20 mL) was added, and the mixture was stirred at −20° C. for 75 minutes. The mixture was quenched with saturated NH$_4$Cl (about 100 mL) and diluted with water to dissolve the solids. After separation, the aqueous layer was washed with methylene chloride (3×). The combined organics were washed with water (2×), dried over Na$_2$SO$_4$ and concentrated in vacuo. The recovered oil was subjected to chromatography on SiO$_2$ eluting with 8:1 hexanes/ethyl acetate. (S)-tert-Butyl 2-((S)-2-((R)-4-benzyl-2-oxooxazolidin-3-yl)-1-(4-chlorophenyl)-2-oxoethyl)pyrrolidine-1-carboxylate was recovered as a sticky foam, (1.8 g, 40%). MS (APCI+) [M+Na] 521.1.

Step 4:

Lithium hydroxide hydrate (0.04709 g, 1.122 mmol) was added to a solution of THF/water (3:1, 19 mL) and stirred until dissolved. The mixture was cooled to 0° C. and treated with 30% hydrogen peroxide (0.2314 mL, 2.244 mmol) and stirred for 10 minutes. A solution of (S)-tert-butyl 2-((S)-2-((R)-4-benzyl-2-oxooxazolidin-3-yl)-1-(4-chlorophenyl)-2-oxoethyl)pyrrolidine-1-carboxylate (0.280 g, 0.5611 mmol) in THF (2 mL) was added. The reaction was stirred for 30 minutes at 0° C. Thin layer chromatography ("TLC") did not show much progress, therefore. The reaction was allowed to warm to ambient temperature and stirred overnight. The reaction was quenched by addition of 1.5 M Na$_2$SO$_3$ (1 mL) and stirred for 15 minutes. The reaction mixture was diluted with Et$_2$O and separated. The aqueous portion was washed (2×) with Et$_2$O then adjusted to a pH of 1 with 3N HCl. The aqueous portion was extracted (3×) with ethyl acetate. The combined organic layers were washed with water (2×), saturated NaCl, dried over Na$_2$SO$_4$ and concentrated in vacuo to a thick oil which slowly solidified (0.15 g, 81%). $^1$H NMR (CDCl$_3$, 400 MHz) δ 7.30 (d, 2H), 7.21 (d, 2H), 4.53-4.40 (m, 1H), 4.37-4.27 (m, 1H), 3.34-3.22 (m, 1H), 2.98-2.90 (m, 1H), 2.02-1.90 (m, 1H), 1.83-1.74 (m, 1H), 1.64-1.53 (m, 2H), 1.50 (s, 9H).

Step 5:

(5R,7R)-7-Fluoro-5-methyl-4-(piperazin-1-yl)-6,7-dihydro-5H-cyclopenta[d]pyrimidine di-hydrochloride (0.050 g, 0.16 mmol) was combined with (S)-2-((S)-1-(tert-butoxycarbonyl)pyrrolidin-2-yl)-2-(4-chlorophenyl)acetic acid (0.055 g, 0.16 mmol) in dichloromethane (10 mL). Diisopropylethylamine (0.1 mL, 0.57 mmol) and HBTU (0.061 g, 0.16 mmol) were added, and the mixture was stirred at ambient temperature for 1 hour. The solvent was removed by concentration in vacuo and the residue was purified by column chromatography on SiO$_2$, eluting with 2:1 hexanes/ethyl acetate. The product was dissolved in dioxane (1 mL) and treated with a solution of 4M HCl in dioxane (2 mL). After stirring at ambient temperature for 2 hours, the mixture was concentrated in vacuo to yield (S)-2-(4-chlorophenyl)-1-(4-((5R,7R)-7-fluoro-5-methyl-6,7-dihydro-5H-cyclopenta[d]pyrimidin-4-yl)piperazin-1-yl)-2-((S)-pyrrolidin-2-yl)ethanone hydrochloride (0.060 g, 81% yield). MS (APCI+) [M+H] 458.2.

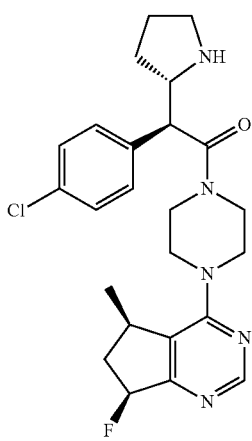 [SMILES: C[C@@H]1C[C@H](F)c2ncnc(N3CCN(C(=O)[C@@H](c4ccc(Cl)cc4)[C@@H]4CCCN4)CC3)c21]

(S)-2-(4-chlorophenyl)-1-(4-((5R,7S)-7-fluoro-5-methyl-6,7-dihydro-5H-cyclopenta[d]pyrimidin-4-yl)piperazin-1-yl)-2-((S)-pyrrolidin-2-yl)ethanone Step 1:

tert-Butyl 4-((5R,7R)-7-hydroxy-5-methyl-6,7-dihydro-5H-cyclopenta[d]pyrimidin-4-yl)piperazine-1-carboxylate (1.190 g, 3.558 mmol) was dissolved in methylene chloride (55 mL) and cooled to −20° C. The solution was treated with DAST (1.410 mL, 10.68 mmol) and stirred at −20° C. for 1 hour. The reaction was quenched with ice and then warmed to ambient temperature. The mixture was diluted with saturated NH$_4$Cl and separated. The aqueous phase was extracted with methylene chloride (2×), and the combined organics were dried over Na$_2$SO$_4$ and concentrated to an oil. This oil was subjected to chromatography on SiO$_2$ (Biotage 40S, load with methylene chloride) then eluted with 2.5% MeOH/DCM then 3.5% MeOH/DCM. The mixed fractions were concentrated, and the material was re-chromatographed on SiO$_2$ (Biotage 40S, load with DCM) and eluted with 2 hexane/EtOAc. The product was collected as an oil to give tert-butyl 4-((5R,7S)-7-fluoro-5-methyl-6,7-dihydro-5H-cyclopenta[d]pyrimidin-4-yl)piperazine-1-carboxylate (0.725 g, 61%). LCMS (APCI+) m/z 337.0 [M+H]$^+$; Rf 3.13 min.

Step 2:

tert-Butyl 4-((5R,7S)-7-fluoro-5-methyl-6,7-dihydro-5H-cyclopenta[d]pyrimidin-4-yl)piperazine-1-carboxylate (0.725 g, 2.155 mmol) was dissolved in dioxane (5 mL) and cooled to 0° C. A solution of HCl in dioxane (13.47 mL, 53.88 mmol; 4M) was added dropwise. The reaction mixture was allowed to warm to ambient temperature and stirred for 16 hours. A white precipitate had formed after about 8 hours. The reaction mixture was concentrated in vacuo, re-suspended in MeOH, and re-concentrated (3×). The residue was dissolved in MeOH (about 2 to 3 mL) and added dropwise to a rapidly stirring flask containing ether (80 mL). The white solid was filtered under a blanket of nitrogen gas and dried under nitrogen gas to give (5R,7S)-7-fluoro-5-methyl-4-(piperazin-1-yl)-6,7-dihydro-5H-cyclopenta[d]pyrimidine di-hydrochloride a white solid (555 mg, 83%). LCMS (ESI+) m/z 237.2 [M+H]$^+$; Rf: 1.70 min.

Step 3:

(S)-2-(4-chlorophenyl)-1-(4-((5R,7S)-7-fluoro-5-methyl-6,7-dihydro-5H-cyclopenta[d]pyrimidin-4-yl)piperazin-1-yl)-2-((S)-pyrrolidin-2-yl)ethanone di-hydrochloride was prepared according to the procedure described for Example 1, using (5R,7S)-7-fluoro-5-methyl-4-(piperazin-1-yl)-6,7-dihydro-5H-cyclopenta[d]pyrimidine di-hydrochloride (0.66 g, 89%). MS (APCI+) [M+H] 458.2

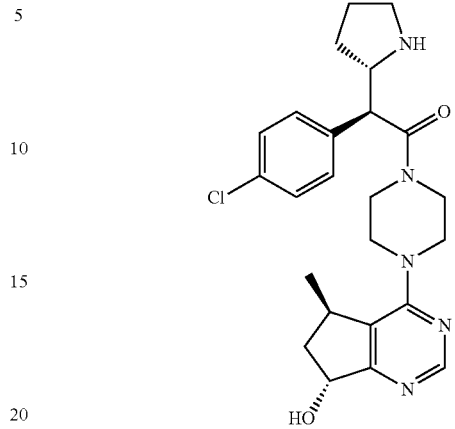

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone Step 1:

Ethyl pulegenate (130 g, 662 mmol) in EtOAc (900 mL) was cooled to −78° C. using a dry ice-isopropanol bath. This mixture was subjected to ozonolysis until the reaction turned purple in color. At this point, ozone generation ceased, and the reaction was removed from the dry-ice bath. Oxygen was bubbled through the reaction mixture until it turned yellow. The reaction mixture was concentrated under vacuum, and the resulting residue was dissolved in glacial acetic acid (400 mL). The solution was cooled to 0° C., and Zn dust (65 g, 993 mmol) was added portionwise over 30 minutes. The reaction was then allowed to stir for 2 hours, at which point the reaction mixture was filtered through a pad of celite to remove the zinc dust. The acetic acid was neutralized to pH 7 with aqueous NaOH and NaHCO$_3$ and extracted with ether (3×800 mL). The combined organics were dried with brine, MgSO$_4$ and concentrated to give (2R)-ethyl 2-methyl-5-oxocyclopentanecarboxylate as a brown liquid (107 g, 95%).

Step 2:

Ammonium acetate (240.03 g, 3113.9 mmol) was added to a solution of (R)-ethyl 2-methyl-5-oxocyclopentanecarboxylate (106.0 g, 622.78 mmol) in MeOH (1.2 L). The reaction mixture was stirred at room temperature under nitrogen for 20 hours, after which it was complete as judged by TLC and HPLC. The reaction mixture was concentrated to remove MeOH. The resulting residue was dissolved in DCM, washed twice with H$_2$O, once with brine, dried (Na$_2$SO$_4$), filtered, and concentrated to give (R)-ethyl 2-amino-5-methylcyclopent-1-enecarboxylate (102 g, 97% yield) as an orange oil. LC/MS (APCI+) m/z 170 [M+H]+.

Step 3:

A solution containing (R)-ethyl 2-amino-5-methylcyclopent-1-enecarboxylate (161.61 g, 955.024 mmol) and ammonium formate (90.3298 g, 1432.54 mmol) in formamide (303.456 mL, 7640.19 mmol) was heated to an internal temperature of 150° C. and stirred for 17 hours. The reaction mixture was cooled, and transferred to a 2 L single nextracted flask. Then excess formamidine was removed by high vacuum distillation. Once formamidine stopped coming over, the remaining oil in the still pot was dissolved in DCM and washed with brine (3×200 mL). The combined aqueous washes were extracted with DCM. The combined organic extracts were dried ($Na_2SO_4$), filtered, and concentrated. The resulting oil was dissolved in minimal DCM, and this solution was added using a separatory funnel to a stirred solution of ether (about 5 volumes of ether vs. DCM solution), causing some precipitate to form. This precipitate was removed by filtration through a medium fit funnel which was rinsed with ether and disposed. The filtrate was concentrated, the trituration from ether repeated two more times and then dried on high vacuum line to give (R)-5-methyl-6,7-dihydro-5H-cyclopenta[d]pyrimidin-4-ol (93.225 g, 65.00% yield) as a pasty solid. LC/MS (APCI−) m/z 149.2.

Step 4:

Neat $POCl_3$ (463.9 mL, 5067 mmol) was added slowly by addition funnel to a 0° C. solution of (R)-5-methyl-6,7-dihydro-5H-cyclopenta[d]pyrimidin-4-ol (152.2 g, 1013 mmol) in DCE (1.2 L). After the addition was complete, the reaction mixture was warmed to room temperature, then heated to reflux and stirred for 70 minutes. The reaction was complete as determined by HPLC. The reaction mixture was cooled to room temperature, and the excess $POCl_3$ was quenched in 4 portions as follows: Reaction mixture transferred to separatory funnel and dripped into a beaker containing ice and saturated $NaHCO_3$ solution cooled in an ice bath. Once the addition of each portion of the reaction mixture was completed, the quenched mixture was stirred 30 minutes to ensure complete destruction of $POCl_3$ prior to transfer to separatory funnel. The mixture was transferred to the separatory funnel and extracted twice with DCM. The combined extracts were dried ($Na_2SO_4$), filtered, and concentrated. The crude was purified on silica gel as follows: silica gel (1 kg) was slurried in 9:1 hexane:ethyl acetate onto a 3 L fritted funnel, silica settled under vacuum, topped with sand. The crude was loaded with a DCM/hexane mixture, and the compound was eluted using 1 L sidearm flasks under vacuum. High Rf byproducts eluted first, then (R)-4-chloro-5-methyl-6,7-dihydro-5H-cyclopenta[d]pyrimidine (104.4 g, 61.09% yield) as an oil. Triethylamine (93.0 mL, 534 mmol) and tert-butyl piperazine-1-carboxylate (34.8 g, 187 mmol) was added to a solution of (R)-4-chloro-5-methyl-6,7-dihydro-5H-cyclopenta[d]pyrimidine (30.0 g, 178 mmol) in n-BuOH (250 mL). The reaction mixture was heated to reflux under nitrogen and stirred overnight (17 hours), after which it was concentrated on a rotavap. The resulting oil was dissolved in DCM, washed with $H_2O$, dried ($Na_2SO_4$), filtered, and was concentrated. The resulting oil was purified on silica gel eluting first with 2:1 hexanes:ethyl acetate until product eluting cleanly, then gradient 1:1 to 1:5 DCM:ethyl acetate to give (R)-tertbutyl 4-(5-methyl-6,7-dihydro-5H-cyclopenta[d]pyrimidin-4-yl)piperazine-1-carboxylate (42.0 g, 74.1% yield) as a powder. LC/MS (APCI+) m/z 319.1 [M+H]⁺.

Step 5:

Solid 77% max. m-CPBA (23.9 g, 107 mmol) was added portionwise to a 0° C. solution of (R)-tert-butyl 4-(5-methyl-6,7-dihydro-5H-cyclopenta[d]pyrimidin-4-yl)piperazine-1-carboxylate (20.0 g, 62.8 mmol) in $CHCl_3$ (310 mL). The reaction mixture was stirred 5 for minutes, then warmed to room temperature and stirred for 90 minutes. HPLC looked similar after 7.5 hours. The reaction mixture was cooled to 0° C., then $NaHCO_3$ (13.2 g, 157 mmol) and another 0.5 equivalents of m-CPBA were added. The reaction mixture was stirred overnight (14 hours). The reaction mixture was cooled to 0° C., and a solution of $Na_2S_2O_3$ (29.8 g, 188 mmol) in $H_2O$ (50 mL) was added dropwise by addition funnel. This was followed by a solution of $Na_2CO_3$ (24.6 g, 232 mmol) in $H_2O$ (70 mL) by addition funnel (mixture turns homogeneous). The reaction mixture was stirred for 30 minutes, then the mixture was extracted with $CHCl_3$ (3×150 mL). The combined extracts were dried ($Na_2SO_4$), filtered, and concentrated to give the N-oxide. LC/MS (APCI+) m/z 335.1 [M+H]+.

Step 6:

$Ac_2O$ (77.0 mL, 816 mmol) was added to the N-oxide (21.0 g, 62.8 mmol) from Step 5. The reaction mixture was heated under nitrogen in a 90° C. sand bath and stirred for 100 minutes. The reaction mixture was cooled to room temperature, and excess acetic anhydride was removed by rotary evaporation. The resulting oil was dissolved in DCM, which was then poured carefully into ice saturated $Na_2CO_3$. The mixture was extracted with DCM, and the combined extracts were dried ($Na_2SO_4$), filtered and concentrated to give (5R)-tert-butyl 4-(7-acetoxy-5-methyl-6,7-dihydro-5H-cyclopenta[d]pyrimidin-4-yl)piperazine-1-carboxylate (23.6 g, 100%) as a foam. LC/MS (APCI+) m/z 377.1 [M+H]+.

Step 7:

LiOH—$H_2O$ (6.577 g, 156.7 mmol) was added to a 0° C. solution of (5R)-tert-butyl 4-(7-acetoxy-5-methyl-6,7-dihydro-5H-cyclopenta[d]pyrimidin-4-yl)piperazine-1-carboxylate (23.6 g, 62.69 mmol) in 2:1 THF:$H_2O$ (320 mL). The reaction mixture was stirred for 10 minutes, and then warmed to room temperature. LC/MS looked the same at 3 hours and 4.5 hours. The reaction mixture was cooled to 0° C., and then saturated $NH_4Cl$ was added to the mixture. The mixture was stirred for 5 minutes, and most of the THF was removed by rotary evaporation. The mixture was extracted with EtOAc (3×250 mL), and the combined extracts were dried ($Na_2SO_4$), filtered, and concentrated. The crude was flashed on Biotage 65M: 4:1 DCM:ethyl acetate, then gradient to 1:1 to 1:4 DCM:ethyl acetate. Once the product was eluting, then ethyl acetate was flushed through the column. Then 30:1 DCM: MeOH eluted the rest of the product (8.83 g). The mixed fractions were re-flashed with Biotage 40M using the same conditions to give another 2.99 g which gave a combined yield of (5R)-tert-butyl 4-(7-hydroxy-5-methyl-6,7-dihydro-5H-cyclopenta[d]pyrimidin-4-yl)piperazine-1-carboxylate (11.82 g, 56.38% yield) as a foam. LC/MS (APCI+) m/z 335.1 [M+H]+.

Step 8:

A solution of DMSO (5.45 mL, 76.8 mmol) in DCM (50 mL) was added dropwise by addition funnel to a −78° C. solution of oxalyl chloride (3.35 mL, 38.4 mmol) in DCM (150 mL). The reaction mixture was stirred for 35 minutes, and then a solution of (5R)-tert-butyl 4-(7-hydroxy-5-methyl-6,7-dihydro-5H-cyclopenta[d]pyrimidin-4-yl)piperazine-1-carboxylate (9.17 g, 27.4 mmol) in DCM (80 mL) was added slowly by addition funnel. The reaction mixture was stirred another 1 hour at −78° C., after which neat triethylamine (18.0 mL, 129 mmol) was added to the mixture. The reaction mixture was then allowed to warm to room temperature, and then it was stirred for 30 minutes. $H_2O$ was added. The mixture was extracted with DCM (3×200 mL), and the combined extracts were dried ($Na_2SO_4$), filtered, and concentrated in vacuo. The crude was purified on silica gel (Biotage 65M): the column was flushed with ca. 800 mL 4:1 DCM: EtOAc, then gradient to 1:1 DCM:ethyl acetate until product eluting, then 1:4 DCM:EtOAc eluted product to give (R)-tert-butyl 4-(5-methyl-7-oxo-6,7-dihydro-5H-cyclopenta[d]pyrimidin-4-yl)piperazine-1-carboxylate (7.5 g, 82.3% yield) as a foam. The foam was concentrated (3×) from DCM/hexanes, which gave a foam. HPLC>95% area. LC/MS (APCI+) m/z 333 [M+H]+.

Step 9:

Triethylamine (4.33 mL, 31.1 mmol; degassed with nitrogen 30 minutes prior to use) and formic acid (1.36 mL, 36.1 mmol; degassed with nitrogen 30 minutes prior to use) were added to a solution of (R)-tert-butyl 4-(5-methyl-7-oxo-6,7-dihydro-5H-cyclopenta[d]pyrimidin-4-yl)piperazine-1-carboxylate (9.75 g, 29.3 mmol) in DCM (210 mL; degassed with nitrogen 30 minutes prior to use). The mixture was stirred for 5 minutes, then a Ru catalyst (0.0933 g, 0.147 mmol) was added. The reaction was stirred under positive nitrogen pressure overnight (18 hours). The reaction mixture was concentrated to dryness and dried on high vacuum. The impure material was flashed on Biotage 65M loaded 1:1 DCM:ethyl acetate 500 mL flushed, then 1:4 DCM:ethyl acetate until product (2nd spot), then gradient to neat ethyl acetate, then 25:1 DCM:MeOH eluted rest of product. The fractions were combined and concentrated on a rotary evaporator. The residue was concentrated again from DCM/hexanes to give a mixture of tert-butyl 4-((5R,7R)-7-hydroxy-5-methyl-6,7-dihydro-5H-cyclopenta[d]pyrimidin-4-yl)piperazine-1-carboxylate (major) and tert-butyl 4-((5R,7S)-7-hydroxy-5-methyl-6,7-dihydro-5H-cyclopenta[d]pyrimidin-4-yl)piperazine-1-carboxylate (minor) (9.35 g, 95.3% yield) as a foam. LC/MS (APCI+) m/z 335 [M+H]+. $^1$H NMR (CDCl$_3$) shows 88% diastereoselectivity by integration of carbinol methine.

Step 10:

4-Nitrobenzoyl chloride (4.27 g, 23.0 mmol) was added to a 0° C. solution of tert-butyl 4-((5R,7R)-7-hydroxy-5-methyl-6,7-dihydro-5H-cyclopenta[d]pyrimidin-4-yl)piperazine-1-carboxylate (7.0 g, 20.9 mmol) and triethylamine (4.38 mL, 31.4 mmol) in DCM (110 mL). The reaction mixture was stirred at room temperature overnight, after which saturated NaHCO$_3$ was added. The mixture was stirred 10 minutes, and then extracted with DCM. The combined extracts were dried (Na$_2$SO$_4$), filtered, and concentrated. The crude was flashed on Biotage 65M (3:1 hexanes:ethyl acetate loaded crude, then 2:1 hexanes:ethyl acetate eluted tert-butyl 4-((5R,7R)-5-methyl-7-(4-nitrobenzoyloxy)-6,7-dihydro-5H-cyclopenta[d]pyrimidin-4-yl)piperazine-1-carboxylate and a few mixed fractions). Then tert-butyl 4-((5R,7S)-5-methyl-7-(4-nitrobenzoyloxy)-6,7-dihydro-5H-cyclopenta[d]pyrimidin-4-yl)piperazine-1-carboxylate was eluted using 1:2 hexanes:ethyl acetate. The fractions with product were concentrated by rotary evaporation to give tert-butyl 4-((5R,7R)-5-methyl-7-(4-nitrobenzoyloxy)-6,7-dihydro-5H-cyclopenta[d]pyrimidin-4-yl)piperazine-1-carboxylate (8.55 g, 84.5% yield) as a foam. LC/MS (APCI+) m/z 484 [M+H]+. $^1$H NMR (CDCl$_3$) shows single diastereomer). The fractions with other diastereomer were concentrated by rotary evaporation to give tert-butyl 4-((5R,7S)-5-methyl-7-(4-nitrobenzoyloxy)-6,7-dihydro-5H-cyclopenta[d]pyrimidin-4-yl)piperazine-1-carboxylate (0.356 g, 3.52% yield) as a foam. LC/MS (APCI+) m/z 484 [M+H]+.

Step 11:

LiOH—H$_2$O (0.499 g, 11.9 mmol) was added to a 0° C. solution of tert-butyl 4-((5R,7R)-5-methyl-7-(4-nitrobenzoyloxy)-6,7-dihydro-5H-cyclopenta[d]pyrimidin-4-yl)piperazine-1-carboxylate (2.30 g, 4.76 mmol) in 2:1 THF:H$_2$O (40 mL). The reaction mixture was warmed to room temperature and stirred for 1 hour. The THF was removed by rotary evaporation, saturated NaHCO$_3$ was added, and the mixture was extracted with ethyl acetate. The combined extracts were washed (1×) with saturated NaHCO$_3$, dried (Na$_2$SO$_4$), filtered, and concentrated to give tert-butyl 4-((5R,7R)-7-hydroxy-5-methyl-6,7-dihydro-5H-cyclopenta[d]pyrimidin-4-yl)piperazine-1-carboxylate (1.59 g, 100.0% yield) as a foam. HPLC after workup just product>98 area % pure. LC/MS (APCI+) m/z 335 [M+H]+. The tert-butyl 4-((5R,7S)-7-hydroxy-5-methyl-6,7-dihydro-5H-cyclopenta[d]pyrimidin-4-yl)piperazine-1-carboxylate was prepared using an analogous method.

Step 12:

4M HCl/dioxane (11.2 mL, 44.9 mmol) was added to a solution of tert-butyl 4-((5R,7R)-7-hydroxy-5-methyl-6,7-dihydro-5H-cyclopenta[d]pyrimidin-4-yl)piperazine-1-carboxylate (0.600 g, 1.79 mmol) in dioxane (15 mL). The reaction mixture was stirred at room temperature under nitrogen overnight (20 hours). The mixture was concentrated to dryness and dried on high vacuum line. The crude was suspended in ether, sonicated, and stirred for 5 minutes. The solids were isolated by filtration through a medium frit funnel with nitrogen pressure, rinsed with ether, dried under nitrogen pressure, and dried further on a high vacuum line to give (5R,7R)-5-methyl-4-(piperazin-1-yl)-6,7-dihydro-5H-cyclopenta[d]pyrimidin-7-ol di-hydrochloride (0.440 g, 79.8% yield) as a powder. LC/MS (APCI+) m/z 235. The (5R,7S)-5-methyl-4-(piperazin-1-yl)-6,7-dihydro-5H-cyclopenta[d]pyrimidin-7-ol di-hydrochloride was prepared using an analogous method.

Step 13:

(S)-2-((S)-1-(tert-butoxycarbonyl)pyrrolidin-2-yl)-2-(4-chlorophenyl)acetic acid (0.1765 g, 0.5194 mmol) was combined with (5R,7R)-5-methyl-4-(piperazin-1-yl)-6,7-dihydro-5H-cyclopenta[d]pyrimidin-7-ol dihydrochloride (0.1596 g, 0.5194 mmol) and then slurried in methylene chloride (4.5 mL). The suspension was treated with diisopropylethylamine (0.2714 mL, 1.558 mmol) then with HBTU (0.1970 g, 0.5194 mmol), and the mixture was stirred at ambient temperature for 16 hours. The reaction was quenched with 10% Na$_2$CO$_3$ and then separated. The aqueous portion was washed twice with dichloromethane. The combined organic portions were dried with Na$_2$SO$_4$ and concentrated in vacuo. The residue was subjected to chromatography on SiO$_2$ eluting with 4% MeOH/dichloromethane to yield (S)-tert-butyl 2-((S)-1-(4-chlorophenyl)-2-(4-((5R,7R)-7-hydroxy-5-methyl-6,7-dihydro-5H-cyclopenta[d]pyrimidin-4-yl)piperazin-1-yl)-2-oxoethyl)pyrrolidine-1-carboxylate (0.256 g, 89%). MS (ESI+) [M+H] 556.1/558.1.

Step 14:

(S)-tert-butyl 2-((S)-1-(4-chlorophenyl)-2-(4-((5R,7R)-7-hydroxy-5-methyl-6,7-dihydro-5H-cyclopenta[d]pyrimidin-4-yl)piperazin-1-yl)-2-oxoethyl)pyrrolidine-1-carboxylate (0.74 g, 1.331 mmol) was dissolved in dioxane (3 mL) and treated with 4M hydrogen chloride in dioxane (8.317 mL, 33.27 mmol). The mixture was stirred at ambient temperature for 8 hours. The reaction was concentrated in vacuo, re-dissolved and re-concentrated from MeOH three times. Then the residue was re-dissolved in MeOH (3 mL) and added dropwise to stirred Et$_2$O (100 mL). After stirring for 30 minutes, the solid was collected, washed with Et$_2$O, and then air-dried under a blanket of nitrogen. (S)-2-(4-Chlorophenyl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone was recovered as a white solid, (0.47 g, 79%). MS (ESI+) [M+H] 456.1/458.1

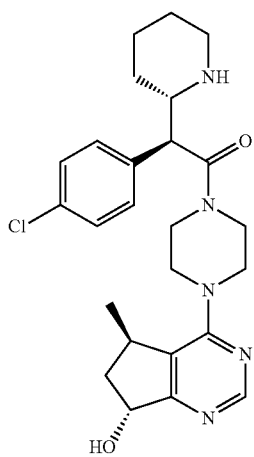 [SMILES: C[C@@H]1C[C@@H](O)c2ncnc(N3CCN(C(=O)[C@@H](c4ccc(Cl)cc4)[C@@H]4CCCCN4)CC3)c21]

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-piperidin-2-yl)ethanone Step 1:

(S)-tert-Butyl 2-((S)-2-((R)-4-benzyl-2-oxooxazolidin-3-yl)-1-(4-chlorophenyl)-2-oxoethyl)piperidine-1-carboxylate was prepared according to the procedure described for Example 1, using tert-butyl 2-oxopiperidine-1-carboxylate. $^1$H NMR (CDCl$_3$, 400 MHz) δ 7.35-7.25 (m, 7H), 7.16-7.10 (m, 2H), 4.71-4.64 (m, 1H), 4.35-4.17 (m, 3H), 3.26 (dd, 1H), 3.17-3.05 (m, 3H), 2.76 (dd, 1H), 1.89-1.61 (m, 6H), 1.49 (s, 9H).

Step 2:

(S)-2-((S)-1-(tert-Butoxycarbonyl)piperidin-2-yl)-2-(4-chlorophenyl)acetic acid was prepared according to the procedure described for Example 1 using (S)-tert-butyl 2-((S)-2-((R)-4-benzyl-2-oxooxazolidin-3-yl)-1-(4-chlorophenyl)-2-oxoethyl)piperidine-1-carboxylate. MS (APCI−) [M−H] 352.1/354.1.

Step 3:

(S)-tert-Butyl 2-((S)-1-(4-chlorophenyl)-2-(4-((5R,7R)-7-hydroxy-5-methyl-6,7-dihydro-5H-cyclopenta[d]pyrimidin-4-yl)piperazin-1-yl)-2-oxoethyl)piperidine-1-carboxylate was prepared according to the procedure described for Example 3 using (S)-2-((S)-1-(tert-butoxycarbonyl)piperidin-2-yl)-2-(4-chlorophenyl)acetic acid. MS (APCI+) [M+H] 570.1.

Step 4:

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-piperidin-2-yl)ethanone was prepared according to the procedure described for Example 3 using (S)-tert-butyl 2-((S)-1-(4-chlorophenyl)-2-(4-((5R,7R)-7-hydroxy-5-methyl-6,7-dihydro-5H-cyclopenta[d]pyrimidin-4-yl)piperazin-1-yl)-2-oxoethyl)piperidine-1-carboxylate. MS (APCI+) [M+H] 470.2; 2.28 minutes.

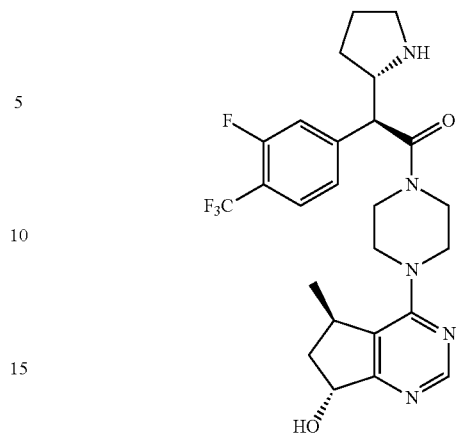

(S)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone Step 1:

(R)-4-Benzyl-3-(2-(3-fluoro-4-(trifluoromethyl)phenyl)acetyl)oxazolidin-2-one: A solution of 2-(3-fluoro-4-(trifluoromethyl)phenyl)acetic acid (5.0 g, 22.5 mmol) dissolved in ether (100 mL) was cooled to 0° C. and then treated with triethylamine (3.3 mL, 23.7 mmol) and pivaloyl chloride (2.9 mL, 23.5 mmol). The resulting solution was stirred at 0° C. for 1 hour and then cooled to −78° C. Meanwhile, a solution of (R)-4-benzyloxazolidin-2-one (3.99 g, 22.5 mmol) dissolved in THF (100 mL) was cooled to −78° C. and treated slowly with butyl lithium (12 mL, 25.2 mmol). The resulting solution was stirred at −78° C. for 15 minutes, and then added via cannula into the solution of the mixed anhydride. The mixture was stirred at −78° C. for 15 minutes and then warmed to 0° C. for 30 minutes. Saturated NH$_4$Cl (50 mL) was added to quench the reaction. The reaction was concentrated in vacuo, and the residue was extracted with ethyl acetate (3×150 mL). The organic phase was dried over Na$_2$SO$_4$ and concentrated. The residue was purified by column chromatography, eluting with hexane/ethyl acetate (4:1), (4.9 g, 57.1% yield). $^1$H NMR (CDCl$_3$, 400 MHz) δ 7.59 (t, J=8.2, 1H), 7.34-7.12 (m, 7H), 4.74-4.66 (m, 1H), 4.39 (d, J=16, 1H), 4.29 (d, J=16, 1H), 4.27-4.19 (m, 2H), 3.27 (dd, 1H), 2.78 (dd, 1H).

Step 2:

(S)-tert-Butyl 2-((S)-2-((R)-4-benzyl-2-oxooxazolidin-3-yl)-1-(3-fluoro-4-(trifluoromethyl)phenyl)-2-oxoethyl)pyrrolidine-1-carboxylate: A solution of (R)-4-benzyl-3-(2-(3-fluoro-4-(trifluoromethyl)phenyl)acetyl)oxazolidin-2-one (1.6 g, 4.20 mmol) was dissolved in dichloromethane (40 mL), cooled to −78° C. and treated slowly with titanium (IV) chloride (4.4 mL, 4.40 mmol). This was followed by treatment with diisopropylethylamine (0.76 mL, 4.36 mmol). The mixture was stirred at −78° C. for 15 minutes, and tert-butyl 2-methoxypyrrolidine-1-carboxylate (1.0 g, 4.97 mmol) was added. After 15 minutes, the reaction was allowed to warm to ambient temperature for one hour. The reaction was quenched with saturated NH$_4$Cl (20 mL) and extracted with dichloromethane (3×100 mL). The organic phase was dried over Na$_2$SO$_4$ and concentrated in vacuo. The residue was purified by column chromatography, eluting with hexane/ethyl acetate (4:1), (1.44 g, 62.3% yield). 7.55 (t, J=8.2, 1H), 7.38-

7.18 (m, 7H), 5.61-5.51 (m, 1H), 4.72-4.56 (m, 2H), 4.16-4.02 (m, 2H), 3.43-3.34 (m, 1H), 3.28-3.15 (m, 1H), 2.77-2.61 (m, 1H), 1.96-1.80 (m, 1H), 1.75-1.56 (m, 4H), 1.48 (s, 9H).

Step 3:

(S)-2-((S)-1-(tert-Butoxycarbonyl)pyrrolidin-2-yl)-2-(3-fluoro-4-(trifluoromethyl)phenyl)acetic acid: Lithium hydroxide hydrate (0.22 g, 5.24 mmol) was dissolved in THF (20 mL) and water (10 mL) and then treated with hydrogen peroxide (35 wt %) (1.00 g, 10.3 mmol). After stirring at ambient temperature for 30 minutes, the solution was cooled to 0° C. (S)-tert-Butyl 2-((S)-2-((R)-4-benzyl-2-oxooxazolidin-3-yl)-1-(3-fluoro-4-(trifluoromethyl)phenyl)-2-oxoethyl)pyrrolidine-1-carboxylate (1.44 g, 2.62 mmol) was added as a solution in THF (10 mL). The mixture was stirred at 0° C. for 1 hour and then warmed to ambient temperature overnight. The reaction was quenched with 10% $K_2SO_3$ (4 mL) and saturated $NaHCO_3$ (4 mL) and stirred at ambient temperature for 20 minutes. The reaction was concentrated in vacuo, and the aqueous phase was washed with ether (3×50 mL). The aqueous phase was diluted with ethyl acetate (50 mL), cooled to 0° C., and acidified with 1N HCl to a pH of 3. The organic phase was separated, and the aqueous phase was extracted with ethyl acetate (3×50 mL). The combined organic phase was washed with 1N HCl (2×20 mL), dried over $Na_2SO_4$ and then concentrated in vacuo (0.036 g, 3.52% yield). MS (APCI−) [M−H] 389.8.

Step 4:

(S)-tert-Butyl 2-((S)-1-(3-fluoro-4-(trifluoromethyl)phenyl)-2-(4-((5R,7R)-7-hydroxy-5-methyl-6,7-dihydro-5H-cyclopenta[d]pyrimidin-4-yl)piperazin-1-yl)-2-oxoethyl)pyrrolidine-1-carboxylate: (S)-2-((S)-1-(tert-Butoxycarbonyl)pyrrolidin-2-yl)-2-(3-fluoro-4-(trifluoromethyl)phenyl)acetic acid (0.036 g, 0.092 mmol) and (5R,7R)-5-methyl-4-(piperazin-1-yl)-6,7-dihydro-5H-cyclopenta[d]pyrimidin-7-ol di-hydrochloride (0.028 g, 0.092 mmol) were slurried in dichloromethane (5 mL) and then treated with diisopropylethylamine (0.06 mL, 0.34 mmol). This was followed by treatment with HBTU (0.036 g, 0.095 mmol). The mixture was stirred at ambient temperature for 1 hour. The reaction was concentrated in vacuo and purified by column chromatography, eluting with ethyl acetate. (0.040 g, 72% yield). MS (APCI+) [M+H] 608.2.

Step 5:

(S)-2-(3-Fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone: (S)-tert-Butyl 2-((S)-1-(3-fluoro-4-(trifluoromethyl)phenyl)-2-(4-((5R,7R)-7-hydroxy-5-methyl-6,7-dihydro-5H-cyclopenta[d]pyrimidin-4-yl)piperazin-1-yl)-2-oxoethyl)pyrrolidine-1-carboxylate (0.040 g, 0.066 mmol) was dissolved in dichloromethane (4 mL) and MeOH (1 mL) and treated with HCl in dioxane (2 mL, 8.0 mmol). The mixture was stirred at ambient temperature overnight. The reaction was concentrated in vacuo to produce the desired product (0.033 g, 99% yield). MS (APCI+) [M+H] 508.1; 2.13 minutes.

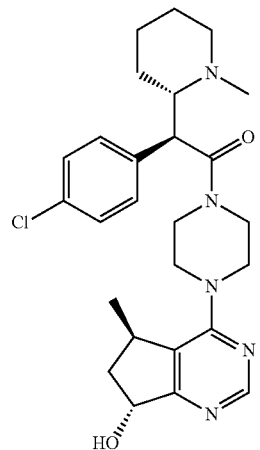 [SMILES: C[C@@H]1C[C@@H](O)c2ncnc(N3CCN(C(=O)[C@@H](c4ccc(Cl)cc4)[C@@H]4CCCCN4C)CC3)c21]

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-methylpiperidin-2-yl)ethanone Prepared according to the procedure described for Example 7 using (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-piperidin-2-yl)ethanone, (0.0056 g, 50%). MS (ESI+) [M+H] 484.2.

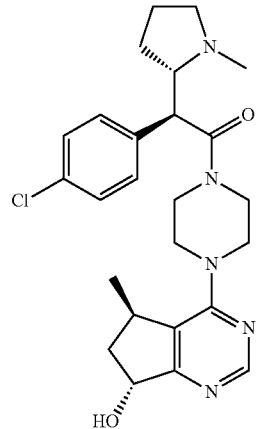 [SMILES: C[C@@H]1C[C@@H](O)c2ncnc(N3CCN(C(=O)[C@@H](c4ccc(Cl)cc4)[C@@H]4CCCN4C)CC3)c21]

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-methylpyrrolidin-2-yl)ethanone (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone di-hydrochloride (0.213 g, 0.4027 mmol) was treated with 37% aqueous formaldehyde (0.1109 mL, 4.027 mmol), formic acid (0.1519 mL, 4.027 mmol) and water (400 uL). The mixture was heated to reflux for 6 hours. After cooling, the reaction was neutralized with saturated $NaHCO_3$ and then extracted with methylene chloride. The aqueous was extracted with methylene chloride (2×). The combined organic portions were dried over $Na_2SO_4$ and concentrated in vacuo. The residue was subjected to chromatography on SiO₂ and eluted with a stepped gradient from 2% MeOH/1% NH₄OH/dichloromethane to 5% MeOH/1% NH₄OH/dichloromethane. The free base was collected and concentrated in vacuo. The residue was concentrated from MeOH and then re-dissolved in MeOH. The solution was treated with HCl in dioxane (4M, 1 mL, 4 mmol). The solution was concentrated in vacuo, re-suspended in MeOH and re-concentrated three times. The solution was re-dissolved in MeOH (0.25 mL+0.125 mL wash) and added dropwise to a stirred flask containing Et₂O (15 mL). The suspension was stirred for 30 minutes. The suspension was then filtered, washed with Et₂O and dried under a blanket of nitrogen. (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-methylpyrrolidin-2-yl)ethanone dihydrochloride was recovered as a solid (0.117 g, 62%). MS (ESI+) [M+H] 470.1/472.1. ¹H NMR (CD₃OD, 400 MHz) δ 8.57 (s, 1H), 7.47-7.41 (dd, 4H), 5.31 (t, J=8.0 Hz, 1H), 4.54 (d, J=9.1 Hz, 1H), 4.25-4.16 (m, 2H), 4.11-4.05 (m, 1H), 3.93-3.62 (m, 6H), 3.51-3.42 (m, 1H), 3.26-3.17 (m, 1H), 2.95 (s, 3H), 2.34-2.26 (m, 1H), 2.23-2.06 (m, 3H), 2.05-1.92 (m, 1H), 1.85-1.73 (m, 1H), 1.21-1.16 (d, 3H).

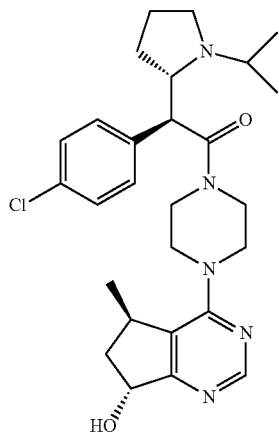 [SMILES: CC(C)N1CCC[C@H]1[C@@H](C(=O)N1CCN(c2ncnc3c2[C@H](C)C[C@H]3O)CC1)c1ccc(Cl)cc1]

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-isopropylpyrrolidin-2-yl)ethanone (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone di-hydrochloride (0.074 g, 0.1399 mmol) was dissolved in 1,2-dichloroethane (0.50 mL) and treated with diisopropylethylamine (0.04874 mL, 0.2798 mmol), propan-2-one (0.03082 mL, 0.4197 mmol) and sodium triacetoxyborohydride (0.1483 g, 0.6996 mmol). The mixture was stirred at 40° C. for 18 hours. The reaction was quenched with 3N HCl and stirred for 30 minutes. The reaction was neutralized to a pH of about 8 to about 8.5 with slow addition of saturated NaHCO₃. The reaction was diluted with methylene chloride and separated. The aqueous layer was washed with methylene chloride (2×), and the combined organics were dried over Na₂SO₄ and concentrated in vacuo. The material was subjected to chromatography on SiO₂ eluting with 5% MeOH/1% NH₄OH/methylene chloride. The recovered free base (51.2 mg) was dissolved in dioxane (1 mL) and treated with 4N HCl in dioxane (1.5 mL). After stirring for 5 minutes, the mixture was concentrated in vacuo. The mixture was re-dissolved and re-concentrated in vacuo three times from MeOH. The mixture was re-dissolved in MeOH (0.5 mL+0.25 mL wash) and added dropwise to stirred Et₂O (30 mL). The resultant solid was stirred for 30 minutes. The solid was then filtered, washed with Et₂O and dried under a blanket of nitrogen. (S)-2-(4-Chlorophenyl)-1-(4-((5R,7R)-7-hydroxy-5-methyl-6,7-dihydro-5H-cyclopenta[d]pyrimidin-4-yl)piperazin-1-yl)-2-((S)-1-isopropylpyrrolidin-2-yl)ethanone dihydrochloride was recovered as a solid (0.026 g, 59%). MS (ESI+) [M+H] 498.2/500.1. ¹H NMR (CD₃OD, 400 MHz) δ 8.56 (s, 1H), 7.44 (dd, 4H), 5.29 (t, J=8.1 Hz, 1H), 4.56 (d, J=10.3, 1H), 4.44-4.35 (m, 1H), 4.29-4.06 (m, 3H), 3.87-3.75 (m, 3H), 3.72-3.62 (m, 1H), 3.60-3.35 (m, 5H), 2.31-2.25 (m, 1H), 2.23-2.08 (m, 2H), 2.07-1.95 (m, 1H), 1.90-1.78 (m, 1H), 1.78-1.68 (m, 1H), 1.39 (d, 3H), 1.32 (d, 3H), 1.18 (d, 3H).

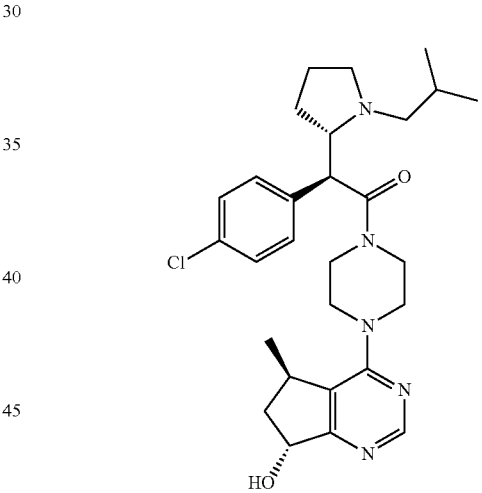

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-isobutylpyrrolidin-2-yl)ethanone Prepared according to the procedure described for Example 8 using isobutyraldehyde. MS (ESI+) [M+H] 512.2. ¹H NMR (CD₃OD, 400 MHz) δ 8.56 (s, 1H), 7.44 (dd, 4H), 5.28 (t, 1H), 4.60 (d, J=8.9 Hz, 1H), 4.30-4.16 (m, 2H), 4.11-4.02 (m, 1H), 3.93-3.59 (m, 5H), 3.55-3.42 (m, 2H), 3.37-3.23 (m, 1H), 3.09-3.03 (dd, 1H), 2.32-2.24 (m, 1H), 2.22-1.94 (m, 5H), 1.85-1.75 (m, 1H), 1.17 (d, 3H), 1.08 (d, 3H), 1.00 (d, 3H).

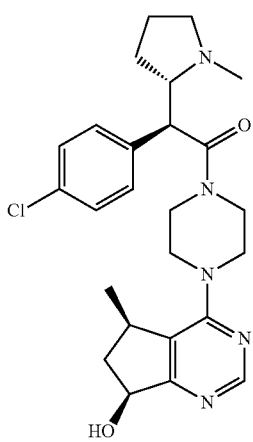 [SMILES: C[C@@H]1C[C@H](O)c2ncnc(N3CCN(C(=O)[C@@H](c4ccc(Cl)cc4)[C@@H]4CCCN4C)CC3)c21]

(S)-2-(4-chlorophenyl)-1-(4-((5R,7S)-7-hydroxy-5-methyl-6,7-dihydro-5H-cyclopenta[d]pyrimidin-4-yl)piperazin-1-yl)-2-((S)-1-methylpyrrolidin-2-yl)ethanone Prepared according to the procedure described for Example 7 using (S)-2-(4-chlorophenyl)-1-(4-((5R,7S)-7-hydroxy-5-methyl-6,7-dihydro-5H-cyclopenta[d]pyrimidin-4-yl)piperazin-1-yl)-2-((S)-pyrrolidin-2-yl)ethanone. MS (ESI+) [M+H] 470.1/472.1. $^1$H NMR (CDCl$_3$, 400 MHz) δ 8.59 (s, 1H), 7.43 (dd, 4H), 5.13 (dd, Hi), 4.53 (d, 1H), 4.30-4.13 (m, 2H), 3.97-3.88 (m, 1H), 3.80-3.64 (m, 3H), 3.57-3.41 (m, 2H), 3.26-3.17 (m, 1H), 2.95 (s, 3H), 2.84-2.75 (m, 1H), 2.16-2.06 (m, 2H), 2.03-1.92 (m, 1H), 1.85-1.74 (m, 1H), 1.65-1.58 (dt, 1H), 1.24 (d, 3H).

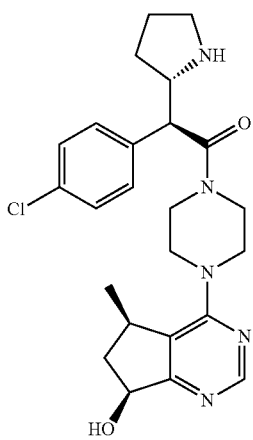 [SMILES: C[C@@H]1C[C@H](O)c2ncnc(N3CCN(C(=O)[C@@H](c4ccc(Cl)cc4)[C@@H]4CCCN4)CC3)c21]

(S)-2-(4-chlorophenyl)-1-(4-((5R,7S)-7-hydroxy-5-methyl-6,7-dihydro-5H-cyclopenta[d]pyrimidin-4-yl)piperazin-1-yl)-2-((S)-pyrrolidin-2-yl)ethanone Step 1:
(S)-tert-Butyl 2-((S)-1-(4-chlorophenyl)-2-(4-((5R,7S)-7-hydroxy-5-methyl-6,7-dihydro-5H-cyclopenta[d]pyrimidin-4-yl)piperazin-1-yl)-2-oxoethyl)pyrrolidine-1-carboxylate was prepared according to the procedure described for Example 3 using (5R,7S)-5-methyl-4-(piperazin-1-yl)-6,7-dihydro-5H-cyclopenta[d]pyrimidin-7-ol di-hydrochloride (0.22 g, 87%). MS (ESI+) [M+H] 556.0/558.0.

Step 2:
(S)-2-(4-chlorophenyl)-1-(4-((5R,7S)-7-hydroxy-5-methyl-6,7-dihydro-5H-cyclopenta[d]pyrimidin-4-yl)piperazin-1-yl)-2-((S)-pyrrolidin-2-yl)ethanone was prepared according to the procedure described for Example 3 using (S)-tert-butyl 2-((S)-1-(4-chlorophenyl)-2-(4-((5R,7S)-7-hydroxy-5-methyl-6,7-dihydro-5H-cyclopenta[d]pyrimidin-4-yl)piperazin-1-yl)-2-oxoethyl)pyrrolidine-1-carboxylate (0.175 g, 84%). MS (ESI+) [M+H] 456.1/458.1. $^1$H NMR (CD$_3$OD, 400 MHz) δ 8.59 (s, 1H), 7.43 (dd, 4H), 5.12 (dd, 1H), 4.45 (d, J=9.8 Hz, 1H), 4.26-4.16 (m, 1H), 4.14-4.05 (m, 1H), 3.94-3.82 (m, 2H), 3.79-3.67 (m, 3H), 3.56-3.47 (m, 1H), 3.46-3.37 (m, 1H), 3.37-3.31 (m, 2H), 2.84-2.75 (m, 1H), 2.16-2.05 (m, 1H), 1.98-1.74 (m, 3H), 1.65-1.58 (dt, 1H), 1.40-1.34 (m, 3H), 1.23 (d, 3H).

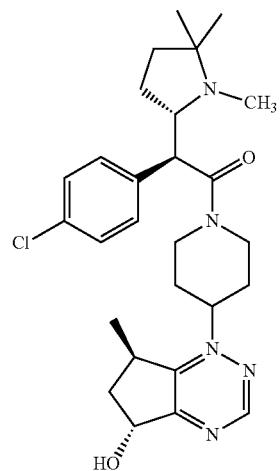

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1,5,5-trimethylpyrrolidin-2-yl)ethanone Step 1:
5,5-Dimethylpyrrolidin-2-one (0.1078 g, 0.95265 mmol) [Ganem, B. and Osby, J O; Tet Lett 26:6413 (1985)] was dissolved in THF (3 mL) and cooled to −20° C. The solution was treated with lithium hexamethyldisilazide ("LHMDS"; 1.0479 mL, 1.0479 mmol) and stirred at −20° C. for 30 minutes. di-tert-Butyl dicarbonate (0.24950 g, 1.1432 mmol) was added, and the reaction mixture was allowed to warm to ambient temperature. The reaction was stirred at ambient temperature for two hours and then quenched with saturated NH$_4$Cl, diluted with ethyl acetate and separated. The organic layer was washed with saturated NH$_4$Cl, saturated NaHCO$_3$, saturated NaCl, dried over Na$_2$SO$_4$ and concentrated in vacuo to an oil. The crude product was subjected to chromatography on SiO$_2$ and eluted with 4:1 hexanes/ethyl acetate. tert-Butyl 2,2-dimethyl-5-oxopyrrolidine-1-carboxylate (Rf of 0.11 in 4:1 hexanes/ethyl acetate) was recovered as a solid (0.087 g, 43%). $^1$H NMR (CDCl$_3$, 400 MHz) δ 2.48 (t, J=7.8, 2H), 1.85 (t, 2H), 1.54 (s, 9H), 1.47 (s, 6H).

Step 2:
tert-Butyl 2,2-dimethyl-5-oxopyrrolidine-1-carboxylate (1.170 g, 5.4859 mmol) was dissolved in Et$_2$O (15 mL) and cooled to −78° C. The solution was treated with DIBAL-H (3.7304 mL, 5.5956 mmol). The mixture was stirred at −78° C. for 2 hours and then warmed to ambient temperature overnight. The reaction was quenched by addition of an aliquot (7 mL) of a solution of p-toluenesulfonic acid hydrate (0.012 g) in MeOH (12 mL). The mixture was stirred at ambient temperature for 60 hours. The suspension was concentrated in vacuo and re-suspended in a mixture of Rochelle's salt (0.5N) and ethyl acetate. After separation, the aqueous portion was washed with ethyl acetate (2×). The combined organics were then washed with saturated NaCl, dried over $Na_2SO_4$ and concentrated in vacuo to a light oil (92%). A solution of titanium(IV) chloride (3.7128 ml, 3.7128 mmol) in toluene was cooled to 0° C. and treated with a solution of (R)-4-benzyl-3-(2-(4-chlorophenyl)acetyl)oxazolidin-2-one (1.1131 g, 3.3753 mmol) dissolved in dichloromethane (7 mL). After 5 minutes, diisopropylethylamine (0.64671 mL, 3.7128 mmol) was added. The resultant solution was stirred for 1 hour at 0° C. and then cooled to −20° C. A solution of tert-butyl 5-methoxy-2,2-dimethylpyrrolidine-1-carboxylate (1.090 g, 5.0630 mmol) in dichloromethane (7 mL) was added, and the mixture was stirred at −20° C. for 75 minutes. The reaction was quenched with saturated $NH_4Cl$ (about 4 mL) and diluted with water to dissolve the solids. After separation, the aqueous portion was washed with methylene chloride (3×). The combined organics were washed with water (2×), dried over $Na_2SO_4$ and concentrated in vacuo. The crude product was subjected to chromatography on $SiO_2$ and eluted with 9:1 hexanes/ethyl acetate to produce (S)-tert-butyl 5-((S)-2-((R)-4-benzyl-2-oxooxazolidin-3-yl)-1-(4-chlorophenyl)-2-oxoethyl)-2,2-dimethylpyrrolidine-1-carboxylate (1.09 g, 61%). MS (ESI+) [M+H] 526.7/528.8

Step 3:

(S)-2-((S)-1-(tert-Butoxycarbonyl)-5,5-dimethylpyrrolidin-2-yl)-2-(4-chlorophenyl)acetic acid was prepared according to the procedure described for Example 1 using (S)-tert-butyl 5-((S)-2-((R)-4-benzyl-2-oxooxazolidin-3-yl)-1-(4-chlorophenyl)-2-oxoethyl)-2,2-dimethylpyrrolidine-1-carboxylate (0.55 g, 72%). $^1$H NMR (CDCl$_3$, 400 MHz) δ 7.33-7.21 (m, 4H), 4.60-4.51 (m, 1H), 4.39-4.32 (m, 1H), 2.04-1.92 (m, 2H), 1.78-1.68 (m, 2H), 1.51 (s, 9H), 1.22 (s, 6H).

Step 4:

(S)-tert-Butyl 5-((S)-1-(4-chlorophenyl)-2-(4-((5R,7R)-7-hydroxy-5-methyl-6,7-dihydro-5H-cyclopenta[d]pyrimidin-4-yl)piperazin-1-yl)-2-oxoethyl)-2,2-dimethylpyrrolidine-1-carboxylate was prepared according to the procedure described for Example 3 using (S)-2-((S)-1-(tert-butoxycarbonyl)-5,5-dimethylpyrrolidin-2-yl)-2-(4-chlorophenyl)acetic acid (0.315 g, 79%). MS (ESI+) [M+H] 584.0/586.1.

Step 5:

(S)-2-(4-Chlorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone was prepared according to the procedure described for Example 3 using (S)-tert-butyl 5-((S)-1-(4-chlorophenyl)-2-(4-((5R,7R)-7-hydroxy-5-methyl-6,7-dihydro-5H-cyclopenta[d]pyrimidin-4-yl)piperazin-1-yl)-2-oxoethyl)-2,2-dimethylpyrrolidine-1-carboxylate, (0.278 g, 93%). MS (ESI+) [M+H] 484.2/486.2.

Step 6:

(S)-2-(4-Chlorophenyl)-1-(4-((5R,7R)-7-hydroxy-5-methyl-6,7-dihydro-5H-cyclopenta[d]pyrimidin-4-yl)piperazin-1-yl)-2-((S)-1,5,5-trimethylpyrrolidin-2-yl)ethanone was prepared according to the procedure described for Example 7 using (S)-2-(4-chlorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone (0.016 g, 62%). MS (ESI+) [M+H] 498.2/500.1. $^1$H NMR (CD$_3$OD, 400 MHz) δ 8.57 (s, 1H), 7.52-7.42 (m, 4H), 5.28 (t, J=7.8 Hz, 1H), 4.81-4.76 (m, 1H), 4.40-4.31 (q, 1H), 4.22-4.12 (m, 1H), 4.05-3.97 (m, 1H), 3.96-3.63 (m, 5H), 3.56-3.49 (m, 1H), 2.55 (s, 3H), 2.32-2.24 (m, 1H), 2.23-1.96 (m, 4H), 1.86-1.76 (m, 1H), 1.55 (s, 3H), 1.34 (s, 3H), 1.19 (d, 3H).

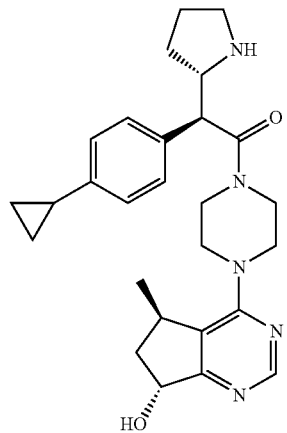 [SMILES: C[C@@H]1C[C@@H](O)c2ncnc(N3CCN(C(=O)[C@@H](c4ccc(C5CC5)cc4)[C@@H]4CCCN4)CC3)c21]

(S)-2-(4-cyclopropylphenyl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone Step 1:

Cyclopropylmagnesium bromide (64.0 mL, 32.00 mmol) in THF was treated with a solution of zinc (II) chloride (64.00 mL, 32.00 mmol) in THF. The mixture was stirred at ambient temperature for 20 minutes. 2-(4-Bromophenyl)acetonitrile (5.228 g, 26.67 mmol) and bis[tri-t-butyl phosphine]palladium (0.6814 g, 1.333 mmol) were added as a solution in THF (2 mL). The reaction was stirred at ambient temperature under nitrogen for 12 hours. The reaction was quenched with saturated $NH_4Cl$, diluted with methylene chloride and separated. The aqueous layer was washed with methylene chloride (2×), and then the combined organic layers were washed with water (3×), dried over $Na_2SO_4$ and concentrated in vacuo. The crude product was subjected to chromatography on $SiO_2$ eluting with 25:1 hexanes/ethyl acetate to yield 2-(4-cyclopropylphenyl)acetonitrile (2.76 g, 66%). $^1$H NMR (CDCl$_3$, 400 MHz) δ 7.20 (d, J=8.2, 2H), 7.07 (d, J=8.2, 2H), 3.70 (s, 2H), 1.94-1.85 (m, 1H), 1.01-0.95 (m, 2H), 0.71-0.66 (m, 2H).

Step 2:

Methanol (65 mL) was cooled to 0° C. and saturated with HCl (g). This solution was treated with a solution of 2-(4-cyclopropylphenyl)acetonitrile (2.76 g, 17.56 mmol) in methanol (6 mL). The reaction mixture was heated to reflux overnight under a drying tube containing $CaSO_4$. The reaction was cooled and concentrated in vacuo. The crude mixture was re-suspended in ethyl acetate and water and then separated. The organic layer was washed with saturated $NaHCO_3$, saturated NaCl, dried over $Na_2SO_4$ and concentrated in vacuo to provide methyl 2-(4-cyclopropylphenyl)acetate as an oil (3.10 g, 93%). ¹H NMR (CDCl₃, 400 MHz) δ 7.16 (d, J=8.3, 2H), 7.02 (d, 2H), 3.68 (s, 3H), 3.58 (s, 2H), 1.92-1.83 (m, 1H), 0.97-0.91 (m, 2H), 0.70-0.64 (m, 2H).

Step 3:

Methyl 2-(4-cyclopropylphenyl)acetate (3.10 g, 16.30 mmol) was dissolved in a mixture of THF/MeOH/water (2:2:1, 80 mL), and the solution was treated with lithium hydroxide hydrate (0.8548 g, 20.37 mmol). The mixture was then stirred at ambient temperature for 4 hours. The reaction mixture was neutralized to a pH of 4 with 3N HCl and concentrated in vacuo. The solids were re-dissolved in ethyl acetate and water. The pH was re-adjusted to a pH of about 3 to about 4 with 3N HCl. The layers were then separated. The aqueous layer was washed with ethyl acetate (2×). The combined organic layers were then washed with saturated NaCl, dried over Na₂SO₄ and concentrated to yield 2-(4-cyclopropylphenyl)acetic acid (2.82 g, 98%). ¹H NMR (CDCl₃, 400 MHz) δ 7.16 (d, J=8.2, 2H), 7.03 (d, 2H), 3.60 (s, 2H), 1.92-1.83 (m, 1H), 098-0.91 (m, 2H), 0.70-0.64 (m, 2H).

Step 4:

2-(4-Cyclopropylphenyl)acetic acid (2.82 g, 16.003 mmol) was combined with (R)-4-benzyloxazolidin-2-one (3.4030 g, 19.204 mmol) in toluene (14 mL). The suspension was treated with triethylamine (6.6917 mL, 48.010 mmol) and then heated to 80° C. The solution was treated dropwise with a solution of pivaloyl chloride (1.9893 mL, 16.003 mmol) in toluene (3.5 mL). The reaction was heated overnight at 80° C. The reaction was cooled and washed with 2N HCl and then separated. The aqueous layer was washed with toluene, and the combined organics were then washed with 2N HCl, water, saturated NaHCO₃ (2×), saturated NaCl, dried over Na₂SO₄ and concentrated in vacuo. The crude product was subjected to chromatography on SiO₂ eluting with 9:1 hexanes/ethyl acetate to yield (R)-4-benzyl-3-(2-(4-cyclopropylphenyl)acetyl)oxazolidin-2-one (3.43 g, 64%). ¹H NMR (CDCl₃, 400 MHz) δ 7.33-7.20 (m, 5H), 7.16-7.11 (m, 2H), 7.05 (d, J=8.2, 2H), 4.70-4.63 (m, 1H), 4.32-4.14 (m, 4H), 3.26 (dd, J1=3.2, J2=13.3, 1H), 2.75 (dd, J1=9.5, J2=13.3, 1H), 1.93-1.85 (m, 1H), 0.98-0.92 (m, 2H), 0.72-0.66 (m, 2H).

Step 5:

(S)-2-((S)-1-(tert-Butoxycarbonyl)pyrrolidin-2-yl)-2-(4-cyclopropylphenyl)acetic acid was prepared according to the procedure described for Example 1, using (R)-4-benzyl-3-(2-(4-cyclopropylphenyl)acetyl)oxazolidin-2-one (0.287 g, 26%). MS (ESI+) [M+H] 345.7.

Step 6:

(S)-tert-Butyl 2-((S)-1-(4-cyclopropylphenyl)-2-(4-((5R,7R)-7-hydroxy-5-methyl-6,7-dihydro-5H-cyclopenta[d]pyrimidin-4-yl)piperazin-1-yl)-2-oxoethyl)pyrrolidine-1-carboxylate was prepared according to the procedure described for Example 3 using (S)-2-((S)-1-(tert-butoxycarbonyl)pyrrolidin-2-yl)-2-(4-cyclopropylphenyl)acetic acid, (0.199 g, 94%). MS (ESI+) [M+H] 562.1.

Step 7:

(S)-2-(4-Cyclopropylphenyl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone was prepared according to the procedure described for Example 3 using (S)-tert-butyl 2-((S)-1-(4-cyclopropylphenyl)-2-(4-((5R,7R)-7-hydroxy-5-methyl-6,7-dihydro-5H-cyclopenta[d]pyrimidin-4-yl)piperazin-1-yl)-2-oxoethyl)pyrrolidine-1-carboxylate (0.145 g, 77%). MS (ESI+) [M+H] 462.2. ¹H NMR (CD₃OD, 400 MHz) δ 8.56 (s, 1H), 7.26 (d, 2H), 7.13 (d, 2H), 5.29 (dd, 1H), 5.32-5.26 (dd, 1H), 4.32 (d, 1H), 4.29-4.18 (m, 1H), 4.12-3.95 (m, 2H), 3.88-3.61 (m, 6H), 3.51-3.38 (m, 1H), 3.35-3.30 (m, 1H), 2.32-2.24 (m, 1H), 2.22-2.03 (m, 2H), 1.95-1.85 (m, 2H), 1.82-1.73 (m, 2H), 1.40-1.34 (m, 1H), 1.16 (d, 3H), 1.01-0.95 (m, 2H), 0.69-0.64 (m, 2H).

Examples 14-32 shown in Table 1 can also be made according to the above described methods.

TABLE 1

| Ex. # | Structure | Name | LCMS NMR |
|---|---|---|---|
| 14 | 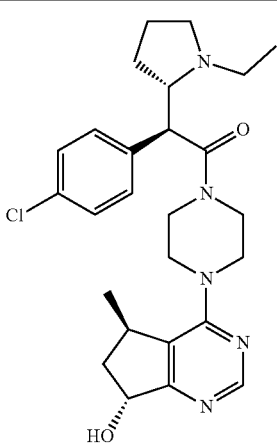 | S)-2-(4-chlorophenyl)-2-((S)-1-ethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone | m/z 484.2/486.1; ¹H NMR (400 MHz, CD₃OD) d ppm 8.51 (s, 1H), 7.31-7.24 (m, 4H), 5.10 (t, 1H), 3.86-3.34 (m, 13 H), 3.12-3.04 (m, 1H), 2.97-2.86 (m, 1H), 2.48-2.36 (m, 1H), 2.31-2.10 (m, 3H), 1.87-1.53 (m, 4H), 1.46-1.32 (m, 2H), 1.29-1.23 (m, 1H), 1.16 (d, 3H), 1.08 (t, 3H) |

TABLE 1-continued

| Ex. # | Structure | Name | LCMS NMR |
|---|---|---|---|
| 15 | 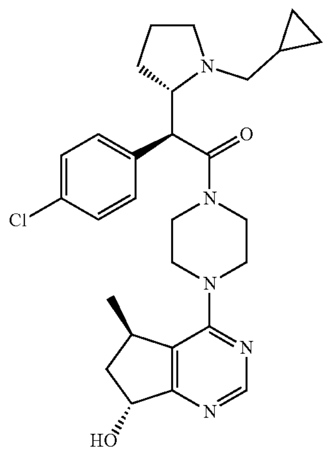 [SMILES: C[C@@H]1C[C@@H](O)c2ncnc(N3CCN(C(=O)[C@@H](c4ccc(Cl)cc4)[C@@H]4CCCN4CC4CC4)CC3)c21] | (S)-2-(4-chlorophenyl)-2-((S)-1-(cyclopropylmethyl)pyrrolidin-2-yl)-1-(4-((5R,7R)-7-hydroxy-5-methyl-6,7-dihydro-5H-cyclopenta[d]pyrimidin-4-yl)piperazin-1-yl)ethanone | m/z 510.2/512.2; $^1$H NMR (400 MHz, CD$_3$OD) d ppm 8.55 (s, 1H), 7.46 (d, 2H), 7.40 (d, 2H), 5.27 (t, 1H), 4.45 (d, 1H), 4.30-4.16 (m, 2H), 4.09-4.00 (m, 1H), 3.92-3.83 (m, 1H), 3.78-3.61 (m, 5H), 3.59-3.45 (m, 2H), 3.43-3.34 (m, 1H), 3.27-3.19 (m, 1H), 2.31-2.24 (m, 1H), 2.22-2.04 (m, 3H), 1.97-1.86 (m, 1H), 1.83-1.72 (m, 1H), 1.24-1.12 (m, 4H), 0.83-0.68 (m, 2H), 0.49-0.39 (m, 2H) |
| 16 | 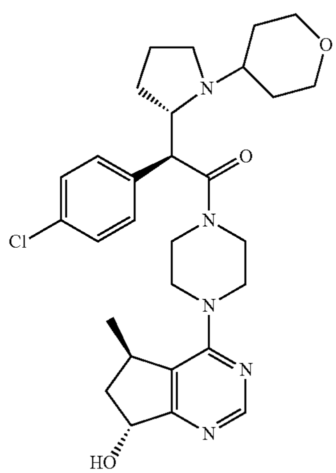 [SMILES: C[C@@H]1C[C@@H](O)c2ncnc(N3CCN(C(=O)[C@@H](c4ccc(Cl)cc4)[C@@H]4CCCN4C4CCOCC4)CC3)c21] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-(tetrahydro-2H-pyran-4-yl)pyrrolidin-2-yl)ethanone | m/z 540.1/542.1; $^1$H NMR (400 MHz, CD$_3$OD) d ppm 8.57 (s, 1H), 7.50-7.40 (m, 4H), 5.29 (t, 1H), 4.58-4.47 (m, 2H), 4.31-4.20 (m, 1H), 4.16-3.96 (m, 4H), 3.89-3.73 (m, 4H), 3.72-3.37 (m, 7H), 2.33-2.25 (m, 1H), 2.23-2.10 (m, 3H), 2.08-1.95 (m, 2H), 1.91-1.67 (m, 4H), 1.22-1.14 (m, 3H) |
| 17 | 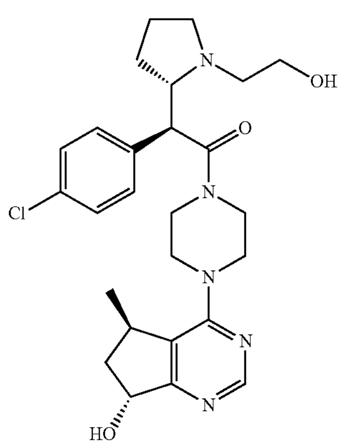 [SMILES: C[C@@H]1C[C@@H](O)c2ncnc(N3CCN(C(=O)[C@@H](c4ccc(Cl)cc4)[C@@H]4CCCN4CCO)CC3)c21] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-(2-hydroxyethyl)pyrrolidin-2-yl)ethanone | m/z 500.1/502.1; $^1$H NMR (400 MHz, CD$_3$OD) d ppm 8.57 (s, 1H), 74.49-7.40 (dd, 4H), 5.30 (t, 1H), 4.55 (d, J = 8.6 Hz, 1H), 4.34-4.18 (m, 2H), 4.09-4.01 (m, 1H), 3.89-3.63 (m, 8H), 3.61-3.44 (m, 4H), 3.26-3.19 (dt, 1H), 2.34-2.25 (m, 1H), 2.22-1.97 (m, 4H), 1.84-1.74 (m, 1H), 1.18 (d, 3H) |

TABLE 1-continued

| Ex. # | Structure | Name | LCMS NMR |
|---|---|---|---|
| 18 | 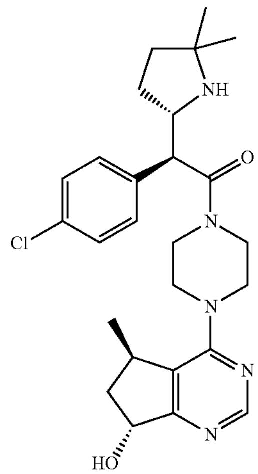 [SMILES: C[C@@H]1C[C@@H](O)c2ncnc(N3CCN(C(=O)[C@@H](c4ccc(Cl)cc4)[C@@H]4CCC(C)(C)N4)CC3)c21] | (S)-2-(4-chlorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone | m/z 484.2/486.2; $^1$H NMR (400 MHz, CD$_3$OD) d ppm 8.58 (s, 1H), 7.49-7.41 (m, 4H), 5.32 (t, 1H), 4.56 (d, 1H), 4.32 (q, 1H), 4.23-4.11 (m, 1H), 4.09-4.01 (m, 1H), 3.96-3.62 (m, 6H), 3.50-3.41 (m, 1H), 3.33-3.29 (m, 1H), 2.33-2.26 (m, 1H), 2.24-2.14 (m, 1H), 2.04-1.79 (m, 4H), 1.56 (s, 3H), 1.45 (s, 3H), 1.18 (d, 3H) |
| 19 | 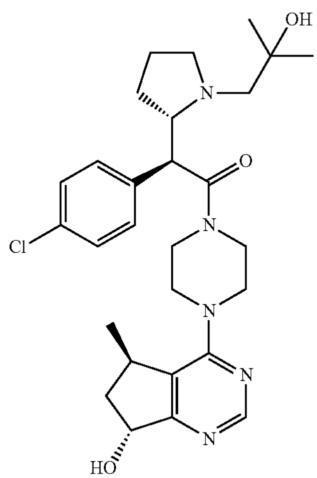 [SMILES: C[C@@H]1C[C@@H](O)c2ncnc(N3CCN(C(=O)[C@@H](c4ccc(Cl)cc4)[C@@H]4CCCN4CC(C)(C)O)CC3)c21] | (S)-2-(4-chlorophenyl)-2-((S)-1-(2-hydroxy-2-methylpropyl)pyrrolidin-2-yl)-1-(4-((5R,7R)-7-hydroxy-5-methyl-6,7-dihydro-5H-cyclopenta[d]pyrimidin-4-yl)piperazin-1-yl)ethanone | m/z 528.2/530.1; $^1$H NMR (400 MHz, CDCl$_3$) d ppm 8.51 (s, 1H), 7.31-7.27 (m, 4H), 5.09 (t, 1H), 3.88-3.29 (m, 12H), 3.19-3.08 (m, 1H), 2.90-2.82 (m, 1H), 2.64-2.53 (m, 1H), 2.43-2.37 (dd, 1H), 2.19-2.11 (m, 2H), 1.82-1.54 (m, 5H), 1.37-1.23 (m, 1H), 1.21-1.11 (m, 9H) |
| 20 | 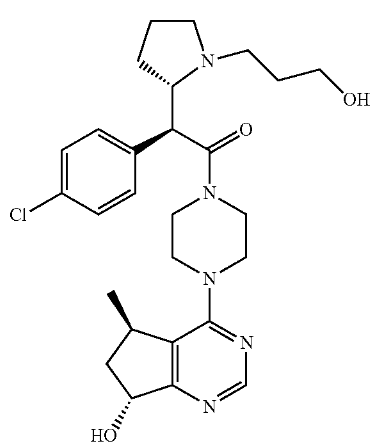 [SMILES: C[C@@H]1C[C@@H](O)c2ncnc(N3CCN(C(=O)[C@@H](c4ccc(Cl)cc4)[C@@H]4CCCN4CCCO)CC3)c21] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-(3-hydroxypropyl)pyrrolidin-2-yl)ethanone | m/z 514.1/516.1; $^1$H NMR (400 MHz, CDCl$_3$) d ppm 8.50 (s, 1H), 7.32-7.26 (m, 4H), 5.09 (t, 1H), 3.90-3.42 (m, 13H), 3.39-3.19 (m, 2H), 2.76-2.68 (m, 1H), 2.47-2.37 (m, 1H), 2.19-2.12 (m, 2H), 1.87-1.46 (m, 5H), 1.39-1.23 (m, 2H), 1.16 (d, 3H) |

TABLE 1-continued

| Ex. # | Structure | Name | LCMS NMR |
|---|---|---|---|
| 21 | 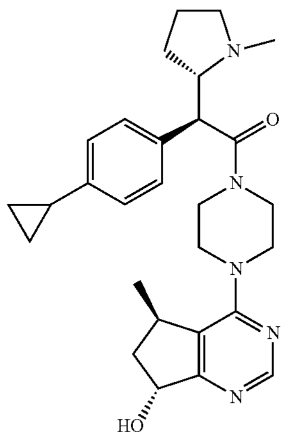 [SMILES: C[C@@H]1C[C@@H](O)c2ncnc(N3CCN(C(=O)[C@@H](c4ccc(C5CC5)cc4)[C@@H]4CCCN4C)CC3)c21] | (S)-2-(4-cyclopropylphenyl)-1-(4-((5R,7R)-7-hydroxy-5-methyl-6,7-dihydro-5H-cyclopenta[d]pyrimidin-4-yl)piperazin-1-yl)-2-((S)-1-methylpyrrolidin-2-yl)ethanone | m/z 476.2; $^1$H NMR (400 MHz, CD$_3$OD) d ppm 8.55 (s, 1H), 7.27 (d, 2H), 7.14 (d, 2H), 5.27 (t, J = 8.2 Hz, 1H), 4.43 (d, 1H), 4.28-4.18 (m, 1H), 4.16-4.08 (q, 1H), 4.03-3.95 (m, 1H), 3.88-3.61 (m, 6H), 3.53-3.40 (m, 2H), 3.24-3.16 (m, 1H), 2.89 (s, 3H), 2.31-2.22 (m, 1H), 2.21-1.76 (m, 6H), 1.16 (d, 3H), 1.02-0.96 (m, 2H), 0.70-0.64 (m, 2H) |
| 22 | 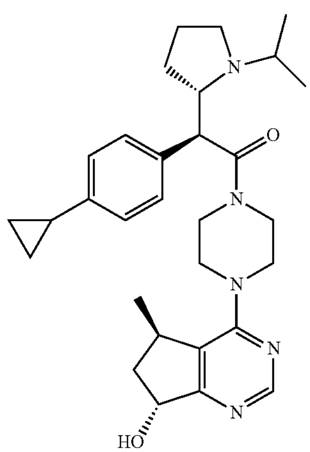 [SMILES: CC(C)N1CCC[C@H]1[C@@H](C(=O)N1CCN(c2ncnc3c2[C@H](C)C[C@H]3O)CC1)c1ccc(C2CC2)cc1] | (S)-2-(4-cyclopropylphenyl)-1-(4-((5R,7R)-7-hydroxy-5-methyl-6,7-dihydro-5H-cyclopenta[d]pyrimidin-4-yl)piperazin-1-yl)-2-((S)-1-isopropylpyrrolidin-2-yl)ethanone | m/z 504.2; $^1$H NMR (400 MHz, CD$_3$OD) d ppm 8.55 (s, 1H), 7.27 (d, 2H), 7.14 (d, 2H), 5.27 (t, 1H), 4.43 (d, 1H), 4.38-4.24 (m, 2H), 4.16-4.01 (m, 2H), 3.92-3.83 (m, 1H), 3.77-3.35 (m, 6H), 2.31-2.24 (m, 1H), 2.21-1.71 (m, 6H), 1.36 (d, 3H), 1.30 (d, 3H), 1.02-0.95 (m, 2H), 0.70-0.64 (m, 2H) |
| 23 | 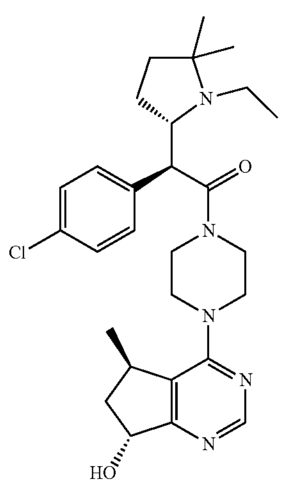 [SMILES: CCN1[C@H]([C@@H](C(=O)N2CCN(c3ncnc4c3[C@H](C)C[C@H]4O)CC2)c2ccc(Cl)cc2)CCC1(C)C] | (S)-2-(4-chlorophenyl)-2-((S)-1-ethyl-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone | m/z 512.1/514.1; $^1$H NMR (400 MHz, CD$_3$OD) d ppm 8.58 (s, 1H), 7.55-7.43 (m, 4H), 5.30 (t, 1H), 4.51-4.43 (m, 1H), 4.26-4.14 (m, 1H), 4.09-3.99 (m, 1H), 3.94-3.80 (m, 3H), 3.77-3.51 (m, 5H), 3.30-3.22 (m, 1H), 3.08-2.97 (m, 1H), 2.33-2.25 (m, 1H), 2.24-1.93 (m, 4H), 1.87-1.77 (m, 1H), 1.61 (s, 3H), 1.43 (s, 3H), 1.33-1.17 (m, 6H) |

TABLE 1-continued

| Ex. # | Structure | Name | LCMS NMR |
|---|---|---|---|
| 24 | 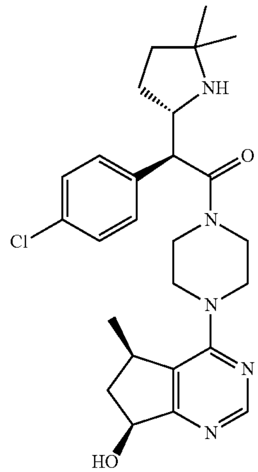 [SMILES: C[C@@H]1C[C@H](O)c2ncnc(N3CCN(C(=O)[C@@H](c4ccc(Cl)cc4)[C@@H]4CCC(C)(C)N4)CC3)c21] | (S)-2-(4-chlorophenyl)-2-((S)-5,5-dimethylpyrrolidin-2-yl)-1-(4-((5R,7S)-7-hydroxy-5-methyl-6,7-dihydro-5H-cyclopenta[d]pyrimidin-4-yl)piperazin-1-yl)ethanone | m/z 484.2; $^1$H NMR (400 MHz, CD$_3$OD) d ppm 8.59 (s, 1H), 7..51-7.40 (m, 4H), 5.13 (m, 1H), 4.45 (d, 1H) 4.33-4.15 (m, 2H), 3.93-3.65 (m, 5H), 3.59-3.43 (m, 1H), 3.26-3.19 (q, 1H), 2.85-2.74 (m, 1H), 2.03-1.80 (m, 4H), 1.66-1.57 (m, 1H), 1.54 (s, 3H), 1.44 (s, 3H), 1.40-1.33 (m, 6H), 1.23 (d, 3H) |
| 25 | 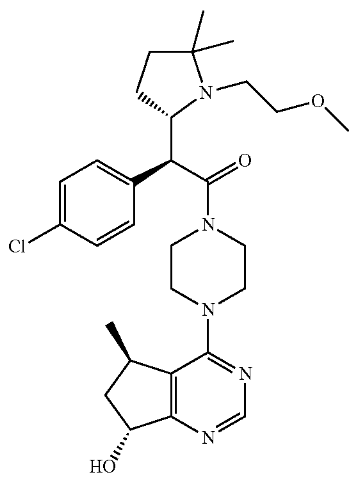 [SMILES: COCCN1[C@H]([C@@H](C(=O)N2CCN(c3ncnc4c3[C@H](C)C[C@H]4O)CC2)c2ccc(Cl)cc2)CCC1(C)C] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-(2-methoxyethyl)-5,5-dimethylpyrrolidin-2-yl)ethanone | m/z 542.1/544.1; $^1$H NMR (400 MHz, CD$_3$OD) d ppm 8.58 (s, 1H), 7.51-7.40 (m, 4H), 5.29 (t, 1H), 4.83-4.75 (m, 1H), 4.44-4.38 (m, 1H), 4.28-4.18 (m, 1H), 4.05-3.63 (m, 614), 3.61-3.46 (m, 2H), 3.38 (s, 3H), 2.94-2.84 (m, 1H), 2.41-2.25 (m, 2H), 2.23-2.07 (m, 2H), 2.04-1.95 (m, 1H), 1.92-1.81 (m, 1H), 1.59 (s, 3H), 1.42 (s, 3H), 1.19 (d, 3H) |
| 26 | 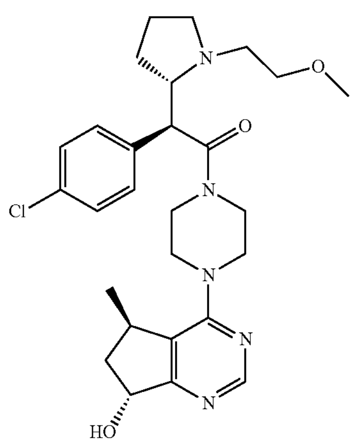 [SMILES: COCCN1CCC[C@H]1[C@@H](C(=O)N1CCN(c2ncnc3c2[C@H](C)C[C@H]3O)CC1)c1ccc(Cl)cc1] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-(2-methoxyethyl)pyrrolidin-2-yl)ethanone | m/z 514.2/516.1; $^1$HNMR (400 MHz, CD$_3$OD) d ppm 8.57 (s, 1H), 7.49-7.39 (dd, 4H), 5.30 (t, 1H), 4.52 (s, 1H), 4.35-4.20 (m, 2H), 4.10-4.02 (m, 1H), 3.89-3.64 (m, 9H), 3.55-3.44 (m, 2H), 3.41 (s, 3H), 2.33-2.26 (m, 1H), 2.23-1.91 (m, 4H), 1.82-1.72 (m, 1H), 1.18 (d, 3H) |

TABLE 1-continued

| Ex. # | Structure | Name | LCMS NMR |
|---|---|---|---|
| 27 | 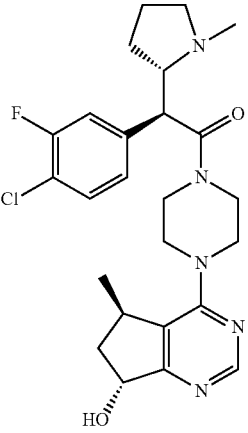 [SMILES: C[C@@H]1C[C@@H](O)c2ncnc(N3CCN(C(=O)[C@@H](c4ccc(Cl)c(F)c4)[C@@H]4CCCN4C)CC3)c21] | (S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-2-((S)-1-methylpyrrolidin-2-yl)ethanone | m/z 488.3/490.2; $^1$HNMR (400 MHz, D$_2$O) d ppm 8.37 (s, 1H), 7.44 (dd, J = 8.0, 8.0 Hz, 1H), 7.18 (d, J = 8.0 Hz, 1H), 7.07 (d, J = 8.0 Hz, 1H), 5.25 (t, J = 8.0 Hz, 1H), 4.38-4.32 (m, 2H), 3.80-3.23 (m, 14H), 2.69 (s, 3H), 2.21-2.16 (m, 1H), 1.96-1.82 (m, 4H), 1.01-0.96 (m, 2H) |
| 28 | 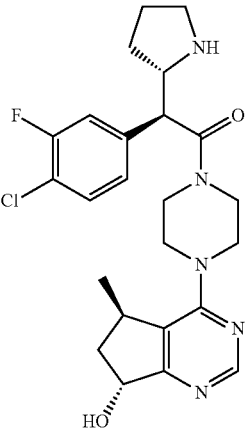 [SMILES: C[C@@H]1C[C@@H](O)c2ncnc(N3CCN(C(=O)[C@@H](c4ccc(Cl)c(F)c4)[C@@H]4CCCN4)CC3)c21] | (S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone | m/z 474.1/476.2; $^1$HNMR (400 MHz, D$_2$O) d ppm 8.42 (s, 1H), 7.57 (dd, J = 8.0, 8.0 Hz, 1H), 7.26-7.22 (m, 2H), 5.06 (t, J = 8.0 Hz, 1H), 4.10-4.02 (m, 2H), 3.81-3.19 (m, 12H), 2.66-2.63 (m, 1H), 1.94-1.88 (m, 1H), 1.82-1.49 (m, 4H), 1.05-1.01 (m, 2H) |
| 29 | 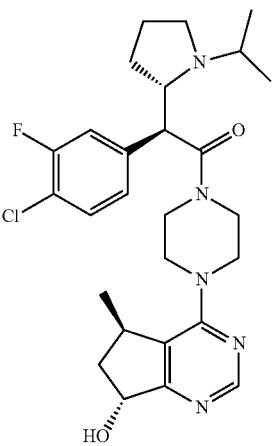 [SMILES: CC(C)N1CCC[C@H]1[C@@H](C(=O)N1CCN(c2ncnc3c2[C@H](C)C[C@H]3O)CC1)c1ccc(Cl)c(F)c1] | (S)-2-(4-chloro-3-fluorophenyl)-1-(4-((5R 7R)-7-hydroxy-5-methyl-6,7-dihydro-5H-cyclopenta[d]pyrimidin-4-yl)piperazin-1-yl)-2-((S)-1-isopropylpyrrolidin-2-yl)ethanone | m/z 516.2/518.2; $^1$HNMR (400 MHz, D$_2$O) d ppm 8.37 (s, 1H), 7.44 (dd, J = 8.0, 8.0 Hz, 1H), 7.17 (d, J = 8.0 Hz, 1H), 7.08 (d, J = 8.0 Hz, 1H), 5.25 (t, J = 8.0 Hz, 1H), 4.28-4.22 (m, 2H), 3.80-3.23 (m, 14H), 2.21-2.16 (m, 1H), 2.04-1.79 (m, 4H), 1.78-1.62 (m, 1H), 1.17 (d, J = 6.4 Hz, 3H), 1.13 (d, J = 6.4 Hz, 3H), 1.01-0.96 (m, 2H) |

TABLE 1-continued

| Ex. # | Structure | Name | LCMS NMR |
|---|---|---|---|
| 30 | 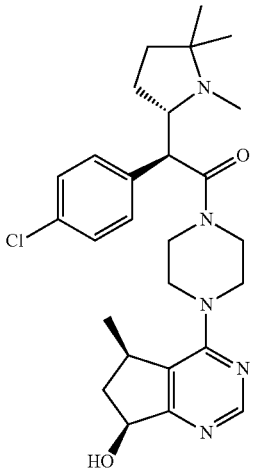 [SMILES: C[C@@H]1C[C@H](O)c2ncnc(N3CCN(C(=O)[C@@H](c4ccc(Cl)cc4)[C@@H]4CCC(C)(C)N4C)CC3)c21] | (S)-2-(4-chlorophenyl)-1-(4-((5R,7S)-7-hydroxy-5-methyl-6,7-dihydro-5H-cyclopenta[d]pyrimidin-4-yl)piperazin-1-yl)-2-((S)-1,5,5-trimethylpyrrolidin-2-yl)ethanone | m/z 498.2/500.2; $^1$HNMR (400 MHz, CD$_3$OD) d ppm 8.60 (s, 1H), 7.50-7.41 (m, 4H), 5.17-5.09 (m, 1H), 4.82-4.76 (m, 1H), 4.41-4.31 (m, 1H), 4.26-4.14 (m, 1H), 4.96-4.69 (m, 7H), 3.58-3.45 (m, 2H), 2.84-2.74 (m, 1H), 2.56 (s, 3H), 2.17-1.95 (m, 3H), 1.86-1.74 (m, 1H), 1.67-1.58 (m, 1H), 1.55 (s, 3H), 1.34 (s, 3H), 1.25 (d, 3H) |
| 31 | 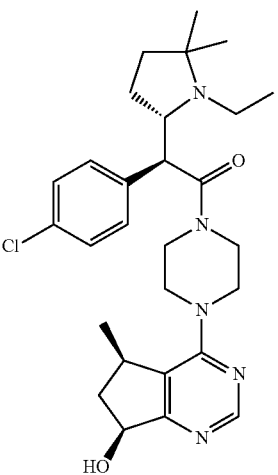 [SMILES: CCN1[C@H]([C@@H](C(=O)N2CCN(c3ncnc4c3[C@H](C)C[C@@H]4O)CC2)c2ccc(Cl)cc2)CCC1(C)C] | (S)-2-(4-chlorophenyl)-2-((S)-1-ethyl-5,5-dimethylpyrrolidin-2-yl)-1-(4-((5R,7S)-7-hydroxy-5-methyl-6,7-dihydro-5H-cyclopenta[d]pyrimidin-4-yl)piperazin-1-yl)ethanone | m/z 512.2/514.2; $^1$H NMR (400 MHz, CD$_3$OD) d ppm 8.60 (s, 1H), 7.51-7.43 (m, 4H), 5.15-5.10 (m, 1H), 4.52-4.44 (m, 1H), 4.26-4.17 (m, 1H), 3.94-3.61 (m, 6H), 3.60-3.46 (m, 2H), 3.29-3.22 (m, 1H), 3.11-3.00 (m, 1H), 3.84-3.74 (m, 1H), 2.16-1.77 (m, 4H), 1.65-1.57 (m, 1H), 1.61 (s, 3H), 1.42 (s, 3H), 1.29-1.23 (m, 6H) |
| 32 | 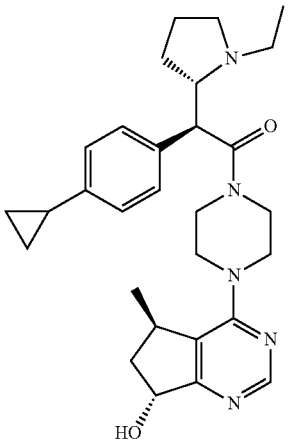 [SMILES: CCN1CCC[C@H]1[C@@H](C(=O)N1CCN(c2ncnc3c2[C@H](C)C[C@H]3O)CC1)c1ccc(C2CC2)cc1] | 2-(4-cyclopropylphenyl)-2-((S)-1-ethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone | m/z 490.2; $^1$HNMR (400 MHz, CD$_3$OD) d ppm 8.56 (s, 1H), 7.26 (d, 2H), 7.13 (d, 2H), 5.29 (t, 1H), 4.38 (d, 1H), 4.34-4.17 (m, 2H), 4.09-4.01 (m, 1H), 3.91-3.81 (m, 1H), 3.79-3.45 (m, 9H), 3.36-3.29 (m, 1H), 3.21-3.10 (m, 1H), 2.33-2.24 (m, 1H), 2.22-2.00 (m, 3H), 1.96-1.85 (m, 2H), 1.82-1.72 (m, 1H), 1.37-1.27 (m, 51-1), 1.16 (d, 3H), 1.03-0.95 (m, 2H), 0.72-0.63 (m, 2H) |

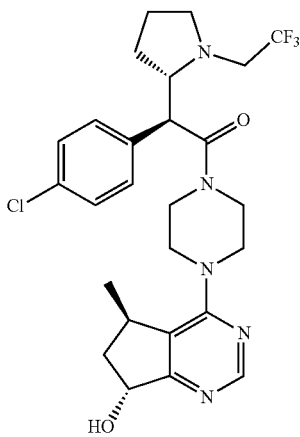 [SMILES: C[C@@H]1C[C@@H](O)c2ncnc(N3CCN(C(=O)[C@@H](c4ccc(Cl)cc4)[C@@H]4CCCN4CC(F)(F)F)CC3)c21]

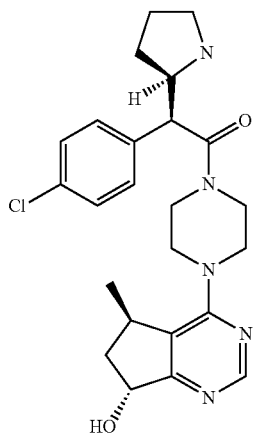 [SMILES: C[C@@H]1C[C@@H](O)c2ncnc(N3CCN(C(=O)[C@@H](c4ccc(Cl)cc4)[C@H]4CCCN4)CC3)c21]

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-(2,2,2-trifluoroethyl)pyrrolidin-2-yl)ethanone (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone (28 mg, 0.53 mmol; see Example 3) was slurried in acetone (0.4 mL) and treated with diisopropylethylamine (0.032 mL, 0.18 mmol), 4-dimethylaminopyridine ("DMAP"; 0.0006 g, 0.005 mmol) and 3,3,3-trifluoropropyl trifluoromethanesulfonate (0.016 g, 0.066 mmol). The reaction mixture was heated to reflux for 9 hours. Additional 3,3,3-trifluoropropyl trifluoromethanesulfonate (0.016 g, 0.066 mmol) was added and the mixture was heated at reflux for 16 hours. The reaction was concentrated using $N_2$ (g) and chromatographed on $SiO_2$ eluting with 2% MeOH/methylene chloride. After chromatography, the product was dissolved in ethyl acetate and washed 3 times with saturated $NH_4Cl$, once with saturated $NaHCO_3$, once with saturated NaCl, dried over $Na_2SO_4$ and concentrated in vacuo. The residue was concentrated from dioxane, treated with 4M HCl in dioxane (2 mL) and concentrated in vacuo. The salt was redissolved in MeOH and re-concentrated three times. The salt was dissolved in a minimal amount of MeOH and added dropwise to $Et_2O$. The salt was filtered and washed with $Et_2O$ then dried under vacuum (12.8 mg, 39%). MS (ESI+) [M+H] 538.2/540.1. $^1H$ NMR ($CD_3OD$, 400 MHz) δ ☐8.58 (s, 1H), 7.47-7.36 (m, 4H), 5.31 (t, 1H), 4.48-3.96 (m, 3H), 3.91-3.44 (m, 7H), 2.35-2.27 (m, 1H), 2.23-2.13 (m, 1H), 2.05-1.88 (m, 2H), 1.84-1.71 (m, 1H), 1.68-1.56 (m, 1H), 1.19 (d, 3H).

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((R)-pyrrolidin-2-yl)ethanone Step 1:
KOH (8.3 g, 147.9 mmol) in water (60 mL) was added to a solution of a mixture of (2R)-ethyl 2-methyl-5-oxocyclopentanecarboxylate (20 g, 117.5 mmol) and thiourea (9.2 g, 120.9 mmol) in ethanol (100 mL). The mixture was refluxed for 10 hours. After cooling, the solvent was removed. The resulting residue was neutralized with concentrated HCl (12 mL) at 0° C. and then extracted with DCM (3×150 mL). The solvent was removed, and the resulting residue was purified by silica gel chromatography, eluting with hexane/ethyl acetate (2:1) to give (R)-2-mercapto-5-methyl-6,7-dihydro-5H-cyclopenta[d]pyrimidin-4-ol (12 g, 56%). MS (APCI+) [M+H]$^+$ 183.

Step 2:
Raney Nickel (15 g) and $NH_4OH$ (20 mL) was added to a suspension of (R)-2-mercapto-5-methyl-6,7-dihydro-5H-cyclopenta[d]pyrimidin-4-ol (12 g, 65.8 mmol) in distilled water (100 mL). The mixture was refluxed for 3 hours and then filtered. The filtrate was concentrated to afford (R)-5-methyl-6,7-dihydro-5H-cyclopenta[d]pyrimidin-4-ol (9.89 g, 99%). MS (APCI+) [M+H]$^+$151.

Step 3:
(R)-5-Methyl-6,7-dihydro-5H-cyclopenta[d]pyrimidin-4-ol was converted to (5R)-tert-butyl 4-(7-hydroxy-5-methyl-6,7-dihydro-5H-cyclopenta[d]pyrimidin-4-yl)piperazine-1-carboxylate according to the procedures from Example 3; Steps 4-7.

Step 4:
(R)-tert-Butyl 4-(7-hydroxy-5-methyl-6,7-dihydro-5H-cyclopenta[d]pyrimidin-4-yl)piperazine-1-carboxylate (2.50 g, 7.48 mmol) was dissolved in methylene chloride (30 mL), cooled to 0° C. and treated with 4-bromobenzyl chloride (1.81 g, 8.22 mmol) and triethylamine (3.13 mL, 22.4 mmol). The ice bath was removed immediately, and the reaction was stirred at ambient temperature for 3 hours. The reaction was poured into saturated $NaHCO_3$ and separated. The aqueous layer was washed with methylene chloride (2×). The combined organic layers were then washed with saturated $NaHCO_3$ (2×), 6% $NaHCO_3$ (1×), dried over $Na_2SO_4$ and concentrated in vacuo. The residue was columned (Biotage 40M) eluting with 2:1 hexanes:ethyl acetate to give (R)-tert-butyl 4-(7-(4-bromobenzoyloxy)-5-methyl-6,7-dihydro-5H-cyclopenta[d]pyrimidin-4-yl)piperazine-1-carboxylate (1.29 g, 33%).

Step 5:

(R)-tert-Butyl 4-(7-(4-bromobenzoyloxy)-5-methyl-6,7-dihydro-5H-cyclopenta[d]pyrimidin-4-yl)piperazine-1-carboxylate (0.832 g, 1.608 mmol) was subjected to chromatography on SiO$_2$ eluting with 2:1 hexanes:ethyl acetate to give tert-butyl 4-((5R,7R)-7-(4-bromobenzoyloxy)-5-methyl-6,7-dihydro-5H-cyclopenta[d]pyrimidin-4-yl)piperazine-1-carboxylate (0.31 g, 37%); then switching to 1:1 hexane:ethyl acetate to give tert-butyl 4-((5R,7S)-7-(4-bromobenzoyloxy)-5-methyl-6,7-dihydro-5H-cyclopenta[d]pyrimidin-4-yl)piperazine-1-carboxylate (415.3 mg, 49%).

Step 6:

Lithium hydroxide hydrate (0.779 mL, 28.0 mmol) was added to a solution of tert-butyl 4-((5R,7R)-7-(4-bromobenzoyloxy)-5-methyl-6,7-dihydro-5H-cyclopenta[d]pyrimidin-4-yl)piperazine-1-carboxylate (5.8 g, 11.2 mmol) in THF:H$_2$O (150 mL, 2:1) at 0° C. The mixture was allowed to warm to room temperature and stirred at for 1 hour. The mixture was concentrated in vacuo, taken up into saturated sodium bicarbonate (100 mL) and extracted into EtOAc (2×200 mL). The reaction was dried over Na$_2$SO$_4$ and concentrated in vacuo to give tert-butyl 4-((5R,7R)-7-hydroxy-5-methyl-6,7-dihydro-5H-cyclopenta[d]pyrimidin-4-yl)piperazine-1-carboxylate (3.8 g, 11.4 mmol, 100% yield) as a foam. Similarly, tert-butyl 4-05R,7S)-7-(4-bromobenzoyloxy)-5-methyl-6,7-dihydro-5H-cyclopenta[d]pyrimidin-4-yl)piperazine-1-carboxylate (1.29 g, 2.49 mmol) was dissolved in THF:H$_2$O (10 mL, 2:1), cooled to 0° C. and then treated with solid lithium hydroxide hydrate. The solution was stirred at ambient temperature for 16 hours. The reaction was quenched with saturated NH$_4$Cl and concentrated in vacuo. The resulting residue was diluted with ethyl acetate and a small amount of water. The layers were separated, and the aqueous layer was washed with ethyl acetate. The combined organic layers were washed with saturated NaHCO$_3$ (2×), saturated NaCl, dried over Na$_2$SO$_4$ and concentrated in vacuo. The resulting residue was dried under high vacuum to give tert-butyl 4-((5R,7S)-7-hydroxy-5-methyl-6,7-dihydro-5H-cyclopenta[d]pyrimidin-4-yl)piperazine-1-carboxylate as a foam (0.843 g, 100%).

Step 7:

4M HCl/dioxane (11.2 mL, 44.9 mmol) was added to a solution of tert-butyl 4-((5R,7R)-7-hydroxy-5-methyl-6,7-dihydro-5H-cyclopenta[d]pyrimidin-4-yl)piperazine-1-carboxylate (0.600 g, 1.79 mmol) in dioxane (15 mL). The reaction mixture was stirred at room temperature under nitrogen overnight (20 hours). The mixture was concentrated to dryness and dried on high vacuum line. The crude product was suspended in ether, sonicated, and stirred for 5 minutes. The solids were isolated by filtration through a medium fit funnel under nitrogen pressure, rinsed with ether, dried under nitrogen pressure, and dried further on a high vacuum line to give (5R,7R)-5-methyl-4-(piperazin-1-yl)-6,7-dihydro-5H-cyclopenta[d]pyrimidin-7-ol dihydrochloride (0.440 g, 79.8% yield) as a powder. LC/MS (APCI+) m/z 235. The (5R,7S)-5-methyl-4-(piperazin-1-yl)-6,7-dihydro-5H-cyclopenta[d]pyrimidin-7-ol dihydrochloride was prepared using an analogous method.

Step 8:

Sodium azide (7.8 g, 120 mmol) was charged in a 1 L round bottom flask with water. 4-Acetamidobenzene-1-sulfonyl chloride (23.4 g, 100 mmol) was dissolved in acetone, and this solution was slowly added to the solution of sodium azide. The reaction was then stirred for 16 hours at room temperature and diluted with water. The acetone was then removed. The solid was filtered to give 4-acetamidobenzenesulfonyl azide (21 g, 87%) as a white solid.

Step 9:

A solution of 4-acetamidobenzenesulfonyl azide (1.43 g, 5.96 mmol) and methyl 2-(4-chlorophenyl)acetate (1 g, 5.42 mmol) in acetonitrile (27 mL) was cooled to 0° C. DBU (0.907 g, 0.891 mL, 5.96 mmol) was then added dropwise to the reaction mixture. The mixture was allowed to stir over night, after which it was passed through a plug of silica and purified by column chromatography (EtOAc) to give methyl 2-(4-chlorophenyl)-2-diazoacetate (0.95 g, 83%) as a solid.

Step 10:

Methyl 2-(4-chlorophenyl)-2-diazoacetate (200 mg, 0.95 mmol, 1 eq.) in hexanes (4.7 mL, 0.2M) was added slowly to a stirred solution of tert-butyl pyrrolidine-1-carboxylate (325 mg, 1.9 mmol, 2eq.) and Rh$_2$(S-DOSP)$_4$ (6.25 mg, 0.01 mmol, 0.01 eq) in hexanes (4.7 mL). The solution was cooled to −40° C. The reaction was stirred for 1.5 hours. The reaction was warmed to room temperature, concentrated in vacuo, and passed through a plug of SiO$_2$ eluting with EtOAc. This was concentrated to a foam and use without purification to give material containing (R)-tert-butyl 2-((S)-1-(4-chlorophenyl)-2-methoxy-2-oxoethyl)pyrrolidine-1-carboxylate (336 mg, 100%). MS (ESI+) [M+H] 353.8.

Step 11:

(R)-tert-butyl 2-((S)-1-(4-chlorophenyl)-2-methoxy-2-oxoethyl)pyrrolidine-1-carboxylate (336 mg) was dissolved in THF/H$_2$O (3:1, 4.7 mL), and LiOH (42 mg, 1.05 eq.) was added. The mixture was stirred at room temperature for 3 hours. The reaction was quenched with 10% KHSO$_4$ and EtOAc. The aqueous layer was washed with EtOAc (2×). The combined organic layers were dried over MgSO$_4$, filtered and concentrated to give material containing (S)-2-((R)-1-(tert-butoxycarbonyl)pyrrolidin-2-yl)-2-(4-chlorophenyl)acetic acid (144 mg, 45%). MS (ESI+) [M+H] 337.9.

Step 12:

Using procedures similar to those described in Example 1, Step 5, (S)-2-((R)-1-(tert-butoxycarbonyl)pyrrolidin-2-yl)-2-(4-chlorophenyl)acetic acid (144 mg, 0.424 mmol) was converted to (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((R)-pyrrolidin-2-yl)ethanone (25 mg, 10%). LCMS (apci+) 456.0/458.0 [M+H]+; 1.93 minutes. Some (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone (66 mg, 28%) was also isolated.

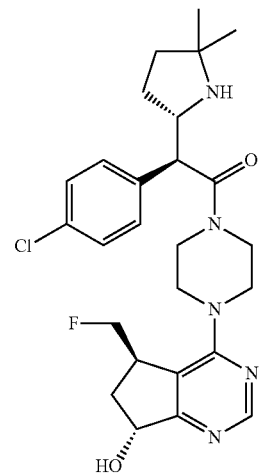 [SMILES: CC1(C)CC[C@@H]([C@@H](C(=O)N2CCN(c3ncnc4c3[C@H](CF)C[C@H]4O)CC2)c2ccc(Cl)cc2)N1]

(S)-2-(4-chlorophenyl)-2-((S)-5,5-dimethylpyrrolidin-2-yl)-1-(4-((5R,7R)-5-(fluoromethyl)-7-hydroxy-6,7-dihydro-5H-cyclopenta[d]pyrimidin-4-yl)piperazin-1-yl)ethanone Step 1:

Ethyl 2-oxo-5-vinylcyclopentanecarboxylate (Nugent, W. A.; Hobbs, Jr, F. W., J. Org. Chem, 1986, 51, 3376-3378) was converted into tert-butyl 4-(5-vinyl-6,7-dihydro-5H-cyclopenta[d]pyrimidin-4-yl)piperazine-1-carboxylate using procedures described in Example 3, Steps 2-4.

Step 2:

A solution of tert-butyl 4-(5-vinyl-6,7-dihydro-5H-cyclopenta[d]pyrimidin-4-yl)piperazine-1-carboxylate (566 mg) in DCM (20 mL) was cooled to −78° C. A stream of ozone was bubbled for 15 minutes. Oxygen was bubbled, followed by nitrogen at −78° C. Ethyl methyl sulfide (2 mL) was added. The mixture was allowed to warm up to room temperature over 1 hour. The contents were concentrated. The resulting residue was partitioned between DCM and half saturated NaCl solution. The organic layer was separated. The aqueous layer was extracted with DCM (2×). The combined organic solutions were dried ($Na_2SO_4$). The crude was dissolved in MeOH (10 mL) and cooled to 0° C. $NaBH_4$ (150 mg) was added in portions. The mixture was stirred at 0° C. for 2 hours. The reaction was quenched with 10% HOAc (5 mL). The mixture was concentrated and portioned between water and EtOAc. The organic layer was separated. The aqueous layer was extracted with EtOAc (2×). The combined organic solutions were dried ($Na_2SO_4$). The crude material was purified with flash chromatography to give tert-butyl 4-(5-(hydroxymethyl)-6,7-dihydro-5H-cyclopenta[d]pyrimidin-4-yl)piperazine-1-carboxylate (73 mg, 13%). MS: 335.2 (M+1). This material could be resolved using chiral column chromatography.

Step 3:

(R)-tert-Butyl 4-(5-(hydroxymethyl)-6,7-dihydro-5H-cyclopenta[d]pyrimidin-4-yl)piperazine-1-carboxylate (30.0 mg, 0.0897 mmol) was dissolved in tetrahydrofuran (0.080 mL). Perfluoro-1-butanesulfonylfluoride (0.0644 mL, 0.359 mmol) and triethylamine trishydrofluoride (0.0584 mL, 0.359 mmol) were added to this solution, followed by triethylamine (0.150 mL, 0.726 mmol). The reaction mixture was allowed to stir for 12 hours at room temperature. The reaction was concentrated, and the material was subjected to chromatography on $SiO_2$ and eluted with 10% MeOH/DCM. The desired 4-((R)-5-fluoromethyl-6,7-dihydro-5H-cyclopentapyrimidin-4-yl)-piperazine-1-carboxylic acid tert-butyl ester (25.0 mg, 83%) was isolated. LC/MS (APCI)+ m/z 337.2.

Step 4:

Using procedures similar to those described in Example 3, Steps 12-14, 4-((R)-5-fluoromethyl-6,7-dihydro-5H-cyclopentapyrimidin-4-yl)-piperazine-1-carboxylic acid tert-butyl ester was converted to (S)-2-(4-chlorophenyl)-2-((S)-5,5-dimethylpyrrolidin-2-yl)-1-(4-((5R,7R)-5-(fluoromethyl)-7-hydroxy-6,7-dihydro-5H-cyclopenta[d]pyrimidin-4-yl)piperazin-1-yl)ethanone. m/z 502.2; $^1$H NMR (500 MHz, $CD_3OD$) δ ppm 8.60 (s, 1H), 7.44 (q, J=8.73 Hz, 4H), 5.29-5.20 (m, 1H), 4.61-4.52 (m, 1H), 4.50-4.36 (m, 1H), 4.34-4.13 (m, 2H), 4.13-3.95 (m, 2H), 3.90-3.83 (m, 1H), 3.80-3.73 (m, 1H), 3.70-3.62 (m, 1H), 3.60-3.54 (m, 2H), 3.52-3.41 (m, 2H), 2.54-2.43 (m, 1H), 2.27-2.13 (m, 1H), 2.05-1.85 (m, 4H), 1.54 (s, 3H), 1.44 (s, 3H)

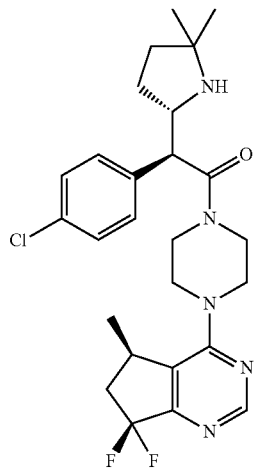

(S)-2-(4-chlorophenyl)-1-(4-((R)-7,7-difluoro-5-methyl-6,7-dihydro-5H-cyclopenta[d]pyrimidin-4-yl)piperazin-1-yl)-2-((S)-5,5-dimethylpyrrolidin-2-yl)ethanone Step 1:

(R)-tert-Butyl 4-(5-methyl-7-oxo-6,7-dihydro-5H-cyclopenta[d]pyrimidin-4-yl)piperazine-1-carboxylate (1.0 g, 3.0 mmol, see Example 3) was dissolved in DCM (15 mL) in a plastic bottle, and then DAST was added neat over approximately 5 minutes. The reaction was quenched after 42 hours at room temperature by pouring into saturated aqueous sodium bicarbonate solution mixed with ice. The organic layer was diluted with EtOAc, washed 3 times with water, once with brine and then dried over sodium sulfate. After filtration, the residue was concentrated and purified via column chromatography (70:30 hexane/ethyl acetate, then 1:1 hexane/ethyl acetate) to give (R)-tert-butyl 4-(7,7-difluoro-5-methyl-6,7-dihydro-5H-cyclopenta[d]pyrimidin-4-yl)piperazine-1-carboxylate (300 mg, 28%).

Step 2:

4M HCl/dioxane (2.27 mL, 9.09 mmol) was added to a solution of (R)-tert-butyl 4-(7,7-difluoro-5-methyl-6,7-dihydro-5H-cyclopenta[d]pyrimidin-4-yl)piperazine-1-carboxylate (0.092 g, 0.260 mmol) in dioxane (2 mL.) The reaction mixture was stirred at room temperature overnight, after which it was concentrated to dryness and dried on under high vacuum to give (R)-7,7-difluoro-5-methyl-4-(piperazin-1-yl)-6,7-dihydro-5H-cyclopenta[d]pyrimidine dihydrochloride (0.079 g, 93.0% yield) as a solid.

Step 3:

Using procedures described in Example 3, Steps 13 and 14, (R)-7,7-difluoro-5-methyl-4-(piperazin-1-yl)-6,7-dihydro-5H-cyclopenta[d]pyrimidine dihydrochloride was converted to (S)-2-(4-chlorophenyl)-1-(4-((R)-7,7-difluoro-5-methyl-6,7-dihydro-5H-cyclopenta[d]pyrimidin-4-yl)piperazin-1-yl)-2-((S)-5,5-dimethylpyrrolidin-2-yl)ethanone. LCMS (apci+) 578.6 [M+H]+; 2.22 min; $^1$H NMR (400 MHz, $D_2O$) δ ppm (8.38 (s, 1H), 7.31 (d, J=8.6 Hz, 2H), 7.22 (d, J=8.2 Hz, 2H), 4.26-4.20 (m, 1H), 4.18-3.98 (m, 2H), 3.89-3.80 (m, 1H), 3.71-3.63 (m, 1H), 3.57-3.43 (m, 4H), 3.18-3.10 (m, 1H), 2.81-2.62 (m, 1H), 2.26-2.12 (m, 1H), 1.87-1.69 (m, 4H), 1.35 (s, 3H), 1.30 (s, 3H), 1.02 (d, J=6.6, 3H).

Examples 37-96 shown in Table 2 can also be made according to the above described methods.

TABLE 2

| Ex. # | Structure | Name | LCMS NMR |
|---|---|---|---|
| 37 | 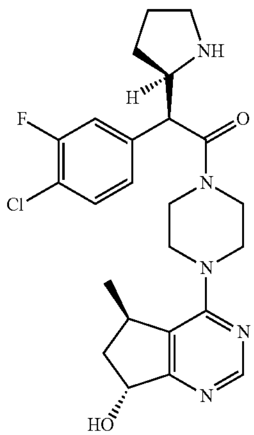 [SMILES: C[C@@H]1C[C@@H](O)c2ncnc(N3CCN(C(=O)[C@@H](c4ccc(Cl)c(F)c4)[C@H]4CCCN4)CC3)c21] | (S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-2-((R)-pyrrolidin-2-yl)ethanone | MS (ESI+) [M + H] 474.1/ 476.0 |
| 38 | 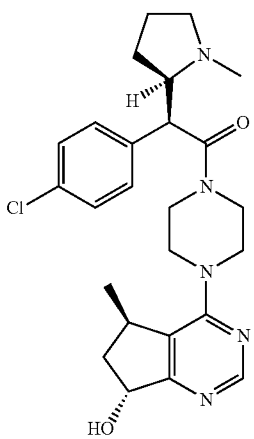 [SMILES: C[C@@H]1C[C@@H](O)c2ncnc(N3CCN(C(=O)[C@@H](c4ccc(Cl)cc4)[C@H]4CCCN4C)CC3)c21] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((R)-1-methylpyrrolidin-2-yl)ethanone | MS (ESI+) [M + H] 470.1/ 472.1 |
| 39 | 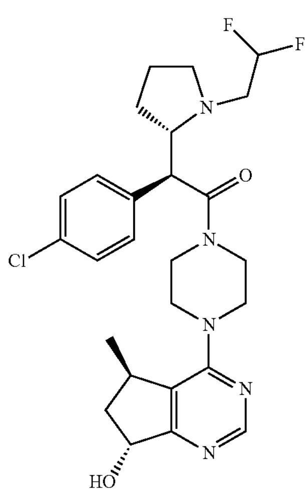 [SMILES: C[C@@H]1C[C@@H](O)c2ncnc(N3CCN(C(=O)[C@@H](c4ccc(Cl)cc4)[C@@H]4CCCN4CC(F)F)CC3)c21] | (S)-2-(4-chlorophenyl)-2-((S)-1-(2,2-difluoroethyl)pyrrolidin-2-yl)-1-(4-((5R,7R)-7-hydroxy-5-methyl-6,7-dihydro-5H-cyclopenta[d]pyrimidin-4-yl)piperazin-1-yl)ethanone | m/z 520.2/522.1; $^1$HNMR (400 MHz, CD$_3$OD) d ppm 8.57 (s, 1H), 7.50-7.39 (m, 4H), 5.30 (t, 1H), 4.59-4.50 (m, 1H), 4.45-4.34 (m, 1H), 4.31-4.16 (m, 1H), 4.14-4.05 (m, 1H), 3.88-3.62 (m, 6H), 3.59-3.39 (m, 2H), 2.34-2.26 (m, 1H), 2.23-2.05 (m, 3H), 1.96-1.84 (m, 1H), 1.84-1.72 (m, 1H), 1.18 (d, 3H) |

TABLE 2-continued

| Ex. # | Structure | Name | LCMS NMR |
|---|---|---|---|
| 40 | 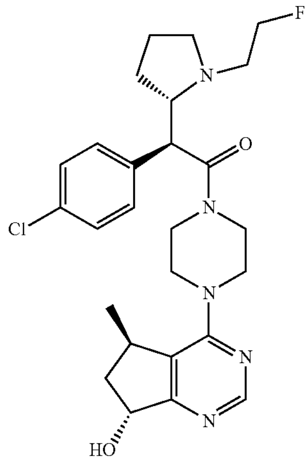 [SMILES: C[C@@H]1C[C@@H](O)c2ncnc(N3CCN(C(=O)[C@@H](c4ccc(Cl)cc4)[C@@H]4CCCN4CCF)CC3)c21] | (S)-2-(4-chlorophenyl)-2-((S)-1-(2-fluoroethyl)pyrrolidin-2-yl)-1-(4-((5R,7R)-7-hydroxy-5-methyl-6,7-dihydro-5H-cyclopenta[d]pyrimidin-4-yl)piperazin-1-yl)ethanone | m/z 502.2/504.1; $^1$H NMR (400 MHz, CD$_3$OD) d ppm 8.56 (s, 1H), 7.46 (d, 2H), 7.42 (d, 2H), 5.29 (t, 1H), 4.52 (d, 1H), 4.42-4.32 (m, 1H), 4.30-4.18 (m, 1H), 4.14-3.98 (m, 2H), 3.85-3.71 (m, 5H), 3.72-3.41 (m, 5H), 2.33-2.25 (m, 1H), 2.23-2.04 (m, 3H), 1.99-1.88 (m, 1H), 1.84-1.72 (m, 1H), 1.17 (d, 3H) |
| 41 | 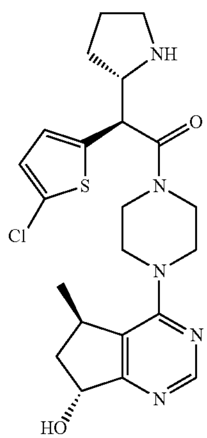 [SMILES: C[C@@H]1C[C@@H](O)c2ncnc(N3CCN(C(=O)[C@@H](c4ccc(Cl)s4)[C@@H]4CCCN4)CC3)c21] | (S)-2-(5-chlorothiophen-2-yl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone | m/z 462.2; $^1$HNMR (400 MHz, D$_2$O) d ppm 8.54 (s, 1H), 7.00 (d, J = 4.0 Hz, 1H), 6.97 (d, J = 4.0 Hz, 1H), 5.42 (t, J = 8.0 Hz, 1H), 4.72 (d, J = 8.8 Hz, 1H), 4.30-4.00 (m, 4H), 3.85-3.64 (m, 7H), 3.41-3.36 (m, 2H), 2.38-2.32 (m, 1H), 2.22-1.81 (m, 5H), 1.14 (d, 6.8 Hz, 3H) |
| 42 | 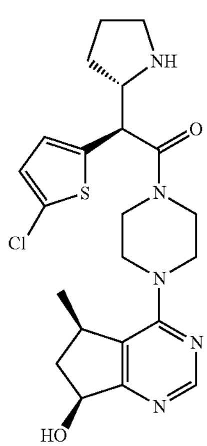 [SMILES: C[C@@H]1C[C@H](O)c2ncnc(N3CCN(C(=O)[C@@H](c4ccc(Cl)s4)[C@@H]4CCCN4)CC3)c21] | (S)-2-(5-chlorothiophen-2-yl)-1-(4-((5R,7S)-7-hydroxy-5-methyl-6,7-dihydro-5H-cyclopenta[d]pyrimidin-4-yl)piperazin-1-yl)-2-((S)-pyrrolidin-2-yl)ethanone | m/z 462.2; $^1$HNMR (400 MHz, D$_2$O) d ppm 8.55 (s, 1H), 6.99 (d, 4.0 Hz, 1H), 6.97 (d, J = 4.0 Hz, 1H), 5.24 (q, J = 4.8 Hz, 1H), 4.71 (d, J = 9.2 Hz, 1H), 4.20-3.53 (m, 12H), 3.41-3.31 (m, 2H), 2.86-2.78 (m, 1H), 2.13-1.78 (m, 4H), 1.68-1.63 (m, 1H), 1.21 (d, J = 6.8 Hz, 3H) |

TABLE 2-continued

| Ex. # | Structure | Name | LCMS NMR |
|---|---|---|---|
| 43 | 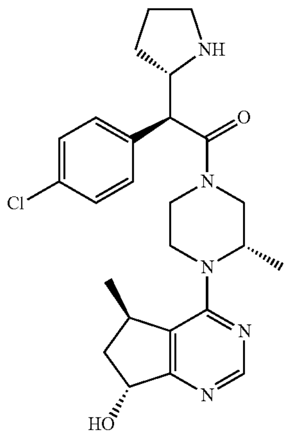 [SMILES: C[C@@H]1C[C@@H](O)c2ncnc(N3CCN(C(=O)[C@@H](c4ccc(Cl)cc4)[C@@H]4CCCN4)C[C@@H]3C)c21] | (S)-2-(4-chlorophenyl)-1-((S)-4-((5R,7R)-7-hydroxy-5-methyl-6,7-dihydro-5H-cyclopenta[d]pyrimidin-4-yl)-3-methylpiperazin-1-yl)-2-((S)-pyrrolidin-2-yl)ethanone | 1.84 min (Mead HPLC); (APCI+) m/z 470 [M + H]+; $^1$H NMR mixture of rotamers (D$_2$O, 400 M Hz) d 8.04 (s, 0.5H), 8.02 (s, 0.4H), 7.07 (d, J = 8.6 Hz, 1H), 6.97 (d, J = 8.6 Hz, 1H), 6.89 (d, J = 8.6 Hz, 1H), 6.80 (d, J = 8.6 Hz, 1H), 4.97-4.89 (m, 1H), 4.02-3.52 (m, 4H), 3.40-2.68 (m, 9H), 1.87 (dd, J = 13.0, 7.5 Hz, 1H), 1.73-1.58 (m, 2H), 1.52-1.26 (m, 3H), 0.84 (d, J = 6.4 Hz, 1.6H), 0.72 (d, J = 6.8 Hz, 1.9H), 0.55 (d, J = 6.8 Hz, 1.6H) |
| 44 | 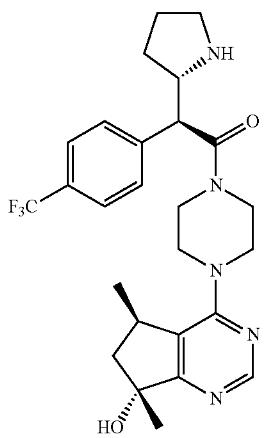 [SMILES: C[C@@H]1C[C@@](C)(O)c2ncnc(N3CCN(C(=O)[C@@H](c4ccc(C(F)(F)F)cc4)[C@@H]4CCCN4)CC3)c21] | (S)-1-(4-((5R,7R)-7-hydroxy-5,7-dimethyl-6,7-dihydro-5H-cyclopenta[d]pyrimidin-4-yl)piperazin-1-yl)-2-((S)-pyrrolidin-2-yl)-2-(4-(trifluoromethyl)phenyl)ethanone | m/z 504.3; $^1$H NMR (500 MHz, DMSO-D6) d ppm 9.11 (m, 1H), 8.80 (m, 1H), 8.58 (s, 1H), 7.81 (d, J = 8.21 Hz, 2H), 7.61 (d, J = 8.11 Hz, 2H), 5.10 (t, 1H), 4.45 (d, 1H), 4.02 (m, 1H), 3.95 (m, 1H), 3.61-3.50 (m, 4H), 3.40 (m, 2H), 3.12-3.02 (m, 3H), 2.00-1.91 (m, 4H), 1.80-1.65 (m, 2H), 1.67-1.50 (m, 2H), 1.38 (s, 3H), 1.09 (d, 3H) |
| 45 | 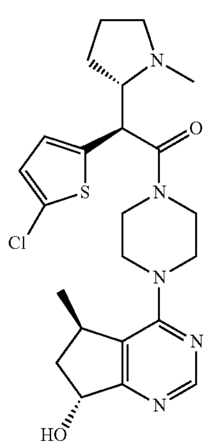 [SMILES: C[C@@H]1C[C@@H](O)c2ncnc(N3CCN(C(=O)[C@@H](c4ccc(Cl)s4)[C@@H]4CCCN4C)CC3)c21] | (S)-2-(5-chlorothiophen-2-yl)-1-(4-((5R,7R)-7-hydroxy-5-methyl-6,7-dihydro-5H-cyclopenta[d]pyrimidin-4-yl)piperazin-1-yl)-2-((S)-1-methylpyrrolidin-2-yl)ethanone | m/z 476.2; $^1$H NMR (500 MHz, DMSO-D6) d ppm 9.82 (s, 1H), 8.61 (s 1H), 7.08 (s, 2H), 5.06 (t, J = 7.5 Hz, 1H), 4.05-3.39 (m, 13 H), 3.17 (s, 3H), 2.88 (d, J = 4.5 Hz, 2H), 2.05-1.73 (m 4H), 1.74-1.67 (m, 1H), 1.09 (d, 7.0 Hz, 3H) |

TABLE 2-continued

| Ex. # | Structure | Name | LCMS NMR |
|---|---|---|---|
| 46 | 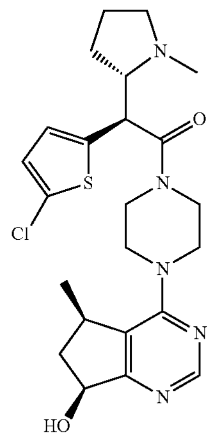 [SMILES: C[C@@H]1C[C@H](O)c2ncnc(N3CCN(C(=O)[C@@H](c4ccc(Cl)s4)[C@@H]4CCCN4C)CC3)c21] | (S)-2-(5-chlorothiophen-2-yl)-1-(4-((5R,7S)-7-hydroxy-5-methyl-6,7-dihydro-5H-cyclopenta[d]pyrimidin-4-yl)piperazin-1-yl)-2-((S)-1-methylpyrrolidin-2-yl)ethanone | m/z 476.2; $^1$HNMR (500 MHz, D$_2$O) d ppm 8.49 (s, 1H), 6.94 (d, J = 6.0 Hz, 2H), 5.17 (t, J = 7.5 Hz, 1H) 4.24-3.47 (m, 10H), 3.30 (s, 3H), 3.20-3.15 (m, 1H), 2.78-2.65 (m, 4H), 2.20-1.56 (m, 5H), 1.16 (d, 6.0 Hz, 3H) |
| 47 | 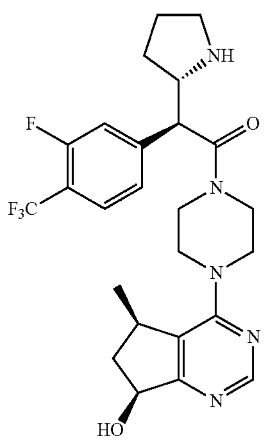 [SMILES: C[C@@H]1C[C@H](O)c2ncnc(N3CCN(C(=O)[C@@H](c4ccc(C(F)(F)F)c(F)c4)[C@@H]4CCCN4)CC3)c21] | (S)-2-(3-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)-2-((S)-pyrrolidin-2-yl)ethanone | m/z 508.4; $^1$H NMR (400 MHz, D$_2$O) d ppm 8.38 (s, 1H), 7.66 (dd, J = 8.0, 8.0 Hz, 1H), 7.26-7.22 (m, 2H), 5.08-5.05 (m, 1H), 4.10-4.00 (m, 2H), 3.81-3.21 (m, 12H), 2.66-2.63 (m, 1H), 1.94-1.89 (m, 1H), 1.80-1.47 (m, 4H), 1.04-1.02 (m, 4H) |
| 48 | 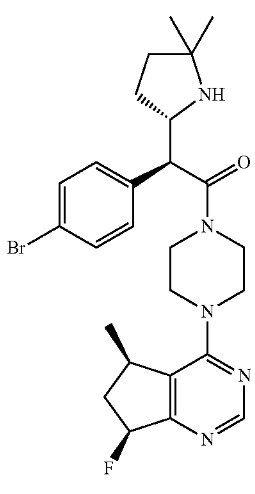 | (S)-2-(5-bromothiophen-2-yl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone | m/z 506.1; $^1$H NMR (400 MHz, D$_2$O) d ppm 8.54 (s, 1H), 7.11 (d, J = 4.0 Hz, 1H), 6.97 (d, J = 4.0 Hz, 1H), 5.42 (t, J = 8.0 Hz, 1H), 4.74 (d, 8.8 Hz, 1H), 4.46-3.65 (m, 12H), 3.39-3.31 (m, 2H), 2.37-2.31 (m, 1H), 2.21-1.78 (m, 5H), 1.14 (d, J = 6.8 Hz, 3H) |

TABLE 2-continued

| Ex. # | Structure | Name | LCMS NMR |
|---|---|---|---|
| 49 | 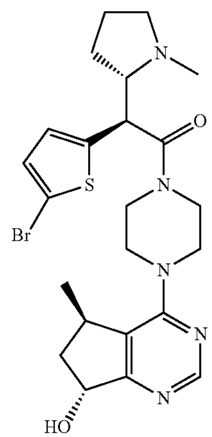 | (S)-2-(5-bromothiophen-2-yl)-1-(4-((5R,7R)-7-hydroxy-5-methyl-6,7-dihydro-5H-cyclopenta[d]pyrimidin-4-yl)piperazin-1-yl)-2-((S)-1-methylpyrrolidin-2-yl)ethanone | m/z 520.2; $^1$H NMR (500 MHz, DMSO-D6) d ppm 9.74 (s, 1H), 8.63 (s, 1H), 7.18 (s, 1H), 7.04 (s, 1H), 5.10 (t, J = 7.0 Hz, 1H), 4.85 (d, J = 9.5 Hz, 1H), 4.04-3.17 (m, 15H0, 2.88 (d, J = 4.5 Hz, 2 H), 2.07-1.91 (m, 4H), 1.73-1.66 (m, 1H), 1.10 (d, 7.0 Hz, 3H) |
| 50 | 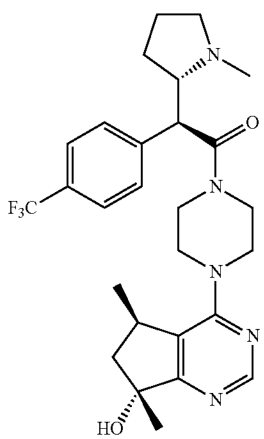 [SMILES: C[C@@H]1C[C@@](C)(O)c2ncnc(N3CCN(C(=O)[C@@H](c4ccc(C(F)(F)F)cc4)[C@@H]4CCCN4C)CC3)c21] | (S)-1-(4-((5R,7R)-7-hydroxy-5,7-dimethyl-6,7-dihydro-5H-cyclopenta[d]pyrimidin-4-yl)piperazin-1-yl)-2-((S)-1-methylpyrrolidin-2-yl)-2-(4-(trifluoromethyl)phenyl)ethanone | m/z 518.3; $^1$H NMR (500 MHz, DMSO-D6) d ppm 8.70 (s, 1H), 7.78 (d, J = 8.15 Hz, 2H), 7.64 (d, J = 8.14 Hz, 2H), 4.72 (m, 1H), 4.18 (m, 1H), 4.10-3.93 (m, 4H), 3.76 (m, 2H), 3.10 (m, 2H), 2.96 (s, 3H), 2.40 (m, 1H), 1.93 (m, 2H), 1.75-1.64 (m, 2H), 1.52 (m, 1H), 1.45 (s, 3H), 1.27 (m, 4H), 1.15 (d, 3H), 1.09 (m, 1H) |
| 51 | 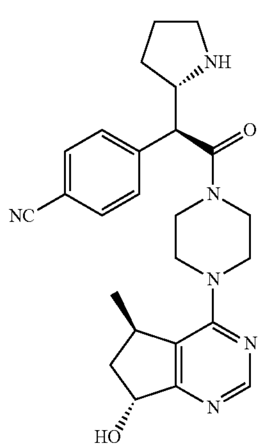 [SMILES: C[C@@H]1C[C@@H](O)c2ncnc(N3CCN(C(=O)[C@@H](c4ccc(C#N)cc4)[C@@H]4CCCN4)CC3)c21] | 4-((S)-2-(4-((5R,7R)-7-hydroxy-5-methyl-6,7-dihydro-5H-cyclopenta[d]pyrimidin-4-yl)piperazin-1-yl)-2-oxo-1-((S)-pyrrolidin-2-yl)ethyl)benzonitrile | m/z 447.3; $^1$H NMR (500 MHz, DMSO-D6) d ppm 9.11 (m, 1H), 8.78 (m, 1H), 8.57 (s, 1H), 7.91 (d, J = 8.28 Hz, 2H) 7.59 (d, J = 8.17 Hz, 2H), 5.02 (m, 1H), 4.44 (m, 1H), 4.00 (m, 2H), 3.92 (m, 2H), 3.38 (m, 2H), 2.01 (m, 2H), 1.95 (m, 1H), 1.86 (m, 1H), 1.58 (m, 2H), 1.04 (d, 3H) |

TABLE 2-continued

| Ex. # | Structure | Name | LCMS NMR |
|---|---|---|---|
| 52 | 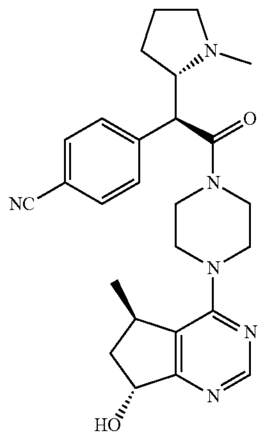 [SMILES: C[C@@H]1C[C@@H](O)c2ncnc(N3CCN(C(=O)[C@@H](c4ccc(C#N)cc4)[C@@H]4CCCN4C)CC3)c21] | 4-((S)-2-(4-((5R,7R)-7-hydroxy-5-methyl-6,7-dihydro-5H-cyclopenta[d]pyrimidin-4-yl)piperazin-1-yl)-1-((S)-1-methylpyrrolidin-2-yl)-2-oxoethyl)benzonitrile | m/z 461.3; $^1$H NMR (500 MHz, DMSO-D6) d ppm 8.65 (s, 1H), 7.85 (d, 2H), 7.65 (d, 2H), 5.10 (t, 1H), 4.80 (d, 1H), 4.10-3.85 (m, 5H), 3.68 (m, 2H), 3.40 (m, 2H), 2.90 (s, 3H), 2.20-2.02 (m, 2H), 1.93 (m, 2H), 1.68 (m, 1H), 1.50 (m, 1H), 1.35-1.25 (m, 11H), 1.10 (d, 3H) |
| 53 | 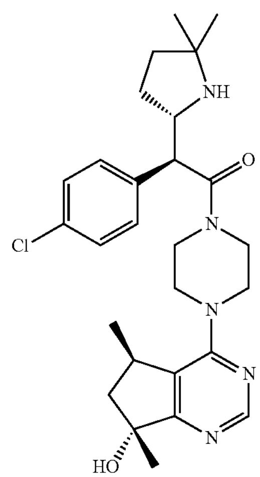 [SMILES: C[C@@H]1C[C@@](C)(O)c2ncnc(N3CCN(C(=O)[C@@H](c4ccc(Cl)cc4)[C@@H]4CCC(C)(C)N4)CC3)c21] | (S)-2-(4-chlorophenyl)-2-((S)-5,5-dimethylpyrrolidin-2-yl)-1-(4-((5R,7R)-7-hydroxy-5,7-dimethyl-6,7-dihydro-5H-cyclopenta[d]pyrimidin-4-yl)piperazin-1-yl)ethanone | m/z 498.3; $^1$H NMR (500 MHz, DMSO-D6) d ppm 8.82 (m, 1H), 8.57 (s, 1H), 8.41 (m, 1H), 7.49 (d, J = 8.62 Hz, 2H) 7.44 (d, J = 8.61 Hz, 2H), 4.34 (m, 2H), 4.16 (m, 2H), 3.90 (m, 2H), 3.79 (m, 2H), 2.92 (m, 2H), 2.30 (m, 1H), 1.79-1.65 (m, 5H), 1.41 (s, 3H), 1.38 (s, 3H), 1.35 (s, 3H), 1.11 (d, 3H) |
| 54 | 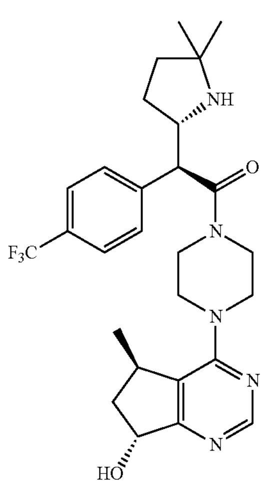 [SMILES: C[C@@H]1C[C@@H](O)c2ncnc(N3CCN(C(=O)[C@@H](c4ccc(C(F)(F)F)cc4)[C@@H]4CCC(C)(C)N4)CC3)c21] | (S)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)-2-(4-(trifluoromethyl)phenyl)ethanone | LCMS (apci+) 518 [M + H]+; 2.59 min; HPLC r.t. = 1.98 min, 98% purity; $^1$H NMR (400 MHz, D$_2$O) d ppm 8.36 (s, 1H), 7.66 (d, J = 8.2 Hz, 2H), 7.45 (d, J = 8.2 Hz, 2H), 5.25 (t, J = 7.8 Hz, 1H), 4.35 (d, J = 8.98 Hz, 1H), 4.24-4.02 (m, 2H), 3.87-3.76 (m, 2H), 3.67-3.38 (m, 5H), 3.23-3.12 (m, 1H), 2.18 (dd, J1 = 7.42 Hz, J2 = 12.88 hz, 1H), 2.06-1.96 (m, 1H) 1.89-1.70 (m, 4H), 1.37 (s, 3H) 1.31 (s, 3H), 0.94 (d, J = 7.03 Hz, 3H) |

TABLE 2-continued

| Ex. # | Structure | Name | LCMS NMR |
|---|---|---|---|
| 55 | 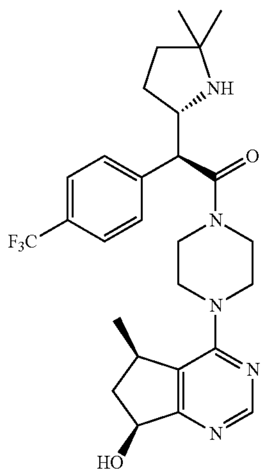 [SMILES: C[C@@H]1C[C@H](O)c2ncnc(N3CCN(C(=O)[C@@H](c4ccc(C(F)(F)F)cc4)[C@@H]4CCC(C)(C)N4)CC3)c21] | (S)-2-((S)-5,5-dimethylpyrrolidin-2-yl)-1-(4-((5R,7S)-7-hydroxy-5-methyl-6,7-dihydro-5H-cyclopenta[d]pyrimidin-4-yl)piperazin-1-yl)-2-(4-(trifluoromethyl)phenyl)ethanone | LCMS (apci+) 518 [M + H]+; 2.58 min; HPLC r.t. = 1.97 min, 96% purity; $^1$H NMR (400 MHz, D$_2$O) d ppm 8.37 (s, 1H), 7.66 (d, J = 8.6 Hz, 2H), 7.45 (, J = 8.2 Hz, 2H), 5.06 (dd, J1 = 4.7 Hz, J2 = 8.2 Hz, 1H), 4.35 (d, J = 8.98 Hz, 1H), 4.24-4.09 (m, 2H), 3.85-3.63 (m, 2H), 3.57-3.41 (m, 5I-1), 3.39-3.27 (m, 1H), 3.20-3.08 (m, 1H), 2.70-2.58 (m, 1H), 1.89-1.70 (m, 4H), 1.49 (dt, J1 = 4.3 Hz, J2 = 14.05 Hz, 1H), 1.37 (s, 3H), 1.31 (s, 3H), 1.00 (d, J = 6.6 Hz, 3H) |
| 56 | 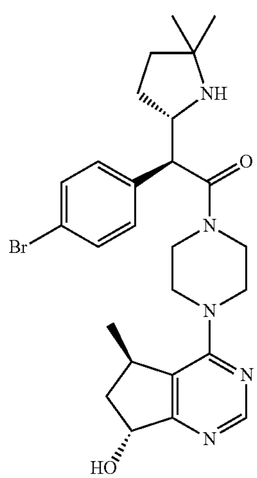 [SMILES: C[C@@H]1C[C@@H](O)c2ncnc(N3CCN(C(=O)[C@@H](c4ccc(Br)cc4)[C@@H]4CCC(C)(C)N4)CC3)c21] | (S)-2-(4-bromophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone | LCMS (apci+) 529 [M + H]+; 2.56 min; HPLC r.t. = 1.92 min, >97% purity |
| 57 | 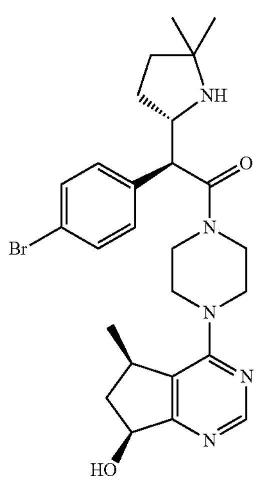 [SMILES: C[C@@H]1C[C@H](O)c2ncnc(N3CCN(C(=O)[C@@H](c4ccc(Br)cc4)[C@@H]4CCC(C)(C)N4)CC3)c21] | (S)-2-(4-bromophenyl)-2-((S)-5,5-dimethylpyrrolidin-2-yl)-1-(4-((5R,7S)-7-hydroxy-5-methyl-6,7-dihydro-5H-cyclopenta[d]pyrimidin-4-yl)piperazin-1-yl)ethanone | LCMS (apci+) 529 [M + H]+; 2.51 min; HPLC r.t. = 1.92 min, >97% purity; $^1$H NMR (400 MHz, D$_2$O) d ppm 8.38 (s, 1H), 7.50 (d, J = 8.2 Hz, 2H), 7.17 (d, J = 8.6 Hz, 2H), 5.08 (dd, J1 = 3.5 Hz, J2 = 8.2 Hz, 1H), 4.22 (d, J = 8.98 Hz, 1H), 4.18-4.07 (m, 2H), 3.88-3.77 (m, 1H), 3.73-3.63 (m, 1H), 3.56-3.40 (m, 4H), 3.39-3.28 (m, 1H), 3.27-3.14 (m, 1H), 2.712.60 (m, 1H), 1.88-1.72 (m, 4H), 1.50 (dt, J1 = 4.3 Hz, J2 = 14.0 Hz, 1H), 1.36 (s, 3H), 1.30 (s, 3H), 1.03 (d, J = 7.0 Hz, 3H) |

TABLE 2-continued

| Ex. # | Structure | Name | LCMS NMR |
|---|---|---|---|
| 58 | 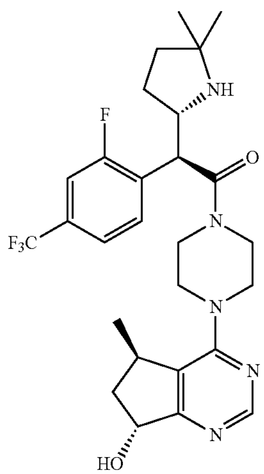 [SMILES: C[C@@H]1C[C@@H](O)c2ncnc(N3CCN(C(=O)[C@@H](c4ccc(C(F)(F)F)cc4F)[C@@H]4CCC(C)(C)N4)CC3)c21] | (S)-2-((S)-5,5-dimethylpyrrolidin-2-yl)-2-(2-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)ethanone | LCMS (apci+) 536 [M + H]+; 2.60 min; HPLC r.t. = 1.98 min, >95% purity; $^1$H NMR (400 MHz, D$_2$O) d ppm 8.37 (s, 1H), 7.55 (d, J = 10.5 Hz, 1H), 7.49 (d, J = 8.2 Hz, 1H), 7.41 (t, J = 7.0 Hz, 1H), 5.25 (t, J = 7.8 Hz, 1H), 4.58 (d, J = 9.4 Hz, 1H), 4.24 (q, J = 8.6 Hz, 1H), 4.13-4.04 (m, 1H), 3.85-3.42 (m, 7H), 3.37-3.25 (m, 2H), 2.22-2.14 (m, 1H), 2.07-1.97 (m, 1H), 1.90-1.73 (m, 5H), 1.38 (s, 3H), 1.32 (s, 3H), 0.96 (d, J = 7.0 Hz, 3H) |
| 59 | 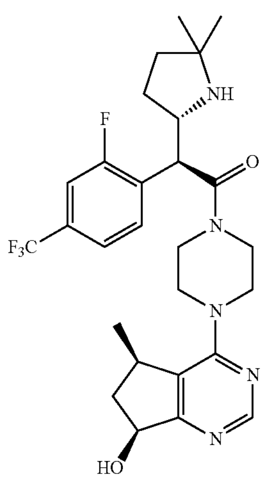 [SMILES: C[C@@H]1C[C@H](O)c2ncnc(N3CCN(C(=O)[C@@H](c4ccc(C(F)(F)F)cc4F)[C@@H]4CCC(C)(C)N4)CC3)c21] | (S)-2-((S)-5,5-dimethylpyrrolidin-2-yl)-2-(2-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)ethanone | LCMS (apci+) 536 [M + H]+; 2.59 min; HPLC r.t. = 1.97 min, >95% purity; $^1$H NMR (400 MHz, D$_2$O) d ppm 8.37 (s, 1H), 7.55 (d, J = 10.5 Hz, 1H), 7.49 (d, J = 8.2 Hz, 1H), 7.41 (t, J = 7.0 Hz, 1H), 5.25 (t, J = 7.8 Hz, 1H), 4.58 (d, J = 9.4 Hz, 1H), 4.24 (q, J = 8.6 Hz, 1H), 4.13-4.04 (m, 1H), 3.85-3.42 (m, 7H), 3.37-3.25 (m, 2H), 2.22-2.14 (m, 1H), 2.07-1.97 (m, 1H), 1.90-1.73 (m, 5H), 1.38 (s, 3H), 1.32 (s, 3H), 0.96 (d, J = 7.0 Hz, 3H) |
| 60 | 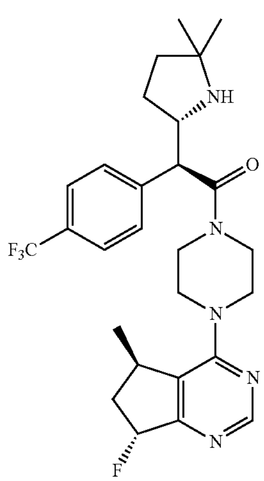 [SMILES: C[C@@H]1C[C@@H](F)c2ncnc(N3CCN(C(=O)[C@@H](c4ccc(C(F)(F)F)cc4)[C@@H]4CCC(C)(C)N4)CC3)c21] | (S)-24(S)-5,5-dimethylpyrrolidin-2-yl)-1-(4-((5R,7R)-7-fluoro-5-methyl-6,7-dihydro-5H-cyclopenta[d]pyrimidin-4-yl)piperazin-1-yl)-2-(4-(trifluoromethyl)phenyl)ethanone | LCMS (apci+) 519.7/521.4; Rf 2.89 min |

TABLE 2-continued

| Ex. # | Structure | Name | LCMS NMR |
|---|---|---|---|
| 61 | 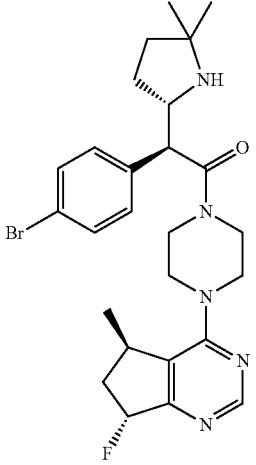 [SMILES: C[C@@H]1C[C@@H](F)c2ncnc(N3CCN(C(=O)[C@@H](c4ccc(Br)cc4)[C@@H]4CCC(C)(C)N4)CC3)c21] | (S)-2-(4-bromophenyl)-2-((S)-5,5-dimethylpyrrolidin-2-yl)-1-(4-((5R,7R)-7-fluoro-5-methyl-6,7-dihydro-5H-cyclopenta[d]pyrimidin-4-yl)piperazin-1-yl)ethanone | LCMS (apci+) 530.3; Rf: 2.83 min |
| 62 | 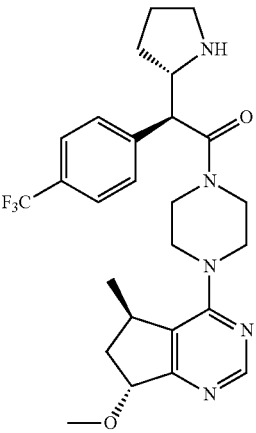 [SMILES: CO[C@@H]1C[C@@H](C)c2c1ncnc2N1CCN(C(=O)[C@@H](c2ccc(C(F)(F)F)cc2)[C@@H]2CCCN2)CC1] | (S)-1-(4-((5R,7R)-7-methoxy-5-methyl-6,7-dihydro-5H-cyclopenta[d]pyrimidin-4-yl)piperazin-1-yl)-2-((S)-pyrrolidin-2-yl)-2-(4-(trifluoromethyl)phenyl)ethanone | m/z 504.3; $^1$H NMR (400 MHz, D$_2$O) d ppm 8.49 (s, 1H), 7.81 (d, J = 8.4 Hz, 2H), 7.58 (d, J = 8.4 Hz, 2H), 5.16 (t, J = 7.6 Hz, 1H), 4.49-3.61 (m, 10H), 3.47 (s, 3H), 3.38-3.33 (m, 3H), 2.37-1.78 (m, 6H), 1.36-1.32 (m, 2H), 1.08 (d, J = 6.8 Hz, 3H) |
| 63 | 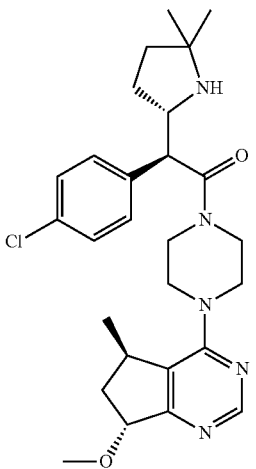 [SMILES: CO[C@@H]1C[C@@H](C)c2c1ncnc2N1CCN(C(=O)[C@@H](c2ccc(Cl)cc2)[C@@H]2CCC(C)(C)N2)CC1] | (S)-2-(4-chlorophenyl)-2-((S)-5,5-dimethylpyrrolidin-2-yl)-1-(4-((5R,7R)-7-methoxy-5-methyl-6,7-dihydro-5H-cyclopenta[d]pyrimidin-4-yl)piperazin-1-yl)ethanone | m/z 498.3; $^1$H NMR (400 MHz, D$_2$O) d ppm 8.49 (s, 1H), 7.47 (d, J = 4.0 Hz, 1H), 7.37 (d, J = 4.0 Hz, 1H), 5.16 (t, J = 7.6 Hz, 1H), 4.46-3.65 (m, 7H), 3.48 (s, 3H), 2.37-2.34 (m, 1H), 2.26-2.18 (m, 1H), 1.98-1.89 (m, 4H), 1.50 (s, 3H), 1.44 (s, 3H), 1.36-1.32 (m, 6H), 1.10 (d, J = 6.8 Hz, 3H) |

TABLE 2-continued

| Ex. # | Structure | Name | LCMS NMR |
|---|---|---|---|
| 64 | 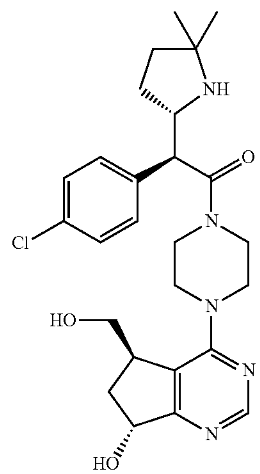 [SMILES: CC1(C)CC[C@@H]([C@@H](C(=O)N2CCN(c3ncnc4c3[C@H](CO)C[C@H]4O)CC2)c2ccc(Cl)cc2)N1] | (S)-2-(4-chlorophenyl)-2-((S)-5,5-dimethylpyrrolidin-2-yl)-1-(4-((5R,7R)-7-hydroxy-5-(hydroxymethyl)-6,7-dihydro-5H-cyclopenta[d]pyrimidin-4-yl)piperazin-1-yl)ethanone | m/z 500.3; $^1$H NMR (500 MHz, CD$_3$OD) d ppm 8.55 (s, 1H), 7.44 (s, 4H) 5.23 (t, J = 7.92 Hz, 1H), 4.53 (d, J = 9.54 Hz, 1H), 4.32-4.25 (m, 1H), 4.2-4.12 (m, 1H), 4.06-3.95 (m, 1H), 3.92-3.69 (m, 5H), 3.68-3.51 (m, 3H), 3.46-3.42 (s, 1H), 2.50 (dd, J = 12.94 Hz, 1H), 2.11 (dd, J = 8.27 Hz, 1H), 2.04-1.81 (m, 4H), 1.55 (s, 3H), 1.47-1.40 (m, 3H) |
| 65 | 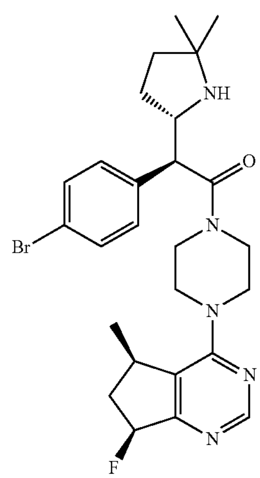 | (S)-2-(4-bromophenyl)-2-((S)-5,5-dimethylpyrrolidin-2-yl)-1-(4-((5R,7S)-7-fluoro-5-methyl-6,7-dihydro-5H-cyclopenta[d]pyrimidin-4-yl)piperazin-1-yl)ethanone | LCMS (apci+) 532.1 [M + H]+ ; 2.22 min |
| 66 | 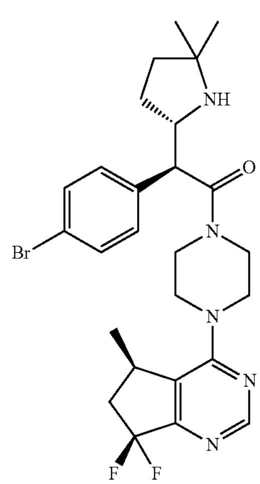 | (S)-2-(4-bromophenyl)-1-(4-((R)-7,7-difluoro-5-methyl-6,7-dihydro-5H-cyclopenta[d]pyrimidin-4-yl)piperazin-1-yl)-2-((S)-5,5-dimethylpyrrolidin-2-yl)ethanone | LCMS (apci+) 550.4 [M + H]+; 2.83 min |

TABLE 2-continued

| Ex. # | Structure | Name | LCMS NMR |
|---|---|---|---|
| 67 | 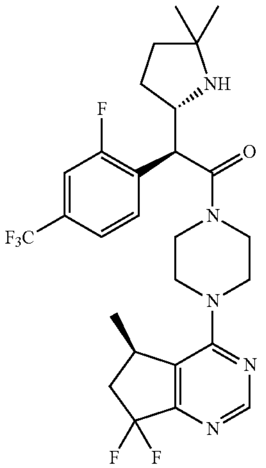 [SMILES: C[C@@H]1CC(F)(F)c2ncnc(N3CCN(C(=O)[C@@H](c4ccc(C(F)(F)F)cc4F)[C@@H]4CCC(C)(C)N4)CC3)c21] | (S)-1-(4-((R)-7,7-difluoro-5-methyl-6,7-dihydro-5H-cyclopenta[d]pyrimidin-4-yl)piperazin-1-yl)-2-((S)-5,5-dimethylpyrrolidin-2-yl)-2-(2-fluoro-4-(trifluoromethyl)phenyl)ethanone | LCMS (apci+) 556.3 [M + H]+; 2.97 min |
| 68 | 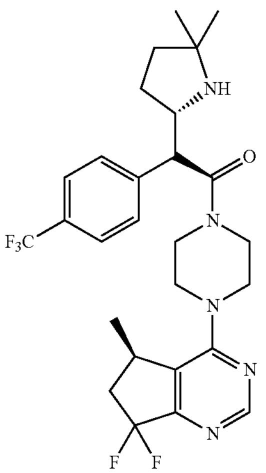 | (R)-1-(4-((R)-7,7-difluoro-5-methyl-6,7-dihydro-5H-cyclopenta[d]pyrimidin-4-yl)piperazin-1-yl)-2-((S)-5,5-dimethylpyrrolidin-2-yl)-2-(4-(trifluoromethyl)phenyl)ethanone | LCMS (apci+) 538.7 [M + H]+ ; 2.95 min; $^1$H NMR (400 MHz, D$_2$O) d ppm (8.35 (s, 1H), 7.65 (d, J = 8.2 Hz, 2H), 7.44 (d, J = 7.8 Hz, 2H), 4.34 (d app, J = 9.0, 1H), 4.24-4.15 (m, 1H), 4.04-3.95 (m, 1H), 3.86-3.78 (m, 1H), 3.68-3.59 (m, 1H), 3.55-3.40 (m, 4H), 3.11-3.01 (m, 1H), 2.78-2.60 (m, 1H), 2.23-2.09 (m, 1H), 1.88-1.68 (m, 4H), 1.37 (s, 3H), 1.31 (s, 3H), 0.99 (d, J = 6.6, 3H) |
| 69 | 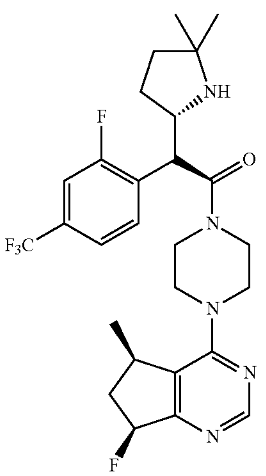 | (R)-2-((S)-5,5-dimethylpyrrolidin-2-yl)-2-(2-fluoro-4-(trifluoromethyl)phenyl)-1-(4-((5R,7S)-7-fluoro-5-methyl-6,7-dihydro-5H-cyclopenta[d]pyrimidin-4-yl)piperazin-1-yl)ethanone | LCMS (apci+) 538.2 [M + H]+ ; 2.22 min |

TABLE 2-continued

| Ex. # | Structure | Name | LCMS NMR |
|---|---|---|---|
| 70 | 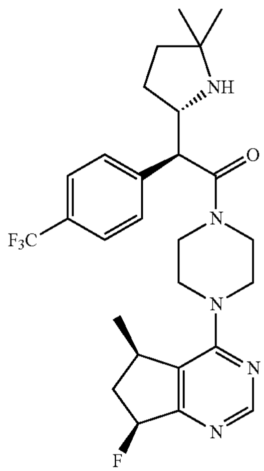 [SMILES: C[C@@H]1C[C@H](F)c2ncnc(N3CCN(C(=O)[C@@H](c4ccc(C(F)(F)F)cc4)[C@@H]4CCC(C)(C)N4)CC3)c21] | (S)-24(S)-5,5-dimethylpyrrolidin-2-yl)-1-(4-45R,7S)-7-fluoro-5-methyl-6,7-dihydro-5H-cyclopenta[d]pyrimidin-4-yl)piperazin-1-yl)-2-(4-(trifluoromethyl)phenyl)ethanone | LCMS (apci+) 520.5 [M + H]+; 2.88 min |
| 71 | 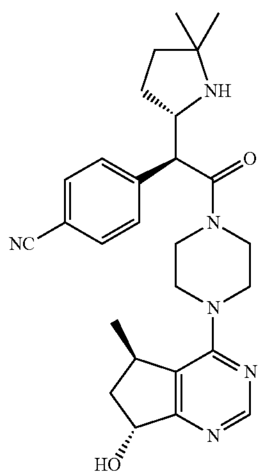 [SMILES: C[C@@H]1C[C@@H](O)c2ncnc(N3CCN(C(=O)[C@@H](c4ccc(C#N)cc4)[C@@H]4CCC(C)(C)N4)CC3)c21] | 4-((S)-1-((S)-5,5-dimethylpyrrolidin-2-yl)-2-(4-((5R,7R)-7-hydroxy-5-methyl-6,7-dihydro-5H-cyclopenta[d]pyrimidin-4-yl)piperazin-1-yl)-2-oxoethyl)benzonitrile | m/z 475.3; $^1$H NMR (500 MHz, DMSO-D6) d ppm 8.85 (m, 1H), 8.55 (s, 1H), 8.47 (m, 1H), 7.91 (d, J = 8.39 Hz, 2H) 7.64 (d, J = 8.37 Hz, 2H), 5.01 (m, 1H), 4.46 (m, 1H), 4.21 (m, 2H), 3.91 (m, 2H), 3.78-3.65 (m, 4H), 2.98 (m, 2H), 1.99 (m, 2H), 1.82-1.69 (m, 3H), 1.66-1.59 (m, 1H), 1.41 (s, 3H), 1.36 (m, 3H), 1.04 (d, 3H) |
| 72 | 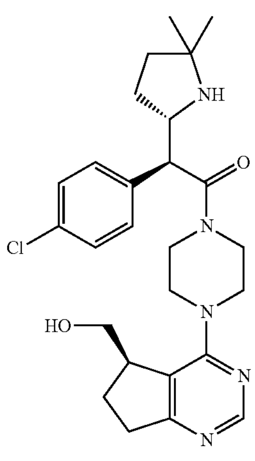 [SMILES: CC1(C)CC[C@@H]([C@@H](C(=O)N2CCN(c3ncnc4c3[C@H](CO)CC4)CC2)c2ccc(Cl)cc2)N1] | (S)-2-(4-chlorophenyl)-2-((S)-5,5-dimethylpyrrolidin-2-yl)-1-(4-((R)-5-(hydroxymethyl)-6,7-dihydro-5H-cyclopenta[d]pyrimidin-4-yl)piperazin-1-yl)ethanone | m/z 484.2; $^1$H NMR (500 MHz, CDCl$_3$) d ppm 8.45 (s, 1H), 7.34 (d, J = 8.29 Hz, 2H), 7.29-7.19 (m, 2H), 4.15-3.97 (m, 1H), 3.87-3.62 (m, 4H), 3.61-3.50 (m, 3H), 3.50-3.35 (m, 2H), 3.35-3.21 (m, 1H), 3.17-3.03 (m, 1H), 2.99-2.78 (m, 2H), 2.24-2.13 (m, 1H), 2.03-1.94 (m, 1H), 1.94-1.22 (m, 13H) |

TABLE 2-continued

| Ex. # | Structure | Name | LCMS NMR |
|---|---|---|---|
| 73 | 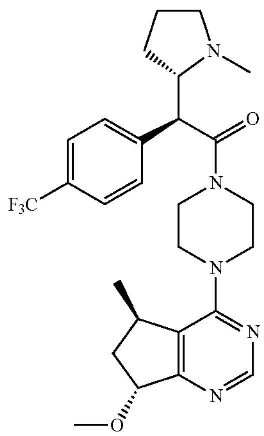 [SMILES: CO[C@@H]1C[C@@H](C)c2c1ncnc2N1CCN(C(=O)[C@@H](c2ccc(C(F)(F)F)cc2)[C@@H]2CCCN2C)CC1] | (S)-1-(4-((5R,7R)-7-methoxy-5-methyl-6,7-dihydro-5H-cyclopenta[d]pyrimidin-4-yl)piperazin-1-yl)-2-((S)-1-methylpyrrolidin-2-yl)-2-(4-(trifluoromethyl)phenyl)ethanone | m/z 518.3; $^1$H NMR (500 MHz, D$_2$O) d ppm 8.42 (s, 1H), 7.80 (d, J = 7.5 Hz, 2H), 7.58 (d, J = 7.5 Hz, 2H), 5.00 (t, J = 7.0 Hz, 1H), 4.21-3.54 (m, 10 H), 3.46 (s, 3H), 3.25-3.18 (m, 2H), 2.81 (s, 3H), 2.22-2.20 (m, 2H), 2.11-2.08 (m, 2H), 1.35-1.33 (m, 3H), 1.06 (s, J = 7.0 Hz, 3H) |
| 74 | 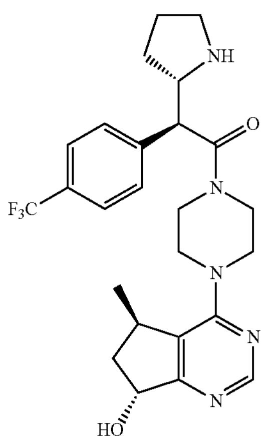 | (S)-1-(4-((5R,7R)-7-hydroxy-5-methyl-6,7-dihydro-5H-cyclopenta[d]pyrimidin-4-yl)piperazin-1-yl)-2-((S) pyrrolidin-2-yl)-2-(4-(trifluoromethyl)phenyl)ethanone | m/z 490.3; $^1$H NMR (500 MHz, DMSO-D6) d ppm 9.18 (m, 1H), 8.85 (m, 1H), 8.57 (s, 1H), 7.78 (d,, 2H), 7.62 (d, 2H), 5.04 (t, 1H), 4.48 (d, 1H), 4.02 (m, 2H), 3.95 (m, 2H), 3.75-3.50 (m, 6H), 3.42 (m, 2H), 3.30-3.10 (m, 4H), 2.10-1.90 (m 3H), 1.75 (m, 1H), 1.70-1.50 (m, 2H), 1.04 (d, 3H) |
| 75 | 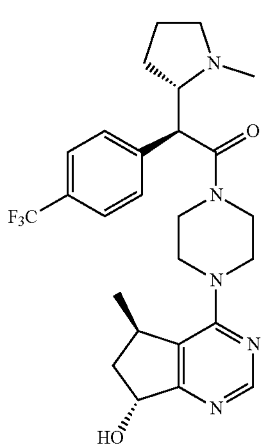 | (S)-1-(4-((5R,7R)-7-hydroxy-5-methyl-6,7-dihydro-5H-cyclopenta[d]pyrimidin-4-yl)piperazin-1-yl)-2-((S)-1-methylpyrrolidin-2-yl)-2-(4-(trifluoromethyl)phenyl)ethanone | m/z 504.3; 1H NMR (500 MHz, DMSO-D6) d ppm 9.87 (m, 1H), 8.57 (s, 1H), 7.80 (d, J = 8.37 Hz, 2H), 7.62 (d, J = 8.13 Hz, 2H), 5.04 (m, 1H), 4.48 (d, 1H), 4.08 (m, 2H), 3.95 (m, 2H), 3.75-3.50 (m, 6H), 3.40 (m, 2H), 3.30-3.10 (m, 4H), 2.95 (s, 3H), 2.10-1.90 (m 4H), 1.85 (m, 1H), 1.60 (m, 1H), 1.04 (d, 3H) |

TABLE 2-continued

| Ex. # | Structure | Name | LCMS NMR |
|---|---|---|---|
| 76 | 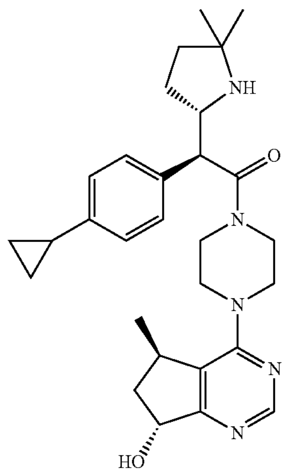 [SMILES: C[C@@H]1C[C@@H](O)c2ncnc(N3CCN(C(=O)[C@@H](c4ccc(C5CC5)cc4)[C@@H]4CCC(C)(C)N4)CC3)c21] | (S)-2-(4-cyclopropylphenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone | LCMS (apci+) 490.2 (M + H)+; Rf: 2.39 min |
| 77 | 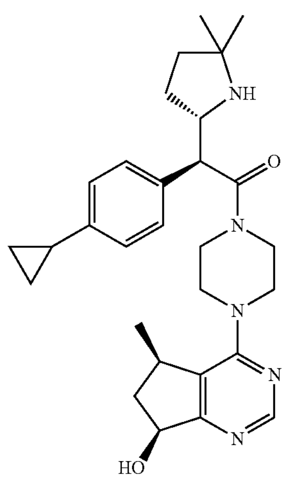 [SMILES: C[C@@H]1C[C@H](O)c2ncnc(N3CCN(C(=O)[C@@H](c4ccc(C5CC5)cc4)[C@@H]4CCC(C)(C)N4)CC3)c21] | (S)-2-(4-cyclopropylphenyl)-2-((S)-5,5-dimethylpyrrolidin-2-yl)-1-(4-((5R,7S)-7-hydroxy-5-methyl-6,7-dihydro-5H-cyclopenta[d]pyrimidin-4-yl)piperazin-1-yl)ethanone | m/z 490.2; $^1$H NMR (400 MHz, CD$_3$OD) d ppm 8.57 (s, 1H), 7.28 (d, 2H), 7.14 (d, 2H), 5.14-5.07 (m, 1H), 4.36-4.21 (m, 3H), 3.93-3.78 (m, 2H), 3.77-3.42 (m, 5H), 2.83-2.73 (m, 1H), 2.02-1.81 (m, 5H), 1.65-1.56 (m, 1H), 1.52 (s, 3H), 1.44 (s, 3H), 1.40-1.33 (m, 1H), 1.20 (d, 3H), 1.03-0.95 (m, 2H), 0.71-0.64 (m, 2H) |
| 78 | 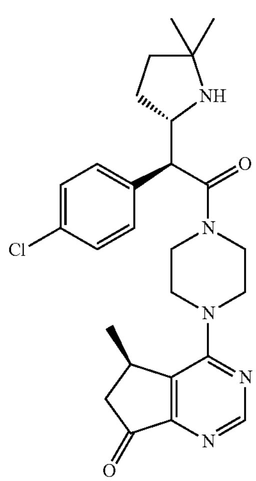 | (R)-4-(4-((S)-2-(4-chlorophenyl)-2-((S)-5,5-dimethylpyrrolidin-2-yl)acetyl)piperazin-1-yl)-5-methyl-5H-cyclopenta[d]pyrimidin-7(6H)-one | LCMS (apci+) 387.0 [M + H]+; 1.61 min; $^1$H NMR (400 MHz, D$_2$O) d ppm 8.46 (s, 1H), 7.35 (d, J = 8.6 Hz, 2H), 7.24 (d, J = 8.6 Hz, 2H), 4.26 (d app, 2H), 4.15 (m, 1H), 3.92-3.82 (m, 2H), 3.76-3.50 (m, 5H), 3.36-3.26 (m, 1H), 3.03-2.93 (m, 1H), 2.38 (d, J = 20.3 1H), 1.88-1.72 (m, 4H), 1.36 (s, 3H), 1.31 (s, 3H), 1.07 (d, J = 7.0, 3H) |

TABLE 2-continued

| Ex. # | Structure | Name | LCMS NMR |
|---|---|---|---|
| 79 | 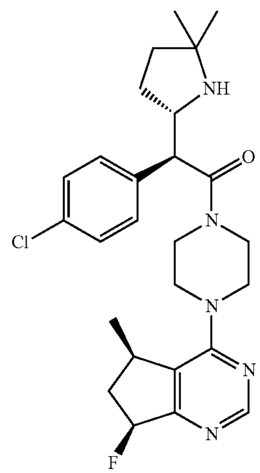 [SMILES: C[C@@H]1C[C@H](F)c2ncnc(N3CCN(C(=O)[C@@H](c4ccc(Cl)cc4)[C@@H]4CCC(C)(C)N4)CC3)c21] | (S)-2-(4-chlorophenyl)-2-((S)-5,5-dimethylpyrrolidin-2-yl)-1-(4-((5R,7S)-7-fluoro-5-methyl-6,7-dihydro-5H-cyclopenta[d]pyrimidin-4-yl)piperazin-1-yl)ethanone | LCMS (apci+) 487.4 [M + H]+; 2.18 min |
| 80 | 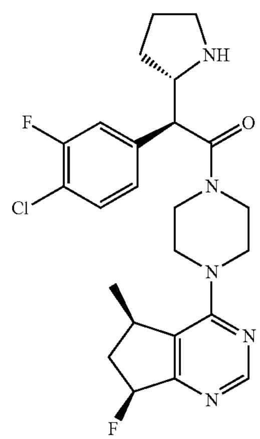 [SMILES: C[C@@H]1C[C@H](F)c2ncnc(N3CCN(C(=O)[C@@H](c4ccc(Cl)c(F)c4)[C@@H]4CCCN4)CC3)c21] | (S)-2-(4-chloro-3-fluorophenyl)-1-(4-((5R,7S)-7-fluoro-5-methyl-6,7-dihydro-5H-cyclopenta[d]pyrimidin-4-yl)piperazin-1-yl)-2-((S)-pyrrolidin-2-yl)ethanone | rt = 2.07 min; $^1$H NMR (400 MHz, D$_2$O) d ppm (8.41 (s, 1H), 7.44 (t app, J = 8.0 Hz, 1H), 7.15 (d, J = 9.7 Hz, 1H), 7.06 (d, J = 8.2 Hz, 1H), 5.82 (dm, J = 55.1 Hz, 1H), 4.24 (d, J = 9.4, 1H), 4.14-4.06 (m, 1H), 4.02-3.93 (m, 1H), 3.86-3.72 (m, 1H), 3.67-3.58 (m, 1H), 3.57-3.40 (m, 4H), 3.35-3.15 (m, 3H), 2.68-2.50 (m, 2H), 2.00-1.59 (m, 4H), 1.06 (d, 3H) |
| 81 | 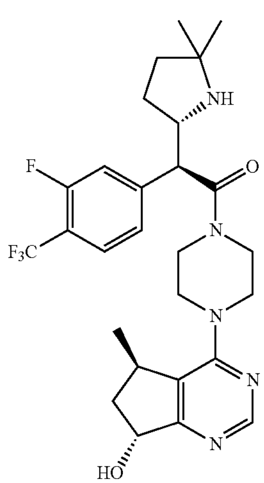 [SMILES: C[C@@H]1C[C@@H](O)c2ncnc(N3CCN(C(=O)[C@@H](c4ccc(C(F)(F)F)c(F)c4)[C@@H]4CCC(C)(C)N4)CC3)c21] | (S)-2-((S)-5,5-dimethylpyrrolidin-2-yl)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)ethanone | LCMS (apci+) 536 [M + H]+; 2.70 min; $^1$H NMR (400 MHz, D$_2$O) d ppm 8.37 (s, 1H), 7.66 (t, J = 8.2 Hz, 1H), 7.32-7.21 (m, 2H), 5.25 (t, J = 7.8 Hz, 1H), 4.37 (d, J = 8.6 Hz, 1H), 4.24-4.04 (m, 1H), 3.90-3.38 (m, 7H), 2.58 (s, 2H), 2.25-1.96 (m, 1H), 1.90-1.71 (m, 4H), 1.36 (s, 3H), 1.31 (s, 3H), 0.96 (d, J = 6.2 Hz, 3H) |

TABLE 2-continued

| Ex. # | Structure | Name | LCMS NMR |
|---|---|---|---|
| 82 | 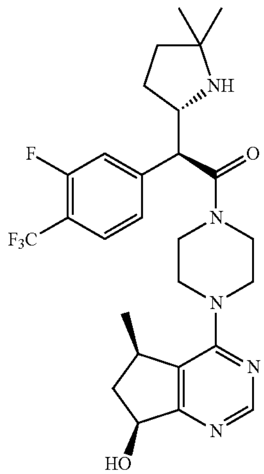 [SMILES: C[C@@H]1C[C@H](O)c2ncnc(N3CCN(C(=O)[C@@H](c4ccc(C(F)(F)F)c(F)c4)[C@@H]4CCC(C)(C)N4)CC3)c21] | (S)-2-((S)-5,5-dimethylpyrrolidin-2-yl)-2-(3-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)ethanone | LCMS (apci+) 536 [M + H]+; 2.67 min; $^1$H NMR (400 MHz, D$_2$O) d ppm 8.37 (s, 1H), 7.67 (t, J = 7.8 Hz, 1H), 7.30-7.22 (m, 2H), 5.10-5.04 (m, 1H), 4.37 (d, J = 9.4 Hz, 1H), 4.25-4.04 (m, 2H), 3.81-3.67 (m, 2H), 3.65-3.22 (m, 7H), 2.72-2.60 (m, 1H), 1.90-1.71 (m, 4H), 1.55-1.44 (m, 1H), 1.36 (s, 3H), 1.31 (s, 3H), 1.04 (d, J = 7.0 Hz, 3H) |
| 83 | 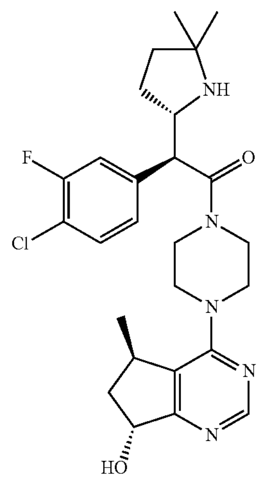 [SMILES: C[C@@H]1C[C@@H](O)c2ncnc(N3CCN(C(=O)[C@@H](c4ccc(Cl)c(F)c4)[C@@H]4CCC(C)(C)N4)CC3)c21] | (S)-2-(4-chloro-3-fluorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone | LCMS (apci+) 502 [M + H]+; 2.68 min; HPLC r.t. = 1.98 min, >97% purity; $^1$H NMR (400 MHz, D$_2$O) d ppm 8.37 (s, 1H), 7.43 (t, J = 8.2 Hz, 1H), 7.16 (d, J = 9.8 Hz, 1H), 7.06 (d, J = 8.2 Hz, 1H), 5.24 (t, J = 7.8 Hz, 1H), 4.27 (d, J = 9.4 Hz, 1H), 4.22-4.02 (m, 1H), 3.88-3.75 (m, 2H), 3.72-3.60 (m, 1H), 3.59-3.41 (m, 4H0, 3.37-3.22 (m, 1H), 2.24-2.11 (m, 0.5H), 2.10-1.94 (m, 0.5H), 1.89-1.71 (m, 4H), 1.36 (s, 3H), 1.30 (s, 3H), 0.96 (d, J = 7.0 Hz, 3H) |
| 84 | 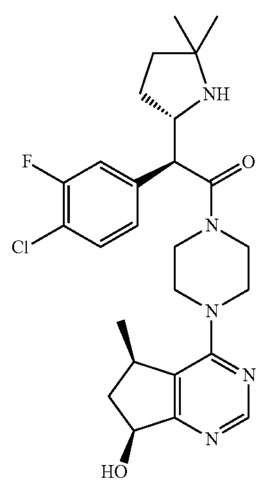 [SMILES: C[C@@H]1C[C@H](O)c2ncnc(N3CCN(C(=O)[C@@H](c4ccc(Cl)c(F)c4)[C@@H]4CCC(C)(C)N4)CC3)c21] | (S)-2-(4-chloro-3-fluorophenyl)-2((S)-5,5-dimethylpyrrolidin-2-yl)-1-(4-((5R 7S)-7-hydroxy-5-methyl-6,7-dihydro-5H-cyclopenta[d]pyrimidin-4-yl)piperazin-1-yl)ethanone | LCMS (apci+) 502 [M + H]+; 2.60 min; HPLC r.t.= 1.99 min, >95% purity; $^1$H NMR (400 MHz, D$_2$O) d ppm 8.37 (s, 1H), 7.43 (t, J = 8.2 Hz 1H), 7.16 (d, J = 9.8 Hz, 1H), 7.06 (d, J = 8.2 Hz, 1H), 5.11-5.04 (m, 1H), 4.27 (d, J = 9.4 Hz, 1H), 4.22-4.02 (m, 1H), 3.88-3.22 (m, 7H), 2.72-2.59 (m, 1H), 1.89-1.71 (m, 4H), 1.55-1.44 (m, 1H), 1.36 (s, 3H), 1.30 (s, 3H), 1.03 (d, J = 7.0 Hz, 3H) |

TABLE 2-continued

| Ex. # | Structure | Name | LCMS NMR |
|---|---|---|---|
| 85 | 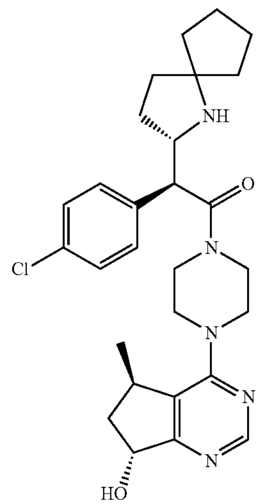 [SMILES: C[C@@H]1C[C@@H](O)c2ncnc(N3CCN(C(=O)[C@@H](c4ccc(Cl)cc4)[C@@H]4CCC5(CCCC5)N4)CC3)c21] | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-azaspiro[4.4]nonan-2-yl)ethanone | 2.03 min (HPLC); (APCI+) m/z 510 [M + H]+; $^1$H NMR mixture of rotamers (D$_2$O, 400 MHz) d 8.35 (s, 1H), 7.33 (d, J = 8.4 Hz, 2H) 7.22 (d, J = 8.2 Hz, 2H), 5.22 (dd, J = 7.7, 7.7 Hz, 1H), 4.20 (d, J = 9.4 Hz, 1H), 4.16-4.04 (m, 2H), 3.88-3.74 (m, 2H), 3.66-3.42 (m, 5H), 3.24-3.14 (m, 1H), 2.17 (dd, J = 13.0, 7.7 Hz, 1H), 2.06-1.96 (m, 1H), 1.94-1.50 (m, 13H), 0.95 (d, J = 6.8 Hz, 3H) |
| 86 | 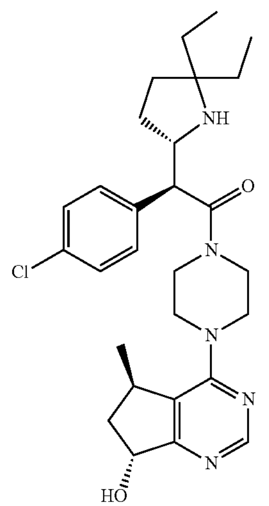 [SMILES: CCC1(CC)CC[C@@H]([C@@H](C(=O)N2CCN(c3ncnc4c3[C@H](C)C[C@H]4O)CC2)c2ccc(Cl)cc2)N1] | (S)-2-(4-chlorophenyl)-2-((S)-5,5-diethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone | 2.04 min (HPLC); (APCI+) m/z 512 [M + H]+; $^1$H NMR mixture of rotamers (D$_2$O, 400 MHz) d 8.36 (s, 1H), 7.33 (d, J = 7.8 Hz, 2H), 7.21 (d, J = 8.0 Hz, 2H), 5.25 (dd, J = 7.7, 7.7 Hz, 1H), 4.24 (d, J = 8.6 Hz, 1H), 4.14-4.02 (m, 2H), 3.90-3.76 (m, 2H), 3.70-3.60 (m, 1H), 3.58-3.42 (m, 4H), 3.30-3.20 (m, 1H), 2.23.2.14 (m, 1H), 2.07-1.96 (m, 1H), 1.88-1.56 (m, 8H), 0.95 (d, J = 7.4 Hz, 3H), 0.85-0.74 (m, 6H) |
| 87 | 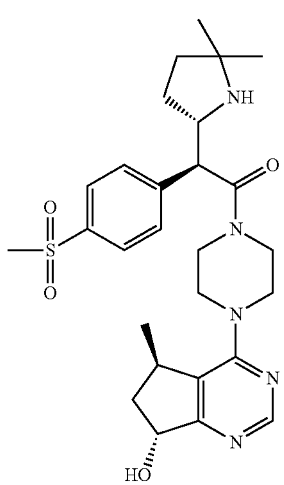 [SMILES: C[C@@H]1C[C@@H](O)c2ncnc(N3CCN(C(=O)[C@@H](c4ccc(S(C)(=O)=O)cc4)[C@@H]4CCC(C)(C)N4)CC3)c21] | (S)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)-2-(4-(methylsulfonyl)phenyl)ethanone | m/z 528.2; $^1$H NMR (500 MHz, D$_2$O) d ppm 8.51 (s, 1H), 8.05 (d, J = 8.0 Hz, 2H), 7.71 (d, J = 8.0 Hz, 2H), 5.39 (t, 7.5 Hz, 1H), 4.56 (d, J = 9.0 Hz, 1H), 4.38-4.22 (m, 2H), 3.96-3.54 (m, 9H), 3.36-3.30 (m, 1H), 3.29 (s, 3H), 2.34-2.30 (m, 1H), 2.19-2.13 (m, 1H), 2.02-1.87 (m, 4H), 1.52 (s, 3H), 1.46 (m, 3H), 1.08 (d, J = 7.0 Hz, 3H) |

TABLE 2-continued

| Ex. # | Structure | Name | LCMS NMR |
|---|---|---|---|
| 88 | 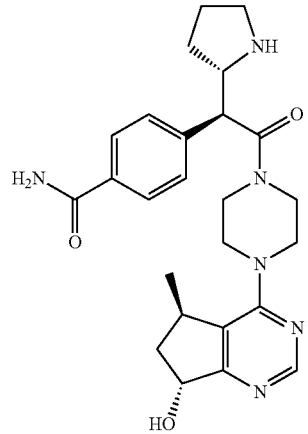 [SMILES: C[C@@H]1C[C@@H](O)c2ncnc(N3CCN(C(=O)[C@@H](c4ccc(C(N)=O)cc4)[C@@H]4CCCN4)CC3)c21] | 4-((S)-2-(4-((5R,7R)-7-hydroxy-5-methyl-6,7-dihydro-5H-cyclopenta[d]pyrimidin-4-yl)piperazin-1-yl)-2-oxo-1-((S)-pyrrolidin-2-yl)ethyl)benzamide | m/z 465.2; $^1$H NMR (500 MHz, DMSO-D6) d ppm 9.06 (m, 1H), 8.69 (m, 1H), 8.47 (s, 1H), 7.91 (d, J = 8.12 Hz, 2H), 7.46 (d, J = 8.14 Hz, 2H), 4.90 (m, 1H), 4.35 (m, 1H), 4.00 (m, 2H), 3.84-3.70 (m, 3H), 2.93 (m, 2H), 1.98-1.83 (m, 4H), 1.81-1.72 (m, 2H), 1.66-1.51 (m, 3H), 1.01 (d, 3H) |
| 89 | 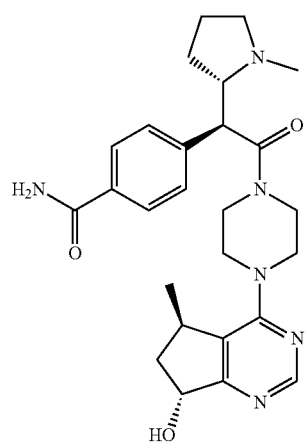 [SMILES: C[C@@H]1C[C@@H](O)c2ncnc(N3CCN(C(=O)[C@@H](c4ccc(C(N)=O)cc4)[C@@H]4CCCN4C)CC3)c21] | 4-((S)-2-(4-((5R,7R)-7-hydroxy-5-methyl-6,7-dihydro-5H-cyclopenta[d]pyrimidin-4-yl)piperazin-1-yl)-1-((S)--methylpyrrolidin-2-yl)-2-oxoethyl)benzamide | m/z 479.3; $^1$H NMR (500 MHz, DMSO-D6) d ppm 11.06 (m, 1H), 8.92 (m, 1H), 8.71 (s, 1H), 7.88 (d, J = 8.07 Hz, 2H), 7.47 (d, J = 8.00 Hz, 2H), 5.23 (m, 1H), 4.59 (m, 1H), 4.20-3.86 (m, 4H), 3.13 (m, 4H), 2.89 (s, 3H), 2.15-1.80 (m, 5H), 1.68-1.50 (m, 2H), 1.30-1.25 (m, 9H), 1.11-1.07 (m, 3H) |
| 90 | 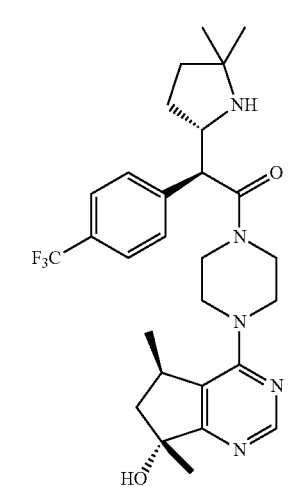 [SMILES: C[C@@H]1C[C@@](C)(O)c2ncnc(N3CCN(C(=O)[C@@H](c4ccc(C(F)(F)F)cc4)[C@@H]4CCC(C)(C)N4)CC3)c21] | (S)-2-((S)-5,5-dimethylpyrrolidin-2-yl)-1-(4-((5R,7R)-7-hydroxy-5,7-dimethyl-6,7-dihydro-5H-cyclopenta[d]pyrimidin-4-yl)piperazin-1-yl)-2-(4-(trifluoromethyl)phenyl)ethanone | m/z 532.3; $^1$H NMR (500 MHz, DMSO-D6) d ppm 8.85 (m, 1H), 8.58 (s, 1H), 8.50 (m, 1H), 7.81 (d, J = 8.15 Hz, 2H), 7.67 (d, J = 8.14 Hz, 2H), 4.48 (m, 1H), 4.21 (m, 2H), 2.90 (m, 2H), 2.31 (m, 1H), 1.81-1.64 (m, 5H), 1.42 (s, 3H), 1.38 (s, 3H), 1.36 (s, 3H), 1.09 (d, 3H) |

TABLE 2-continued

| Ex. # | Structure | Name | LCMS NMR |
|---|---|---|---|
| 91 | 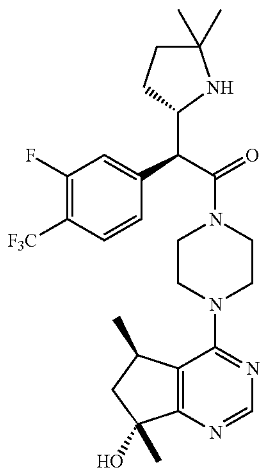 [SMILES: C[C@@H]1C[C@@](C)(O)c2ncnc(N3CCN(C(=O)[C@@H](c4ccc(C(F)(F)F)c(F)c4)[C@@H]4CCC(C)(C)N4)CC3)c21] | (S)-2-((S)-5,5-dimethylpyrrolidin-2-yl)-2-(3-fluoro-4-(trifluoromethyl)phenyl)-1-(4-((5R,7R)-7-hydroxy-5,7-dimethyl-6,7-dihydro-5H-cyclopenta[d]pyrimidin-4-yl)piperazin-1-yl)ethanone | m/z 550.3; $^1$H NMR (500 MHz, DMSO-D6) d ppm 8.85 (m, 1H), 8.58 (s, 1H), 8.48 (m, 1H), 7.86 (t, J = 7.86 Hz, 1H), 7.64 (d, J = 8.40 Hz, 1H), 7.47 (d, J = 8.54 Hz, 1H), 4.51 (m, 1H), 4.23 (m, 2H), 3.89 (m 2H), 3.10 (m, 2H), 2.31 (m, 1H), 1.78-1.67 (m, 5H), 1.42 (s, 3H), 1.38 (s, 3H), 1.36 (s, 3H), 1.11 (d, 3H) |
| 92 | 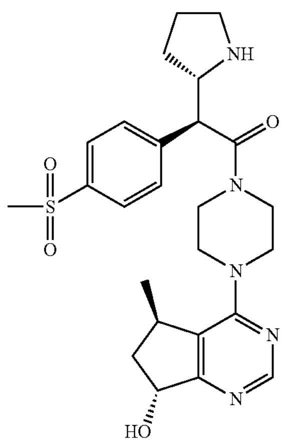 [SMILES: C[C@@H]1C[C@@H](O)c2ncnc(N3CCN(C(=O)[C@@H](c4ccc(S(C)(=O)=O)cc4)[C@@H]4CCCN4)CC3)c21] | (S)-1-(4-((5R,7R)-7-hydroxy-5-methyl-6,7-dihydro-5H-cyclopenta[d]pyrimidin-4-yl)piperazin-1-yl)-2-(4-(methylsulfonyl)phenyl)-2-((S)-pyrrolidin-2-yl)ethanone | $^1$H NMR (500 MHz, D$_2$O) d ppm 8.60 (s, 1H), 8.14 (d, J = 7.5 Hz, 2H), 7.79 (d, J = 7.5 Hz, 2H), 5.49 (t, J = 2.5 Hz, 1H), 4.63 (d, J = 9.5 Hz, 1H), 4.40-4.25 (m, 2H), 4.05-4.02 (m, 2H), 3.91-3.63 (m, 6H), 3.50-3.40 (m, 2H), 3.38 (s, 3H), 2.42-2.39 (m, 1H), 2.26-2.18 (m, 2H), 2.03-2.02 (m, 1 H), 1.92-1.89 (m, 2H), 1.27 (t, J = 7.0 Hz, 2H), 1.17 (d, J = 26.0 Hz, 3H); m/z: 500.3 |
| 93 | 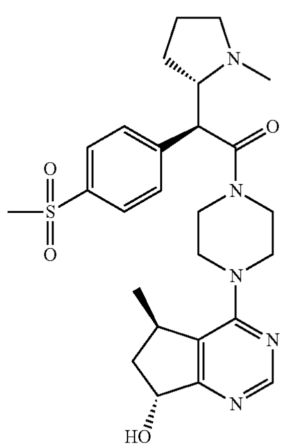 [SMILES: C[C@@H]1C[C@@H](O)c2ncnc(N3CCN(C(=O)[C@@H](c4ccc(S(C)(=O)=O)cc4)[C@@H]4CCCN4C)CC3)c21] | (S)-1-(4-((5R,7R)-7-hydroxy-5-methyl-6,7-dihydro-5H-cyclopenta[d]pyrimidin-4-yl)piperazin-1-yl)-2-((S)-1-methylpyrrolidin-2-yl)-2-(4-(methylsulfonyl)phenyl)ethanone | $^1$H NMR (500 MHz, DMSO-d6) d ppm 8.56 (s, 1H), 7.98 (d, J = 8.5 Hz, 2H), 7.65 (d, J = 8.5 Hz, 2H), 5.01 (t, J = 2.5 Hz, 1H), 4.59 (d, J = 9.5 Hz, 1H), 3.89-3.84 (m, 13H), 3.20 (s, 3H), 3.19-3.17 (m, 2H), 2.92 (d, J = 6.0 Hz, 2H), 2.01-1.96 (m, 3H), 1.77-1.72 (m, 1H), 1.57-1.52 (m, 1H), 1.04 (d, J = 7.0 Hz, 3H).; m/z: 514.3 |

TABLE 2-continued

| Ex. # | Structure | Name | LCMS NMR |
|---|---|---|---|
| 94 | 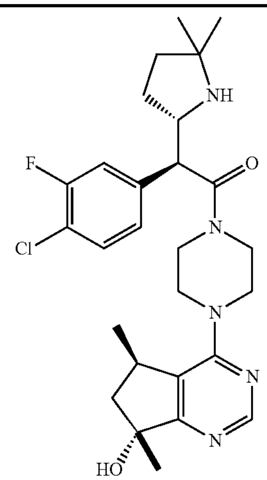 | (S)-2-(4-chloro-3-fluorophenyl)-2-((S)-5,5-dimethylpyrrolidin-2-yl)-1-(4-((5R,7R)-7-hydroxy-5,7-dimethyl-6,7-dihydro-5H-cyclopenta[d]pyrimidin-4-yl)piperazin-1-yl)ethanone | $^1$H NMR (500 MHz, DMSO-D6) d ppm 8.80 (m, 1H), 8.55 (s, 1H), 8.41 (m, 1H), 7.66 (t, J = 8.21 Hz, 1H), 7.52 (d, J = 8.41 Hz, 1H), 7.29 (d, J = 8.51 Hz, 1H), 4.38 (m, 1H), 4.19 (m, 2H), 3.88-3.74 (m 4H), 3.03 (m, 2H), 2.30 (m, 1H), 1.77-1.67 (m, 5H), 1.41 (s, 3H), 1.38 (s, 3H), 1.36 (s, 3H), 1.12 (d, 3H); m/z: 516.3 |
| 95 | 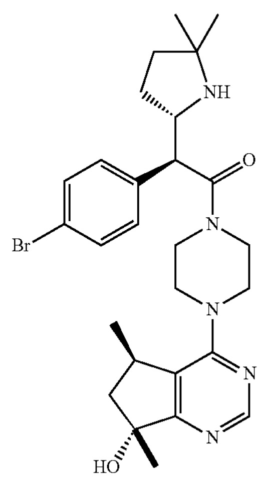 [SMILES: C[C@@H]1C[C@@](C)(O)c2ncnc(N3CCN(C(=O)[C@@H](c4ccc(Br)cc4)[C@@H]4CCC(C)(C)N4)CC3)c21] | (S)-2-(4-bromophenyl)-2-((S)-5,5-dimethylpyrrolidin-2-yl)-1-(4-((5R,7R)-7-hydroxy-5,7-dimethyl-6,7-dihydro-5H-cyclopenta[d]pyrimidin-4-yl)piperazin-1-yl)ethanone | $^1$H NMR (500 MHz, DMSO-D6) d ppm 8.78 (m, 1H), 8.55 (s, 1H), 8.39 (m, 1H), 7.62 (d, J = 8.49 Hz, 2H), 7.38 (d, J = 8.47 Hz, 2H), 4.32 (m, 1H), 4.16 (m, 2H), 3.89-3.76 (m, 4H), 2.28 (m, 1H), 1.81-1.64 (m, 5H), 1.41 (s, 3H), 1.38 (s, 3H), 1.36 (s, 3H), 1.12 (d, 3H); m/z: 542.2 |
| 96 | 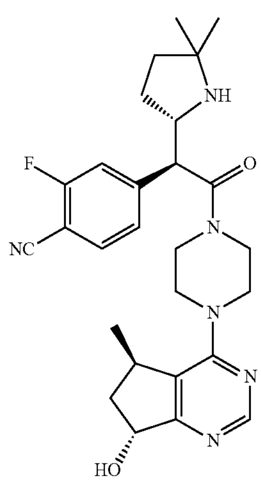 [SMILES: C[C@@H]1C[C@@H](O)c2ncnc(N3CCN(C(=O)[C@@H](c4ccc(C#N)c(F)c4)[C@@H]4CCC(C)(C)N4)CC3)c21] | 4-((S)-1-((S)-5,5-dimethylpyrrolidin-2-yl)-2-(4-((5R,7R)-7-hydroxy-5-methyl-6,7-dihydro-5H-cyclopenta[d]pyrimidin-4-yl)piperazin-1-yl)-2-oxoethyl)-2-fluorobenzonitrile | $^1$H NMR (500 MHz, DMSO-D6) d ppm 8.87 (m, 1H), 8.64 (s, 1H), 8.52 (m, 1H), 8.00 (t, J = 7.80 Hz, 1H), 7.62 (d, J = 8.45 Hz, 1H), 7.46 (d, J = 8.25 Hz, 1H), 5.13 (m, 1H), 4.49 (m, 2H), 4.22 (m 2H), 3.26 (m, 2H), 2.09-1.97 (m, 3H), 1.78-1.64 (m, 5H), 1.39 (s, 3H), 1.34 (s, 3H), 1.05 (d, 3H); m/z: 493.3; m/z: 493.3 |

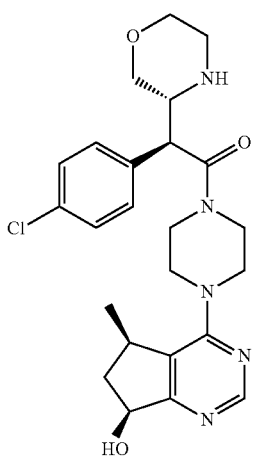 [SMILES: C[C@@H]1C[C@H](O)c2ncnc(N3CCN(C(=O)[C@@H](c4ccc(Cl)cc4)[C@@H]4COCCN4)CC3)c21]

(S)-2-(4-chlorophenyl)-1-(4-((5R,7S)-7-hydroxy-5-methyl-6,7-dihydro-5H-cyclopenta[d]pyrimidin-4-yl)piperazin-1-yl)-2-((R)-morpholin-3-yl)ethanone Step 1:

tert-Butyl 3-oxomorpholine-4-carboxylate (8.65 g, 43.0 mmol; prepared as described in Chandrakumar, N. S.; et al.; J Med Chem 35:2928 (1992)) was dissolved in Et$_2$O (45 mL) and cooled to −78° C. The solution was treated dropwise with DIBAL-H (1.5M solution in toluene; 29.2 mL, 43.8 mmol), and the mixture was stirred at −78° C. for 90 minutes. The mixture was then warmed to ambient temperature and stirred overnight. The reaction was quenched with saturated NH$_4$Cl (50 mL) and stirred for 20 minutes. The reaction was diluted with ethyl acetate (100 mL) and Rochelle's salt (50 mL of 0.5N solution) and then stirred for 20 minutes. Additional Rochelle's salt (75 mL, 0.5N) was added, and then the reaction was stirred for 20 minutes and separated. The aqueous portion was washed with ethyl acetate (2×). Then the combined organics were washed twice with Rochelle's salt (0.5 N), saturated NaHCO$_3$, saturated NaCl, dried over Na$_2$SO$_4$ and concentrated to an oil, tert-butyl 3-hydroxymorpholine-4-carboxylate (7.0 g, 80%).

Step 2:

tert-Butyl 3-hydroxymorpholine-4-carboxylate (7.0 g, 34.4 mmol) was dissolved in MeOH (65 mL) and treated with p-toluenesulfonic acid hydrate (0.65 g, 3.4 mmol). The reaction was stirred for 40 hours at ambient temperature. The reaction mixture was concentrated in vacuo. The resulting residue was then dissolved in ethyl acetate and washed with 10% Na$_2$CO$_3$ (2×), saturated NaCl, dried over Na$_2$SO$_4$ and concentrated in vacuo to an oil, tert-butyl 3-methoxymorpholine-4-carboxylate (5.85 g, 78%). $^1$H NMR (CDCl$_3$, 400 MHz) δ 4.00-3.91 (m, 2H), 3.81-3.58 (m, 1H), 3.58-3.46 (m, 2H), 3.38-3.21 (m, 2H), 3.32 (s, 3H), 1.49 (s, 9H).

Step 3:

A solution of titanium (IV) chloride (2.00 mL, 2.00 mmol; 1M in toluene) was cooled to 0° C. and treated with a solution of (R)-4-benzyl-3-(2-(4-chlorophenyl)acetyl)oxazolidin-2-one (0.60 g, 1.82 mmol) dissolved in dichloromethane (3.5 mL). After 5 minutes, diisopropylethylamine (0.348 mL, 2.00 mmol) was added. The resulting solution was stirred for 1 hour at 0° C. and then cooled to −20° C. A solution of tert-butyl 3-methoxymorpholine-4-carboxylate (0.592 g, 2.72 mmol) dissolved in dichloromethane (3.5 mL) was added, and the mixture was stirred at −20° C. for 15 minutes. The reaction was then warmed to 0° C. The reaction was allowed to warm slowly to 10° C. in a bath over 3 hours. The reaction was quenched with saturated NH$_4$Cl (about 4 mL) and diluted with water to dissolve the solids. After separation, the aqueous portion was washed with methylene chloride (3×). The combined organics were washed with water (2×), dried over Na$_2$SO$_4$ and concentrated in vacuo. The crude product was subjected to chromatography on SiO$_2$ eluting with a gradient from 10 to 25% ethyl acetate/hexanes. (R)-tert-Butyl 3-((S)-2-((R)-4-benzyl-2-oxooxazolidin-3-yl)-1-(4-chlorophenyl)-2-oxoethyl)morpholine-4-carboxylate was recovered as a foam (0.607 g, 65%). MS (APCI+) [M+H] 514.7/516.8.

Step 4:

Lithium hydroxide hydrate (0.098 g, 2.3 mmol) was dissolved in water (28 mL), cooled to 0° C. and diluted with THF (83 mL). The solution was treated with 30% hydrogen peroxide (0.48 mL, 4.7 mmol) and stirred for 10 minutes. A solution of (R)-tert-butyl 3-((S)-2-((R)-4-benzyl-2-oxooxazolidin-3-yl)-1-(4-chlorophenyl)-2-oxoethyl)morpholine-4-carboxylate (0.607 g, 1.17 mmol) dissolved in THF (3 mL) was added. The reaction mixture was allowed to warm to ambient temperature in a bath and stirred for 20 hours. The reaction was quenched with Na$_2$SO$_3$ (about 7 mL, 1.5M) until the reaction mixture was negative to starch-iodine test paper. The reaction was then concentrated in vacuo. The aqueous layer was extracted with ethyl acetate (2×). The aqueous layer was adjusted to a pH of about 1 to about 2 with 3N HCl and extracted with ethyl acetate (3×). The final ethyl acetate extracts were dried over Na$_2$SO$_4$ and concentrated in vacuo to a solid, (S)-2-((R)-4-(tert-butoxycarbonyl)morpholin-3-yl)-2-(4-chlorophenyl)acetic acid (310 mg, 74%). MS (APCI+) [M+H-Boc] 256.0/258.0

Step 5:

(S)-2-((R)-4-(tert-Butoxycarbonyl)morpholin-3-yl)-2-(4-chlorophenyl)acetic acid (0.051 g, 0.143 mmol) was combined with (5R,7S)-5-methyl-4-(piperazin-1-yl)-6,7-dihydro-5H-cyclopenta[d]pyrimidin-7-ol dihydrochloride (0.0440 g, 0.143 mmol), and then slurried in methylene chloride (1.4 mL). The suspension was treated with diisopropylethylamine (0.0749 mL, 0.430 mmol) and then with HBTU (0.0544 g, 0.143 mmol). The mixture was then stirred at ambient temperature for 60 hours. The reaction was quenched with 10% Na$_2$CO$_3$ and separated. The reaction mixture was washed with methylene chloride (3×), and the combined organics were then dried with Na$_2$SO$_4$ and concentrated in vacuo. The resulting residue was subjected to chromatography on SiO$_2$ (Biotage 12M) eluting with methylene chloride (96 mL) then 0% to 5% MeOH/methylene chloride (500 mL) and 5% MeOH/methylene chloride (96 mL). The desired material eluted cleanly in approximately 1% MeOH/methylene chloride to yield (R)-tert-butyl 3-((S)-1-(4-chlorophenyl)-2-(4-((5R,7S)-7-hydroxy-5-methyl-6,7-dihydro-5H-cyclopenta[d]pyrimidin-4-yl)piperazin-1-yl)-2-oxoethyl)morpholine-4-carboxylate as an oil. (81.2 mg, 99%).

Step 6:

(R)-tert-Butyl 3-((S)-1-(4-chlorophenyl)-2-(4-((5R,7S)-7-hydroxy-5-methyl-6,7-dihydro-5H-cyclopenta[d]pyrimidin-4-yl)piperazin-1-yl)-2-oxoethyl)morpholine-4-carboxylate (0.0389 g, 0.0680 mmol) was dissolved in dioxane (1 mL) and treated with 4M hydrogen chloride in dioxane (0.425 mL, 1.70 mmol). The solution was stirred at ambient temperature overnight. The reaction was concentrated in vacuo, resuspended in dioxane and concentrated in vacuo. The residue was concentrated from MeOH (3 times) and then dissolved in MeOH. The solution was then added dropwise to Et$_2$O to afford (S)-2-(4-chlorophenyl)-1-(4-((5R,7S)-7-hydroxy-5-methyl-6,7-dihydro-5H-cyclopenta[d]pyrimidin-4-yl)piperazin-1-yl)-2-((R)-morpholin-3-yl)ethanone dihydrochloride (20 mg, 54%). m/z 472.1/474.0; $^1$H NMR (400 MHz, CD$_3$OD) δ ppm 8.57 (s, 1H), 7.48 (d, 2H), 7.40 (d, 2H), 5.13-5.07 (m, 1H), 4.50 (d, 1H), 4.15-4.05 (m, 1H), 4.01-3.55 (m, 13H), 3.53-3.39 (m, 1H), 2.83-2.73 (m, 1H), 1.65-1.56 (m, 1H), 1.23 (d, 3H).

Examples 98-100 shown in Table 3 can also be made according to the above described methods.

TABLE 3

| Ex. # | Structure | Name | LCMS NMR |
|---|---|---|---|
| 98 | 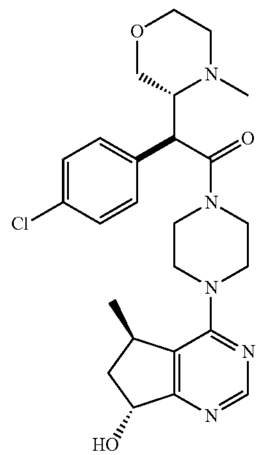 [SMILES: C[C@@H]1C[C@@H](O)c2ncnc(N3CCN(C(=O)[C@@H](c4ccc(Cl)cc4)[C@@H]4COCCN4C)CC3)c21] | (S)-2-(4-chlorophenyl)-1-(4-((5R,7S)-7-hydroxy-5-methyl-6,7-dihydro-5H-cyclopenta[d]pyrimidin-4-yl)piperazin-1-yl)-2-((R)-4-methylmorpholin-3-yl)ethanone | m/z 486.1/488.0; $^1$H NMR (400 MHz, CD$_3$OD) d ppm 8.57 (s, 1H), 7.51-7.36 (m, 4H), 5.29 (t, 1H), 4.25-4.13 (m, 1H), 4.13-3.35 (m, 9H), 3.22-2.96 (m, 3H), 2.33-2.25 (m, 1H), 2.23-2.13 (m, 1H), 1.18 (d, 3H) |
| 99 | 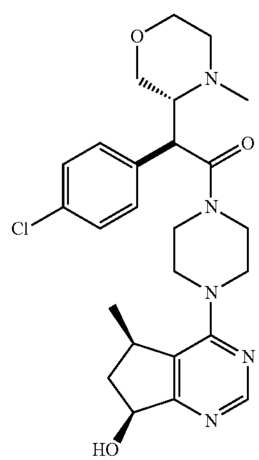 [SMILES: C[C@@H]1C[C@H](O)c2ncnc(N3CCN(C(=O)[C@@H](c4ccc(Cl)cc4)[C@@H]4COCCN4C)CC3)c21] | (S)-2-(4-chlorophenyl)-1-(4-((5R,7S)-7-hydroxy-5-methyl-6,7-dihydro-5H-cyclopenta[d]pyrimidin-4-yl)piperazin-1-yl)-2-((R)-4-methylmorpholin-3-yl)ethanone | m/z 486.1/488.0; $^1$H NMR (400 MHz, CD$_3$OD) d ppm 8.58 (s, 1H), 7.51-7.35 (dd, 4H), 5.13-5.10 (m, 1H), 4.26-4.14 (m, 1H), 4.09-3.61 (m, 7H), 3.61-3.34 (m, 3H), 3.22-2.96 (m, 3H), 2.84-2.74 (m, 1H), 1.65-1.57 (m, 1H), 1.23 (d, 3H) |
| 100 | 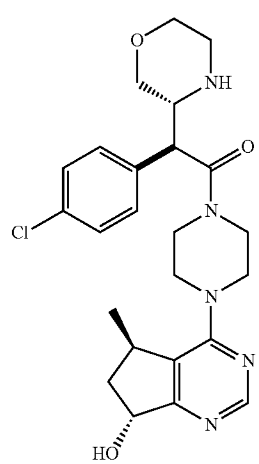 | (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((R)-morpholin-3-yl)ethanone | m/z 472.1/474.1; $^1$H NMR (400 MHz, CD$_3$OD) d ppm 8.56 (s, 1H), 7.48 (d, 2H), 7.41 (d, 2H), 5.28 (t, 1H), 4.51 (d, 1H), 4.18-4.07 (m, 1H), 4.03-3.73 (m, 7H), 3.73-3.56 (m, 4H), 3.53-3.41 (m, 1H), 3.41-3.20 (m, 2H), 2.33-2.24 (m, 1H), 2.23-2.13 (m, 1H), 1.18 (d, 3H) |

133

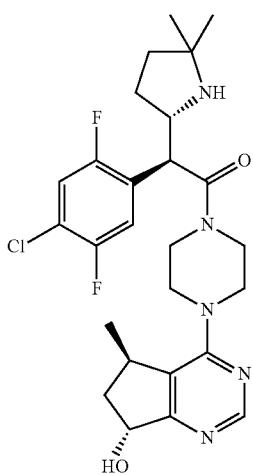 [SMILES: C[C@@H]1C[C@@H](O)c2ncnc(N3CCN(C(=O)[C@@H](c4cc(F)c(Cl)cc4F)[C@@H]4CCC(C)(C)N4)CC3)c21]

(S)-2-(4-chloro-2,5-difluorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone Step 1:
Trifluoromethanesulfonic acid (9.9 mL, 110 mmol) was added to 2-chloro-1,4-difluorobenzene (2.2 g, 15 mmol) at room temperature and then cooled to 0° C. N-Iodosuccinimide (3.16 g, 14.1 mmol) was then added in multiple portions. After 10 minutes, the reaction mixture was allowed to warm to room temperature and stirred for 2 hours. The reaction mixture was poured over ice-water and extracted with hexane. The organic layer was washed with saturated $Na_2SO_4$, dried and concentrated. The crude product was purified by silica gel chromatography (100% hexanes) to give 1-chloro-2,5-difluoro-4-iodobenzene (3.0 g, 74%). $^1$H NMR (400 MHz, $CDCl_3$) δ 7.52 (dd, J=5.4, 7.8, 1H), 7.17-7.08 (m, 1H).

Step 2:
Copper(I) iodide (69.4 mg, 0.364 mmol), 2-phenylphenol (93.0 mg, 0.546 mmol) and cesium carbonate (1.78 g, 5.46 mmol) were added to a dry flask under nitrogen. Ethyl malonate (1.11 mL, 7.29 mmol) was added to the mixture, followed by 1-chloro-2,5-difluoro-4-iodobenzene (1.00 g, 3.64 mmol) in tetrahydrofuran (3.64 mL, 44.9 mmol). The reaction mixture was sealed and heated to 90° C. After 12 hours, the reaction mixture was allowed to cool to room temperature and then diluted with saturated $NH_4Cl$ and EtOAc. The organic layer was separated, dried and filtered through Celite. The brown oil was purified via silica gel chromatography (0-30% EtOAc-hexane) to give diethyl 2-(4-chloro-2,5-difluorophenyl)malonate (0.65 g, 58%). $^1$H NMR (400 MHz, $CDCl_3$) δ 7.37 (dd, J=6.3, 9.3, 1H), 7.17 (dd, J=6.1, 8.9, 1H), 4.91 (s, 1H), 4.33-4.14 (m, 4H), 1.28 (t, J=7.2, 6H).

Step 3:
Diethyl 2-(4-chloro-2,5-difluorophenyl)malonate (330 mg, 1.08 mmol) was dissolved in EtOH (1 mL), and then NaOH (0.6 mL, 5N) was added. The resulting solution was stirred at ambient for 12 hours. At this time, the reaction mixture was heated to 60° C. for 3 hours, after which it was acidified to a pH of 1 with HCl (1N). The reaction was diluted with water (1 mL) and then extracted twice with diethyl ether. The combined organics were dried over magnesium sulfate, filtered and concentrated to give 2-(4-chloro-2,5-difluorophenyl)acetic acid which was used without further purification.

134

Step 4:
(S)-2-((S)-1-(tert-butoxycarbonyl)-5,5-dimethylpyrrolidin-2-yl)-2-(4-chloro-2,5-difluorophenyl)acetic acid was prepared as described in Example B, Steps 1-3, starting with 2-(4-chloro-2,5-difluorophenyl)acetic acid.

Step 5:
(S)-2-(4-Chloro-2,5-difluorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone was prepared as described in Example 1, Step 5, using (S)-2-4S)-1-(tert-butoxycarbonyl)-5,5-dimethylpyrrolidin-2-yl)-2-(4-chloro-2,5-difluorophenyl)acetic acid. $^1$H NMR (400 MHz, $D_2O$) δ 8.37 (s, 1H), 7.37 (dd, J=6.2, 9.2, 1H), 7.16-7.08 (m, 1H), 5.24 (t, J=7.9, 1H), 4.49 (d, J=9.1, 1H), 4.25-4.13 (m, 1H), 4.11-3.99 (m, 1H), 3.85-3.66 (m, J=19.2, 3H), 3.64-3.29 (m, 4H), 2.23-2.13 (m, 1H), 2.08-1.96 (m, J=13.2, 1H), 1.93-1.71 (m, 4H), 1.37 (s, 3H), 1.31 (s, 3H), 1.20 (d, J=5.9, 3H), 0.98 (d, J=7.0, 3H).

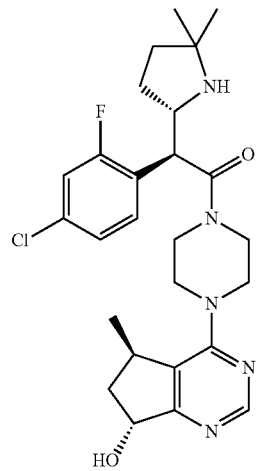 [SMILES: C[C@@H]1C[C@@H](O)c2ncnc(N3CCN(C(=O)[C@@H](c4ccc(Cl)cc4F)[C@@H]4CCC(C)(C)N4)CC3)c21]

(S)-2-(4-chloro-2-fluorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone Step 1:
(5R,7R)-5-Methyl-4-(piperazin-1-yl)-6,7-dihydro-5H-cyclopenta[d]pyrimidin-7-ol dihydrochloride (0.109 g, 0.356 mmol; see Example 3, Step 12), HATU (0.123 g, 0.324 mmol), and collidine (0.171 mL, 1.30 mmol) were added to a solution of (S)-2-((S)-1-(tert-butoxycarbonyl)-5,5-dimethylpyrrolidin-2-yl)-2-(4-chloro-2-fluorophenyl)acetic acid (0.125 g, 0.324 mmol; prepared analogously to that described in Example B) in DCM (25 mL). The reaction was stirred overnight at room temperature. The reaction was partitioned between water (20 mL) and DCM (50 mL), and the layers were separated. The organics were washed with water (2×10 mL). The aqueous portion was back extracted with DCM (25 mL), dried ($MgSO_4$) and concentrated to an oil that was purified by flash chromatography (5% MeOH/DCM) to give (S)-tert-butyl 5-((S)-1-(4-chloro-2-fluorophenyl)-2-(4-((5R,7R)-7-hydroxy-5-methyl-6,7-dihydro-5H-cyclopenta[d]pyrimidin-4-yl)piperazin-1-yl)-2-oxoethyl)-2,2-dimethylpyrrolidine-1-carboxylate (0.116 g, 0.193 mmol, 59.5% yield). LC/MS=3.79 minutes, (APCI+) m/z=602 [M+H]+.

Step 2:

4N HCl in dioxane (3 mL, 0.191 mmol) was added to a solution of (S)-tert-butyl 5-((S)-1-(4-chloro-2-fluorophenyl)-2-(4-((5R,7R)-7-hydroxy-5-methyl-6,7-dihydro-5H-cyclopenta[d]pyrimidin-4-yl)piperazin-1-yl)-2-oxoethyl)-2,2-dimethylpyrrolidine-1-carboxylate (0.115 g, 0.191 mmol) in dry DCM (30 mL) and stirred at room temperature for 2 hours. The reaction was concentrated to dryness to reveal (S)-2-(4-chloro-2-fluorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone dihydrochloride (0.093 g, 0.162 mmol, 84.7% yield). HPLC, 220 nM=1.93 minutes, 100% purity. LC/MS=2.22 minutes, (APCI+) m/z=502 [M+H]+. $^1$H NMR (400 MHz, D$_2$O) 8.38 (s, 1H), 7.27 (d, J=10.54 Hz, 1H), 7.21-7.15 (m, 2H), 5.22 (t, J=7.81 Hz, 1H), 4.43 (d, J=8.98 Hz, 1H), 4.19 (dd, J1=8.59 Hz, J2=14.8 Hz, 1H), 4.15-4.05 (m, 1H), 3.87-3.75 (m, 2H), 3.74-3.46 (m, 5H), 3.42 (q, J=7.03 Hz, 2H), 3.39-3.25 (m, 2H), 2.19 (dd, J1=7.08 Hz, J2=13.27 Hz, 1H), 2.07-1.97 (m, 1H), 1.90-1.72 (m, 4H), 1.36 (s, 3H), 1.31 (s, 3H), 1.04 (t, J=7.03 Hz, 2H), 0.97 (d, J=7.03 Hz, 3H).

Step 2:

4.0M HCl/Dioxane (0.121 mL, 0.483 mmol) was added to a solution of (S)-tert-butyl 5-((S)-1-(4-bromo-2-fluorophenyl)-2-(4-((5R,7R)-7-hydroxy-5-methyl-6,7-dihydro-5H-cyclopenta[d]pyrimidin-4-yl)piperazin-1-yl)-2-oxoethyl)-2,2-dimethylpyrrolidine-1-carboxylate (0.104 g, 0.161 mmol) in DCM (1 mL). The solution stirred overnight, and the solvent was removed to yield (S)-2-(4-bromo-2-fluorophenyl)-2-((R)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone dihydrochloride (0.0618 g, 0.0998 mmol, 62.0% yield). HPLC, 254 nm=1.988 minutes, 99.66% purity, LCMS (APCI+) 547.7 m/z [M+H]+; Retention time=2.45 minutes. $^1$H NMR (400 MHz, D$_2$O) 8.58 (s, 1H), 7.54 (dd, J1=1.952 Hz, J2=9.761 Hz, 1H), 7.46 (dd, J1=1.562 Hz, J2=8.199 Hz, 1H), 7.35 (t, J=7.809 Hz, 1H), 5.32 (t, J=8.199 Hz, 1H), 4.79 (d, J=9.761 Hz, 1H), 4.40-4.31 (m, 1H), 4.0-3.9 (m, 2H), 3.82-3.62 (m, 3H), 2.30-2.28 (m, 1H), 2.27-2.15 (m, 1H), 2.02-1.84 (m, 4H), 1.58 (s, 3H), 1.44 (s, 3H), 1.29 (d, J=6.637 Hz, 3H).

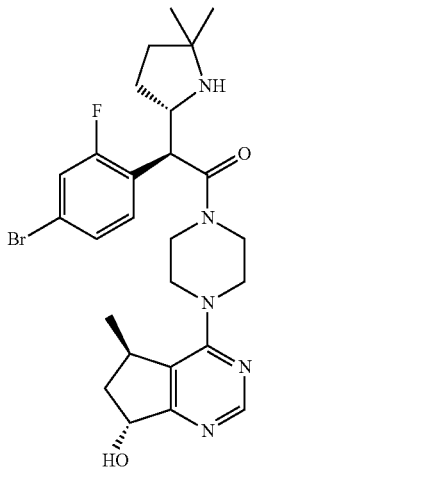

(S)-2-(4-bromo-2-fluorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone

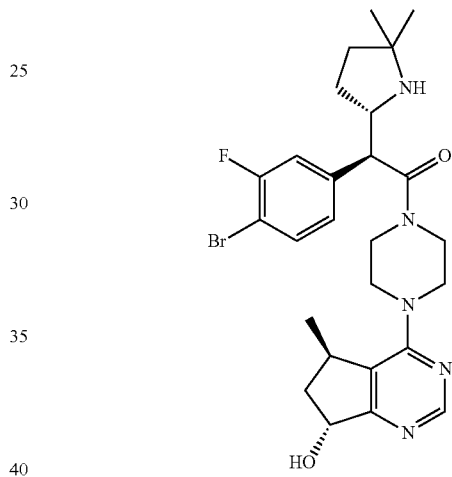

(S)-2-(4-bromo-3-fluorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone Step 1:

HATU (0.149 g, 0.391 mmol) was added to a solution of (R)-2-(4-bromo-2-fluorophenyl)-2-((S)-1-(tert-butoxycarbonyl)-5,5-dimethylpyrrolidin-2-yl)acetic acid (0.168 g, 0.391 mmol; prepared analogously to that described in Example B), (5R,7R)-5-methyl-4-(piperazin-1-yl)-6,7-dihydro-5H-cyclopenta[d]pyrimidin-7-ol dihydrochloride (0.1 g, 0.326 mmol; see Example 3, Step 12), and N-ethyl-N-isopropylpropan-2-amine (0.171 mL, 0.977 mmol) in DCM (8 mL), and the reaction mixture was stirred overnight at room temperature. The reaction was then quenched with H$_2$O. The reaction was washed with H$_2$O (3×30 mL). The organic layer was dried with MgSO$_4$, filtered and concentrated. Purification by flash chromatography yielded (S)-tert-butyl 5-((S)-1-(4-bromo-2-fluorophenyl)-2-(4-((5R,7R)-7-hydroxy-5-methyl-6,7-dihydro-5H-cyclopenta[d]pyrimidin-4-yl)piperazin-1-yl)-2-oxoethyl)-2,2-dimethylpyrrolidine-1-carboxylate (0.0334 g, 0.0517 mmol, 15.9% yield). LCMS (APCI+) 646.4, 648.5 m/z [M+H]+; Retention time=4.25 minutes.

Step 1:

N-Ethyl-N-isopropylpropan-2-amine (0.045 mL, 0.26 mmol) was added to a solution of (S)-2-(4-bromo-3-fluorophenyl)-2-((S)-1-(tert-butoxycarbonyl)-5,5-dimethylpyrrolidin-2-yl)acetic acid (0.035 g, 0.081 mmol; prepared analogously to that described in Example B), (5R,7R)-5-methyl-4-(piperazin-1-yl)-6,7-dihydro-5H-cyclopenta[d]pyrimidin-7-ol dihydrochloride (0.025 g, 0.081 mmol; see Example 3, Step 12), and 2-(3H-[1,2,3]triazolo[4,5-b]pyridin-3-yl)-1,1,3,3-tetramethylisouronium hexafluorophosphate(V) (0.031 g, 0.081 mmol) in DCM (5 mL). The reaction was stirred overnight at room temperature. The reaction was then quenched with H$_2$O, washed with H$_2$O (3×30 mL), dried with MgSO$_4$, filtered and concentrated. The resulting residue was purified by flash chromatography to give (S)-tert-butyl 5-((S)-1-(4-bromo-3-fluorophenyl)-2-(4-((5R,7R)-7-hydroxy-5-methyl-6,7-dihydro-5H-cyclopenta[d]pyrimidin-4-yl)piperazin-1-yl)-2-oxoethyl)-2,2-dimethylpyrrolidine-1-carboxylate (23% yield). LCMS (APCI+) 648.2 m/z [M+H]+; Retention time=4.28 minutes.

Step 2:

4.0M HCl in dioxanes (1.5 mL) was added to a solution of (S)-tert-butyl 5-((S)-1-(4-bromo-3-fluorophenyl)-2-(4-((5R,7R)-7-hydroxy-5-methyl-6,7-dihydro-5H-cyclopenta[d]pyrimidin-4-yl)piperazin-1-yl)-2-oxoethyl)-2,2-dimethylpyrrolidine-1-carboxylate (0.012 g, 0.0186 mmol) in DCM (5 mL). This solution was stirred at room temperature overnight, and then the solvent was removed to yield (S)-2-(4-bromo-3-fluorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone dihydrochloride (0.00367 g, 0.00593 mmol, 31.9% yield). HPLC, 254 nm=1.99 minutes, 96.93% purity, LCMS (APCI+) 548.3 m/z [M+H]+; Retention time=2.56 minutes, $^1$H NMR (400 MHz, CD$_3$OD) 8.59 (s, 1H), 7.71 (t, J=7.418 Hz, 1H), 7.39 (dd, J1=1.562 Hz, J2=9.761 Hz, 1H), 7.22 (d, J=7.418 Hz, 1H), 5.30 (t, J=7.809 Hz, 1H), 4.53 (d, J=9.371 Hz, 1H), 3.81-3.65 (m, 6H), 2.30 (dd, J1=7.809 Hz, J2=12.884 Hz, 1H), 2.21-2.15 (m, 1H), 2.02-1.85 (m, 4H), 1.55 (s, 3H), 1.45 (s, 3H), 1.19 (d, J=7.028 Hz, 3H).

Step 2:

4M HCl in dioxane (6 mL, 24 mmol) was added to a solution of (S)-tert-butyl 5-((S)-1-(3-chlorophenyl)-2-(4-((5R,7R)-7-hydroxy-5-methyl-6,7-dihydro-5H-cyclopenta[d]pyrimidin-4-yl)piperazin-1-yl)-2-oxoethyl)-2,2-dimethylpyrrolidine-1-carboxylate (0.020 g, 0.034 mmol) in dry DCM (15 mL) and stirred overnight. The solvent was evaporated to dryness to reveal (S)-2-(3-chlorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone dihydrochloride (0.015 g, 0.027 mmol, 79% yield). HPLC, 220 nm, retention time=1.91 minutes, 92% purity. LC/MS, retention time=2.15 minutes, (APCI+) m/z=484 [M+H]+. $^1$H NMR (400 MHz, D$_2$O) 8.35 (s, 1H), 7.35-7.28 (m, 3H), 7.25-7.15 (m, 1H), 5.22 (t, J=8.20 Hz, 1H), 4.28-4.00 (m, 2H), 3.88-3.71 (m, 1H), 3.67-3.55 (m, 1H), 3.55-3.42 (m, 4H), 3.36-3.05 (m, 1H), 2.16 (dd, J1=7.81 Hz, J2=13.27 Hz, 1H), 2.10-1.93 (m, 1H), 1.88-1.70 (m, 4H), 1.36 (s, 3H), 1.30 (s, 3H), 0.94 (d, J=7.03 Hz, 3H).

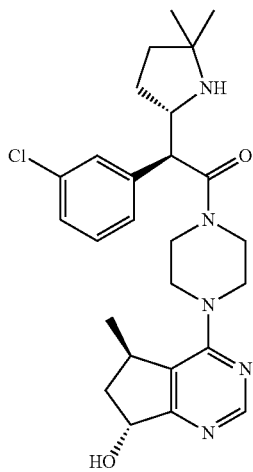 [SMILES: C[C@@H]1C[C@@H](O)c2ncnc(N3CCN(C(=O)[C@@H](c4cccc(Cl)c4)[C@@H]4CCC(C)(C)N4)CC3)c21]

(S)-2-(3-chlorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone Step 1:

(5R,7R)-5-methyl-4-(piperazin-1-yl)-6,7-dihydro-5H-cyclopenta[d]pyrimidin-7-ol dihydrochloride (0.0661 g, 0.215 mmol), HATU (0.0744 g, 0.196 mmol), and DIEA (d 0.742; 0.0341 mL, 0.196 mmol) were added to a solution of (S)-2-((S)-1-(tert-butoxycarbonyl)-5,5-dimethylpyrrolidin-2-yl)-2-(3-chlorophenyl)acetic acid (0.072 g, 0.196 mmol, see Example B, Step 3) in DCM (25 mL). The reaction was stirred overnight at room temperature. The reaction was partitioned between water (20 mL) and DCM (50 mL), and the layers were separated. The organics were washed with water (2×10 mL). The aqueous portion was back extracted with DCM (25 mL), dried (MgSO$_4$), concentrated to an oil and purified by flash chromatography (5% MeOH/DCM) to give (S)-tert-butyl 5-((S)-1-(3-chlorophenyl)-2-(4-((5R,7R)-7-hydroxy-5-methyl-6,7-dihydro-5H-cyclopenta[d]pyrimidin-4-yl)piperazin-1-yl)-2-oxoethyl)-2,2-dimethylpyrrolidine-1-carboxylate (0.090 g, 0.154 mmol, 78.7% yield). LC/MS=3.79 minutes, (APCI+) m/z=584 [M+H]+.

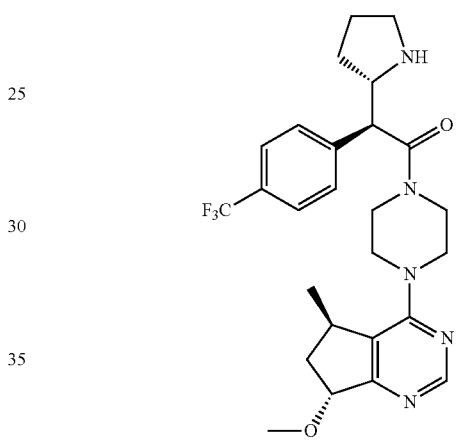

(S)-1-(4-((5R,7R)-7-methoxy-5-methyl-6,7-dihydro-5H-cyclopenta[d]pyrimidin-4-yl)piperazin-1-yl)-2-((S)-pyrrolidin-2-yl)-2-(4-(trifluoromethyl)phenyl)ethanone Step 1:

A solution of tert-butyl 4-((5R,7R)-7-hydroxy-5-methyl-6,7-dihydro-5H-cyclopenta[d]pyrimidin-4-yl)piperazine-1-carboxylate in DMF (2 mL) was added dropwise to a suspension of NaH (50 mg, 1.98 mmol) in DMF (5 mL) at 0° C. A solution of methyl iodide (700 mg, 5 mmol) in DMF (1 mL) was then added dropwise. The reaction mixture was stirred at 0° C. for 1 hour. The reaction was quenched with ice/saturated NH$_4$Cl, extracted with DCM (2×10 mL). The combined organics were dried (Na$_2$SO$_4$), filtered and concentrated to afford tert-butyl 4-((5R,7R)-7-methoxy-5-methyl-6,7-dihydro-5H-cyclopenta[d]pyrimidin-4-yl)piperazine-1-carboxylate as an oil, which was used without purification. MS (APCI+) [M+H]+ 349.0. This material was used to prepare the title compound as described analogously in Example 3, Steps 12-14, substituting the appropriate starting materials. m/z 504.3; $^1$H NMR (400 MHz, D$_2$O) d ppm 8.49 (s, 1H), 7.81 (d, J=8.4 Hz, 2H), 7.58 (d, J=8.4 Hz, 2H), 5.16 (t, J=7.6 Hz, 1H), 4.49-3.61 (m, 10H), 3.47 (s, 3H), 3.38-3.33 (m, 3H), 2.37-1.78 (m, 6H), 1.36-1.32 (m, 2H), 1.08 (d, J=6.8 Hz, 3H).

Examples 107-141 shown in Table 4 can also be made according to the above described methods.

TABLE 4

| Ex. # | Structure | Name | LCMS NMR |
|---|---|---|---|
| 107 | 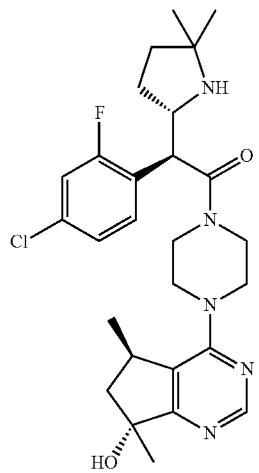 | (S)-2-(4-chloro-2-fluorophenyl)-2-((S)-5,5-dimethylpyrrolidin-2-yl)-1-(4-((5R,7R)-7-hydroxy-5,7-dimethyl-6,7-dihydro-5H-cyclopenta[d]pyrimidin-4-yl)piperazin-1-yl)ethanone dihydrochloride | LC/MS = 3.89 minutes, (APCI+) m/z = 616 [M + H]+ |
| 108 | 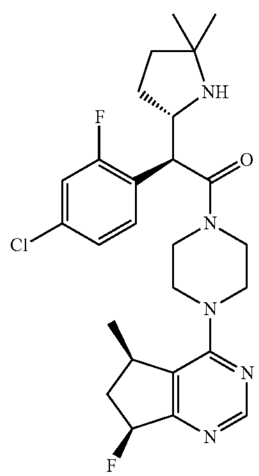 [SMILES: C[C@@H]1C[C@H](F)c2ncnc(N3CCN(C(=O)[C@@H](c4ccc(Cl)cc4F)[C@@H]4CCC(C)(C)N4)CC3)c21] | (S)-2-(4-chloro-2-fluorophenyl)-2-((S)-5,5-dimethylpyrrolidin-2-yl)-1-(4-((5R,7S)-7-fluoro-5-methyl-6,7-dihydro-5H-cyclopenta[d]pyrimidin-4-yl)piperazin-1-yl)ethanone dihydrochloride | HPLC, 220 nm, 100% purity = 2.22 minutes, LC/MS = 2.42 minutes, (APCI+) HPLC, 220 nm, 100% purity, r.t. = 2.22 min. LC/MS, r.t. = 2.42 min, (APCI+) m/z = 504 [M + H]+ = 504 [M + H]+ |
| 109 | 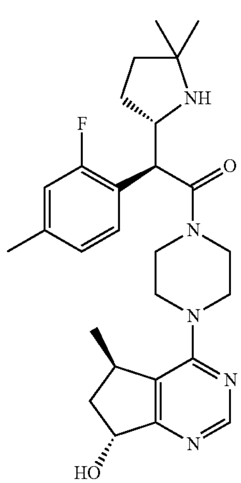 [SMILES: Cc1ccc([C@H](C(=O)N2CCN(c3ncnc4c3[C@H](C)C[C@H]4O)CC2)[C@@H]2CCC(C)(C)N2)c(F)c1] | (S)-2-((S)-5,5-dimethylpyrrolidin-2-yl)-2-(2-fluoro-4-methylphenyl)-1-(4-((5R,7R)-7-hydroxy-5-methyl-6,7-dihydro-5H-cyclopenta[d]pyrimidin-4-yl)piperazin-1-yl)ethanone dihydrochloride | HPLC, 220 nM = 1.95 minutes, 99.6% purity, LC/MS = 2.12 minutes, (APCI+) m/z = 482 [M + H]+ |

TABLE 4-continued

| Ex. # | Structure | Name | LCMS NMR |
|---|---|---|---|
| 110 | 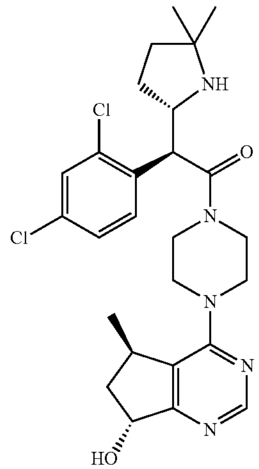 | (S)-2-(2,4-dichlorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone dihydrochloride | HPLC, 254 nm = 2.05 minutes, 95.6% purity, LC/MS = 2.23 minutes, (APCI+) m/z = 518 [M + H]+ |
| 111 | 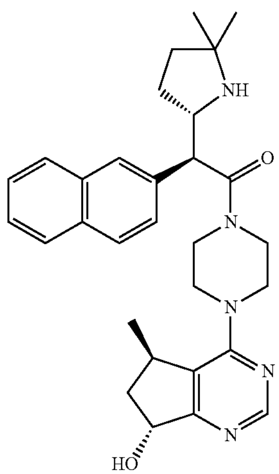 | (S)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)-2-(naphthalen-2-yl)ethanone dihydrochloride | HPLC, 220 nm = 1.98 minutes, 100% purity, LC/MS = 2.28 minutes, (APCI+) m/z = 500 [M + H]+ |
| 112 | 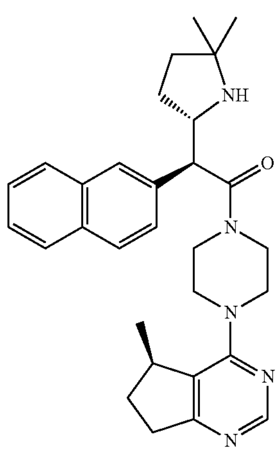 [SMILES: C[C@@H]1CCc2ncnc(N3CCN(C(=O)[C@@H](c4ccc5ccccc5c4)[C@@H]4CCC(C)(C)N4)CC3)c21] | (S)-2-((S)-5,5-dimethylpyrrolidin-2-yl)-1-(4-((R)-5-methyl-6,7-dihydro-5H-cyclopenta[d]pyrimidin-4-yl)piperazin-1-yl)-2-(naphthalen-2-yl)ethanone dihydrochloride | HPLC, 220 nm = 2.01 minutes, 100% purity, LC/MS = 2.50 minutes, (APCI+) m/z = 484 [M + H]+ |

TABLE 4-continued

| Ex. # | Structure | Name | LCMS NMR |
|---|---|---|---|
| 113 | 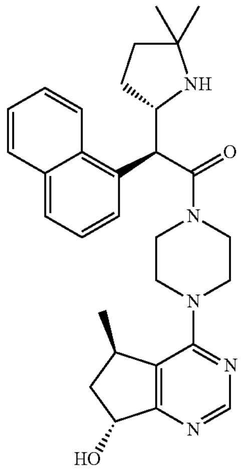 | (S)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)-2-(naphthalen-1-yl)ethanone dihydrochloride | HPLC, 254 nm = 1.99 minutes, 100% purity, LC/MS = 2.24 minutes, (APCI+) m/z = 500 [M + H]+ |
| 114 | 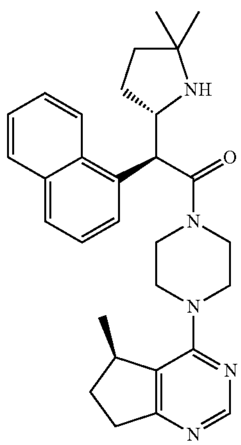 [SMILES: C[C@@H]1CCc2ncnc(N3CCN(C(=O)[C@@H](c4cccc5ccccc45)[C@@H]4CCC(C)(C)N4)CC3)c21] | (S)-2-((S)-5,5-dimethylpyrrolidin-2-yl)-1-(4-((R)-5-methyl-6,7-dihydro-5H-cyclopenta[d]pyrimidin-4-yl)piperazin-1-yl)-2-(naphthalen-1-yl)ethanone dihydrochloride | HPLC, 220 nm = 1.95 minutes, 98% purity, LC/MS = 2.51 minutes, (APCI+) m/z = 484 [M + H]+ |
| 115 | 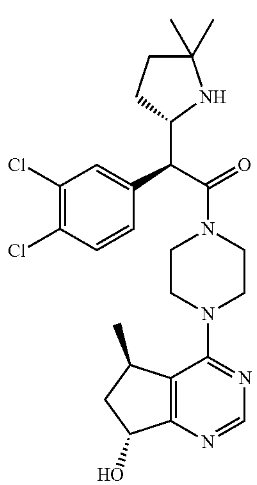 [SMILES: C[C@@H]1C[C@@H](O)c2ncnc(N3CCN(C(=O)[C@@H](c4ccc(Cl)c(Cl)c4)[C@@H]4CCC(C)(C)N4)CC3)c21] | (S)-2-(3,4-dichlorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone dihydrochloride | HPLC, 254 nm = 2.01 minutes, 99.90% purity, LCMS (APCI+) 519.8 m/z [M + H]+; Rt = 2.80; $^1$H NMR (400 MHz, CD$_3$OD) 8.57 (s, 1H), 7.67 (d, J = 2.34 Hz, 1H), 7.61 (d, J = 8.59 Hz, 1H), 7.39 (dd, J1 = 2.34 Hz, J2 = 8.59 Hz, 1H), 5.29 (t, J = 7.809 Hz, 1H), 4.51 (d, J = 9.37 Hz, 1H), 3.95-3.65 (m, 6H), 2.33-2.25 (m, 1H), 2.23-2.16 (m, 1H), 2.00-1.87 (m, 4H, 1.54 (s, 3H), 1.44 (s, 3H), 1.36 (d, J = 5.857 Hz, 3H) |

TABLE 4-continued

| Ex. # | Structure | Name | LCMS NMR |
|---|---|---|---|
| 116 | 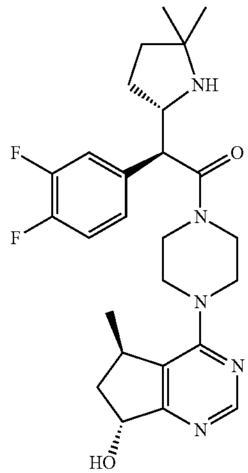 [SMILES: C[C@@H]1C[C@@H](O)c2ncnc(N3CCN(C(=O)[C@@H](c4ccc(F)c(F)c4)[C@@H]4CCC(C)(C)N4)CC3)c21] | (S)-2-(3,4-difluorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone dihydrochloride | HPLC, 254 nm = 1.96 minutes, 99.90% purity, LCMS (APCI+) 486.2 m/z [M + H]+; Rt = 2.49 |
| 117 | 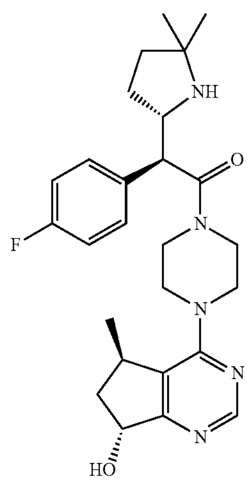 [SMILES: C[C@@H]1C[C@@H](O)c2ncnc(N3CCN(C(=O)[C@@H](c4ccc(F)cc4)[C@@H]4CCC(C)(C)N4)CC3)c21] | (S)-2-((S)-5,5-dimethylpyrrolidin-2-yl)-2-(4-fluorophenyl)-1-(4-((5R,7R)-7-hydroxy-5-methyl-6,7-dihydro-5H-cyclopenta[d]pyrimidin-4-yl)piperazin-1-yl)ethanone dihydrochloride | HPLC, 220 nm = 1.85 minutes, 99.90% yield, LCMS (APCI+) 468.1 m/z [M + H]+; Rt = 2.35 |
| 118 | 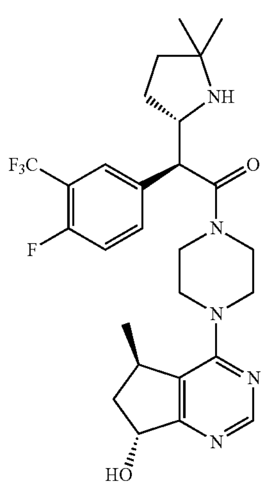 [SMILES: C[C@@H]1C[C@@H](O)c2ncnc(N3CCN(C(=O)[C@@H](c4ccc(F)c(C(F)(F)F)c4)[C@@H]4CCC(C)(C)N4)CC3)c21] | (S)-2-((S)-5,5-dimethylpyrrolidin-2-yl)-2-(4-fluoro-3-(trifluoromethyl)phenyl)-1-(4-((5R,7R)-7-hydroxy-5-methyl-6,7-dihydro-5H-cyclopenta[d]pyrimidin-4-yl)piperazin-1-yl)ethanone dihydrochloride | HPLC, 220 nm = 2.02 minutes, 99.99% purity, LCMS (APCI+) 536.1 m/z [M + H]+; Rt = 2.66 |

TABLE 4-continued

| Ex. # | Structure | Name | LCMS NMR |
|---|---|---|---|
| 119 | 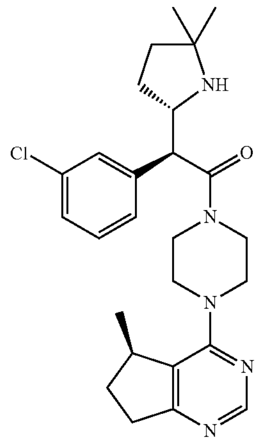 [SMILES: C[C@@H]1CCc2ncnc(N3CCN(C(=O)[C@@H](c4cccc(Cl)c4)[C@@H]4CCC(C)(C)N4)CC3)c21] | (S)-2-(3-chlorophenyl)-2-((S)-5,5-dimethylpyrrolidin-2-yl)-1-(4-((R)-5-methyl-6,7-dihydro-5H-cyclopenta[d]pyrimidin-4-yl)piperazin-1-yl)ethanone dihydrochloride | HPLC, 220 nm = 2.00 minutes, 98.9% purity. LC/MS = 2.76 minutes, (APCI+) m/z = 468 [M + H]+. $^1$H NMR (400 MHz, D$_2$O) 8.26 (s, 1H), 7.33-7.28 (m, 3H), 7.23-7.16 (m, 1H), 4.23 (d, J = 8.18 Hz, 1H), 4.19-4.00 (m, 2H), 3.90-3.79 (m, 1H), 3.79-3.66 (m, 1H), 3.66-3.56 (m, 2H), 3.56-3.38 (m, 4H), 3.03-2.88 (m, 1H), 2.87-2.73 (m, 1H), 2.30-2.14 (m, 1H), 1.88-1.70 (m, 5H), 1.36 (s, 3H), 1.30 (s, 3H), 0.92 (d, J6.64 Hz, 3H) |
| 120 | 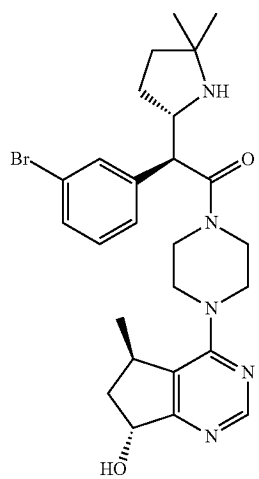 [SMILES: C[C@@H]1C[C@@H](O)c2ncnc(N3CCN(C(=O)[C@@H](c4cccc(Br)c4)[C@@H]4CCC(C)(C)N4)CC3)c21] | (S)-2-(3-bromophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone dihydrochloride | HPLC, 254 nm = 2.01 minutes, 99.09% purity, LCMS (APCI+) 530.0 m/z [M + H]+; Retention time = 2.31 minutes. $^1$H NMR (400 MHz, D$_2$O) 8.39 (s, 1H), 7.46 (s, 2H), 7.24 (d, J = 4.685 Hz, 2H), 5.25 (t, J = 7.809 Hz, 1H), 4.25-4.20 (m, 1H), 3.87-3.75 (m, 2H), 3.7-3.58 (m, 1H), 3.55-3.42 (m, 3H), 2.22-2.16 (m, 1H), 2.1-1.95 (m, 1H), 1.85-1.75 (m, 4H), 1.36 (s, 3H), 1.30 (s, 3H), 0.95 (d, J = 7.028 Hx, 3H) |
| 121 | 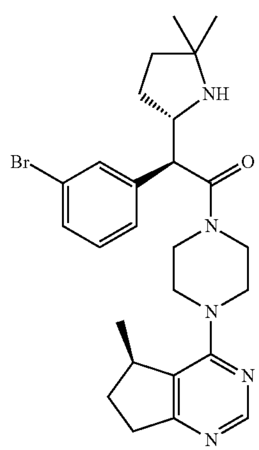 | (S)-2-(3-bromophenyl)-2-((S)-5,5-dimethylpyrrolidin-2-yl)-1-(4-((R)-5-methyl-6,7-dihydro-5H-cyclopenta[d]pyrimidin-4-yl)piperazin-1-yl)ethanone dihydrochloride | HPLC, 254 nm = 2.00 minutes, 96.92% purity LCMS (APCI+) = 2.56 minutes. $^1$H NMR (400 MHz, D$_2$O) 8.22 (s, 1H), 7.52-7.41 (m, 2H), 7.25-7.21 (m, 2H), 4.21-4.0 (m, 1H), 3.9-3.8 (m, 1H), 3.78-3.5 (m, 1H), 3.62-3.56 (m, 1H), 3.5-3.45 (m, 3H), 2.95 (dd, J1 = 9.371 Hz, J2 = 18.351 Hz, 1H), 2.85-2.75 (m, 1H), 2.28-2.18 (m, 1H), 1.86-1.66 (m, 5H), 1.35 (s, 3H), 1.29 (s, 3H), 0.91 (d, J = 7.028 Hz, 3H) |

TABLE 4-continued

| Ex. # | Structure | Name | LCMS NMR |
|---|---|---|---|
| 122 | 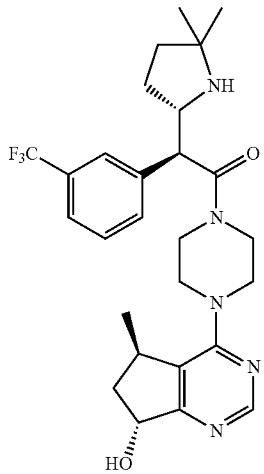 [SMILES: C[C@@H]1C[C@@H](O)c2ncnc(N3CCN(C(=O)[C@@H](c4cccc(C(F)(F)F)c4)[C@@H]4CCC(C)(C)N4)CC3)c21] | (S)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)-2-(3-(trifluoromethyl)phenyl)ethanone dihydrochloride | HPLC, 254 nm = 2.05 minutes, 95.92% purity, LCMS (APCI+) 518.0 m/z [M + H]+; Retention time = 2.40, $^1$H NMR (400 MHz, $D_2O$) 8.39 (s, 1H), 7.65-7.6 (m, 2H), 7.52 (d, J = 5.466 Hz, 2H), 5.25 (t, J = 7.809 Hz, 1H), 4.35 (d, J = 9.371 Hz, 1H), 3.87-3.79 (m, 2H), 3.62-3.4 (m, 4H), 2.20-2.16 (m, 1H), 2.09-1.90 (m, 1H), 1.87-1.75 (m, 4H), 1.37 (s, 3H), 1.32 (s, 3H), 0.94 (d, J = 7.028 Hz, 3H) |
| 123 | 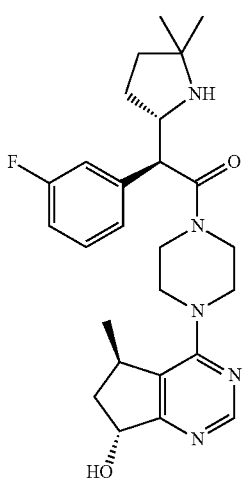 [SMILES: C[C@@H]1C[C@@H](O)c2ncnc(N3CCN(C(=O)[C@@H](c4cccc(F)c4)[C@@H]4CCC(C)(C)N4)CC3)c21] | (S)-2-((S)-5,5-dimethylpyrrolidin-2-yl)-2-(3-fluorophenyl)-1-(4-((5R,7R)-7-hydroxy-5-methyl-6,7-dihydro-5H-cyclopenta[d]pyrimidin-4-yl)piperazin-1-yl)ethanone dihydrochloride | HPLC, 220 nm = 1.85 minutes, 99.99% purity, LCMS (APCI+) 468.4 m/z [M + H]+; Retention time = 2.49 minutes, $^1$H NMR (400 MHz, $CD_3OD$) 8.6 (s, 1H), 7.5-7.42 (1H), 7.3-7.2 (m, 2H), 7.18-7.10 (m, 1H), 5.32 (t, J = 7.809 Hz, 1H), 4.57 (d, J = 9.761 Hz, 1H), 4.38-4.28 (m, 1H), 4.21-4.15 (m, 1H), 4.1-4.02 (m, 1H), 3.92-3.85 (m, 2H), 3.5-3.4 (m, 1H) 2.4-2.31 (m, 1H), 2.3-2.1 (m, 1H), 2.0-1.8 (m, 4H), 1.56 (s, 3H), 1.45 (s, 3H), 1.18 (d, J = 7.028 Hz, 3H) |

TABLE 4-continued

| Ex. # | Structure | Name | LCMS NMR |
|---|---|---|---|
| 124 | 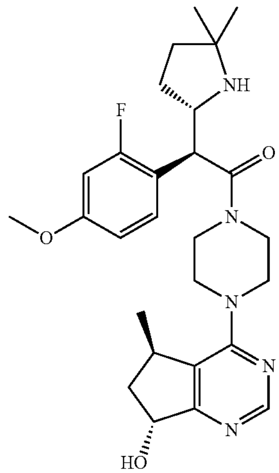 [SMILES: COc1ccc([C@H](C(=O)N2CCN(c3ncnc4c3[C@H](C)C[C@H]4O)CC2)[C@@H]2CCC(C)(C)N2)c(F)c1] | (S)-2-((S)-5,5-dimethylpyrrolidin-2-yl)-2-(2-fluoro-4-methoxyphenyl)-1-(4-((5R,7R)-7-hydroxy-5-methyl-6,7-dihydro-5H-cyclopenta[d]pyrimidin-4-yl)piperazin-1-yl)ethanone dihydrochloride | HPLC purity at 254 nm 98%, Retention time = 1.84 minutes. LCMS (APCI+) M + H+: 498 (100%); retention time = 2.08 minutes. $^1$H NMR (400 MHz, CDCl$_3$) δ 9.76 (br s, 1H), 8.73 (s, 1H), 8.55 (br s, 1H), 7.26 (t, J = 8.6 Hz, 1H), 6.94 (dd, J = 8.6, 2.3 Hz, 1H), 6.84 (dd, J = 8.6, 2.3 Hz, 1H), 5.24 (t, J = 7.8 Hz, 1H), 4.83 (d, J = 10.1 Hz, 1H), 4.21 (m, 1H), 4.07 (m, 1H), 3.97 (m, 1H), 3.84 (m, 2H), 3.77 (s, 3H), 3.68 (m, 4H), 3.49 (m, 2H), 3.30 (m, 1H), 2.09 (m, 2H), 1.80 (m, 3H), 1.47 (s, 3H), 1.33 (s, 3H), 1.09 (d, J = 7.0 Hz, 3H) |
| 125 | 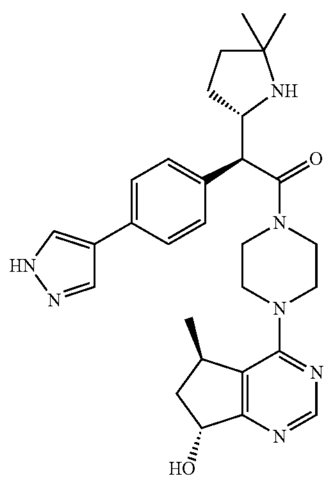 [SMILES: C[C@@H]1C[C@@H](O)c2ncnc(N3CCN(C(=O)[C@@H](c4ccc(-c5cn[nH]c5)cc4)[C@@H]4CCC(C)(C)N4)CC3)c21] | (S)-2-(4-(1H-pyrazol-4-yl)phenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone | $^1$H NMR (400 MHz, DMSO) δ 8.40 (s, 1H), 8.01 (s, 2H), 7.54 (d, J = 8.2, 3H), 7.31 (d, J = 8.2, 3H), 5.33 (s, 1H), 4.81 (t, J = 6.7, 1H), 3.84-3.40 (m, 12H), 3.02 (d, J = 9.5, 1H), 2.02-1.82 (m, 4H), 1.48 (ddd, J = 6.4, 14.0, 17.8, 5H), 1.09 (d, J = 5.2, 8H), 1.00 (d, J = 6.9, 4H) |
| 126 | 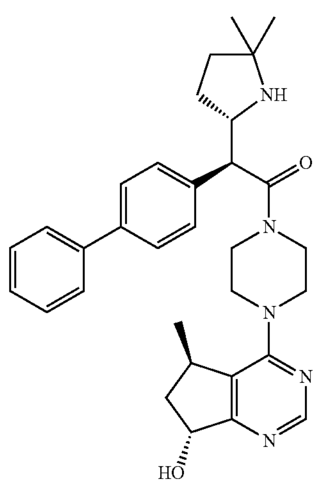 [SMILES: C[C@@H]1C[C@@H](O)c2ncnc(N3CCN(C(=O)[C@@H](c4ccc(-c5ccccc5)cc4)[C@@H]4CCC(C)(C)N4)CC3)c21] | (S)-2-(biphenyl-4-yl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone | $^1$H NMR (400 MHz, DMSO) δ 8.40 (s, 1H), 7.69-7.58 (m, 4H), 7.48-7.40 (m, 4H), 7.34 (t, J = 7.3, 1H), 5.33 (d, J = 5.6, 1H), 4.81 (dd, J = 6.3, 12.7, 1H), 3.83 (s, 2H), 3.74-3.40 (m, 7H), 3.16-3.11 (m, 1H), 2.01-1.82 (m, 2H), 1.58-1.36 (m, 4H), 1.11 (s, 3H), 1.10 (s, 3H), 1.01 (d, J = 6.9, 3H) |

TABLE 4-continued

| Ex. # | Structure | Name | LCMS NMR |
|---|---|---|---|
| 127 | 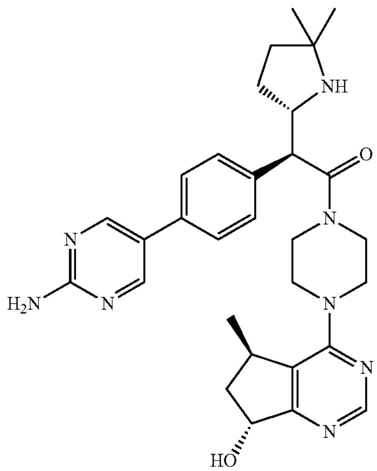 [SMILES: C[C@@H]1C[C@@H](O)c2ncnc(N3CCN(C(=O)[C@@H](c4ccc(-c5cnc(N)nc5)cc4)[C@@H]4CCC(C)(C)N4)CC3)c21] | (S)-2-(4-(2-aminopyrimidin-5-yl)phenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone | $^1$H NMR (400 MHz, DMSO) δ 8.56 (s, 2H), 8.40 (s, 1H), 7.58 (d, J = 8.3, 2H), 7.41 (d, J = 8.3, 2H), 6.72 (s, 2H), 4.82 (t, J = 6.7, 1H), 3.80 (s, 2H), 3.73-3.41 (m, 8H), 2.05-1.81 (m, 3H), 1.55-1.40 (m, 4H), 1.10 (s, 3H), 1.09 (s, 3H), 1.01 (d, J = 6.9, 3H) |
| 128 | 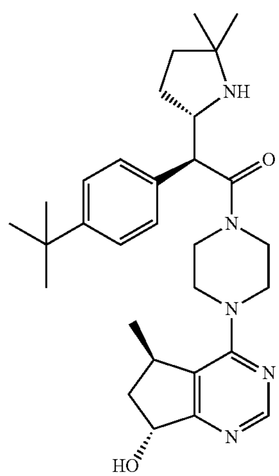 [SMILES: C[C@@H]1C[C@@H](O)c2ncnc(N3CCN(C(=O)[C@@H](c4ccc(C(C)(C)C)cc4)[C@@H]4CCC(C)(C)N4)CC3)c21] | (S)-2-(4-tert-butylphenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone dihydrochloride | $^1$H NMR (400 MHz, D$_2$O) δ 8.47 (s, 1H), 7.54 (d, J = 8.0, 2H), 7.32 (d, J = 8.1, 2H), 5.33 (t, J = 7.8, 1H), 4.32-4.28 (m, 3H), 4.00-3.83 (m, 2H), 3.68-3.48 (m, 5H), 3.17-3.05 (m, 1H), 2.29-4.24 (m, 1H), 2.17-2.06 (m, 1H), 1.96-1.87 (m, 4H), 1.47 (s, 3H), 1.41 (s, 3H), 1.26 (s, 9H), 1.04 (d, J = 6.9, 3H) |
| 129 | 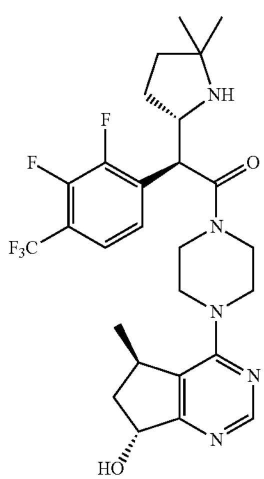 [SMILES: C[C@@H]1C[C@@H](O)c2ncnc(N3CCN(C(=O)[C@@H](c4ccc(C(F)(F)F)c(F)c4F)[C@@H]4CCC(C)(C)N4)CC3)c21] | (S)-2-(2,3-difluoro-4-(trifluoromethyl)phenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone | $^1$H NMR (400 MHz, D$_2$O) δ 8.39 (s, 1H), 7.46 (t, J = 7.2 Hz, 1H), 7.18 (t, J = 7.1 Hz, 1H), 5.27 (t, J = 8.0 Hz, 1H), 4.62 (d, J = 9.1 Hz, 1H), 4.29-4.18 (m, 1H), 4.10-4.02 (m, 1H), 3.87-3.64 (m, 4H), 3.60-3.40 (m, 4H), 3.33-3.26 (m, 1H), 2.22-2.28 (m, 1H), 2.05-1.99 (m, 1H), 1.89-1.76 (m, 4H), 1.38 (s, 4H), 1.32 (s, 4H), 0.99 (d, J = 7.0 Hz, 3H) |

TABLE 4-continued

| Ex. # | Structure | Name | LCMS NMR |
|---|---|---|---|
| 130 | 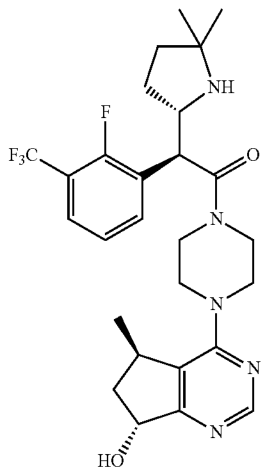 [SMILES: C[C@@H]1C[C@@H](O)c2ncnc(N3CCN(C(=O)[C@@H](c4cccc(C(F)(F)F)c4F)[C@@H]4CCC(C)(C)N4)CC3)c21] | (S)-2-((S)-5,5-dimethylpyrrolidin-2-yl)-2-(2-fluoro-3-(trifluoromethyl)phenyl)-1-(4-((5R,7R)-7-hydroxy-5-methyl-6,7-dihydro-5H-cyclopenta[d]pyrimidin-4-yl)piperazin-1-yl)ethanone | $^1$H NMR (400 MHz, D$_2$O) δ 8.16 (s, 1H), 7.49 (t, J = 7.0 Hz, 1H), 7.31 (t, J = 6.8 Hz, 1H), 7.11 (t, J = 7.9 Hz, 1H), 5.03 (t, J = 7.8 Hz, 1H), 4.42 (d, J = 9.1 Hz, 1H), 4.11-3.99 (m, 1H), 3.91-3.85 (m, 1H), 3.62-3.55 (m, 2H), 3.41-2.96 (m, 6H), 2.00-1.94 (m, 1H), 1.85-1.79 (m, 1H), 1.73-1.53 (m, 4H), 1.19 (s, 3H), 1.13 (s, 3H), 0.76 (d, J = 7.0 Hz, 3H) |
| 131 | 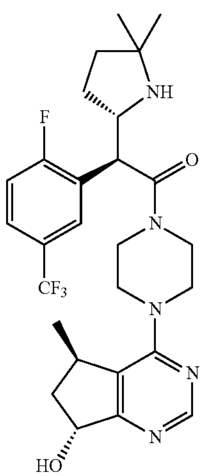 [SMILES: C[C@@H]1C[C@@H](O)c2ncnc(N3CCN(C(=O)[C@@H](c4cc(C(F)(F)F)ccc4F)[C@@H]4CCC(C)(C)N4)CC3)c21] | (S)-2-((S)-5,5-dimethylpyrrolidin-2-yl)-2-(2-fluoro-5-(trifluoromethyl)phenyl)-1-(4-((5R,7R)-7-hydroxy-5-methyl-6,7-dihydro-5H-cyclopenta[d]pyrimidin-4-yl)piperazin-1-yl)ethanone | $^1$H NMR (400 MHz, DMSO) δ 9.63-9.50 (m, 1H), 8.68 (s, 1H), 7.89-7.80 (m, 2H), 7.61 (t, J = 8.0 Hz, 1H), 5.17 (t, J = 8.0 Hz, 1H), 5.02 (d, J = 10.3 Hz, 1H), 4.48-4.32 (m, 1H), 4.00-3.61 (m, 11H), 2.12-1.99 (m, 2H), 1.86-1.71 (m, 4H), 1.67-1.56 (m, 1H), 1.47 (s, 3H), 1.35 (s, 4H), 1.30-1.21 (m, 1H), 1.08 (d, J = 6.9 Hz, 3H) |
| 132 | 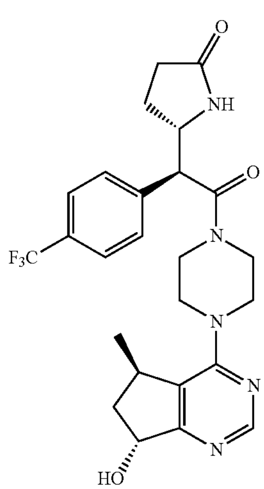 [SMILES: C[C@@H]1C[C@@H](O)c2ncnc(N3CCN(C(=O)[C@@H](c4ccc(C(F)(F)F)cc4)[C@@H]4CCC(=O)N4)CC3)c21] | (S)-5-((S)-2-(4-((5R,7R)-7-hydroxy-5-methyl-6,7-dihydro-5H-cyclopenta[d]pyrimidin-4-yl)piperazin-1-yl)-2-oxo-1-(4-(trifluoromethyl)phenyl)ethyl)pyrrolidin-2-one | $^1$H NMR (400 MHz, DMSO) δ 8.43 (s, 1H), 7.75 (d, J = 8.2, 2H), 7.68 (s, 1H), 7.63 (d, J = 8.1, 2H), 5.40 (d, J = 5.5, 1H), 4.83 (d, J = 6.2, 1H), 4.24 (d, J = 8.9, 1H), 4.19 (s, 1H), 3.71 (s, 3H), 3.44 (m, 4H), 3.28 (m, 1H), 2.11-1.84 (m, 5H), 1.70 (m, 1H), 1.03 (d, J = 6.9, 3H), 0.94 (d, J = 6.6, 1H) |

TABLE 4-continued

| Ex. # | Structure | Name | LCMS NMR |
|---|---|---|---|
| 133 | 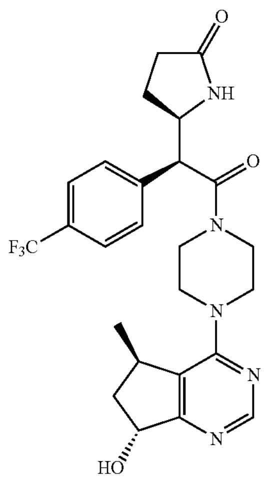 [SMILES: C[C@@H]1C[C@@H](O)c2ncnc(N3CCN(C(=O)[C@@H](c4ccc(C(F)(F)F)cc4)[C@H]4CCC(=O)N4)CC3)c21] | (R)-5-((S)-2-(4-((5R,7R)-7-hydroxy-5-methyl-6,7-dihydro-5H-cyclopenta[d]pyrimidin-4-yl)piperazin-1-yl)-2-oxo-1-(4-(trifluoromethyl)phenyl)ethyl)pyrrolidin-2-one | $^1$H NMR (400 MHz, DMSO) δ 8.43 (s, 1H), 7.75 (d, J = 8.2, 2H), 7.68 (s, 1H), 7.63 (d, J = 8.1, 2H), 5.40 (d, J = 5.5, 1H), 4.83 (q, J = 6.2, 1H), 4.24 (d, J = 8.9, 1H), 4.21-4.12 (m, 1H), 3.80-3.62 (m, 4H), 3.54-3.38 (m, J = 10.2, 6H), 3.29-3.20 (m, 1H), 2.11-1.84 (m, 4H), 1.76-1.64 (m, 1H), 1.61-1.48 (m, 1H), 1.03 (d, J = 6.9, 3H), 0.94 (d, J = 6.6, 1H) |
| 134 | 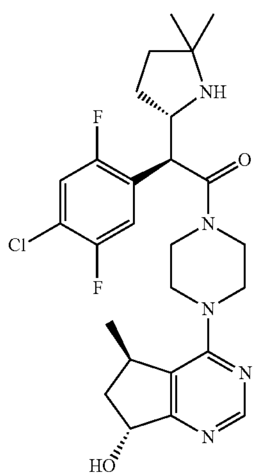 [SMILES: C[C@@H]1C[C@@H](O)c2ncnc(N3CCN(C(=O)[C@@H](c4cc(F)c(Cl)cc4F)[C@@H]4CCC(C)(C)N4)CC3)c21] | (S)-2-(4-chloro-2,5-difluorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone | $^1$H NMR (400 MHz, D$_2$O) δ 8.37 (s, 1H), 7.37 (dd, J = 6.2, 9.2, 1H), 7.16-7.08 (m, 1H), 5.24 (t, J = 7.9, 1H), 4.49 (d, J = 9.1, 1H), 4.25-4.13 (m, 1H), 4.11-3.99 (m, 1H), 3.85-3.66 (m, J = 19.2, 3H), 3.64-3.29 (m, 4H), 2.23-2.13 (m, 1H), 2.08-1.96 (m, J = 13.2, 1H), 1.93-1.71 (m, 4H), 1.37 (s, 3H), 1.31 (s, 3H), 1.20 (d, J = 5.9, 3H), 0.98 (d, J = 7.0, 3H) |
| 135 | 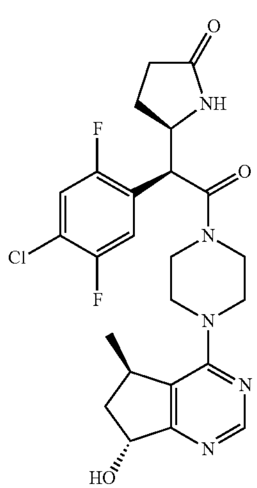 [SMILES: C[C@@H]1C[C@@H](O)c2ncnc(N3CCN(C(=O)[C@@H](c4cc(F)c(Cl)cc4F)[C@H]4CCC(=O)N4)CC3)c21] | (R)-5-((S)-1-(4-chlorophenyl)-2-(4-((5R,7R)-7-hydroxy-5-methyl-6,7-dihydro-5H-cyclopenta[d]pyrimidin-4-yl)piperazin-1-yl)-2-oxoethyl)pyrrolidin-2-one | $^1$H NMR (400 MHz, CDCl$_3$) δ 8.50 (s, 1H), 7.37 (d, J = 8.4, 2H), 7.22 (d, J = 8.5, 2H), 6.15 (s, 1H), 5.08 (t, J = 7.1, 1H), 4.25-4.13 (m, 1H), 3.88-3.75 (m, 2H), 3.69-3.53 (m, J = 9.6, 3H), 3.50-3.29 (m, J = 16.3, 4H), 3.20 (br s, 1H), 3.15-3.05 (m, 1H), 2.32 (dd, J = 7.1, 16.4, 2H), 2.15 (dd, J = 5.0, 12.0, 2H), 1.98-1.83 (m, J = 9.1, 1H), 1.81-1.67 (m, 1H), 1.14 (d, J = 7.0, 3H) |

TABLE 4-continued

| Ex. # | Structure | Name | LCMS NMR |
|---|---|---|---|
| 136 | 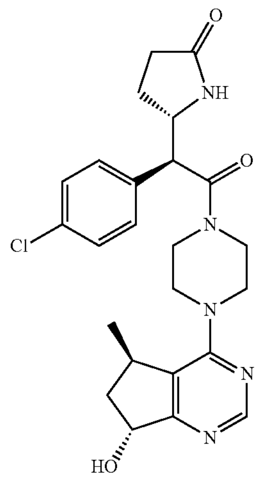 [SMILES: C[C@@H]1C[C@@H](O)c2ncnc(N3CCN(C(=O)[C@@H](c4ccc(Cl)cc4)[C@@H]4CCC(=O)N4)CC3)c21] | (S)-5-((S)-1-(4-chlorophenyl)-2-(4-((5R,7R)-7-hydroxy-5-methyl-6,7-dihydro-5H-cyclopenta[d]pyrimidin-4-yl)piperazin-1-yl)-2-oxoethyl)pyrrolidin-2-one | $^1$H NMR (400 MHz, CDCl$_3$) δ 8.49 (s, 1H), 7.37 (d, J = 8.4, 2H), 7.23 (d, J = 8.4, 2H), 5.95 (s, 1H), 5.07 (t, J = 7.1, 1H), 4.35-4.20 (m, 1H), 3.86 (d, J = 9.9, 2H), 3.68 (d, J = 5.8, 1H), 3.65-3.51 (m, J = 14.3, 2H), 3.48-3.29 (m, J = 12.8, 4H), 3.13-3.03 (m, 1H), 2.99 (s, 1H), 2.44-2.33 (m, 1H), 2.22-2.06 (m, 3H), 1.94-1.68 (m, 2H), 1.13 (d, J = 7.0, 3H) |
| 137 | 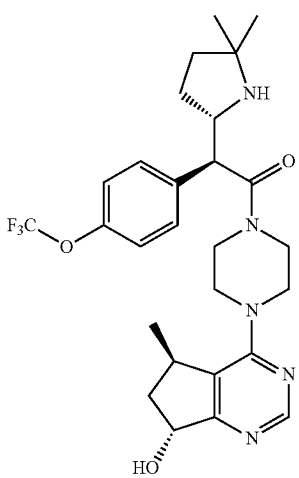 [SMILES: C[C@@H]1C[C@@H](O)c2ncnc(N3CCN(C(=O)[C@@H](c4ccc(OC(F)(F)F)cc4)[C@@H]4CCC(C)(C)N4)CC3)c21] | (S)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)-2-(4-(trifluoromethoxy)phenyl)ethanone | $^1$H NMR (400 MHz, D$_2$O) δ 8.45 (s, 1H), 7.46 (d, J = 8.7 Hz, 2H), 7.38 (d, J = 8.4 Hz, 2H), 5.31 (t, J = 7.7 Hz, 1H), 4.40-4.38 (m, 1H), 4.30-4.16 (m, 2H), 3.95-3.85 (m, 2H), 3.70-3.55 (m, 6H), 3.26-3.15 (m, 1H), 2.28-2.22 (m, 1H), 2.15-2.09 (m, 1H), 1.95-1.85 (m, 4H), 1.47 (s, 3H), 1.42 (s, 3H), 1.05 (d, J = 7.0 Hz, 3H) |
| 138 | 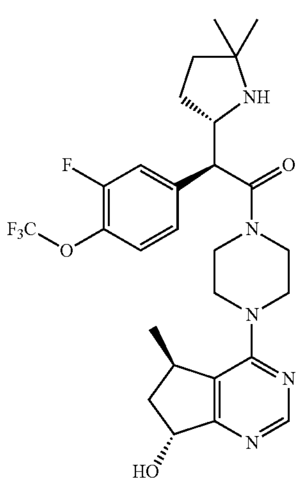 [SMILES: C[C@@H]1C[C@@H](O)c2ncnc(N3CCN(C(=O)[C@@H](c4ccc(OC(F)(F)F)c(F)c4)[C@@H]4CCC(C)(C)N4)CC3)c21] | (S)-2-((S)-5,5-dimethylpyrrolidin-2-yl)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)ethanone | $^1$H NMR (400 MHz, D$_2$O) δ 8.46 (s, 1H), 7.52 (s, 1H), 7.37 (d, J = 10.9 Hz, 1H), 7.26 (d, J = 8.6 Hz, 1H), 5.31 (t, J = 7.7 Hz, 1H), 4.42-4.39 (m, 1H), 4.30-4.15 (m, 2H), 3.97-3.87 (m, 2H), 3.77-3.51 (m, 7H), 3.39-3.27 (m, 1H), 2.28-2.22 (m, 1H), 2.15-2.09 (m, 1H), 1.99-1.84 (m, 4H), 1.47 (s, 3H), 1.42 (s, 3H), 1.06 (d, J = 7.0 Hz, 3H) |

TABLE 4-continued

| Ex. # | Structure | Name | LCMS NMR |
|---|---|---|---|
| 139 | 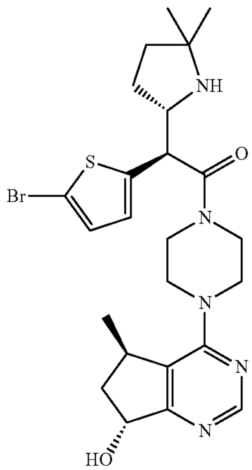 [SMILES: C[C@@H]1C[C@@H](O)c2ncnc(N3CCN(C(=O)[C@@H](c4ccc(Br)s4)[C@@H]4CCC(C)(C)N4)CC3)c21] | (S)-2-(5-bromothiophen-2-yl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone | $^1$H NMR (400 MHz, D$_2$O) δ 8.50 (s, 1H), 7.08 (d, J = 3.8 Hz, 1H), 6.94 (d, J = 3.8 Hz, 1H), 5.36 (t, J = 7.9 Hz, 1H), 4.27-4.20 (m, 2H), 4.05-3.95 (m, 2H), 3.83-3.46 (m, 8H), 2.33-2.27 (m, 1H), 2.16-2.05 (m, 2H), 2.02-1.86 (m, 3H), 1.46 (s, 3H), 1.41 (s, 3H), 1.11 (d, J = 7.0 Hz, 3H) |
| 140 | 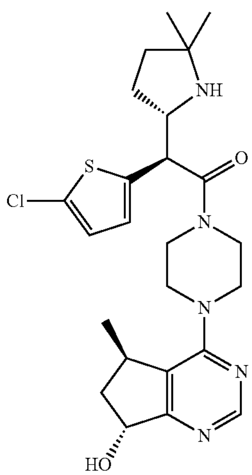 [SMILES: C[C@@H]1C[C@@H](O)c2ncnc(N3CCN(C(=O)[C@@H](c4ccc(Cl)s4)[C@@H]4CCC(C)(C)N4)CC3)c21] | (S)-2-(5-chlorothiophen-2-yl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone | $^1$H NMR (400 MHz, D$_2$O) δ 8.54 (s, 1H), 6.98 (d, J = 3.8 Hz, 1H), 6.94 (d, J = 3.8 Hz, 1H), 5.40 (t, J = 7.9 Hz, 1H), 4.35-4.21 (m, 2H), 4.11-3.95 (m, 2H), 3.87-3.46 (m, 8H), 2.36-2.31 (m, 1H), 2.23-1.89 (m, 5H), 1.49 (s, 3H), 1.44 (s, 3H), 1.14 (d, J = 7.0 Hz, 3H) |
| 141 | 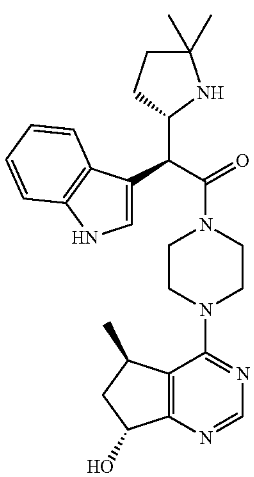 [SMILES: C[C@@H]1C[C@@H](O)c2ncnc(N3CCN(C(=O)[C@@H](c4c[nH]c5ccccc45)[C@@H]4CCC(C)(C)N4)CC3)c21] | (S)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)-2-(1H-indol-3-yl)ethanone | LC/MS, retention time = 2.42 minutes, (APCI+) m/z = 489 [M + H]+ |

While the invention has been described in conjunction with the enumerated embodiments, it will be understood that they are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

The invention claimed is:
1. A compound of the Formula 10:

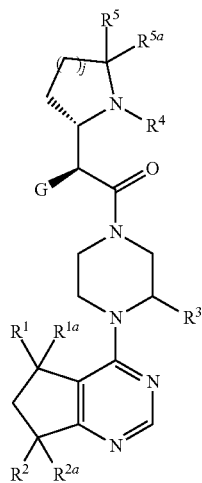

and enantiomers and salts thereof, wherein:
G is phenyl, naphthalene, a 5-6 membered heteroaryl or a 9-10 membered bicyclic heteroaryl wherein the phenyl, naphthalene, 5-6 membered heteroaryl or 9-10 membered bicyclic heteroaryl is optionally substituted with one to four $R^a$ groups;
$R^1$ and $R^{1a}$ are independently selected from H, Me, Et, —CH=CH$_2$, —CH$_2$OH, CF$_3$, CHF$_2$ or CH$_2$F;
$R^2$ is H, —OH, —OMe or F;
$R^{2a}$ is H, Me or F, or
$R^2$ and $R^{2a}$ are oxo;
$R^3$ is H, Me, Et, or CF$_3$;
$R^4$ is H, 4-6 membered heterocycle, cyclopropylmethyl or $C_1$-$C_4$ alkyl optionally substituted with F, —OH or —O($C_1$-$C_3$ alkyl);
$R^5$ and $R^{5a}$ are independently selected from H and $C_1$-$C_4$ alkyl, or $R^5$ and $R^{5a}$ together with the atom to which they are attached form a carbonyl group, a 5-6 membered cycloalkyl or a 5-6 membered heterocycle, wherein the heterocycle has an oxygen heteroatom;
each $R^a$ is independently halogen, $C_1$-$C_6$-alkyl, $C_3$-$C_6$-cycloalkyl, —O—($C_1$-$C_6$-alkyl), CF$_3$, —OCF$_3$, S($C_1$-$C_6$-alkyl), CN, phenyl, —OCH$_2$-phenyl, NH$_2$, —NO$_2$, —NH—($C_1$-$C_6$-alkyl), —N—($C_1$-$C_6$-alkyl)$_2$, piperidine, pyrrolidine, pyrazole, pyridine, 2-aminopyrimidine, CH$_2$F, CHF$_2$, —OCH$_2$F, —OCHF$_2$, —OH, —SO$_2$($C_1$-$C_6$-alkyl), C(O)NH$_2$, C(O)NH($C_1$-$C_6$-alkyl), and C(O)N($C_1$-$C_6$-alkyl)$_2$; and
j is 1 or 2; and when j is 2, the j ring carbon opposite NR$^4$ may be replaced with an O heteroatom.

2. The compound of claim 1, wherein $R^2$ is selected from H, —OH, —OMe or F;
$R^{2a}$ is selected from H, Me or F;
$R^4$ is H, 4-6 membered heterocycle, cyclopropylmethyl or $C_1$-$C_4$ alkyl optionally substituted with —OH or —O($C_1$-$C_3$ alkyl);
$R^5$ and $R^{5a}$ are independently selected from H and $C_1$-$C_4$ alkyl; and
j is 1 or 2.

3. The compound of claim 1, wherein $R^3$ is H.
4. The compound of claim 1, wherein $R^5$ is H.
5. The compound of claim 1, wherein $R^{5a}$ is H.
6. The compound of claim 1, wherein $R^5$ is methyl.
7. The compound of claim 1, wherein $R^{5a}$ is methyl.
8. The compound of claim 1, wherein $R^5$ is ethyl.
9. The compound of claim 1, wherein $R^{5a}$ is ethyl.
10. The compound of claim 1, wherein $R^5$ and $R^{5a}$ together with the atom to which they are attached form a 5-6 membered cycloalkyl.
11. The compound of claim 1, wherein $R^5$ and $R^{5a}$ together with the atom to which they are attached form a 5-6 membered heterocycle, wherein the heterocycle has an oxygen heteroatom.
12. The compound of claim 1, wherein $R^1$ is methyl.
13. The compound of claim 1, wherein $R^1$ is methyl in the (R) configuration.
14. The compound of claim 1, wherein $R^{1a}$ is H.
15. The compound of claim 1, wherein $R^{1a}$ is methyl.
16. The compound of claim 1, wherein $R^1$ is H.
17. The compound of claim 1, wherein $R^1$ is ethyl.
18. The compound of claim 1, wherein $R^1$ is CH=CH$_2$.
19. The compound of claim 1, wherein $R^1$ is CH$_2$OH.
20. The compound of claim 1, wherein $R^1$ is CH$_2$F.
21. The compound of claim 13, wherein $R^{1a}$ is H.
22. The compound of claim 1, wherein $R^{2a}$ is H.
23. The compound of claim 1, wherein $R^2$ is F.
24. The compound of claim 1, wherein $R^2$ is OH.
25. The compound of claim 1, wherein $R^{2a}$ is F.
26. The compound of claim 1, wherein $R^2$ is F.
27. The compound of claim 1, wherein $R^2$ is —OMe.
28. The compound of claim 1, wherein G is selected from 4-chlorophenyl, 3-fluoro-4-chlorophenyl, 3-fluoro-4-trifluoromethylphenyl and 4-cyclopropylphenyl.
29. The compound of claim 1, wherein G is selected from 4-chlorophenyl, 4-bromophenyl, 4-cyclopropylphenyl, 4-trifluoromethylphenyl, 4-cyanophenyl, 4-benzamide, 4-(methylsulfonyl)phenyl, 2-fluoro-4-trifluoromethylphenyl, 3-fluoro-4-chlorophenyl, 3-fluoro-4-trifluoromethylphenyl or 3-fluoro-4-cyanophenyl.
30. The compound of claim 1, wherein $R^4$ is $C_1$-$C_4$ alkyl optionally substituted with OH or O($C_1$-$C_3$ alkyl).
31. The compound of claim 1, wherein $R^4$ is selected from methyl, ethyl, isopropyl, isobutyl, CH$_2$CH$_2$OH, CH$_2$CH$_2$CH$_2$OH, CH$_2$C(CH$_3$)$_2$OH and CH$_2$CH$_2$OCH$_3$.
32. The compound of claim 1, wherein $R^4$ is cyclopropylmethyl.
33. The compound of claim 1, wherein $R^4$ is a 4-6 membered heterocycle.
34. The compound of claim 1, wherein $R^4$ is tetrahydropyranyl.
35. The compound of claim 1, wherein $R^4$ is H.
36. The compound of claim 1, wherein $R^4$ is $C_1$-$C_4$ alkyl optionally substituted with F.
37. The compound of claim 1, wherein $R^4$ is CH$_2$CF$_3$, CH$_2$CH$_2$F or CH$_2$CHF$_2$.
38. The compound of claim 1, wherein j is 1.
39. The compound of claim 1, wherein j is 2.
40. The compound of claim 1, wherein G is 4-chlorophenyl, 4-bromophenyl, 4-cyclopropylphenyl, 4-trifluoromethylphenyl, 4-cyanophenyl, 4-benzamide, 4-(methylsulfonyl)phenyl, 2-fluoro-4-trifluoromethylphenyl, 3-fluoro-4-chlorophenyl, 3-fluoro-4-trifluoromethylphenyl, 3-fluoro-4-cyanophenyl, 4-chloro-2,5-difluorophenyl, 4-chloro-2-fluorophenyl, 4-bromo-2-fluorophenyl, 4-bromo-3-fluorophenyl, 3-chlorophenyl, 2-fluoro-4-methylphenyl, 2,4-dichlorophenyl, 3,4-dichlorophenyl, 4-fluorophenyl, 4-fluoro-3-trifluoromethylphenyl, 3-bromophenyl, 3-trifluoromethylphenyl, 3-fluorophenyl, 2-fluoro-4-methoxyphenyl, 4-(1H-pyrazol-4-yl)phenyl, biphenyl-4-yl, 4-(2-aminopyrimidin-5-yl)phenyl, 4-tert-butylphenyl, 2,3-difluoro-4-(trifluoromethyl)phenyl, 2-fluoro-3-(trifluoromethyl)phenyl, 2-fluoro-5-(trifluoromethyl)phenyl, 4-(trifluoromethoxy)phenyl, and 3-fluoro-4-(trifluoromethoxy)phenyl.

41. A pharmaceutical composition comprising a compound as claimed in claim 1.

42. A method of inhibiting the activity of AKT protein kinase in a mammal, which comprises administering to said mammal an effective amount of a compound as claimed in claim 1.

43. A kit, wherein said kit comprises:
    a) a first pharmaceutical composition comprising a compound as claimed in claim 1; and
    b) instructions for use.

44. The compound of claim 1 selected from the group consisting of:
    (S)-2-(4-chlorophenyl)-1-(4-((5R,7R)-7-fluoro-5-methyl-6,7-dihydro-5H-cyclopenta[d]pyrimidin-4-yl)piperazin-1-yl)-2-((S)-pyrrolidin-2-yl)ethanone;
    (S)-2-(4-chlorophenyl)-1-(4-((5R,7S)-7-fluoro-5-methyl-6,7-dihydro-5H-cyclopenta[d]pyrimidin-4-yl)piperazin-1-yl)-2-((S)-pyrrolidin-2-yl)ethanone;
    (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone;
    (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2((S)-piperidin-2-yl)ethanone;
    (S)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone;
    (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-methylpiperidin-2-yl)ethanone;
    (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-methylpyrrolidin-2-yl)ethanone;
    (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-isopropylpyrrolidin-2-yl)ethanone;
    (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-isobutylpyrrolidin-2-yl)ethanone;
    (S)-2-(4-chlorophenyl)-1-(4-((5R,7S)-7-hydroxy-5-methyl-6,7-dihydro-5H-cyclopenta[d]pyrimidin-4-yl)piperazin-1-yl)-2-((S)-1-methylpyrrolidin-2-yl)ethanone;
    (S)-2-(4-chlorophenyl)-1-(4-((5R,7S)-7-hydroxy-5-methyl-6,7-dihydro-5H-cyclopenta[d]pyrimidin-4-yl)piperazin-1-yl)-2-((S)-pyrrolidin-2-yl)ethanone;
    (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1,5,5-trimethylpyrrolidin-2-yl)ethanone;
    (S)-2-(4-cyclopropylphenyl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone;
    (S)-2-(4-chlorophenyl)-2-((S)-1-ethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone;
    (S)-2-(4-chlorophenyl)-2-((S)-1-(cyclopropylmethyl)pyrrolidin-2-yl)-1-(4-((5R,7R)-7-hydroxy-5-methyl-6,7-dihydro-5H-cyclopenta[d]pyrimidin-4-yl)piperazin-1-yl)ethanone;
    (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-(tetrahydro-2H-pyran-4-yl)pyrrolidin-2-yl)ethanone;
    (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-(2-hydroxyethyl)pyrrolidin-2-yl)ethanone;
    (S)-2-(4-chlorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone;
    (S)-2-(4-chlorophenyl)-2-((S)-1-(2-hydroxy-2-methylpropyl)pyrrolidin-2-yl)-1-(4-((5R,7R)-7-hydroxy-5-methyl-6,7-dihydro-5H-cyclopenta[d]pyrimidin-4-yl)piperazin-1-yl)ethanone;
    (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-(3-hydroxypropyl)pyrrolidin-2-yl)ethanone;
    (S)-2-(4-cyclopropylphenyl)-1-(4-((5R,7R)-7-hydroxy-5-methyl-6,7-dihydro-5H-cyclopenta[d]pyrimidin-4-yl)piperazin-1-yl)-2-4S)-1-methylpyrrolidin-2-yl)ethanone;
    (S)-2-(4-cyclopropylphenyl)-1-(4-((5R,7R)-7-hydroxy-5-methyl-6,7-dihydro-5H-cyclopenta[d]pyrimidin-4-yl)piperazin-1-yl)-2-((S)-1-isopropylpyrrolidin-2-yl)ethanone;
    (S)-2-(4-chlorophenyl)-2-((S)-1-ethyl-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone;
    (S)-2-(4-chlorophenyl)-2-((S)-5,5-dimethylpyrrolidin-2-yl)-1-(4-((5R,7S)-7-hydroxy-5-methyl-6,7-dihydro-5H-cyclopenta[d]pyrimidin-4-yl)piperazin-1-yl)ethanone;
    (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-(2-methoxyethyl)-5,5-dimethylpyrrolidin-2-yl)ethanone;
    (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-(2-methoxyethyl)pyrrolidin-2-yl)ethanone;
    (S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-2-((S)-1-methylpyrrolidin-2-yl)ethanone;
    (S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone;
    (S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-2-((S)-1-isopropylpyrrolidin-2-yl)ethanone;
    (S)-2-(4-chlorophenyl)-1-(4-((5R,7S)-7-hydroxy-5-methyl-6,7-dihydro-5H-cyclopenta[d]pyrimidin-4-yl)piperazin-1-yl)-2-((S)-1,5,5-trimethylpyrrolidin-2-yl)ethanone;
    (S)-2-(4-chlorophenyl)-2-((S)-1-ethyl-5,5-dimethylpyrrolidin-2-yl)-1-(4-((5R,7S)-7-hydroxy-5-methyl-6,7-dihydro-5H-cyclopenta[d]pyrimidin-4-yl)piperazin-1-yl)ethanone; and (S)-2-(4-cyclopropylphenyl)-2-((S)-1-ethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone;

and salts thereof.

45. The compound of claim 1 selected from the group consisting of:

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-(2,2,2-trifluoroethyl)pyrrolidin-2-yl)ethanone;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone;

(S)-2-(4-chlorophenyl)-2-((S)-5,5-dimethylpyrrolidin-2-yl)-1-(4-((5R,7R)-5-(fluoromethyl)-7-hydroxy-6,7-dihydro-5H-cyclopenta[d]pyrimidin-4-yl)piperazin-1-yl)ethanone;

(S)-2-(4-chlorophenyl)-1-(4-((R)-7,7-difluoro-5-methyl-6,7-dihydro-5H-cyclopenta[d]pyrimidin-4-yl)piperazin-1-yl)-2-((S)-5,5-dimethylpyrrolidin-2-yl)ethanone;

(S)-2-(4-chlorophenyl)-2-((S)-1-(2,2-difluoroethyl)pyrrolidin-2-yl)-1-(4-((5R,7R)-7-hydroxy-5-methyl-6,7-dihydro-5H-cyclopenta[d]pyrimidin-4-yl)piperazin-1-yl)ethanone;

(S)-2-(4-chlorophenyl)-2-((S)-1-(2-fluoroethyl)pyrrolidin-2-yl)-1-(4-((5R,7R)-7-hydroxy-5-methyl-6,7-dihydro-5H-cyclopenta[d]pyrimidin-4-yl)piperazin-1-yl)ethanone;

(S)-2-(5-chlorothiophen-2-yl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone;

(S)-2-(5-chlorothiophen-2-yl)-1-(4-((5R,7S)-7-hydroxy-5-methyl-6,7-dihydro-5H-cyclopenta[d]pyrimidin-4-yl)piperazin-1-yl)-2-((S)-pyrrolidin-2-yl)ethanone;

(S)-2-(4-chlorophenyl)-1-((S)-4-((5R,7R)-7-hydroxy-5-methyl-6,7-dihydro-5H-cyclopenta[d]pyrimidin-4-yl)-3-methylpiperazin-1-yl)-2-((S)-pyrrolidin-2-yl)ethanone;

(S)-1-(4-((5R,7R)-7-hydroxy-5,7-dimethyl-6,7-dihydro-5H-cyclopenta[d]pyrimidin-4-yl)piperazin-1-yl)-2-((S)-pyrrolidin-2-yl)-2-(4-(trifluoromethyl)phenyl)ethanone;

(S)-2-(5-chlorothiophen-2-yl)-1-(4-((5R,7R)-7-hydroxy-5-methyl-6,7-dihydro-5H-cyclopenta[d]pyrimidin-4-yl)piperazin-1-yl)-2-((S)-1-methylpyrrolidin-2-yl)ethanone;

(S)-2-(5-chlorothiophen-2-yl)-1-(4-((5R,7S)-7-hydroxy-5-methyl-6,7-dihydro-5H-cyclopenta[d]pyrimidin-4-yl)piperazin-1-yl)-2-((S)-1-methylpyrrolidin-2-yl)ethanone;

(S)-2-(3-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)-2-((S)-pyrrolidin-2-yl)ethanone;

(S)-2-(5-bromothiophen-2-yl)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)ethanone;

(S)-2-(5-bromothiophen-2-yl)-1-(4-((5R,7R)-7-hydroxy-5-methyl-6,7-dihydro-5H-cyclopenta[d]pyrimidin-4-yl)piperazin-1-yl)-2-((S)-1-methylpyrrolidin-2-yl)ethanone;

(S)-1-(4-((5R,7R)-7-hydroxy-5,7-dimethyl-6,7-dihydro-5H-cyclopenta[d]pyrimidin-4-yl)piperazin-1-yl)-2-((S)-1-methylpyrrolidin-2-yl)-2-(4-(trifluoromethyl)phenyl)ethanone;

4-((S)-2-(4-((5R,7R)-7-hydroxy-5-methyl-6,7-dihydro-5H-cyclopenta[d]pyrimidin-4-yl)piperazin-1-yl)-2-oxo-1-((S)-pyrrolidin-2-yl)ethyl)benzonitrile;

4-((S)-2-(4-((5R,7R)-7-hydroxy-5-methyl-6,7-dihydro-5H-cyclopenta[d]pyrimidin-4-yl)piperazin-1-yl)-1-((S)-1-methylpyrrolidin-2-yl)-2-oxoethyl)benzonitrile;

(S)-2-(4-chlorophenyl)-2-((S)-5,5-dimethylpyrrolidin-2-yl)-1-(4-((5R,7R)-7-hydroxy-5,7-dimethyl-6,7-dihydro-5H-cyclopenta[d]pyrimidin-4-yl)piperazin-1-yl)ethanone;

(S)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)-2-(4-(trifluoromethyl)phenyl)ethanone;

(S)-2-((S)-5,5-dimethylpyrrolidin-2-yl)-1-(4-((5R,7S)-7-hydroxy-5-methyl-6,7-dihydro-5H-cyclopenta[d]pyrimidin-4-yl)piperazin-1-yl)-2-(4-(trifluoromethyl)phenyl)ethanone;

(S)-2-(4-bromophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone;

(S)-2-(4-bromophenyl)-2-((S)-5,5-dimethylpyrrolidin-2-yl)-1-(4-((5R,7S)-7-hydroxy-5-methyl-6,7-dihydro-5H-cyclopenta[d]pyrimidin-4-yl)piperazin-1-yl)ethanone;

(S)-2-((S)-5,5-dimethylpyrrolidin-2-yl)-2-(2-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)ethanone;

(S)-2-((S)-5,5-dimethylpyrrolidin-2-yl)-2-(2-fluoro-4-(trifluoromethyl)phenyl)-1-(4-4-((5R,7S)-7-hydroxy-5-methyl-6,7-dihydro-5H-cyclopenta[d]pyrimidin-4-yl)piperazin-1-yl)ethanone;

(S)-2-((S)-5,5-dimethylpyrrolidin-2-yl)-1-(4-((5R,7R)-7-fluoro-5-methyl-6,7-dihydro-5H-cyclopenta[d]pyrimidin-4-yl)piperazin-1-yl)-2-(4-(trifluoromethyl)phenyl)ethanone;

(S)-2-(4-bromophenyl)-2-((S)-5,5-dimethylpyrrolidin-2-yl)-1-(4-((5R,7R)-7-fluoro-5-methyl-6,7-dihydro-5H-cyclopenta[d]pyrimidin-4-yl)piperazin-1-yl)ethanone;

(S)-1-(4-((5R,7R)-7-methoxy-5-methyl-6,7-dihydro-5H-cyclopenta[d]pyrimidin-4-yl)piperazin-1-yl)-2-((S)-pyrrolidin-2-yl)-2-(4-(trifluoromethyl)phenyl)ethanone;

(S)-2-(4-chlorophenyl)-2-((S)-5,5-dimethylpyrrolidin-2-yl)-1-(4-((5R,7R)-7-methoxy-5-methyl-6,7-dihydro-5H-cyclopenta[d]pyrimidin-4-yl)piperazin-1-yl)ethanone;

(S)-2-(4-chlorophenyl)-2-((S)-5,5-dimethylpyrrolidin-2-yl)-1-(4-((5R,7R)-7-hydroxy-5-(hydroxymethyl)-6,7-dihydro-5H-cyclopenta[d]pyrimidin-4-yl)piperazin-1-yl)ethanone (S)-2-(4-bromophenyl)-2-((S)-5,5-dimethylpyrrolidin-2-yl)-1-(4-((5R,7S)-7-fluoro-5-methyl-6,7-dihydro-5H-cyclopenta[d]pyrimidin-4-yl)piperazin-1-yl)ethanone;

(S)-2-(4-bromophenyl)-1-(4-((R)-7,7-difluoro-5-methyl-6,7-dihydro-5H-cyclopenta[d]pyrimidin-4-yl)piperazin-1-yl)-2-((S)-5,5-dimethylpyrrolidin-2-yl)ethanone;

(S)-1-(4-((R)-7,7-difluoro-5-methyl-6,7-dihydro-5H-cyclopenta[d]pyrimidin-4-yl)piperazin-1-yl)-2-((S)-5,5-dimethylpyrrolidin-2-yl)-2-(2-fluoro-4-(trifluoromethyl)phenyl)ethanone;

(R)-1-(4-((R)-7,7-difluoro-5-methyl-6,7-dihydro-5H-cyclopenta[d]pyrimidin-4-yl)piperazin-1-yl)-2-((S)-5,5-dimethylpyrrolidin-2-yl)-2-(4-(trifluoromethyl)phenyl)ethanone;

(R)-2-((S)-5,5-dimethylpyrrolidin-2-yl)-2-(2-fluoro-4-(trifluoromethyl)phenyl)-1-(4-((5R,7S)-7-fluoro-5-methyl-6,7-dihydro-5H-cyclopenta[d]pyrimidin-4-yl)piperazin-1-yl)ethanone;

(S)-2-((S)-5,5-dimethylpyrrolidin-2-yl)-1-(4-((5R,7S)-7-fluoro-5-methyl-6,7-dihydro-5H-cyclopenta[d]pyrimidin-4-yl)piperazin-1-yl)-2-(4-(trifluoromethyl)phenyl)ethanone;

4-((S)-1-((S)-5,5-dimethylpyrrolidin-2-yl)-2-(4-((5R,7R)-7-hydroxy-5-methyl-6,7-dihydro-5H-cyclopenta[d]pyrimidin-4-yl)piperazin-1-yl)-2-oxoethyl)benzonitrile;

(S)-2-(4-chlorophenyl)-2-((S)-5,5-dimethylpyrrolidin-2-yl)-1-(4-((R)-5-(hydroxymethyl)-6,7-dihydro-5H-cyclopenta[d]pyrimidin-4-yl)piperazin-1-yl)ethanone;

(S)-1-(4-((5R,7R)-7-methoxy-5-methyl-6,7-dihydro-5H-cyclopenta[d]pyrimidin-4-yl)piperazin-1-yl)-2-((S)-1-methylpyrrolidin-2-yl)-2-(4-(trifluoromethyl)phenyl)ethanone;

(S)-1-(4-((5R,7R)-7-hydroxy-5-methyl-6,7-dihydro-5H-cyclopenta[d]pyrimidin-4-yl)piperazin-1-yl)-2-((S)-pyrrolidin-2-yl)-2-(4-(trifluoromethyl)phenyl)ethanone;

(S)-1-(4-((5R,7R)-7-hydroxy-5-methyl-6,7-dihydro-5H-cyclopenta[d]pyrimidin-4-yl)piperazin-1-yl)-2-((S)-1-methylpyrrolidin-2-yl)-2-(4-(trifluoromethyl)phenyl)ethanone;

(S)-2-(4-cyclopropylphenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone;

(S)-2-(4-cyclopropylphenyl)-2-((S)-5,5-dimethylpyrrolidin-2-yl)-1-(4-((5R,7S)-7-hydroxy-5-methyl-6,7-dihydro-5H-cyclopenta[d]pyrimidin-4-yl)piperazin-1-yl)ethanone;

(R)-4-(4-((S)-2-(4-chlorophenyl)-2-((S)-5,5-dimethylpyrrolidin-2-yl)acetyl)piperazin-1-yl)-5-methyl-5H-cyclopenta[d]pyrimidin-7(6H)-one;

(S)-2-(4-chlorophenyl)-2-((S)-5,5-dimethylpyrrolidin-2-yl)-1-(4-((5R,7S)-7-fluoro-5-methyl-6,7-dihydro-5H-cyclopenta[d]pyrimidin-4-yl)piperazin-1-yl)ethanone;

(S)-2-(4-chloro-3-fluorophenyl)-1-(4-((5R,7S)-7-fluoro-5-methyl-6,7-dihydro-5H-cyclopenta[d]pyrimidin-4-yl)piperazin-1-yl)-2-((S)-pyrrolidin-2-yl)ethanone;

(S)-2-((S)-5,5-dimethylpyrrolidin-2-yl)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)ethanone;

(S)-2-((S)-5,5-dimethylpyrrolidin-2-yl)-2-(3-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)ethanone;

(S)-2-(4-chloro-3-fluorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone;

(S)-2-(4-chloro-3-fluorophenyl)-2-((S)-5,5-dimethylpyrrolidin-2-yl)-1-(4-((5R,7S)-7-hydroxy-5-methyl-6,7-dihydro-5H-cyclopenta[d]pyrimidin-4-yl)piperazin-1-yl)ethanone;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((S)-1-azaspiro[4.4]nonan-2-yl)ethanone;

(S)-2-(4-chlorophenyl)-2-((S)-5,5-di ethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone;

(S)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)-2-(4-(methylsulfonyl)phenyl)ethanone;

4-((S)-2-(4-((5R,7R)-7-hydroxy-5-methyl-6,7-dihydro-5H-cyclopenta[d]pyrimidin-4-yl)piperazin-1-yl)-2-oxo-1-((S)-pyrrolidin-2-yl)ethyl)benzamide;

4-((S)-2-(4-((5R,7R)-7-hydroxy-5-methyl-6,7-dihydro-5H-cyclopenta[d]pyrimidin-4-yl)piperazin-1-yl)-1-((S)-1-methylpyrrolidin-2-yl)-2-oxoethyl)benzamide;

(S)-2-((S)-5,5-dimethylpyrrolidin-2-yl)-1-(4-((5R,7R)-7-hydroxy-5,7-dimethyl-6,7-dihydro-5H-cyclopenta[d]pyrimidin-4-yl)piperazin-1-yl)-2-(4-(trifluoromethyl)phenyl)ethanone;

(S)-2-((S)-5,5-dimethylpyrrolidin-2-yl)-2-(3-fluoro-4-(trifluoromethyl)phenyl)-1-(4-((5R,7R)-7-hydroxy-5,7-dimethyl-6,7-dihydro-5H-cyclopenta[d]pyrimidin-4-yl)piperazin-1-yl)ethanone;

(S)-1-(4-((5R,7R)-7-hydroxy-5-methyl-6,7-dihydro-5H-cyclopenta[d]pyrimidin-4-yl)piperazin-1-yl)-2-(4-(methylsulfonyl)phenyl)-2-((S)-pyrrolidin-2-yl)ethanone;

(S)-1-(4-((5R,7R)-7-hydroxy-5-methyl-6,7-dihydro-5H-cyclopenta[d]pyrimidin-4-yl)piperazin-1-yl)-2-((S)-1-methylpyrrolidin-2-yl)-2-(4-(methyl sulfonyl)phenyl)ethanone;

(S)-2-(4-chloro-3-fluorophenyl)-2-((S)-5,5-dimethylpyrrolidin-2-yl)-1-(4-((5R,7R)-7-hydroxy-5,7-dimethyl-6,7-dihydro-5H-cyclopenta[d]pyrimidin-4-yl)piperazin-1-yl)ethanone;

(S)-2-(4-bromophenyl)-2-((S)-5,5-dimethylpyrrolidin-2-yl)-1-(4-((5R,7R)-7-hydroxy-5,7-dimethyl-6,7-dihydro-5H-cyclopenta[d]pyrimidin-4-yl)piperazin-1-yl)ethanone;

4-((S)-1-((S)-5,5-dimethylpyrrolidin-2-yl)-2-(4-((5R,7R)-7-hydroxy-5-methyl-6,7-dihydro-5H-cyclopenta[d]pyrimidin-4-yl)piperazin-1-yl)-2-oxoethyl)-2-fluorobenzonitrile;

(S)-2-(4-chlorophenyl)-1-(4-((5R,7S)-7-hydroxy-5-methyl-6,7-dihydro-5H-cyclopenta[d]pyrimidin-4-yl)piperazin-1-yl)-2-((R)-morpholin-3-yl)ethanone;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((R)-4-methylmorpholin-3-yl)ethanone;

(S)-2-(4-chlorophenyl)-1-(4-((5R,7S)-7-hydroxy-5-methyl-6,7-dihydro-5H-cyclopenta[d]pyrimidin-4-yl)piperazin-1-yl)-2-((R)-4-methylmorpholin-3-yl)ethanone; and (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((R)-morpholin-3-yl)ethanone;

and salts thereof.

46. The compound of claim 1 selected from the group consisting of:

(S)-2-(4-chloro-2,5-difluorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone;

(S)-2-(4-chloro-2-fluorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone;

(S)-2-(4-bromo-2-fluorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone;

(S)-2-(4-bromo-3-fluorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone;

(S)-2-(3-chlorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone;

(S)-1-(4-((5R,7R)-7-methoxy-5-methyl-6,7-dihydro-5H-cyclopenta[d]pyrimidin-4-yl)piperazin-1-yl)-2-((S)-pyrrolidin-2-yl)-2-(4-(trifluoromethyl)phenyl)ethanone;

(S)-2-(4-chloro-2-fluorophenyl)-2-((S)-5,5-dimethylpyrrolidin-2-yl)-1-(4-((5R,7R)-7-hydroxy-5,7-dimethyl-6,7-dihydro-5H-cyclopenta[d]pyrimidin-4-yl)piperazin-1-yl)ethanone dihydrochloride;

(S)-2-(4-chloro-2-fluorophenyl)-2-((S)-5,5-dimethylpyrrolidin-2-yl)-1-(4-((5R,7S)-7-fluoro-5-methyl-6,7-dihydro-5H-cyclopenta[d]pyrimidin-4-yl)piperazin-1-yl)ethanone dihydrochloride;

(S)-2-((S)-5,5-dimethylpyrrolidin-2-yl)-2-(2-fluoro-4-methylphenyl)-1-(4-((5R,7R)-7-hydroxy-5-methyl-6,7-dihydro-5H-cyclopenta[d]pyrimidin-4-yl)piperazin-1-yl)ethanone dihydrochloride;

(S)-2-(2,4-dichlorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone dihydrochloride;

(S)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)-2-(naphthalen-2-yl)ethanone dihydrochloride;

(S)-2-((S)-5,5-dimethylpyrrolidin-2-yl)-1-(4-((R)-5-methyl-6,7-dihydro-5H-cyclopenta[d]pyrimidin-4-yl)piperazin-1-yl)-2-(naphthalen-2-yl)ethanone dihydrochloride;

(S)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)-2-(naphthalen-1-yl)ethanone dihydrochloride;

(S)-2-((S)-5,5-dimethylpyrrolidin-2-yl)-1-(4-((R)-5-methyl-6,7-dihydro-5H-cyclopenta[d]pyrimidin-4-yl)piperazin-1-yl)-2-(naphthalen-1-yl)ethanone dihydrochloride;

(S)-2-(3,4-dichlorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone dihydrochloride;

(S)-2-(3,4-difluorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone dihydrochloride;

(S)-2-((S)-5,5-dimethylpyrrolidin-2-yl)-2-(4-fluorophenyl)-1-(4-((5R,7R)-7-hydroxy-5-methyl-6,7-dihydro-5H-cyclopenta[d]pyrimidin-4-yl)piperazin-1-yl)ethanone dihydrochloride;

(S)-2-((S)-5,5-dimethylpyrrolidin-2-yl)-2-(4-fluoro-3-(trifluoromethyl)phenyl)-1-(4-((5R,7R)-7-hydroxy-5-methyl-6,7-dihydro-5H-cyclopenta[d]pyrimidin-4-yl)piperazin-1-yl)ethanone dihydrochloride;

(S)-2-(3-chlorophenyl)-2-((S)-5,5-dimethylpyrrolidin-2-yl)-1-(4-((R)-5-methyl-6,7-dihydro-5H-cyclopenta[d]pyrimidin-4-yl)piperazin-1-yl)ethanone dihydrochloride;

(S)-2-(3-bromophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone dihydrochloride;

(S)-2-(3-bromophenyl)-2-((S)-5,5-dimethylpyrrolidin-2-yl)-1-(4-((R)-5-methyl-6,7-dihydro-5H-cyclopenta[d]pyrimidin-4-yl)piperazin-1-yl)ethanone dihydrochloride;

(S)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)-2-(3-(trifluoromethyl)phenyl)ethanone dihydrochloride;

(S)-2-((S)-5,5-dimethylpyrrolidin-2-yl)-2-(3-fluorophenyl)-1-(4-((5R,7R)-7-hydroxy-5-methyl-6,7-dihydro-5H-cyclopenta[d]pyrimidin-4-yl)piperazin-1-yl)ethanone dihydrochloride;

(S)-2-((S)-5,5-dimethylpyrrolidin-2-yl)-2-(2-fluoro-4-methoxyphenyl)-1-(4-((5R,7R)-7-hydroxy-5-methyl-6,7-dihydro-5H-cyclopenta[d]pyrimidin-4-yl)piperazin-1-yl)ethanone dihydrochloride;

(S)-2-(4-(1H-pyrazol-4-yl)phenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone;

(S)-2-(biphenyl-4-yl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone;

(S)-2-(4-(2-aminopyrimidin-5-yl)phenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone;

(S)-2-(4-tert-butylphenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone dihydrochloride;

(S)-2-(2,3-difluoro-4-(trifluoromethyl)phenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone;

(S)-2-((S)-5,5-dimethylpyrrolidin-2-yl)-2-(2-fluoro-3-(trifluoromethyl)phenyl)-1-(4-((5R,7R)-7-hydroxy-5-methyl-6,7-dihydro-5H-cyclopenta[d]pyrimidin-4-yl)piperazin-1-yl)ethanone;

(S)-2-((S)-5,5-dimethylpyrrolidin-2-yl)-2-(2-fluoro-5-(trifluoromethyl)phenyl)-1-(4-((5R,7R)-7-hydroxy-5-methyl-6,7-dihydro-5H-cyclopenta[d]pyrimidin-4-yl)piperazin-1-yl)ethanone;

(S)-5-((S)-2-(4-((5R,7R)-7-hydroxy-5-methyl-6,7-dihydro-5H-cyclopenta[d]pyrimidin-4-yl)piperazin-1-yl)-2-oxo-1-(4-(trifluoromethyl)phenyl)ethyl)pyrrolidin-2-one;

(S)-2-(4-chloro-2,5-difluorophenyl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone;

(S)-5-((S)-1-(4-chlorophenyl)-2-(4-((5R,7R)-7-hydroxy-5-methyl-6,7-dihydro-5H-cyclopenta[d]pyrimidin-4-yl)piperazin-1-yl)-2-oxoethyl)pyrrolidin-2-one;

(S)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)-2-(4-(trifluoromethoxy)phenyl)ethanone;

(S)-2-((S)-5,5-dimethylpyrrolidin-2-yl)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)ethanone;

(S)-2-(5-bromothiophen-2-yl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone;

(S)-2-(5-chlorothiophen-2-yl)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)ethanone; and (S)-2-((S)-5,5-dimethylpyrrolidin-2-yl)-1-(4-((5R,7R)-7-hydroxy-5-methyl-6,7-dihydro-5H-cyclopenta[d]pyrimidin-4-yl)piperazin-1-yl)-2-(1H-indol-3-yl)ethanone;

and salts thereof.

47. A compound selected from the group consisting of:

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((R)-pyrrolidin-2-yl)ethanone;

(S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-2-((R)-pyrrolidin-2-yl)ethanone;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((R)-1-methylpyrrolidin-2-yl)ethanone;

(R)-5-((S)-2-(4-((5R,7R)-7-hydroxy-5-methyl-6,7-dihydro-5H-cyclopenta[d]pyrimidin-4-yl)piperazin-1-yl)-2-oxo-1-(4-(trifluoromethyl)phenyl)ethyl)pyrrolidin-2-one; and (R)-5-((S)-1-(4-chlorophenyl)-2-(4-((5R,7R)-7-hydroxy-5-methyl-6,7-dihydro-5H-cyclopenta[d]pyrimidin-4-yl)piperazin-1-yl)-2-oxoethyl)pyrrolidin-2-one;

and salts thereof.

48. The compound of claim 47 selected from the group consisting of:

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((R)-pyrrolidin-2-yl)ethanone;

(S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-2-((R)-pyrrolidin-2-yl)ethanone; and (S)-2-(4-chlorophenyl)-1-(4-((5R,7R)-7-hydroxy-5-methyl-6,7-dihydro-5H-cyclopenta[d]pyrimidin-4-yl)piperazin-1-yl)-2-((R)-1-methylpyrrolidin-2-yl)ethanone;

and salts thereof.

49. A pharmaceutical composition comprising a compound as claimed in claim 47.

50. A method of inhibiting the activity of AKT protein kinase in a mammal, which comprises administering to said mammal an effective amount of a compound as claimed in claim 47.

\* \* \* \* \*